(12) United States Patent
Hongyan et al.

(10) Patent No.: US 11,814,354 B2
(45) Date of Patent: Nov. 14, 2023

(54) SOLID FORMS

(71) Applicants: River 3 Renal Corp., New York, NY (US); Hoffmann-La Roche Inc., Little Falls, NJ (US)

(72) Inventors: He Hongyan, Shanghai (CN); Jiang Siyi, Shanghai (CN); Urs Schwitter, Little Falls, NJ (US); Pascal Jean Claude Dott, Littlefalls, NJ (US); Ralph Diodone, Little Falls, NJ (US); Nicole Wyttenbach, Little Falls, NJ (US); Olaf Grassmann, Little Falls, NJ (US)

(73) Assignee: River 3 Renal Corp., New York, NY (US)

( * ) Notice: Subject to any disclaimer, the term of this patent is extended or adjusted under 35 U.S.C. 154(b) by 0 days.

(21) Appl. No.: 17/939,203

(22) Filed: Sep. 7, 2022

(65) Prior Publication Data

US 2023/0242485 A1   Aug. 3, 2023

Related U.S. Application Data

(60) Provisional application No. 63/243,813, filed on Sep. 14, 2021.

(30) Foreign Application Priority Data

Sep. 8, 2021   (CN) .................. 202111049581.4

(51) Int. Cl.
   *C07D 213/64*   (2006.01)

(52) U.S. Cl.
   CPC ........ *C07D 213/64* (2013.01); *C07B 2200/13* (2013.01)

(58) Field of Classification Search
   CPC .................... C07D 213/64; C07B 2200/13
   See application file for complete search history.

(56) References Cited

U.S. PATENT DOCUMENTS

| 8,227,491 B2 | 7/2012 | Roever et al. |
| 2020/0085810 A1* | 3/2020 | Fornoni ............. A61K 31/4245 |

FOREIGN PATENT DOCUMENTS

| WO | WO-2011029827 A1 | 3/2011 |
| WO | WO-2012031817 A1 | 3/2012 |
| WO | WO-2012052444 A1 | 4/2012 |
| WO | WO-2014180741 A1 | 11/2014 |
| WO | WO-2020021097 A1 | 1/2020 |

OTHER PUBLICATIONS

Caira, M., "Crystalline Polymorphism of Organic Compunds," Topics in Current Chemistry 198:Jan. 1, 1998, pp. 163-208, XP001156954.
International Search Report and Written Opinion in PCT/US2022/042905, dated Mar. 2, 2023 18 pages.

* cited by examiner

*Primary Examiner* — Timothy R Rozof
(74) *Attorney, Agent, or Firm* — Goodwin Procter LLP

(57) ABSTRACT

The disclosure is in part directed to crystalline forms of 5-(3,4-dichlorophenyl)-N-((1R,2R)-2-hydroxycyclohexyl)-6-(2,2,2-trifluoroethoxy)nicotinamide and pharmaceutical compositions thereof.

17 Claims, 80 Drawing Sheets

SOLID FORMS

CROSS REFERENCE TO RELATED APPLICATIONS

This application claims the benefit of, and priority to, U.S. Provisional Patent Application No. 63/243,813, filed on Sep. 14, 2021; and Chinese Application Number 202111049581.4, filed on Sep. 8, 2021; the contents of each of which are hereby incorporated by reference in their entirety.

BACKGROUND

Chronic kidney disease is characterized by gradual loss of kidney function over a period of months to years. Chronic kidney disease affected 753 million people globally in 2016, and in 2015 caused 1.2 million deaths. Causes that contribute to the greatest number of deaths include, for example, diabetes, hypertension, and glomerulonephritis. Initial treatments may include, for example, medications to lower blood pressure, blood sugar, and cholesterol, as well as dietary changes, while severe disease may require hemodialysis, peritoneal dialysis, or a kidney transplant for survival. Therefore, there continues to be a need to develop therapeutics, e.g., small molecule therapeutics, for the treatment of kidney diseases.

Polymorphism is the ability of a substance to crystallize in more than one crystal lattice arrangement. Crystallization, or polymorphism, can influence many aspects of the solid-state properties of a drug substance. A crystalline substance may differ considerably from an amorphous form, and different crystal modifications of a substance may differ considerably from one another in many respects including solubility, dissolution rate and/or bioavailability. Generally, it is difficult to predict whether a given compound will form any crystalline solid-state forms. It is even more difficult to predict the physical and pharmaceutical properties of these crystalline solid-state forms. Therefore, it can be advantageous to have a crystalline form of a therapeutic agent for certain formulations and/or for manufacturing processes.

SUMMARY

The present disclosure is directed, at least in part, to crystalline forms of 5-(3,4-dichlorophenyl)-N-((1R,2R)-2-hydroxycyclohexyl)-6-(2,2,2-trifluoroethoxy)nicotinamide and stereoisomers thereof, as well as crystalline anhydrates, hydrates and solvates thereof.

For example, disclosed herein is a crystalline form of 5-(3,4-dichlorophenyl)-N-((1R,2R)-2-hydroxycyclohexyl)-6-(2,2,2-trifluoroethoxy)nicotinamide, anyhdrate, characterized by a powder X-ray diffraction pattern having a characteristic peak in degrees 2θ at about 10.3, for example, characterized by a powder X-ray diffraction pattern having characteristic peaks in degrees 2θ at about 10.3, 15.9, and 20.6, for example, characterized by a powder X-ray diffraction pattern having characteristic peaks in degrees 2θ at about 10.3, 15.9, 17.7, 20.6, 21.4, and 26.1, for example, characterized by a powder X-ray diffraction pattern having characteristic peaks in degrees 2θ at about 10.3, 14.9, 15.9, 17.7, 18.9, 20.6, 21.4, 21.8, 26.1, 29.7, 33.0, and 39.3.

5-(3,4-Dichlorophenyl)-N-((1R,2R)-2-hydroxycyclohexyl)-6-(2,2,2-trifluoroethoxy)nicotinamide is, for example, an ATP-binding cassette transporter A1 protein (ABCA1) inducer (e.g., stabilizes the expression level and/or activity of ABCA1 in plasma membranes), and is represented by:

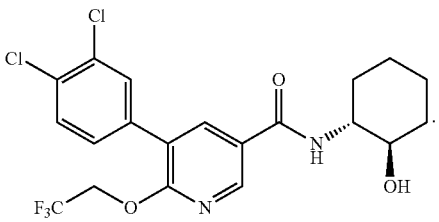 [SMILES: O=C(N[C@@H]1CCCC[C@H]1O)c1cnc(OCC(F)(F)F)c(-c2ccc(Cl)c(Cl)c2)c1]

Further contemplated herein is a pharmaceutical composition comprising a disclosed crystalline form of 5-(3,4-dichlorophenyl)-N-((1R,2R)-2-hydroxycyclohexyl)-6-(2,2,2-trifluoroethoxy)nicotinamide and a pharmaceutically acceptable excipient, for example, a composition that is formulated for oral administration. Further contemplated herein is a drug substance comprising at least a detectable amount of a disclosed form of 5-(3,4-dichlorophenyl)-N-((1R,2R)-2-hydroxycyclohexyl)-6-(2,2,2-trifluoroethoxy)nicotinamide. For example, disclosed herein is a drug substance comprising substantially pure crystalline form of 5-(3,4-dichlorophenyl)-N-((1R,2R)-2-hydroxycyclohexyl)-6-(2,2,2-trifluoroethoxy)nicotinamide.

Also provided herein is a method of treating a kidney disease in a patient in need thereof, comprising administering to the patient an effective amount of a disclosed crystalline form of 5-(3,4-dichlorophenyl)-N-((1R,2R)-2-hydroxycyclohexyl)-6-(2,2,2-trifluoroethoxy)nicotinamide. For example, provided herein is a method of treating a kidney disease in a patient in need thereof, comprising administering to the patient an effective amount of a pharmaceutical composition comprising a disclosed crystalline form of 5-(3,4-dichlorophenyl)-N-((1R,2R)-2-hydroxycyclohexyl)-6-(2,2,2-trifluoroethoxy)nicotinamide.

DETAILED DESCRIPTION

Figure 1:
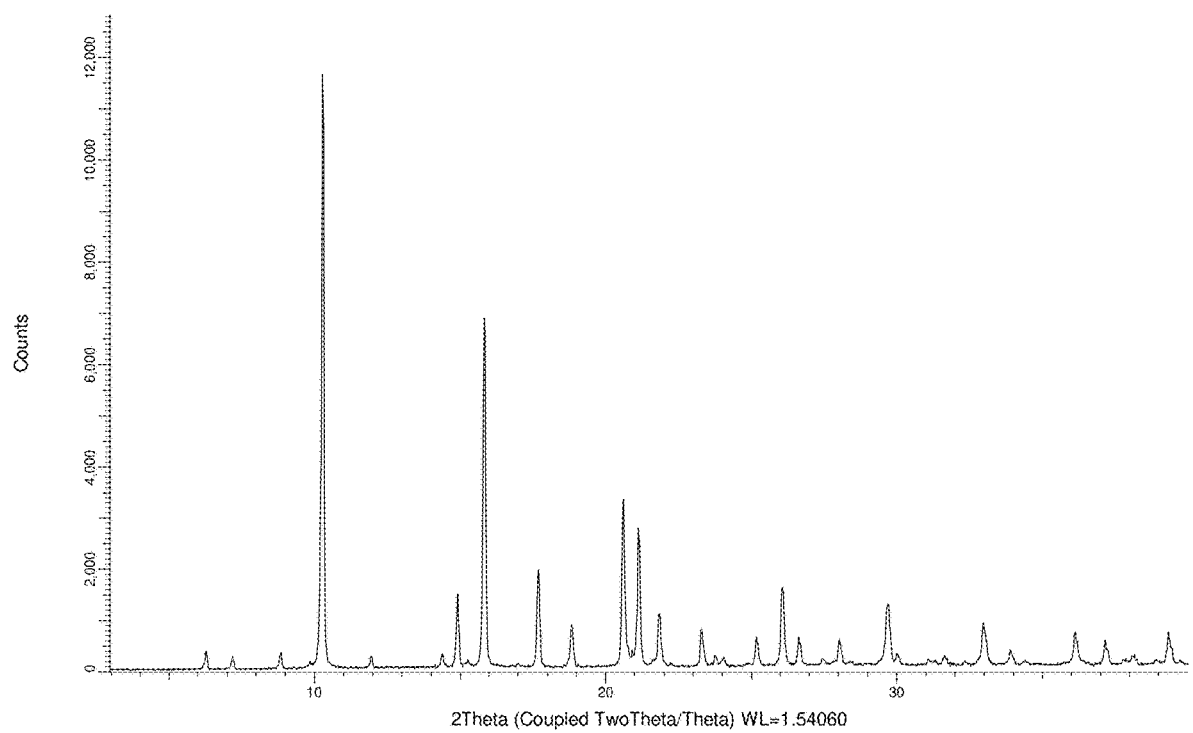
FIG. 1 depicts an X-ray powder diffraction (XRPD) pattern of 5-(3,4-dichlorophenyl)-N-((1R,2R)-2-hydroxycyclohexyl)-6-(2,2,2-trifluoroethoxy)nicotinamide, anhydrate (Form E).

The features and other details of the disclosure will now be more particularly described. Before further description of the present disclosure, certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

Definitions

The term "crystalline form" refers to a crystal form or modification that can be characterized by analytical methods such as, e.g., X-ray powder diffraction (XRPD) and/or Differential scanning calorimetry (DSC). The crystalline compounds disclosed herein can exist in solvated as well as unsolvated forms with solvents such as water, ethanol, and the like. Unless otherwise indicated or inferred, it is intended that disclosed crystalline compounds include both solvated and unsolvated forms.

"Treating" includes any effect, e.g., lessening, reducing, modulating, or eliminating, that results in the improvement of the condition, disease, disorder and the like.

The term "disorder" refers to and is used interchangeably with, the terms "disease," "condition," or "illness," unless otherwise indicated.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable excipient" or "pharmaceutically acceptable carrier" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable excipients.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds of the present disclosure can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods of the present disclosure is desirably a mammal in which treatment, for example, of a kidney disease, a cancer or a blood disorder is desired. "Modulation" includes antagonism (e.g., inhibition), agonism, partial antagonism and/or partial agonism.

In the present specification, the terms "effective amount" or "therapeutically effective amount" means the amount of the subject compound that will elicit the biological or medical response of a tissue, system or animal, (e.g., mammal or human) that is being sought by the researcher, veterinarian, medical doctor or other clinician. The compounds of the present disclosure are administered in therapeutically effective amounts to treat a disease. Alternatively, a therapeutically effective amount of a compound is the quantity required to achieve a desired therapeutic and/or prophylactic effect.

The term "pharmaceutically acceptable salt(s)" as used herein refers to salts of basic groups that may be present in compounds used in the compositions. Compounds included in the present compositions that are basic in nature are capable of forming a wide variety of salts with various inorganic and organic acids.

The term "and/or" is used in this disclosure to mean either "and" or "or" unless indicated otherwise.

As used herein, the words "a" and "an" are meant to include one or more unless otherwise specified. For example, the term "an agent" encompasses both a single agent and a combination of two or more agents.

Where the use of the term "about" is before a quantitative value, the present disclosure also includes the specific quantitative value itself, unless specifically stated otherwise. As used herein, the term "about" refers to a ±10% variation from the nominal value unless otherwise indicated or inferred. The term "about" in the context of peaks at degrees 2θ means that there is an uncertainty in the measurements of the 2θ of ±0.5 (expressed in 2θ) or that there is an uncertainty in the measurements of the 2θ of ±0.2 (expressed in 2θ). Generally, a DSC thermogram may have a variation in the range of ±3° C. Therefore, the temperature values should be understood as including values in the range of about ±3° C.

In general, provided herein are crystalline forms of 5-(3,4-dichlorophenyl)-N-((1R,2R)-2-hydroxycyclohexyl)-6-(2,2,2-trifluoroethoxy)nicotinamide that are substantially free of any other crystalline forms, unless indicated otherwise. As used herein, "substantially free" or substantially free of any other crystalline forms" means that the disclosed crystalline form contains about 20% or less, about 10% or less, about 5% or less, about 2% or less, or about 1% or less, of any other crystalline forms of 5-(3,4-dichlorophenyl)-N-((1R,2R)-2-hydroxycyclohexyl)-6-(2,2,2-trifluoroethoxy) nicotinamide as measured, for example, by XRPD, or less than about 20%, less than about 10%, less than about 5%, less than about 4%, less than about 3%, less than about 2% or less than about 1%, of any other crystalline forms of 5-(3,4-dichlorophenyl)-N-((1R,2R)-2-hydroxycyclohexyl)-6-(2,2,2-trifluoroethoxy)nicotinamide as measured, for example, by XRPD. Thus, a disclosed crystalline form of 5-(3,4-dichlorophenyl)-N-((1R,2R)-2-hydroxycyclohexyl)-6-(2,2,2-trifluoroethoxy)nicotinamide described herein as substantially free of any other crystalline forms would be understood to contain greater than 80% (w/w), greater than 90% (w/w), greater than 95% (w/w), greater than 98% (w/w), or greater than 99% (w/w) of the said crystalline forms of 5-(3,4-dichlorophenyl)-N-((1R,2R)-2-hydroxycyclohexyl)-6-(2,2,2-trifluoroethoxy)nicotinamide. Accordingly, in some embodiments, a disclosed crystalline form of 5-(3,4-dichlorophenyl)-N-((1R,2R)-2-hydroxycyclohexyl)-6-(2,2,2-trifluoroethoxy)nicotinamide may contain from 1% to 20% (w/w), from 5% to 20% (w/w), or from 5% to 10% (w/w) of one or more other crystalline forms of 5-(3,4-dichlorophenyl)-N-((1R,2R)-2-hydroxycyclohexyl)-6-(2,2,2-trifluoroethoxy)nicotinamide.

Crystalline Forms

The present disclosure is directed, at least in part, to crystalline forms of 5-(3,4-dichlorophenyl)-N-((1R,2R)-2-hydroxycyclohexyl)-6-(2,2,2-trifluoroethoxy)nicotinamide.

For example, disclosed herein is a crystalline form of 5-(3,4-dichlorophenyl)-N-((1R,2R)-2-hydroxycyclohexyl)-6-(2,2,2-trifluoroethoxy)nicotinamide, anhydrate, characterized by a powder X-ray diffraction pattern having a characteristic peak in degrees 2θ at about 10.3 (referred to herein as "Form E").

In one embodiment, the crystalline Form E of 5-(3,4-dichlorophenyl)-N-((1R,2R)-2-hydroxycyclohexyl)-6-(2,2,2-trifluoroethoxy)nicotinamide, anhydrate, is characterized by a powder X-ray diffraction pattern that has a characteristic peak in degrees 2θ at about 10.3, is characterized by a powder X-ray diffraction pattern that has a characteristic peak in degrees 2θ at about 14.9, is characterized by a powder X-ray diffraction pattern that has a characteristic peak in degrees 2θ at about 15.9, is characterized by a powder X-ray diffraction pattern that has a characteristic peak in degrees 2θ at about 17.7, is characterized by a powder X-ray diffraction pattern that has a characteristic peak in degrees 2θ at about 18.9, is characterized by a powder X-ray diffraction pattern that has a characteristic peak in degrees 2θ at about 20.6, is characterized by a powder X-ray diffraction pattern that has a characteristic peak in degrees 2θ at about 21.4, is characterized by a powder X-ray diffraction pattern that has a characteristic peak in degrees 2θ at about 21.8, is characterized by a powder X-ray diffraction pattern that has a characteristic peak in degrees 2θ at about 26.1, is characterized by a powder X-ray diffraction pattern that has a characteristic peak in degrees 2θ at about 29.7, is characterized by a powder X-ray diffraction pattern that has a characteristic peak in degrees 2θ at about 33.0, and/or is characterized by a powder X-ray diffraction pattern that has a characteristic peak in degrees 2θ at about 39.3. In another embodiment, crystalline Form E is characterized by a powder X-ray diffraction pattern having at least one or more characteristic peaks in degrees 2θ at about 10.3, 15.9, and 20.6. In a further embodiment, crystalline Form E is characterized by a powder X-ray diffraction pattern having at least one or more characteristic peaks in degrees 2θ at about 10.3, 15.9, 17.7, 20.6, 21.4, and 26.1. In yet another embodiment, crystalline Form E is characterized by a powder X-ray diffraction pattern having at least one or more characteristic peaks in degrees 2θ at about 10.3, 14.9, 15.9, 17.7, 18.9, 20.6, 21.4, 21.8, 26.1, 29.7, 33.0, and 39.3. In another embodiment, crystalline Form E is characterized by a powder X-ray diffraction pattern having at least one or more characteristic peaks in degrees 2θ at about 10.3, 14.9, 15.9, 17.7, 18.9, 20.6, 21.4, 21.8, 23.3, 25.2, 26.1, 26.7, 29.7, 28.0, 33.0, 36.1, 37.2, and 39.3. For example, a contemplated crystalline form has a powder X-ray diffraction pattern shown in FIG. 1. In one embodiment, the powder X-ray diffraction pattern of the crystalline form was obtained using Cu Kα radiation.

In one embodiment, the crystalline Form E of 5-(3,4-dichlorophenyl)-N-((1R,2R)-2-hydroxycyclohexyl)-6-(2,2,2-trifluoroethoxy)nicotinamide, anhydrate, is characterized by a powder X-ray diffraction pattern that has a characteristic peak in degrees 2θ at about 10.2, is characterized by a powder X-ray diffraction pattern that has a characteristic peak in degrees 2θ at about 17.6, is characterized by a powder X-ray diffraction pattern that has a characteristic peak in degrees 2θ at about 18.3, is characterized by a powder X-ray diffraction pattern that has a characteristic peak in degrees 2θ at about 19.0, is characterized by a powder X-ray diffraction pattern that has a characteristic peak in degrees 2θ at about 19.3, is characterized by a powder X-ray diffraction pattern that has a characteristic peak in degrees 2θ at about 21.0, is characterized by a powder X-ray diffraction pattern that has a characteristic peak in degrees 2θ at about 21.6, is characterized by a powder X-ray diffraction pattern that has a characteristic peak in degrees 2θ at about 21.9, is characterized by a powder X-ray diffraction pattern that has a characteristic peak in degrees 2θ at about 23.4, is characterized by a powder X-ray diffraction pattern that has a characteristic peak in degrees 2θ at about 23.6, is characterized by a powder X-ray diffraction pattern that has a characteristic peak in degrees 2θ at about 24.0, and/or is characterized by a powder X-ray diffraction pattern that has a characteristic peak in degrees 2θ at about 26.1. In another embodiment, crystalline Form E is characterized by a powder X-ray diffraction pattern having at least one or more characteristic peaks in degrees 2θ at about 19.3, 21.6, and 21.9. In a further embodiment, crystalline Form E is characterized by a powder X-ray diffraction pattern having at least one or more characteristic peaks in degrees 2θ at about 19.3, 21.0, 21.6, 21.9, 23.4, and 24.0. In yet another embodiment, crystalline Form E is characterized by a powder X-ray diffraction pattern having at least one or more characteristic peaks in degrees 2θ at about 10.2, 17.6, 18.3, 19.0, 19.3, 21.0, 21.6, 21.9, 23.4, 23.6, 24.0, and 26.1. In another embodiment, crystalline Form E is characterized by a powder X-ray diffraction pattern having at least one or more characteristic peaks in degrees 2θ at about 7.1, 10.2, 15.8, 17.6, 18.3, 19.0, 19.3, 20.7, 21.0, 21.6, 21.9, 23.4, 23.6, 24.0, 26.1, 27.8, 29.5, and 32.3. For example, a contemplated crystalline form has a powder X-ray diffraction pattern shown in FIG. 1A. In one embodiment, the powder X-ray diffraction pattern of the crystalline form was obtained using Cu Kα radiation.

The contemplated crystalline Form E of 5-(3,4-dichlorophenyl)-N-((1R,2R)-2-hydroxycyclohexyl)-6-(2,2,2-trifluoroethoxy)nicotinamide, anhydrate, may be characterized by a differential scanning calorimetry (DSC) profile showing a characteristic endotherm with an onset of about 168° C. and a peak of about 169° C. Form E, for example, may be characterized by the differential scanning calorimetry profile shown in FIG. 2.

Figure 3:
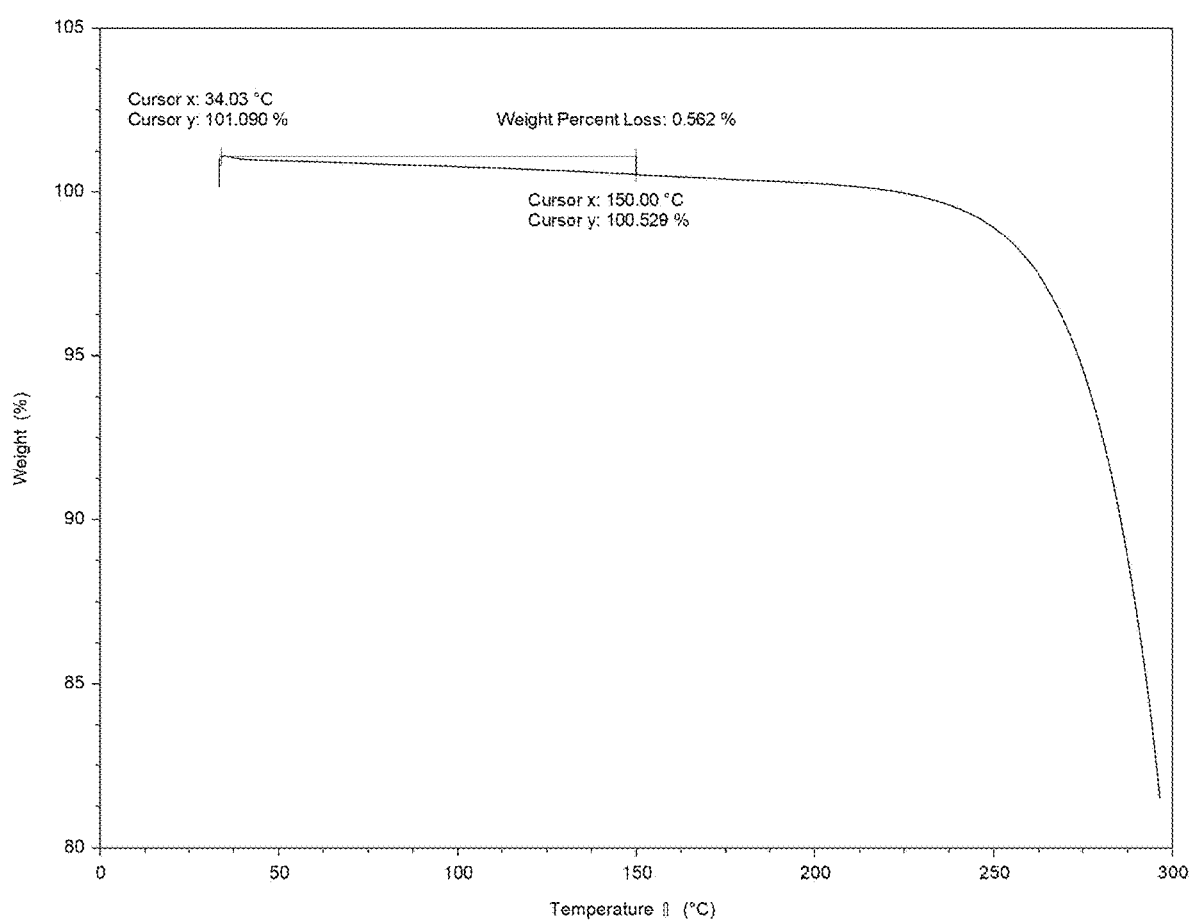
FIG. 3 depicts the thermogravimetric analysis (TGA) profile of Form E.
Figure 4:
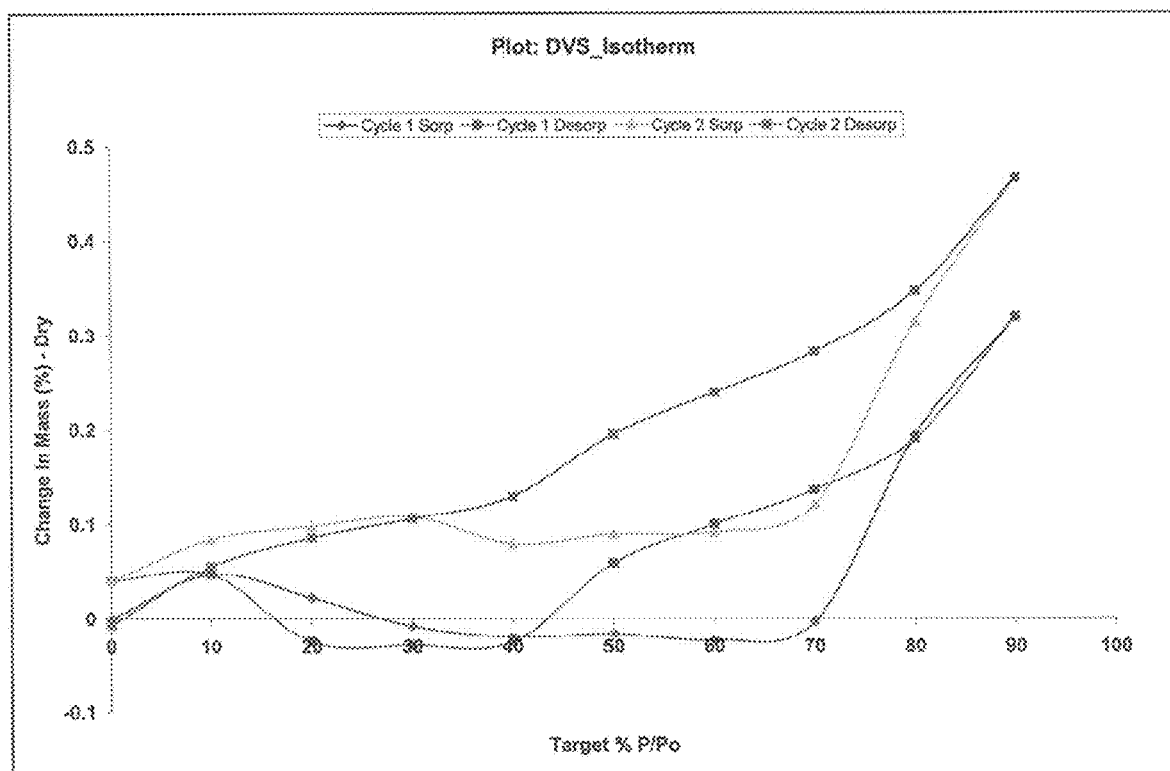
FIG. 4 depicts the dynamic vapor sorption (DVS) profile of Form E.

The contemplated crystalline Form E of 5-(3,4-dichlorophenyl)-N-((1R,2R)-2-hydroxycyclohexyl)-6-(2,2,2-trifluoroethoxy)nicotinamide, anhydrate, may be characterized by a thermogravimetric analysis (TGA) profile showing a mass loss of about 0.6 wt. % up to about 150° C. (FIG. 3). In some embodiments, crystalline Form E may be characterized by a dynamic vapor sorption (DVS) profile showing a reversable total mass change of about 0.3 wt. % between about 0 to about 90% relative humidity (RH) at 25° C. (FIG. 4).

In another embodiment, disclosed herein is a crystalline form of 5-(3,4-dichlorophenyl)-N-((1R,2R)-2-hydroxycyclohexyl)-6-(2,2,2-trifluoroethoxy)nicotinamide, anhydrate, characterized by a powder X-ray diffraction pattern having a characteristic peak in degrees 2θ at about 8.4 (referred to herein as "Form A").

In one embodiment, the crystalline Form A of 5-(3,4-dichlorophenyl)-N-((1R,2R)-2-hydroxycyclohexyl)-6-(2,2,2-trifluoroethoxy)nicotinamide, anhydrate, is characterized by a powder X-ray diffraction pattern that has a characteristic peak in degrees 2θ at about 8.4, is characterized by a powder X-ray diffraction pattern that has a characteristic peak in degrees 2θ at about 11.7, is characterized by a powder X-ray diffraction pattern that has a characteristic peak in degrees 2θ at about 14.9, is characterized by a powder X-ray diffraction pattern that has a characteristic peak in degrees 2θ at about 15.8, is characterized by a powder X-ray diffraction pattern that has a characteristic peak in degrees 2θ at about 17.5, is characterized by a powder X-ray diffraction pattern that has a characteristic peak in degrees 2θ at about 18.4, is characterized by a powder X-ray diffraction pattern that has a characteristic peak in degrees 2θ at about 19.1, is characterized by a powder X-ray diffraction pattern that has a characteristic peak in degrees 2θ at about 20.4, is characterized by a powder X-ray diffraction pattern that has a characteristic peak in degrees 2θ at about 21.6, is characterized by a powder X-ray diffraction pattern that has a characteristic peak in degrees 2θ at about 22.2, is characterized by a powder X-ray diffraction pattern that has a characteristic peak in degrees 2θ at about 23.4, and/or is characterized by a powder X-ray diffraction pattern that has a characteristic peak in degrees 2θ at about 25.1. In another embodiment, crystalline Form A is characterized by a powder X-ray diffraction pattern having at least one or more characteristic peaks in degrees 2θ at about 8.4, 11.7, 14.9, 15.8, 17.5, 18.4, 19.1, 20.4, 21.6, 22.2, 23.4, and 25.1. For example, a contemplated crystalline form has a powder X-ray diffraction pattern shown in FIG. 5. In one embodiment, the powder X-ray diffraction pattern of the crystalline form was obtained using Cu Kα radiation.

In one embodiment, the crystalline Form A of 5-(3,4-dichlorophenyl)-N-((1R,2R)-2-hydroxycyclohexyl)-6-(2,2,2-trifluoroethoxy)nicotinamide, anhydrate, is characterized by a powder X-ray diffraction pattern that has a characteristic peak in degrees 2θ at about 8.4, is characterized by a powder X-ray diffraction pattern that has a characteristic peak in degrees 2θ at about 9.5, is characterized by a powder X-ray diffraction pattern that has a characteristic peak in degrees 2θ at about 17.5, is characterized by a powder X-ray diffraction pattern that has a characteristic peak in degrees 2θ at about 18.1, is characterized by a powder X-ray diffraction pattern that has a characteristic peak in degrees 2θ at about 18.3, is characterized by a powder X-ray diffraction pattern that has a characteristic peak in degrees 2θ at about 19.1, is characterized by a powder X-ray diffraction pattern that has a characteristic peak in degrees 2θ at about 20.0, is characterized by a powder X-ray diffraction pattern that has a characteristic peak in degrees 2θ at about 20.4, is characterized by a powder X-ray diffraction pattern that has a characteristic peak in degrees 2θ at about 20.6, is characterized by a powder X-ray diffraction pattern that has a characteristic peak in degrees 2θ at about 21.0, is characterized by a powder X-ray diffraction pattern that has a characteristic peak in degrees 2θ at about 21.7, and/or is characterized by a powder X-ray diffraction pattern that has a characteristic peak in degrees 2θ at about 22.2. In another embodiment, crystalline Form A is characterized by a powder X-ray diffraction pattern having at least one or more characteristic peaks in degrees 2θ at about 8.4, 9.5, 17.5, 18.1, 18.3, 19.1, 20.0, 20.4, 20.6, 21.0, 21.7, and 22.2. For example, a contemplated crystalline form has a powder X-ray diffraction pattern shown in FIG. 5A. In one embodiment, the powder X-ray diffraction pattern of the crystalline form was obtained using Cu Kα radiation.

The contemplated crystalline Form A of 5-(3,4-dichlorophenyl)-N-((1R,2R)-2-hydroxycyclohexyl)-6-(2,2,2-trifluoroethoxy)nicotinamide, anhydrate, may be characterized by a differential scanning calorimetry (DSC) profile showing a characteristic endotherm with an onset and a peak of about 164° C.; and a characteristic endotherm with an onset of about 168° C. and a peak of about 169° C. Form A, for example, may be characterized by the differential scanning calorimetry profile shown in FIG. 6.

Figure 7:
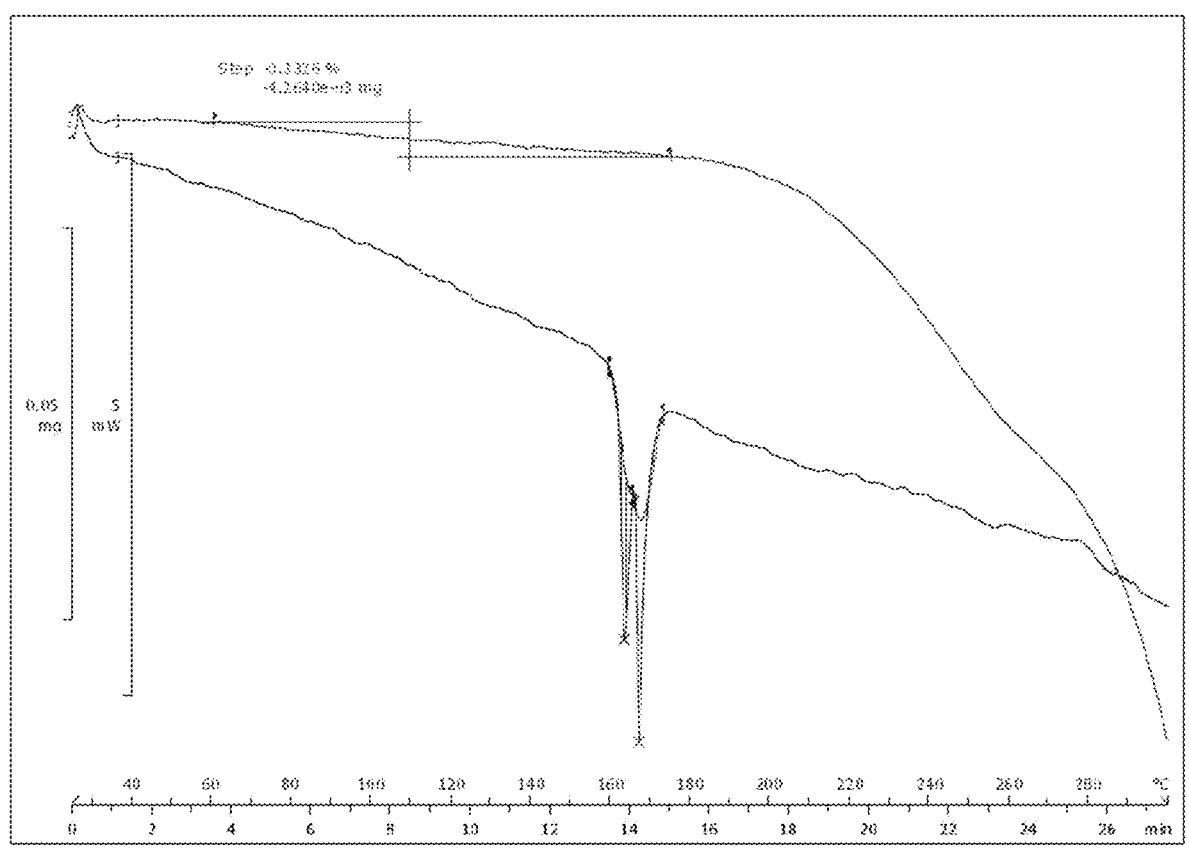
FIG. 7 depicts the thermogravimetric analysis (TGA) profile of Form A.
Figure 8:
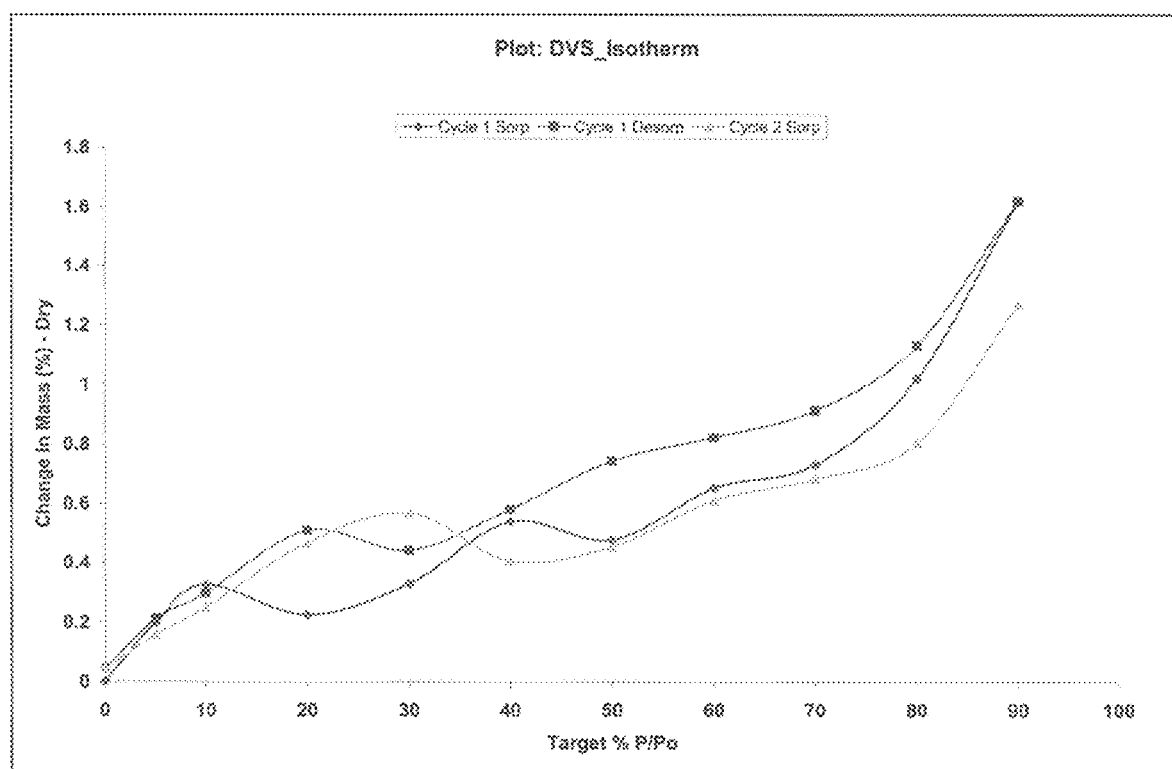
FIG. 8 depicts the dynamic vapor sorption (DVS) profile of Form A.

The contemplated crystalline Form A of 5-(3,4-dichlorophenyl)-N-((1R,2R)-2-hydroxycyclohexyl)-6-(2,2,2-trifluoroethoxy)nicotinamide, anhydrate, may be characterized by a thermogravimetric analysis (TGA) profile showing a mass loss of about 0.33 wt. % up to about 180° C. (FIG. 7). In some embodiments, crystalline Form A may be characterized by a dynamic vapor sorption (DVS) profile showing a reversable total mass change of about 1.8 wt. % between about 0 to about 90% relative humidity (RH) at 25° C. (FIG. 8).

In another embodiment, disclosed herein is a crystalline form of 5-(3,4-dichlorophenyl)-N-((1R,2R)-2-hydroxycyclohexyl)-6-(2,2,2-trifluoroethoxy)nicotinamide, monohydrate, characterized by a powder X-ray diffraction pattern having a characteristic peak in degrees 2θ at about 13.0 (referred to herein as "Form B").

In one embodiment, the crystalline Form B of 5-(3,4-dichlorophenyl)-N-((1R,2R)-2-hydroxycyclohexyl)-6-(2,2,2-trifluoroethoxy)nicotinamide, monohydrate, is characterized by a powder X-ray diffraction pattern that has a characteristic peak in degrees 2θ at about 6.5, is characterized by a powder X-ray diffraction pattern that has a characteristic peak in degrees 2θ at about 11.2, is characterized by a powder X-ray diffraction pattern that has a characteristic peak in degrees 2θ at about 13.0, is characterized by a powder X-ray diffraction pattern that has a characteristic peak in degrees 2θ at about 17.7, is characterized by a powder X-ray diffraction pattern that has a characteristic peak in degrees 2θ at about 19.4, is characterized by a powder X-ray diffraction pattern that has a characteristic peak in degrees 2θ at about 22.5, is characterized by a powder X-ray diffraction pattern that has a characteristic peak in degrees 2θ at about 23.4, is characterized by a powder X-ray diffraction pattern that has a characteristic peak in degrees 2θ at about 26.0, is characterized by a powder X-ray diffraction pattern that has a characteristic peak in degrees 2θ at about 28.2, is characterized by a powder X-ray diffraction pattern that has a characteristic peak in degrees 2θ at about 29.8, is characterized by a powder X-ray diffraction pattern that has a characteristic peak in degrees 2θ at about 32.7, and/or is characterized by a powder X-ray diffraction pattern that has a characteristic peak in degrees 2θ at about 34.0. In another embodiment, crystalline Form B is characterized by a powder X-ray diffraction pattern having at least one or more characteristic peaks in degrees 2θ at about 6.5, 11.2, 13.0, 17.2, 19.4, 22.5, 23.4, 26.0, 28.2, 29.8, 32.7, and 34.0. For example, a contemplated crystalline form has a powder X-ray diffraction pattern shown in FIG. 9. In one embodiment, the powder X-ray diffraction pattern of the crystalline form was obtained using Cu Kα radiation.

In one embodiment, the crystalline Form B of 5-(3,4-dichlorophenyl)-N-((1R,2R)-2-hydroxycyclohexyl)-6-(2,2,2-trifluoroethoxy)nicotinamide, monohydrate, is characterized by a powder X-ray diffraction pattern that has a characteristic peak in degrees 2θ at about 6.4, is characterized by a powder X-ray diffraction pattern that has a characteristic peak in degrees 2θ at about 12.9, is characterized by a powder X-ray diffraction pattern that has a characteristic peak in degrees 2θ at about 17.0, is characterized by a powder X-ray diffraction pattern that has a characteristic peak in degrees 2θ at about 19.1, is characterized by a powder X-ray diffraction pattern that has a characteristic peak in degrees 2θ at about 19.3, is characterized by a powder X-ray diffraction pattern that has a characteristic peak in degrees 2θ at about 20.2, is characterized by a powder X-ray diffraction pattern that has a characteristic peak in degrees 2θ at about 21.6, is characterized by a powder X-ray diffraction pattern that has a characteristic peak in degrees 2θ at about 23.6, is characterized by a powder X-ray diffraction pattern that has a characteristic peak in degrees 2θ at about 24.8, is characterized by a powder X-ray diffraction pattern that has a characteristic peak in degrees 2θ at about 25.7, is characterized by a powder X-ray diffraction pattern that has a characteristic peak in degrees 2θ at about 27.0, and/or is characterized by a powder X-ray diffraction pattern that has a characteristic peak in degrees 2θ at about 28.1. In another embodiment, crystalline Form B is characterized by a powder X-ray diffraction pattern having at least one or more characteristic peaks in degrees 2θ at about 6.4, 12.9, 17.0, 19.1, 19.3, 20.2, 21.6, 23.6, 24.8, 25.7, 27.0, and 28.1. For example, a contemplated crystalline form has a powder X-ray diffraction pattern shown in FIG. 9A. In one embodiment, the powder X-ray diffraction pattern of the crystalline form was obtained using Cu Kα radiation.

The contemplated crystalline Form B of 5-(3,4-dichlorophenyl)-N-((1R,2R)-2-hydroxycyclohexyl)-6-(2,2,2-trifluoroethoxy)nicotinamide, monohydrate, may be characterized by a differential scanning calorimetry (DSC) profile showing a characteristic endotherm with an onset of about 74° C. and a peak of about 87° C.; a characteristic endotherm with an onset of about 163° C. and a peak of about 164° C.; a characteristic exotherm with an onset and a peak of about 165° C.; and a characteristic endotherm with an onset of about 168° C. and a peak of about 169° C. Form B, for example, may be characterized by the differential scanning calorimetry profile shown in FIG. 10.

Figure 11:
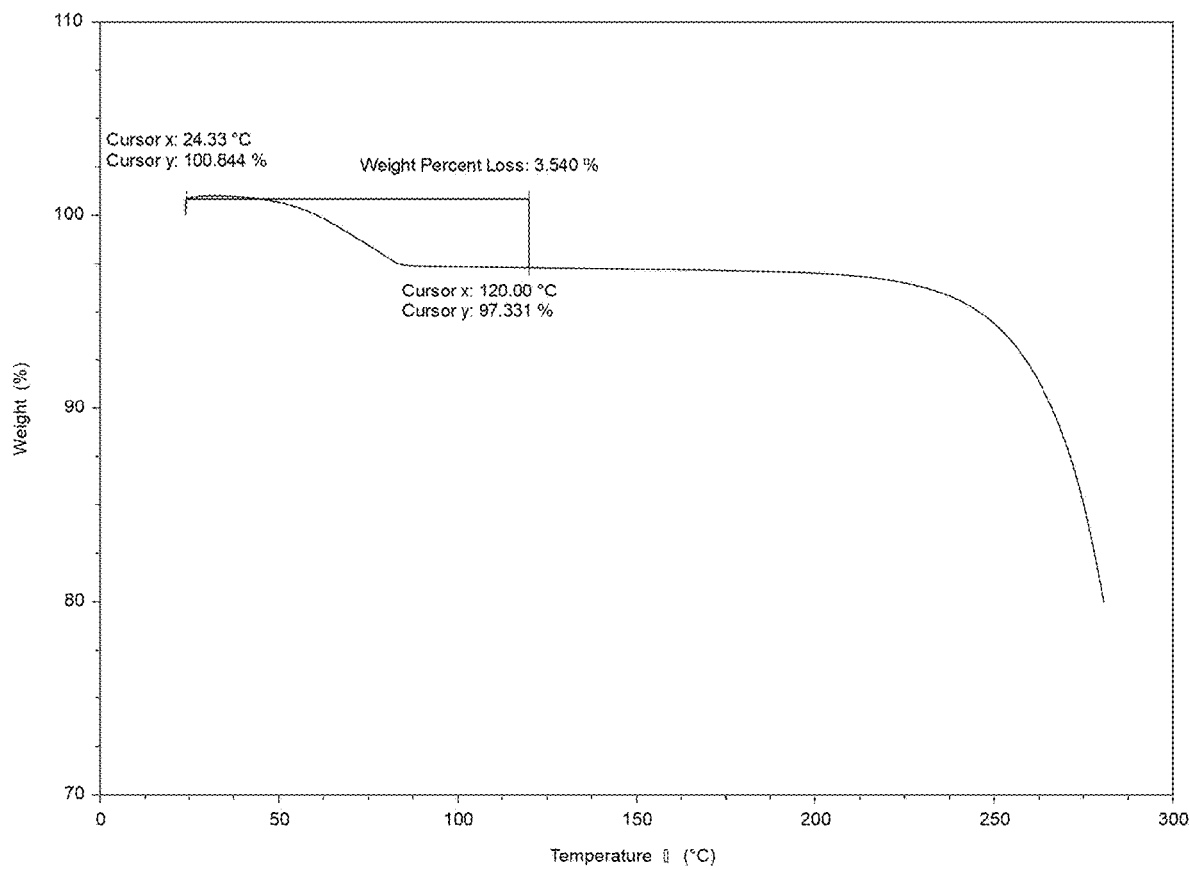
FIG. 11 depicts the thermogravimetric analysis (TGA) profile of Form B.

The contemplated crystalline Form B of 5-(3,4-dichlorophenyl)-N-((1R,2R)-2-hydroxycyclohexyl)-6-(2,2,2-trifluoroethoxy)nicotinamide, monohydrate, may be characterized by a thermogravimetric analysis (TGA) profile showing a mass loss of about 3.5 wt. % up to about 120° C. (FIG. 11). In some embodiments, crystalline Form B may be characterized by Karl Fischer (KF) analysis showing 3.8% water by weight (1.02 equivalent by molar ratio).

In another embodiment, disclosed herein is a crystalline form of 5-(3,4-dichlorophenyl)-N-((1R,2R)-2-hydroxycyclohexyl)-6-(2,2,2-trifluoroethoxy)nicotinamide, anhydrate, characterized by a powder X-ray diffraction pattern having a characteristic peak in degrees 2θ at about 20.9 (referred to herein as "Form C").

In one embodiment, the crystalline Form C of 5-(3,4-dichlorophenyl)-N-((1R,2R)-2-hydroxycyclohexyl)-6-(2,2,2-trifluoroethoxy)nicotinamide, anhydrate, is characterized by a powder X-ray diffraction pattern that has a characteristic peak in degrees 2θ at about 5.1, is characterized by a powder X-ray diffraction pattern that has a characteristic peak in degrees 2θ at about 5.3, is characterized by a powder X-ray diffraction pattern that has a characteristic peak in degrees 2θ at about 6.9, is characterized by a powder X-ray diffraction pattern that has a characteristic peak in degrees 2θ at about 9.0, is characterized by a powder X-ray diffraction pattern that has a characteristic peak in degrees 2θ at about 18.0, is characterized by a powder X-ray diffraction pattern that has a characteristic peak in degrees 2θ at about 18.8, is characterized by a powder X-ray diffraction pattern that has a characteristic peak in degrees 2θ at about 19.7, is characterized by a powder X-ray diffraction pattern that has a characteristic peak in degrees 2θ at about 20.3, is characterized by a powder X-ray diffraction pattern that has a characteristic peak in degrees 2θ at about 20.9, is characterized by a powder X-ray diffraction pattern that has a characteristic peak in degrees 2θ at about 22.2, is characterized by a powder X-ray diffraction pattern that has a characteristic peak in degrees 2θ at about 23.5, and/or is characterized by a powder X-ray diffraction pattern that has a characteristic peak in degrees 2θ at about 24.4. In another embodiment, crystalline Form C is characterized by a powder X-ray diffraction pattern having at least one or more characteristic peaks in degrees 2θ at about 5.1, 5.3, 6.9, 9.0, 18.0, 18.8, 19.7, 20.3, 20.9, 22.2, 23.5, and 24.4. For example, a contemplated crystalline form has a powder X-ray diffraction pattern shown in FIG. 12. In one embodiment, the powder X-ray diffraction pattern of the crystalline form was obtained using Cu Kα radiation.

Figure 13:
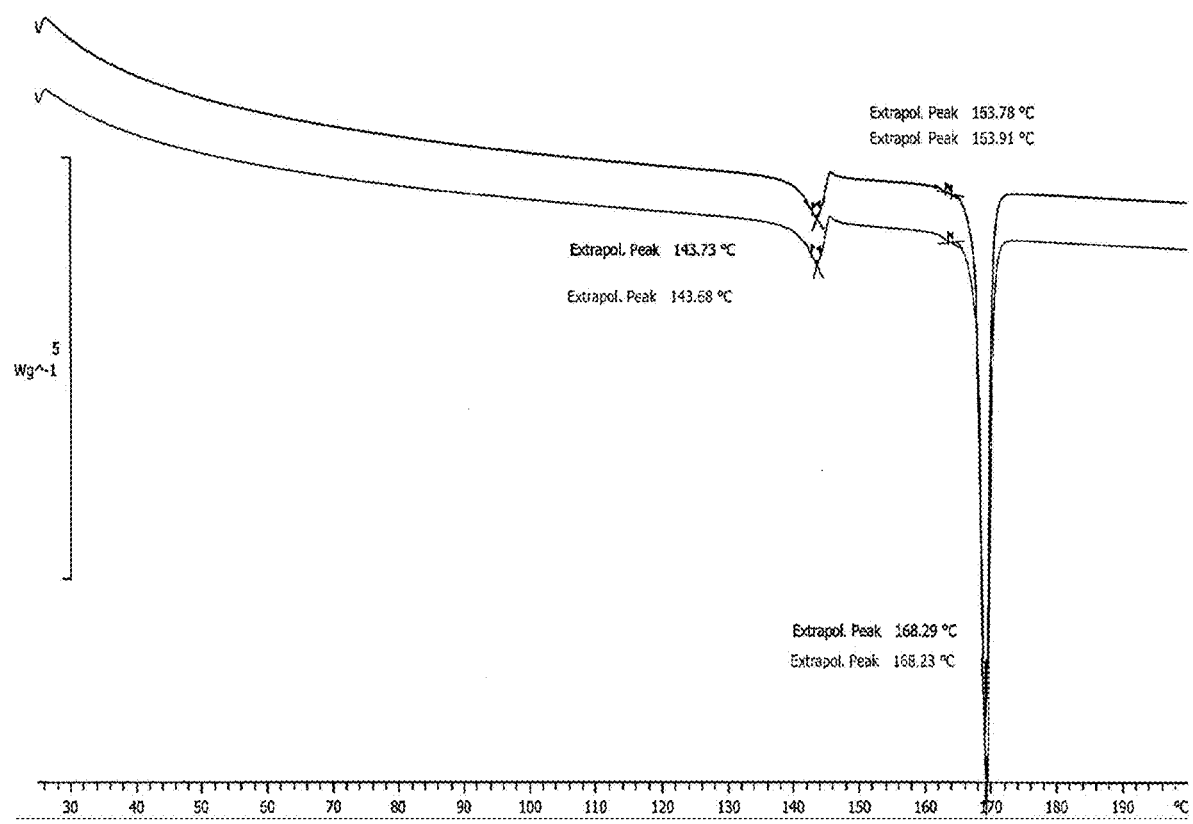
FIG. 13 depicts the characterization of Form C by differential scanning calorimetry (DSC).
Figure 14:
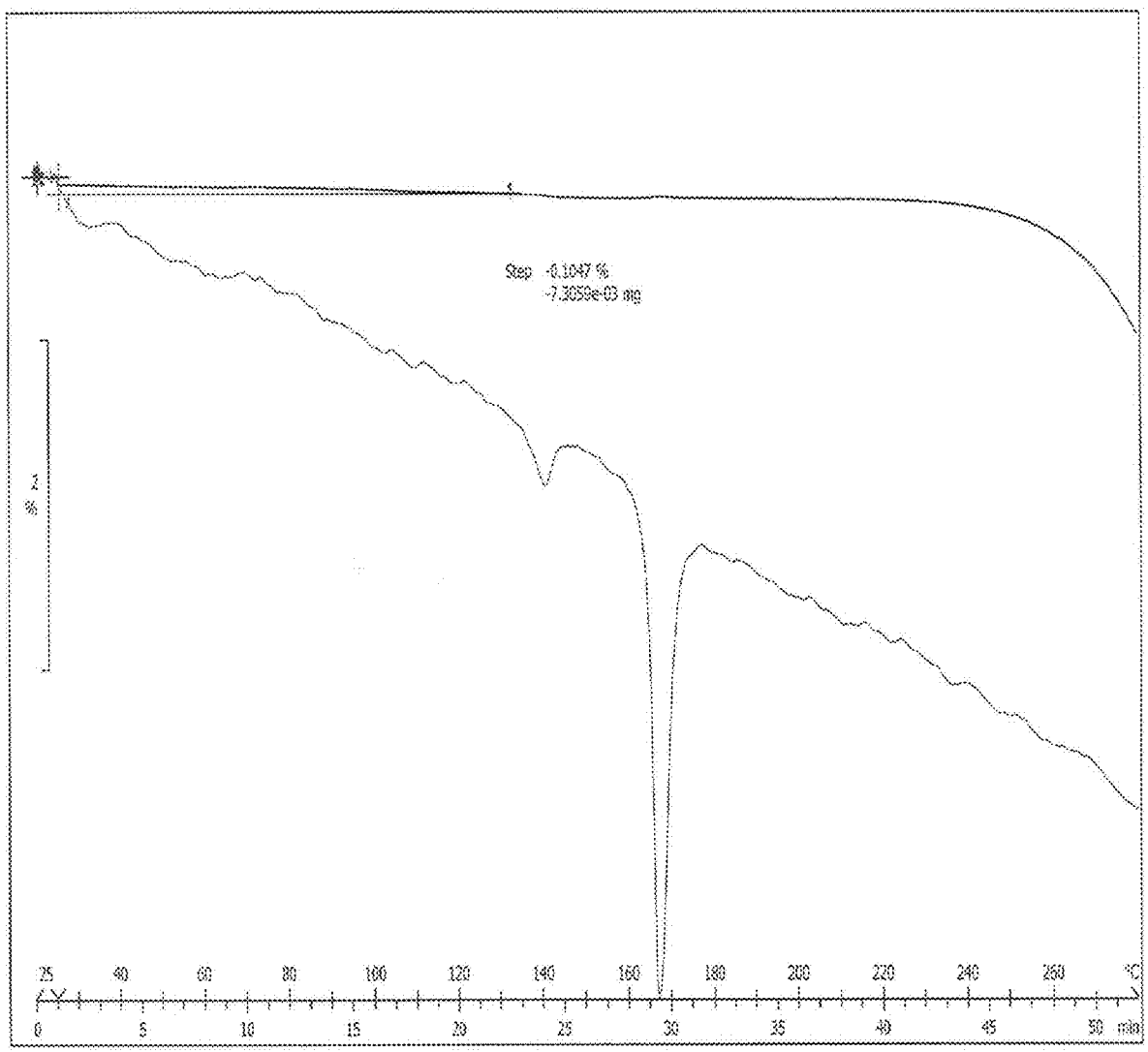
FIG. 14 depicts the thermogravimetric analysis (TGA) profile of Form C.

The contemplated crystalline Form C of 5-(3,4-dichlorophenyl)-N-((1R,2R)-2-hydroxycyclohexyl)-6-(2,2,2-trifluoroethoxy)nicotinamide, anhydrate, may be characterized by a differential scanning calorimetry (DSC) profile showing a characteristic endotherm with an onset of about 144° C.; a characteristic endotherm with an onset of about 164° C.; and a characteristic endotherm with an onset of about 168° C. Form C, for example, may be characterized by the differential scanning calorimetry profile shown in FIG. 13. In some embodiments, Form C may be characterized by a thermogravimetric analysis (TGA) profile showing a mass loss of about 0.1 wt. % up to about 130° C. (FIG. 14).

In another embodiment, disclosed herein is a crystalline form of 5-(3,4-dichlorophenyl)-N-((1R,2R)-2-hydroxycyclohexyl)-6-(2,2,2-trifluoroethoxy)nicotinamide, anhydrate, characterized by a powder X-ray diffraction pattern having a characteristic peak in degrees 2θ at about 19.1 (referred to herein as "Form D").

In one embodiment, the crystalline Form D of 5-(3,4-dichlorophenyl)-N-((1R,2R)-2-hydroxycyclohexyl)-6-(2,2,2-trifluoroethoxy)nicotinamide, anhydrate, is characterized by a powder X-ray diffraction pattern that has a characteristic peak in degrees 2θ at about 7.1, is characterized by a powder X-ray diffraction pattern that has a characteristic peak in degrees 2θ at about 11.8, is characterized by a powder X-ray diffraction pattern that has a characteristic peak in degrees 2θ at about 19.1, is characterized by a powder X-ray diffraction pattern that has a characteristic peak in degrees 2θ at about 19.4, is characterized by a powder X-ray diffraction pattern that has a characteristic peak in degrees 2θ at about 21.0, is characterized by a powder X-ray diffraction pattern that has a characteristic peak in degrees 2θ at about 22.1, is characterized by a powder X-ray diffraction pattern that has a characteristic peak in degrees 2θ at about 22.8, is characterized by a powder X-ray diffraction pattern that has a characteristic peak in degrees 2θ at about 23.1, is characterized by a powder X-ray diffraction pattern that has a characteristic peak in degrees 2θ at about 24.9, is characterized by a powder X-ray diffraction pattern that has a characteristic peak in degrees 2θ at about 26.4, is characterized by a powder X-ray diffraction pattern that has a characteristic peak in degrees 2θ at about 26.6, and/or is characterized by a powder X-ray diffraction pattern that has a characteristic peak in degrees 2θ at about 27.6. In another embodiment, crystalline Form D is characterized by a powder X-ray diffraction pattern having at least one or more characteristic peaks in degrees 2θ at about 7.1, 11.8, 19.1, 19.4, 21.0, 22.1, 22.8, 23.1, 24.9, 26.4, 26.6, and 27.6. For example, a contemplated crystalline form has a powder X-ray diffraction pattern shown in FIG. 15. In one embodiment, the powder X-ray diffraction pattern of the crystalline form was obtained using Cu Kα radiation.

The contemplated crystalline Form D of 5-(3,4-dichlorophenyl)-N-((1R,2R)-2-hydroxycyclohexyl)-6-(2,2,2-trifluoroethoxy)nicotinamide, anhydrate, may be characterized by a differential scanning calorimetry (DSC) profile showing a characteristic endotherm with an onset of about 152° C.; a characteristic endotherm with an onset of about 165° C.; and a characteristic endotherm with an onset of about 168° C. Form D, for example, may be characterized by the differential scanning calorimetry profile shown in FIG. 16.

Figure 17:
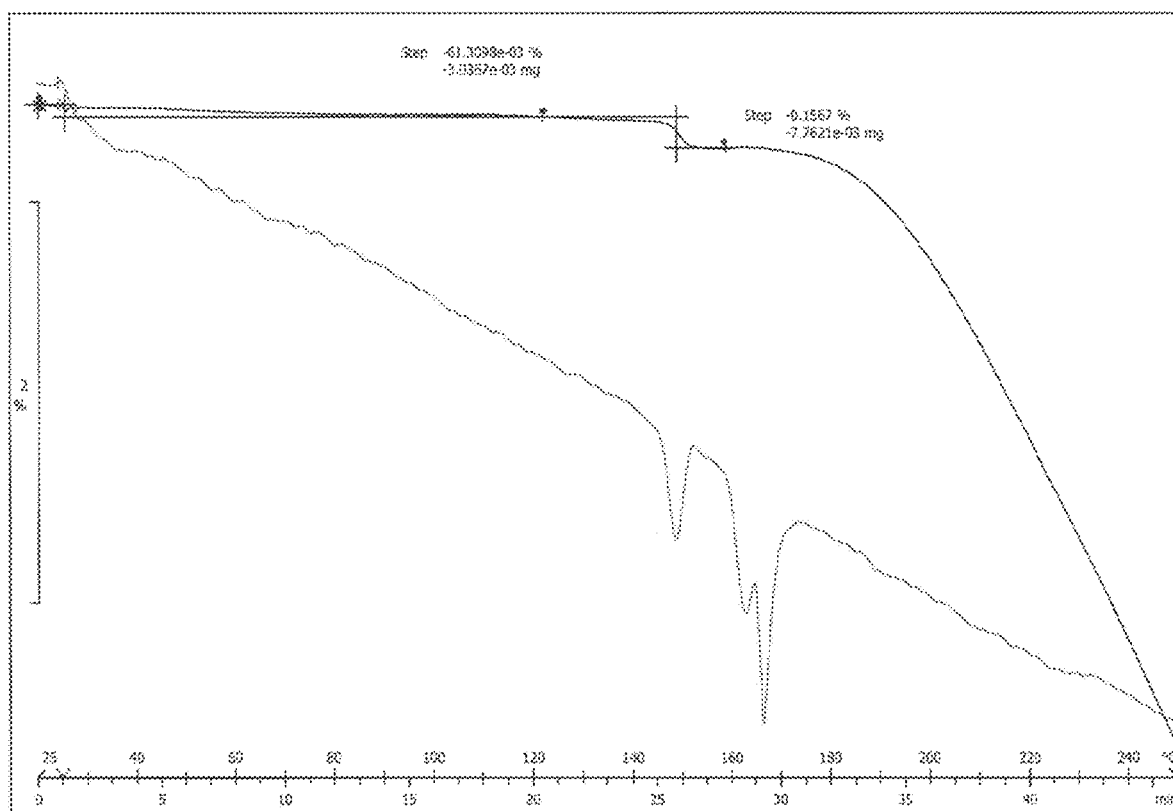
FIG. 17 depicts the thermogravimetric analysis (TGA) profile of Form D.
Figure 18:
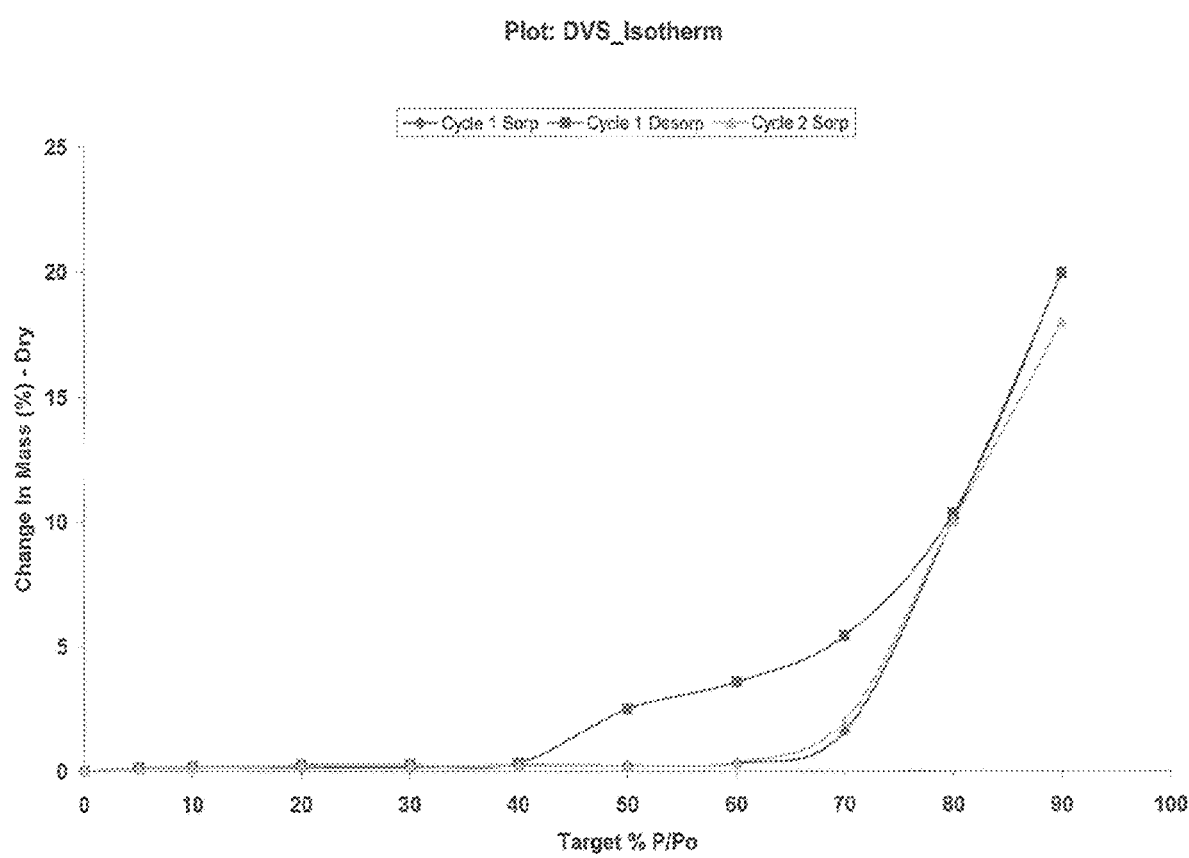
FIG. 18 depicts the dynamic vapor sorption (DVS) profile of Form D.

The contemplated crystalline Form D of 5-(3,4-dichlorophenyl)-N-((1R,2R)-2-hydroxycyclohexyl)-6-(2,2,2-trifluoroethoxy)nicotinamide, anhydrate, may be characterized by a thermogravimetric analysis (TGA) profile showing a mass loss of about 0.16 wt. % up to about 150° C. (FIG. 17). In some embodiments, crystalline Form D may be characterized by a dynamic vapor sorption (DVS) profile showing a reversable total mass change of about 20 wt. % between about 0 to about 90% relative humidity (RH) at 25° C. (FIG. 18).

In another embodiment, disclosed herein is a crystalline form of 5-(3,4-dichlorophenyl)-N-((1R,2R)-2-hydroxycyclohexyl)-6-(2,2,2-trifluoroethoxy)nicotinamide, hydrate, characterized by a powder X-ray diffraction pattern having a characteristic peak in degrees 2θ at about 26.2 (referred to herein as "Form F").

In one embodiment, the crystalline Form F of 5-(3,4-dichlorophenyl)-N-((1R,2R)-2-hydroxycyclohexyl)-6-(2,2,2-trifluoroethoxy)nicotinamide, hydrate, is characterized by a powder X-ray diffraction pattern that has a characteristic peak in degrees 2θ at about 6.0, is characterized by a powder X-ray diffraction pattern that has a characteristic peak in degrees 2θ at about 8.3, is characterized by a powder X-ray diffraction pattern that has a characteristic peak in degrees 2θ at about 11.6, is characterized by a powder X-ray diffraction pattern that has a characteristic peak in degrees 2θ at about 12.0, is characterized by a powder X-ray diffraction pattern that has a characteristic peak in degrees 2θ at about 13.3, is characterized by a powder X-ray diffraction pattern that has a characteristic peak in degrees 2θ at about 16.7, is characterized by a powder X-ray diffraction pattern that has a characteristic peak in degrees 2θ at about 18.0, is characterized by a powder X-ray diffraction pattern that has a characteristic peak in degrees 2θ at about 21.1, is characterized by a powder X-ray diffraction pattern that has a characteristic peak in degrees 2θ at about 21.4, is characterized by a powder X-ray diffraction pattern that has a characteristic peak in degrees 2θ at about 24.0, is characterized by a powder X-ray diffraction pattern that has a characteristic peak in degrees 2θ at about 25.3, and/or is characterized by a powder X-ray diffraction pattern that has a characteristic peak in degrees 2θ at about 26.2. In another embodiment, crystalline Form F is characterized by a powder X-ray diffraction pattern having at least one or more characteristic peaks in degrees 2θ at about 6.0, 8.3, 11.6, 12.0, 13.3, 16.7, 18.0, 21.1, 21.4, 24.0, 25.3, and 26.2. For example, a contemplated crystalline form has a powder X-ray diffraction pattern shown in FIG. 19. In one embodiment, the powder X-ray diffraction pattern of the crystalline form was obtained using Cu Kα radiation.

In one embodiment, the crystalline Form F of 5-(3,4-dichlorophenyl)-N-((1R,2R)-2-hydroxycyclohexyl)-6-(2,2,2-trifluoroethoxy)nicotinamide, hydrate, is characterized by a powder X-ray diffraction pattern that has a characteristic peak in degrees 2θ at about 6.0, is characterized by a powder X-ray diffraction pattern that has a characteristic peak in degrees 2θ at about 13.2, is characterized by a powder X-ray diffraction pattern that has a characteristic peak in degrees 2θ at about 17.0, is characterized by a powder X-ray diffraction pattern that has a characteristic peak in degrees 2θ at about 18.1, is characterized by a powder X-ray diffraction pattern that has a characteristic peak in degrees 2θ at about 19.8, is characterized by a powder X-ray diffraction pattern that has a characteristic peak in degrees 2θ at about 21.1, is characterized by a powder X-ray diffraction pattern that has a characteristic peak in degrees 2θ at about 23.2, is characterized by a powder X-ray diffraction pattern that has a characteristic peak in degrees 2θ at about 23.9, is characterized by a powder X-ray diffraction pattern that has a characteristic peak in degrees 2θ at about 25.2, is characterized by a powder X-ray diffraction pattern that has a characteristic peak in degrees 2θ at about 26.1, is characterized by a powder X-ray diffraction pattern that has a characteristic peak in degrees 2θ at about 29.7, and/or is characterized by a powder X-ray diffraction pattern that has a characteristic peak in degrees 2θ at about 31.7. In another embodiment, crystalline Form F is characterized by a powder X-ray diffraction pattern having at least one or more characteristic peaks in degrees 2θ at about 6.0, 13.2, 17.0, 18.1, 19.8, 21.1, 23.2, 23.9, 25.2, 26.1, 29.7, and 31.7. For example, a contemplated crystalline form has a powder X-ray diffraction pattern shown in FIG. 19A. In one embodiment, the powder X-ray diffraction pattern of the crystalline form was obtained using Cu Kα radiation.

The contemplated crystalline Form F of 5-(3,4-dichlorophenyl)-N-((1R,2R)-2-hydroxycyclohexyl)-6-(2,2,2-trifluoroethoxy)nicotinamide, hydrate, may be characterized by a differential scanning calorimetry (DSC) profile showing a characteristic endotherm with an onset of about 87° C. and a peak of about 100° C.; and a characteristic endotherm with an onset of about 164° C. and a peak of about 165° C.; and a characteristic endotherm with an onset of about 168° C. and a peak of about 169° C. Form F, for example, may be characterized by the differential scanning calorimetry profile shown in FIG. 20.

Figure 21:
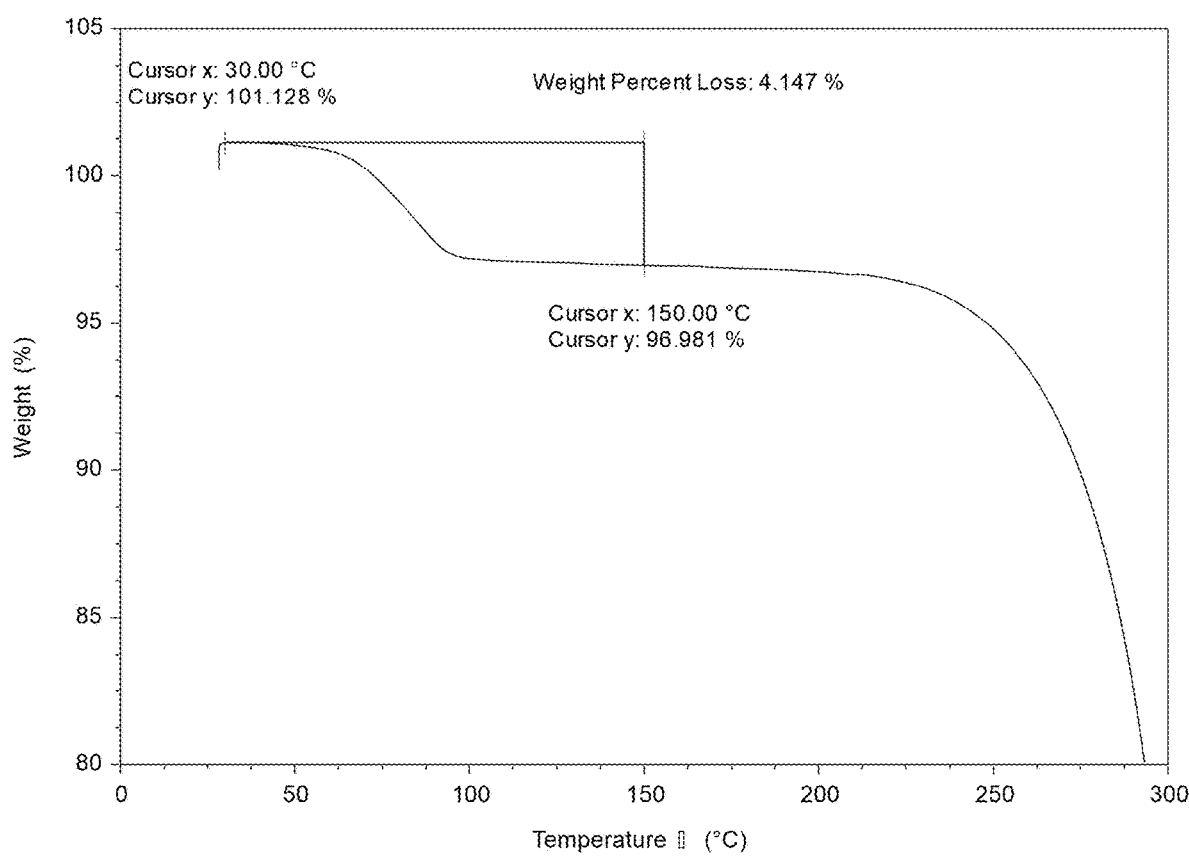
FIG. 21 depicts the thermogravimetric analysis (TGA) profile of Form F.

The contemplated crystalline Form F of 5-(3,4-dichlorophenyl)-N-((1R,2R)-2-hydroxycyclohexyl)-6-(2,2,2-trifluoroethoxy)nicotinamide, hydrate, may be characterized by a thermogravimetric analysis (TGA) profile showing a mass loss of about 4.1 wt. % up to about 150° C. (FIG. 21). In some embodiments, crystalline Form F may be characterized by Karl Fischer (KF) analysis showing 5.0% water by weight (1.35 equivalent by molar ratio).

In another embodiment, disclosed herein is a crystalline form of 5-(3,4-dichlorophenyl)-N-((1R,2R)-2-hydroxycyclohexyl)-6-(2,2,2-trifluoroethoxy)nicotinamide, diisopropylamine monosolvate, characterized by a powder X-ray diffraction pattern having a characteristic peak in degrees 2θ at about 18.2 (referred to herein as "Form G").

In one embodiment, the crystalline Form G of 5-(3,4-dichlorophenyl)-N-((1R,2R)-2-hydroxycyclohexyl)-6-(2,2,2-trifluoroethoxy)nicotinamide, diisopropylamine monosolvate, is characterized by a powder X-ray diffraction pattern that has a characteristic peak in degrees 2θ at about 6.3, is characterized by a powder X-ray diffraction pattern that has a characteristic peak in degrees 2θ at about 9.0, is characterized by a powder X-ray diffraction pattern that has a characteristic peak in degrees 2θ at about 13.4, is characterized by a powder X-ray diffraction pattern that has a characteristic peak in degrees 2θ at about 15.5, is characterized by a powder X-ray diffraction pattern that has a characteristic peak in degrees 2θ at about 16.4, is characterized by a powder X-ray diffraction pattern that has a characteristic peak in degrees 2θ at about 18.2, is characterized by a powder X-ray diffraction pattern that has a characteristic peak in degrees 2θ at about 18.5, is characterized by a powder X-ray diffraction pattern that has a characteristic peak in degrees 2θ at about 19.1, is characterized by a powder X-ray diffraction pattern that has a characteristic peak in degrees 2θ at about 20.3, is characterized by a powder X-ray diffraction pattern that has a characteristic peak in degrees 2θ at about 20.8, is characterized by a powder X-ray diffraction pattern that has a characteristic peak in degrees 2θ at about 22.2, and/or is characterized by a powder X-ray diffraction pattern that has a characteristic peak in degrees 2θ at about 27.8. In another embodiment, crystalline Form G is characterized by a powder X-ray diffraction pattern having at least one or more characteristic peaks in degrees 2θ at about 6.3, 9.0, 13.4, 15.5, 16.4, 18.2, 18.5, 19.1, 20.3, 20.8, 22.2, and 27.8. For example, a contemplated crystalline form has a powder X-ray diffraction pattern shown in FIG. 22. In one embodiment, the powder X-ray diffraction pattern of the crystalline form was obtained using Cu Kα radiation.

In one embodiment, the crystalline Form G of 5-(3,4-dichlorophenyl)-N-((1R,2R)-2-hydroxycyclohexyl)-6-(2,2,2-trifluoroethoxy)nicotinamide, diisopropylamine monosolvate, is characterized by a powder X-ray diffraction pattern that has a characteristic peak in degrees 2θ at about 6.3, is characterized by a powder X-ray diffraction pattern that has a characteristic peak in degrees 2θ at about 16.4, is characterized by a powder X-ray diffraction pattern that has a characteristic peak in degrees 2θ at about 18.2, is characterized by a powder X-ray diffraction pattern that has a characteristic peak in degrees 2θ at about 19.8, is characterized by a powder X-ray diffraction pattern that has a characteristic peak in degrees 2θ at about 20.0, is characterized by a powder X-ray diffraction pattern that has a characteristic peak in degrees 2θ at about 20.8, is characterized by a powder X-ray diffraction pattern that has a characteristic peak in degrees 2θ at about 21.7, is characterized by a powder X-ray diffraction pattern that has a characteristic peak in degrees 2θ at about 22.2, is characterized by a powder X-ray diffraction pattern that has a characteristic peak in degrees 2θ at about 22.4, is characterized by a powder X-ray diffraction pattern that has a characteristic peak in degrees 2θ at about 25.4, is characterized by a powder X-ray diffraction pattern that has a characteristic peak in degrees 2θ at about 27.0, and/or is characterized by a powder X-ray diffraction pattern that has a characteristic peak in degrees 2θ at about 31.7. In another embodiment, crystalline Form G is characterized by a powder X-ray diffraction pattern having at least one or more characteristic peaks in degrees 2θ at about 6.3, 16.4, 18.2, 19.8, 20.0, 20.8, 21.7, 22.2, 22.4, 25.4, 27.0, and 31.7. For example, a contemplated crystalline form has a powder X-ray diffraction pattern shown in FIG. 22A. In one embodiment, the powder X-ray diffraction pattern of the crystalline form was obtained using Cu Kα radiation.

The contemplated crystalline Form G of 5-(3,4-dichlorophenyl)-N-((1R,2R)-2-hydroxycyclohexyl)-6-(2,2,2-trifluoroethoxy)nicotinamide, diisopropylamine monosolvate, may be characterized by a differential scanning calorimetry (DSC) profile showing a characteristic endotherm with an onset of about 88° C. and a peak of about 93° C.; and a characteristic endotherm with an onset and a peak of about 164° C. Form G, for example, may be characterized by the differential scanning calorimetry profile shown in FIG. 23. In some embodiments, Form G may be characterized by a thermogravimetric analysis (TGA) profile showing a mass loss of about 3.9 wt. % up to about 150° C. (FIG. 24).

In another embodiment, disclosed herein is a crystalline form of 5-(3,4-dichlorophenyl)-N-((1R,2R)-2-hydroxycyclohexyl)-6-(2,2,2-trifluoroethoxy)nicotinamide, anhydrate, characterized by a powder X-ray diffraction pattern having a characteristic peak in degrees 2θ at about 22.5 (referred to herein as "Form H").

In one embodiment, the crystalline Form H of 5-(3,4-dichlorophenyl)-N-((1R,2R)-2-hydroxycyclohexyl)-6-(2,2,2-trifluoroethoxy)nicotinamide, anhydrate, is characterized by a powder X-ray diffraction pattern that has a characteristic peak in degrees 2θ at about 9.2, is characterized by a powder X-ray diffraction pattern that has a characteristic peak in degrees 2θ at about 12.1, is characterized by a powder X-ray diffraction pattern that has a characteristic peak in degrees 2θ at about 18.8, is characterized by a powder X-ray diffraction pattern that has a characteristic peak in degrees 2θ at about 19.1, is characterized by a powder X-ray diffraction pattern that has a characteristic peak in degrees 2θ at about 19.9, is characterized by a powder X-ray diffraction pattern that has a characteristic peak in degrees 2θ at about 20.5, is characterized by a powder X-ray diffraction pattern that has a characteristic peak in degrees 2θ at about 21.9, is characterized by a powder X-ray diffraction pattern that has a characteristic peak in degrees 2θ at about 22.5, is characterized by a powder X-ray diffraction pattern that has a characteristic peak in degrees 2θ at about 22.8, is characterized by a powder X-ray diffraction pattern that has a characteristic peak in degrees 2θ at about 24.5, is characterized by a powder X-ray diffraction pattern that has a characteristic peak in degrees 2θ at about 26.0, and/or is characterized by a powder X-ray diffraction pattern that has a characteristic peak in degrees 2θ at about 31.7. In another embodiment, crystalline Form H is characterized by a powder X-ray diffraction pattern having at least one or more characteristic peaks in degrees 2θ at about 9.2, 12.1, 18.8, 19.1, 19.9, 20.5, 21.9, 22.5, 22.8, 24.5, 26.0, and 31.7. For example, a contemplated crystalline form has a powder X-ray diffraction pattern shown in FIG. 25. In one embodiment, the powder X-ray diffraction pattern of the crystalline form was obtained using Cu Kα radiation.

The contemplated crystalline Form H of 5-(3,4-dichlorophenyl)-N-((1R,2R)-2-hydroxycyclohexyl)-6-(2,2,2-trifluoroethoxy)nicotinamide, anhydrate, may be characterized by a differential scanning calorimetry (DSC) profile showing a characteristic exotherm with an onset of about 120° C.; a characteristic endotherm with an onset of about 136° C.; a characteristic endotherm with an onset of about 164° C.; and a characteristic endotherm with an onset of about 169° C. Form H, for example, may be characterized by the differential scanning calorimetry profile shown in FIG. 26.

Figure 27:
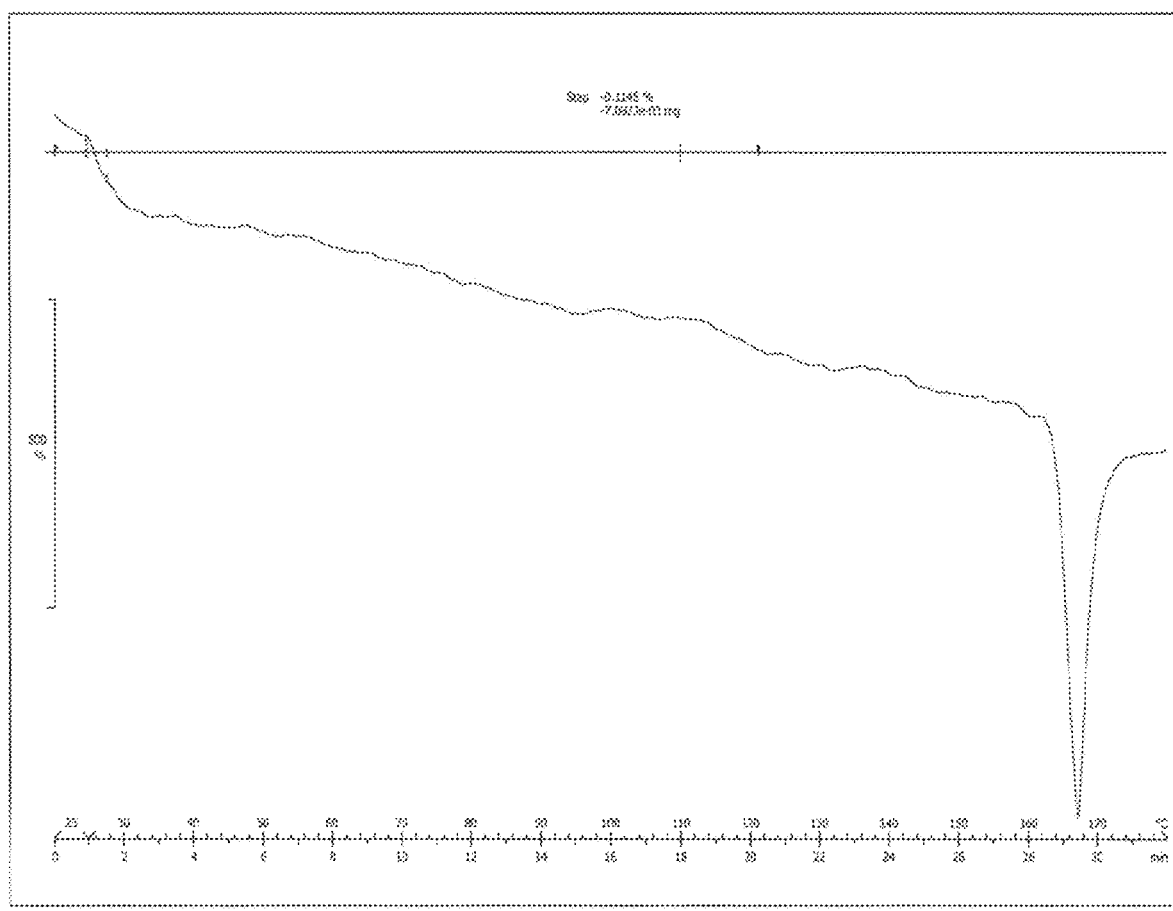
FIG. 27 depicts the thermogravimetric analysis (TGA) profile of Form H.
Figure 28:
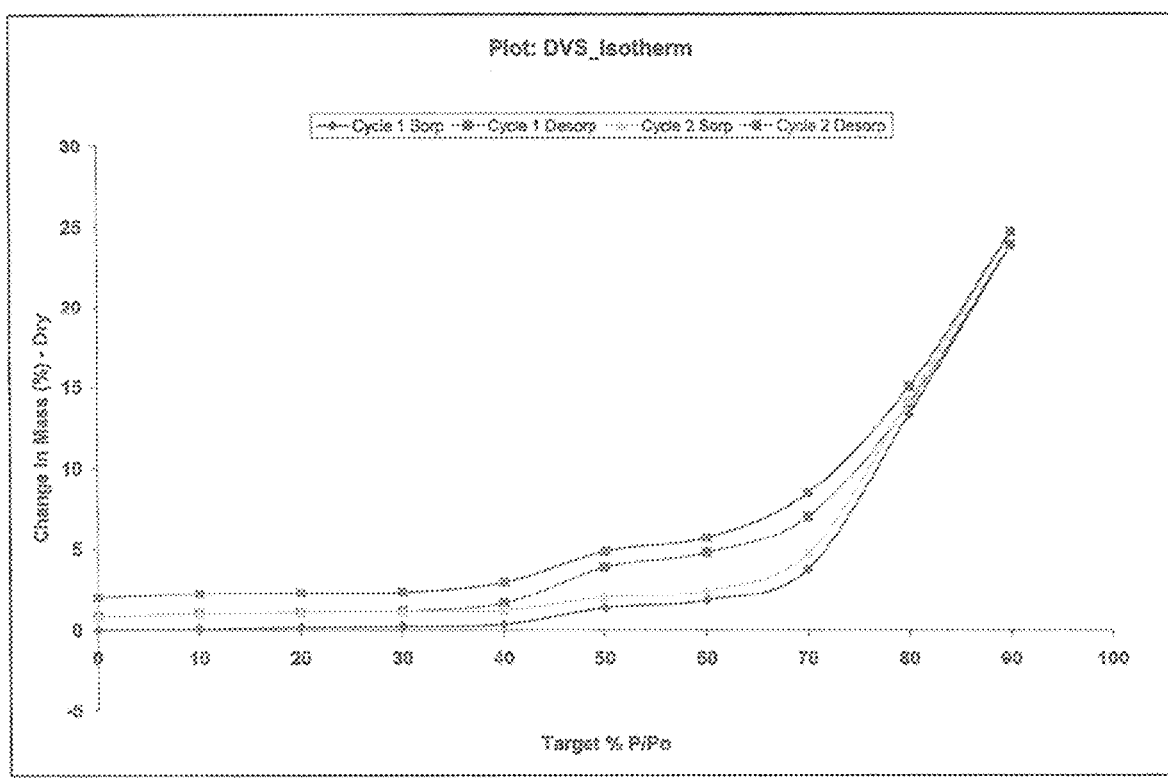
FIG. 28 depicts the dynamic vapor sorption (DVS) profile of Form H.

The contemplated crystalline Form H of 5-(3,4-dichlorophenyl)-N-((1R,2R)-2-hydroxycyclohexyl)-6-(2,2,2-trifluoroethoxy)nicotinamide, anhydrate, may be characterized by a thermogravimetric analysis (TGA) profile showing a mass loss of about 0.11 wt. % up to about 120° C. (FIG. 27). In some embodiments, crystalline Form H may be characterized by a dynamic vapor sorption (DVS) profile showing a total mass change of about 2.5 wt. % between about 0 to about 70% relative humidity (RH) at 25° C., and a total mass change of about 25 wt. % between about 70 to about 90% relative humidity (RH) at 25° C. (FIG. 28).

In another embodiment, disclosed herein is a crystalline form of 5-(3,4-dichlorophenyl)-N-((1R,2R)-2-hydroxycyclohexyl)-6-(2,2,2-trifluoroethoxy)nicotinamide, anhydrate, characterized by a powder X-ray diffraction pattern having a characteristic peak in degrees 2θ at about 17.7 (referred to herein as "Form I").

In one embodiment, the crystalline Form I of 5-(3,4-dichlorophenyl)-N-((1R,2R)-2-hydroxycyclohexyl)-6-(2,2,2-trifluoroethoxy)nicotinamide, anhydrate, is characterized by a powder X-ray diffraction pattern that has a characteristic peak in degrees 2θ at about 7.6, is characterized by a powder X-ray diffraction pattern that has a characteristic peak in degrees 2θ at about 12.2, is characterized by a powder X-ray diffraction pattern that has a characteristic peak in degrees 2θ at about 12.7, is characterized by a powder X-ray diffraction pattern that has a characteristic peak in degrees 2θ at about 17.7, is characterized by a powder X-ray diffraction pattern that has a characteristic peak in degrees 2θ at about 20.1, is characterized by a powder X-ray diffraction pattern that has a characteristic peak in degrees 2θ at about 22.7, is characterized by a powder X-ray diffraction pattern that has a characteristic peak in degrees 2θ at about 22.9, is characterized by a powder X-ray diffraction pattern that has a characteristic peak in degrees 2θ at about 23.4, is characterized by a powder X-ray diffraction pattern that has a characteristic peak in degrees 2θ at about 24.4, is characterized by a powder X-ray diffraction pattern that has a characteristic peak in degrees 2θ at about 25.2, is characterized by a powder X-ray diffraction pattern that has a characteristic peak in degrees 2θ at about 28.5, and/or is characterized by a powder X-ray diffraction pattern that has a characteristic peak in degrees 2θ at about 36.9. In another embodiment, crystalline Form I is characterized by a powder X-ray diffraction pattern having at least one or more characteristic peaks in degrees 2θ at about 9.2, 12.1, 18.8, 19.1, 19.9, 20.5, 21.9, 22.5, 22.8, 24.5, 26.0, and 31.7. For example, a contemplated crystalline form has a powder X-ray diffraction pattern shown in FIG. 29. In one embodiment, the powder X-ray diffraction pattern of the crystalline form was obtained using Cu Kα radiation.

In one embodiment, the crystalline Form I of 5-(3,4-dichlorophenyl)-N-((1R,2R)-2-hydroxycyclohexyl)-6-(2,2,2-trifluoroethoxy)nicotinamide, anhydrate, is characterized by a powder X-ray diffraction pattern that has a characteristic peak in degrees 2θ at about 7.5, is characterized by a powder X-ray diffraction pattern that has a characteristic peak in degrees 2θ at about 12.7, is characterized by a powder X-ray diffraction pattern that has a characteristic peak in degrees 2θ at about 17.6, is characterized by a powder X-ray diffraction pattern that has a characteristic peak in degrees 2θ at about 19.2, is characterized by a powder X-ray diffraction pattern that has a characteristic peak in degrees 2θ at about 20.0, is characterized by a powder X-ray diffraction pattern that has a characteristic peak in degrees 2θ at about 21.3, is characterized by a powder X-ray diffraction pattern that has a characteristic peak in degrees 2θ at about 22.8, is characterized by a powder X-ray diffraction pattern that has a characteristic peak in degrees 2θ at about 23.4, is characterized by a powder X-ray diffraction pattern that has a characteristic peak in degrees 2θ at about 24.3, is characterized by a powder X-ray diffraction pattern that has a characteristic peak in degrees 2θ at about 24.8, is characterized by a powder X-ray diffraction pattern that has a characteristic peak in degrees 2θ at about 26.1, and/or is characterized by a powder X-ray diffraction pattern that has a characteristic peak in degrees 2θ at about 28.5. In another embodiment, crystalline Form I is characterized by a powder X-ray diffraction pattern having at least one or more characteristic peaks in degrees 2θ at about 7.5, 12.7, 17.6, 19.2, 20.0, 21.3, 22.8, 23.4, 24.3, 24.8, 26.1, and 28.5. For example, a contemplated crystalline form has a powder X-ray diffraction pattern shown in FIG. 29A. In one embodiment, the powder X-ray diffraction pattern of the crystalline form was obtained using Cu Kα radiation.

The contemplated crystalline Form I of 5-(3,4-dichlorophenyl)-N-((1R,2R)-2-hydroxycyclohexyl)-6-(2,2,2-trifluoroethoxy)nicotinamide, anhydrate, may be characterized by a differential scanning calorimetry (DSC) profile showing a characteristic endotherm with an onset of about 154° C.; a characteristic exotherm with an onset of about 156° C.; a characteristic endotherm with an onset of about 164° C.; and a characteristic endotherm with an onset of about 168° C. Form I, for example, may be characterized by the differential scanning calorimetry profile shown in FIG. 30.

Figure 31:
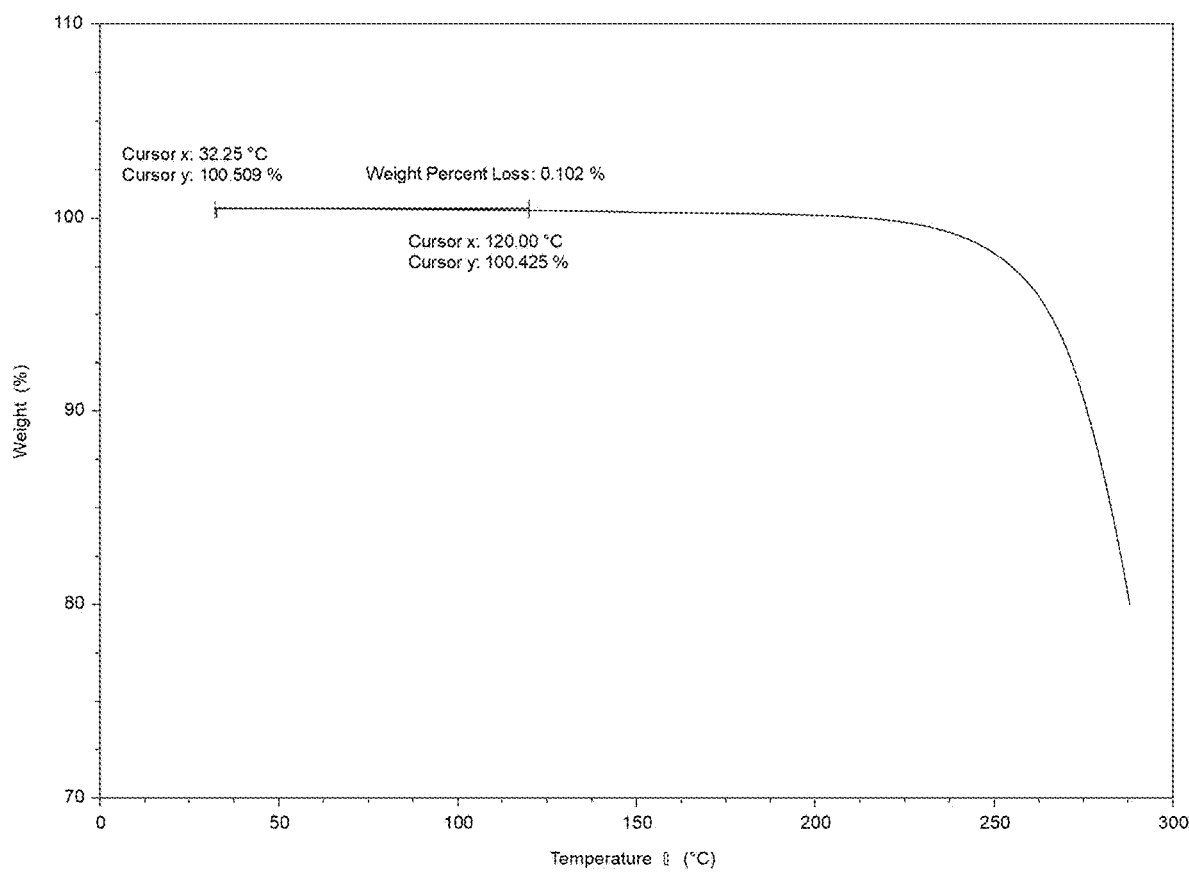
FIG. 31 depicts the thermogravimetric analysis (TGA) profile of Form I.
Figure 32:
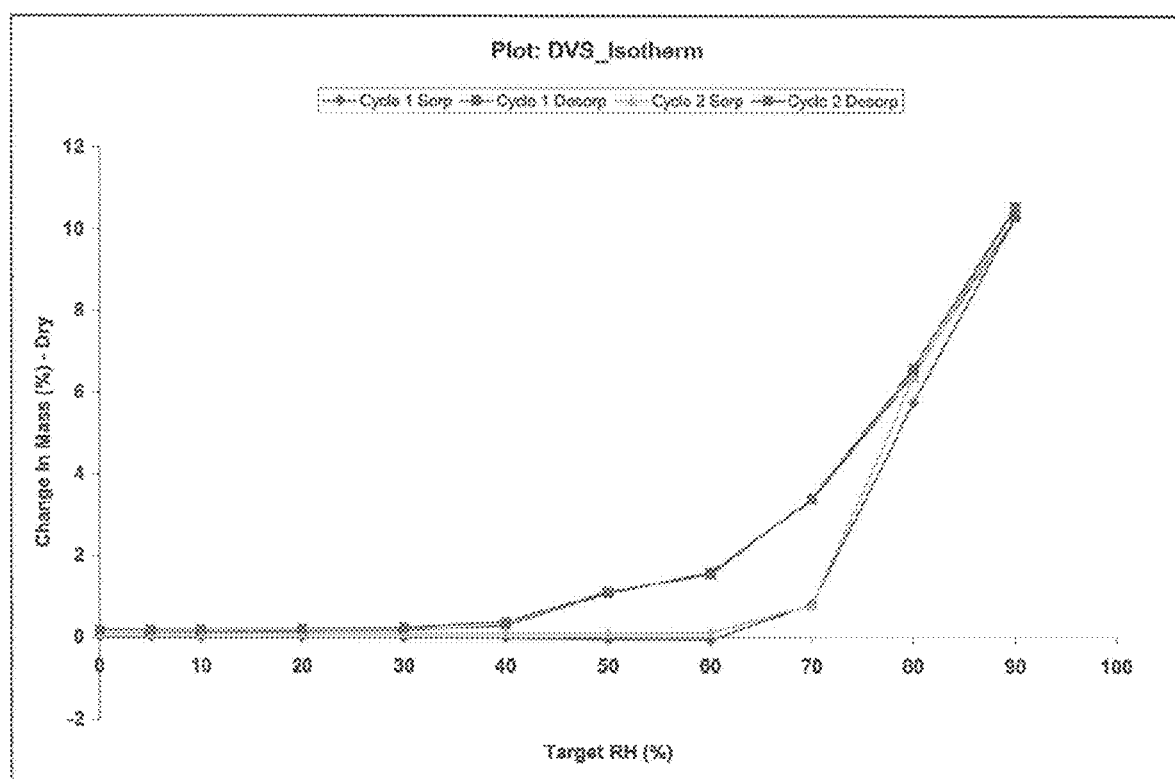
FIG. 32 depicts the dynamic vapor sorption (DVS) profile of Form I.

The contemplated crystalline Form I of 5-(3,4-dichlorophenyl)-N-((1R,2R)-2-hydroxycyclohexyl)-6-(2,2,2-trifluoroethoxy)nicotinamide, anhydrate, may be characterized by a thermogravimetric analysis (TGA) profile showing a mass loss of about 0.1 wt. % up to about 120° C. (FIG. 31). In some embodiments, crystalline Form I may be characterized by a dynamic vapor sorption (DVS) profile showing a total mass change of about 10 wt. % between about 0 to about 90% relative humidity (RH) at 25° C. (FIG. 32).

In another embodiment, disclosed herein is a crystalline form of 5-(3,4-dichlorophenyl)-N-((1R,2R)-2-hydroxycyclohexyl)-6-(2,2,2-trifluoroethoxy)nicotinamide, ethanol solvate, characterized by a powder X-ray diffraction pattern having a characteristic peak in degrees 2θ at about 19.6 (referred to herein as "Form J").

In one embodiment, the crystalline Form J of 5-(3,4-dichlorophenyl)-N-((1R,2R)-2-hydroxycyclohexyl)-6-(2,2,2-trifluoroethoxy)nicotinamide, ethanol solvate, is characterized by a powder X-ray diffraction pattern that has a characteristic peak in degrees 2θ at about 11.5, is characterized by a powder X-ray diffraction pattern that has a characteristic peak in degrees 2θ at about 16.9, is characterized by a powder X-ray diffraction pattern that has a characteristic peak in degrees 2θ at about 19.2, is characterized by a powder X-ray diffraction pattern that has a characteristic peak in degrees 2θ at about 19.6, is characterized by a powder X-ray diffraction pattern that has a characteristic peak in degrees 2θ at about 19.9, is characterized by a powder X-ray diffraction pattern that has a characteristic peak in degrees 2θ at about 23.7, is characterized by a powder X-ray diffraction pattern that has a characteristic peak in degrees 2θ at about 24.1, is characterized by a powder X-ray diffraction pattern that has a characteristic peak in degrees 2θ at about 24.4, is characterized by a powder X-ray diffraction pattern that has a characteristic peak in degrees 2θ at about 24.6, is characterized by a powder X-ray diffraction pattern that has a characteristic peak in degrees 2θ at about 25.0, is characterized by a powder X-ray diffraction pattern that has a characteristic peak in degrees 2θ at about 26.4, and/or is characterized by a powder X-ray diffraction pattern that has a characteristic peak in degrees 2θ at about 40.5. In another embodiment, crystalline Form J is characterized by a powder X-ray diffraction pattern having at least one or more characteristic peaks in degrees 2θ at about 11.5, 16.9, 19.2, 19.6, 19.9, 23.7, 24.1, 24.4, 24.6, 25.0, 26.4, and 40.5. For example, a contemplated crystalline form has a powder X-ray diffraction pattern shown in FIG. 33. In one embodiment, the powder X-ray diffraction pattern of the crystalline form was obtained using Cu Kα radiation.

In another embodiment, disclosed herein is a crystalline form of 5-(3,4-dichlorophenyl)-N-((1R,2R)-2-hydroxycyclohexyl)-6-(2,2,2-trifluoroethoxy)nicotinamide, methanol solvate, characterized by a powder X-ray diffraction pattern having a characteristic peak in degrees 2θ at about 20.2 (referred to herein as "Form K").

In one embodiment, the crystalline Form K of 5-(3,4-dichlorophenyl)-N-((1R,2R)-2-hydroxycyclohexyl)-6-(2,2,2-trifluoroethoxy)nicotinamide, methanol solvate, is characterized by a powder X-ray diffraction pattern that has a characteristic peak in degrees 2θ at about 6.2, is characterized by a powder X-ray diffraction pattern that has a characteristic peak in degrees 2θ at about 12.0, is characterized by a powder X-ray diffraction pattern that has a characteristic peak in degrees 2θ at about 12.8, is characterized by a powder X-ray diffraction pattern that has a characteristic peak in degrees 2θ at about 17.0, is characterized by a powder X-ray diffraction pattern that has a characteristic peak in degrees 2θ at about 18.7 is characterized by a powder X-ray diffraction pattern that has a characteristic peak in degrees 2θ at about 19.5, is characterized by a powder X-ray diffraction pattern that has a characteristic peak in degrees 2θ at about 20.2, is characterized by a powder X-ray diffraction pattern that has a characteristic peak in degrees 2θ at about 24.5, is characterized by a powder X-ray diffraction pattern that has a characteristic peak in degrees 2θ at about 24.9, is characterized by a powder X-ray diffraction pattern that has a characteristic peak in degrees 2θ at about 25.8, is characterized by a powder X-ray diffraction pattern that has a characteristic peak in degrees 2θ at about 26.6, and/or is characterized by a powder X-ray diffraction pattern that has a characteristic peak in degrees 2θ at about 27.2. In another embodiment, crystalline Form K is characterized by a powder X-ray diffraction pattern having at least one or more characteristic peaks in degrees 2θ at about 6.2, 12.0, 12.8, 17.0, 18.7, 19.5, 20.2, 24.5, 24.9, 25.8, 26.6, and 27.2. For example, a contemplated crystalline form has a powder X-ray diffraction pattern shown in FIG. 34. In one embodiment, the powder X-ray diffraction pattern of the crystalline form was obtained using Cu Kα radiation.

In another embodiment, disclosed herein is a crystalline form of 5-(3,4-dichlorophenyl)-N-((1R,2R)-2-hydroxycyclohexyl)-6-(2,2,2-trifluoroethoxy)nicotinamide, hydrate, characterized by a powder X-ray diffraction pattern having a characteristic peak in degrees 2θ at about 12.5 (referred to herein as "Form L").

In one embodiment, the crystalline Form L of 5-(3,4-dichlorophenyl)-N-((1R,2R)-2-hydroxycyclohexyl)-6-(2,2,2-trifluoroethoxy)nicotinamide, hydrate, is characterized by a powder X-ray diffraction pattern that has a characteristic peak in degrees 2θ at about 6.3, is characterized by a powder X-ray diffraction pattern that has a characteristic peak in degrees 2θ at about 12.5, is characterized by a powder X-ray diffraction pattern that has a characteristic peak in degrees 2θ at about 18.1, is characterized by a powder X-ray diffraction pattern that has a characteristic peak in degrees 2θ at about 18.8, is characterized by a powder X-ray diffraction pattern that has a characteristic peak in degrees 2θ at about 20.0, is characterized by a powder X-ray diffraction pattern that has a characteristic peak in degrees 2θ at about 23.1, is characterized by a powder X-ray diffraction pattern that has a characteristic peak in degrees 2θ at about 25.1, is characterized by a powder X-ray diffraction pattern that has a characteristic peak in degrees 2θ at about 25.5, is characterized by a powder X-ray diffraction pattern that has a characteristic peak in degrees 2θ at about 26.1, is characterized by a powder X-ray diffraction pattern that has a characteristic peak in degrees 2θ at about 27.7, is characterized by a powder X-ray diffraction pattern that has a characteristic peak in degrees 2θ at about 28.1, and/or is characterized by a powder X-ray diffraction pattern that has a characteristic peak in degrees 2θ at about 38.2. In another embodiment, crystalline Form L is characterized by a powder X-ray diffraction pattern having at least one or more characteristic peaks in degrees 2θ at about 6.3, 12.5, 18.1, 18.8, 20.0, 23.1, 25.1, 25.5, 26.1, 27.7, 28.1, and 38.2. For example, a contemplated crystalline form has a powder X-ray diffraction pattern shown in FIG. 35. In one embodiment, the powder X-ray diffraction pattern of the crystalline form was obtained using Cu Kα radiation.

The contemplated crystalline Form L of 5-(3,4-dichlorophenyl)-N-((1R,2R)-2-hydroxycyclohexyl)-6-(2,2,2-trifluoroethoxy)nicotinamide, hydrate, may be characterized by a differential scanning calorimetry (DSC) profile showing a characteristic endotherm with an onset of about 35° C. and a peak of about 56° C.; a characteristic endotherm with an onset of about 90° C. and a peak of about 95° C.; a characteristic exotherm with an onset of about 97° C. and a peak of about 100° C.; a characteristic endotherm with an onset and a peak of about 164° C.; and a characteristic endotherm with an onset of about 168° C. and a peak of about 169° C. Form L, for example, may be characterized by the differential scanning calorimetry profile shown in FIG. 36.

Figure 37:
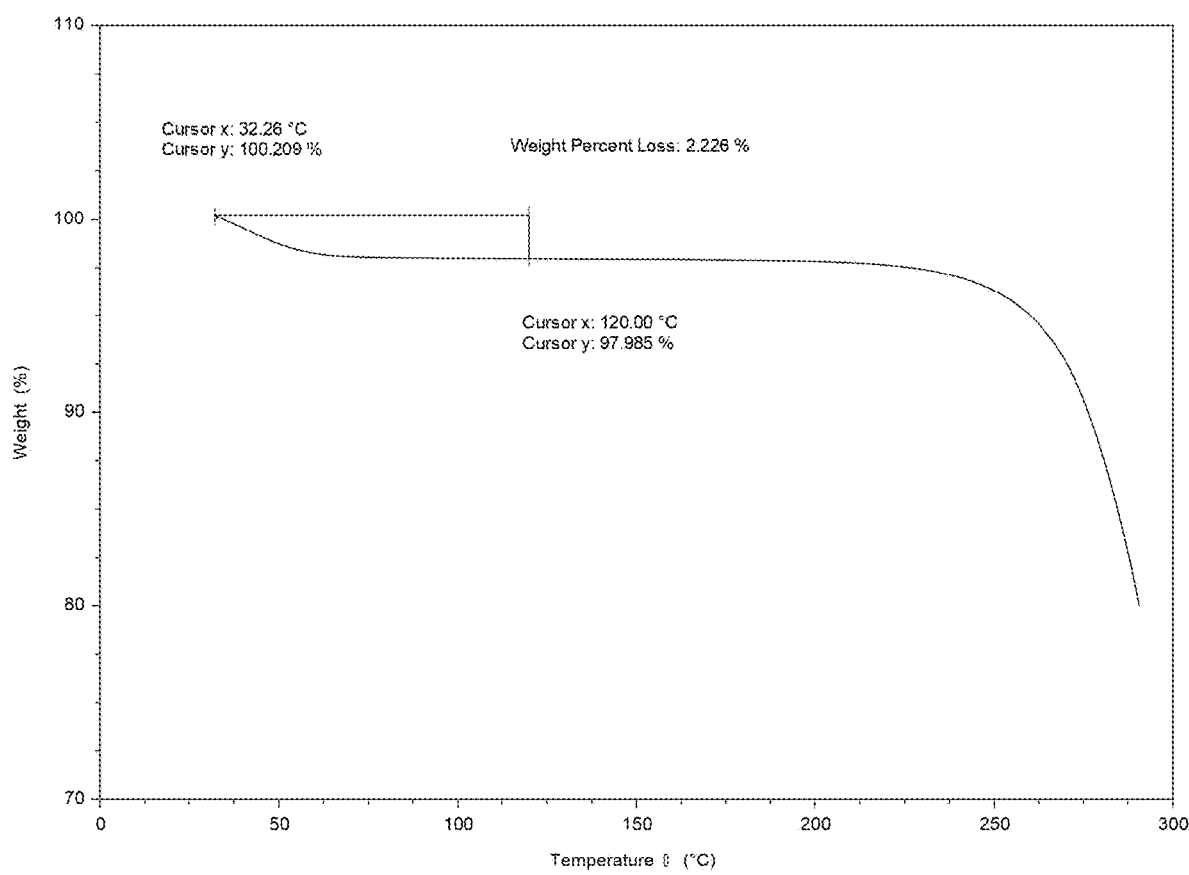
FIG. 37 depicts the thermogravimetric analysis (TGA) profile of Form L.

The contemplated crystalline Form L of 5-(3,4-dichlorophenyl)-N-((1R,2R)-2-hydroxycyclohexyl)-6-(2,2,2-trifluoroethoxy)nicotinamide, hydrate, may be characterized by a thermogravimetric analysis (TGA) profile showing a mass loss of about 2.2 wt. % up to about 120° C. (FIG. 37). In some embodiments, crystalline Form L may be characterized by Karl Fischer (KF) analysis showing 4.4% water by weight (1.18 equivalent by molar ratio).

In another embodiment, disclosed herein is a crystalline form of 5-(3,4-dichlorophenyl)-N-((1R,2R)-2-hydroxycyclohexyl)-6-(2,2,2-trifluoroethoxy)nicotinamide, hydrate, characterized by a powder X-ray diffraction pattern having a characteristic peak in degrees 2θ at about 17.7 (referred to herein as "Form M").

In one embodiment, the crystalline Form M of 5-(3,4-dichlorophenyl)-N-((1R,2R)-2-hydroxycyclohexyl)-6-(2,2,2-trifluoroethoxy)nicotinamide, hydrate, is characterized by a powder X-ray diffraction pattern that has a characteristic peak in degrees 2θ at about 8.5, is characterized by a powder X-ray diffraction pattern that has a characteristic peak in degrees 2θ at about 14.5, is characterized by a powder X-ray diffraction pattern that has a characteristic peak in degrees 2θ at about 17.7, is characterized by a powder X-ray diffraction pattern that has a characteristic peak in degrees 2θ at about 20.9, is characterized by a powder X-ray diffraction pattern that has a characteristic peak in degrees 2θ at about 21.2, is characterized by a powder X-ray diffraction pattern that has a characteristic peak in degrees 2θ at about 21.6, is characterized by a powder X-ray diffraction pattern that has a characteristic peak in degrees 2θ at about 22.7, is characterized by a powder X-ray diffraction pattern that has a characteristic peak in degrees 2θ at about 25.8, is characterized by a powder X-ray diffraction pattern that has a characteristic peak in degrees 2θ at about 24.3, is characterized by a powder X-ray diffraction pattern that has a characteristic peak in degrees 2θ at about 24.5, is characterized by a powder X-ray diffraction pattern that has a characteristic peak in degrees 2θ at about 25.2, and/or is characterized by a powder X-ray diffraction pattern that has a characteristic peak in degrees 2θ at about 34.3. In another embodiment, crystalline Form M is characterized by a powder X-ray diffraction pattern having at least one or more characteristic peaks in degrees 2θ at about 8.5, 14.5, 17.7, 20.9, 21.2, 21.6, 22.7, 23.8, 24.3, 24.5, 25.2, and 34.3. For example, a contemplated crystalline form has a powder X-ray diffraction pattern shown in FIG. 38. In one embodiment, the powder X-ray diffraction pattern of the crystalline form was obtained using Cu Kα radiation.

The contemplated crystalline Form M of 5-(3,4-dichlorophenyl)-N-((1R,2R)-2-hydroxycyclohexyl)-6-(2,2,2-trifluoroethoxy)nicotinamide, hydrate, may be characterized by a differential scanning calorimetry (DSC) profile showing a characteristic endotherm with an onset of about 61° C. and a peak of about 77° C.; a characteristic exotherm with an onset of about 83° C. and a peak of about 90° C.; a characteristic endotherm with an onset of about 147° C. and a peak of about 153° C.; a characteristic endotherm with an onset of about 164° C. and a peak of about 165; and a characteristic endotherm with an onset and a peak of about 169° C. Form M, for example, may be characterized by the differential scanning calorimetry profile shown in FIG. 39.

Figure 40:
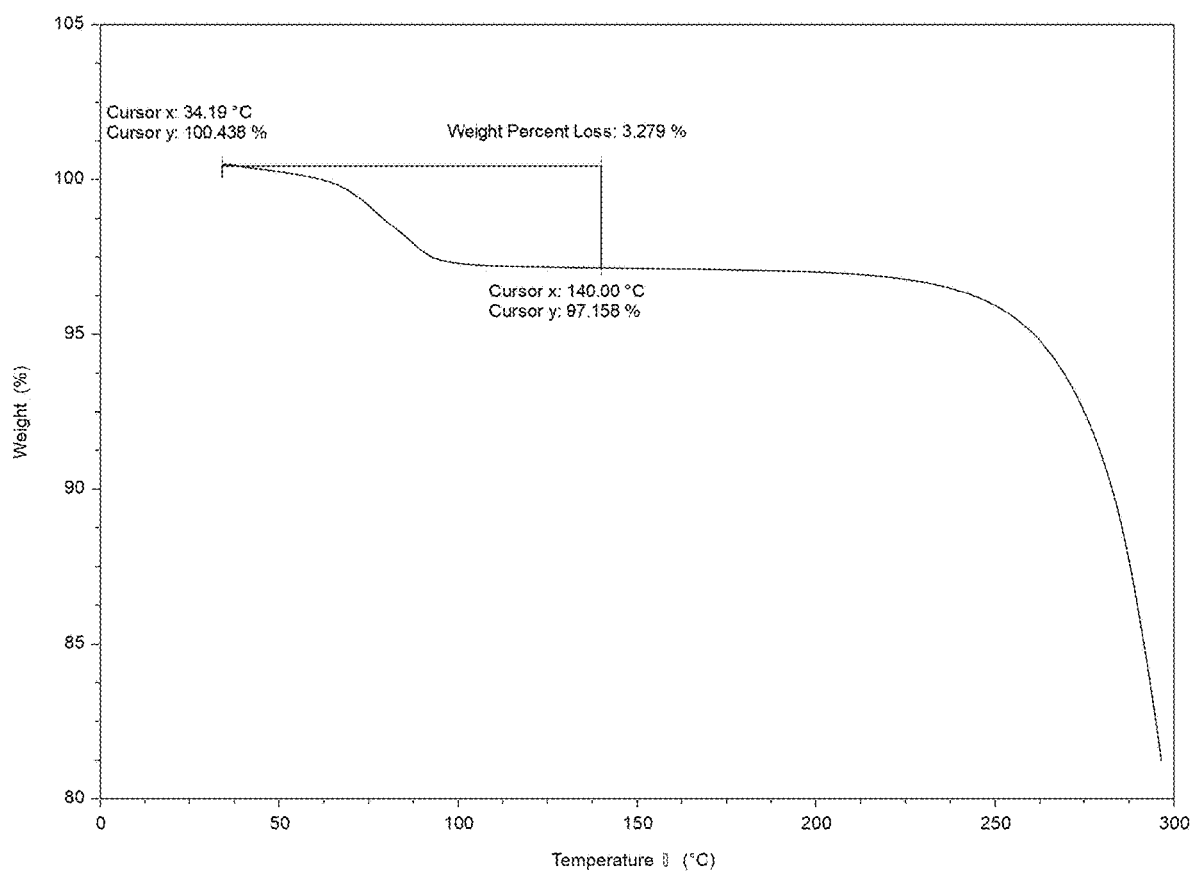
FIG. 40 depicts the thermogravimetric analysis (TGA) profile of Form M.

The contemplated crystalline Form M of 5-(3,4-dichlorophenyl)-N-((1R,2R)-2-hydroxycyclohexyl)-6-(2,2,2-trifluoroethoxy)nicotinamide, hydrate, may be characterized by a thermogravimetric analysis (TGA) profile showing a mass loss of about 3.4 wt. % up to about 120° C. (FIG. 40). In some embodiments, crystalline Form M may be characterized by Karl Fischer (KF) analysis showing 3.5% water by weight (0.93 equivalent by molar ratio).

In another embodiment, disclosed herein is a crystalline form of 5-(3,4-dichlorophenyl)-N-((1R,2R)-2-hydroxycyclohexyl)-6-(2,2,2-trifluoroethoxy)nicotinamide, hydrate, characterized by a powder X-ray diffraction pattern having a characteristic peak in degrees 2θ at about 17.9 (referred to herein as "Form N").

In one embodiment, the crystalline Form N of 5-(3,4-dichlorophenyl)-N-((1R,2R)-2-hydroxycyclohexyl)-6-(2,2,2-trifluoroethoxy)nicotinamide, hydrate, is characterized by a powder X-ray diffraction pattern that has a characteristic peak in degrees 2θ at about 8.2, is characterized by a powder X-ray diffraction pattern that has a characteristic peak in degrees 2θ at about 12.4, is characterized by a powder X-ray diffraction pattern that has a characteristic peak in degrees 2θ at about 17.4, is characterized by a powder X-ray diffraction pattern that has a characteristic peak in degrees 2θ at about 17.6, is characterized by a powder X-ray diffraction pattern that has a characteristic peak in degrees 2θ at about 17.9, is characterized by a powder X-ray diffraction pattern that has a characteristic peak in degrees 2θ at about 20.4, is characterized by a powder X-ray diffraction pattern that has a characteristic peak in degrees 2θ at about 22.4, is characterized by a powder X-ray diffraction pattern that has a characteristic peak in degrees 2θ at about 23.3, is characterized by a powder X-ray diffraction pattern that has a characteristic peak in degrees 2θ at about 28.9, is characterized by a powder X-ray diffraction pattern that has a characteristic peak in degrees 2θ at about 29.0, is characterized by a powder X-ray diffraction pattern that has a characteristic peak in degrees 2θ at about 34.6, and/or is characterized by a powder X-ray diffraction pattern that has a characteristic peak in degrees 2θ at about 35.6. In another embodiment, crystalline Form N is characterized by a powder X-ray diffraction pattern having at least one or more characteristic peaks in degrees 2θ at about 8.2, 12.4, 17.4, 17.6, 17.9, 20.4, 22.4, 23.3, 28.9, 29.0, 34.6, and 35.6. For example, a contemplated crystalline form has a powder X-ray diffraction pattern shown in FIG. 41. In one embodiment, the powder X-ray diffraction pattern of the crystalline form was obtained using Cu Kα radiation.

The contemplated crystalline Form N of 5-(3,4-dichlorophenyl)-N-((1R,2R)-2-hydroxycyclohexyl)-6-(2,2,2-trifluoroethoxy)nicotinamide, hydrate, may be characterized by a differential scanning calorimetry (DSC) profile showing a characteristic endotherm with an onset of about 50° C. and a peak of about 98° C.; a characteristic endotherm with an onset of about 163° C. and a peak of about 164° C.; and a characteristic endotherm with an onset of about 168° C. and a peak of about 169° C. Form N, for example, may be characterized by the differential scanning calorimetry profile shown in FIG. 42.

Figure 43:
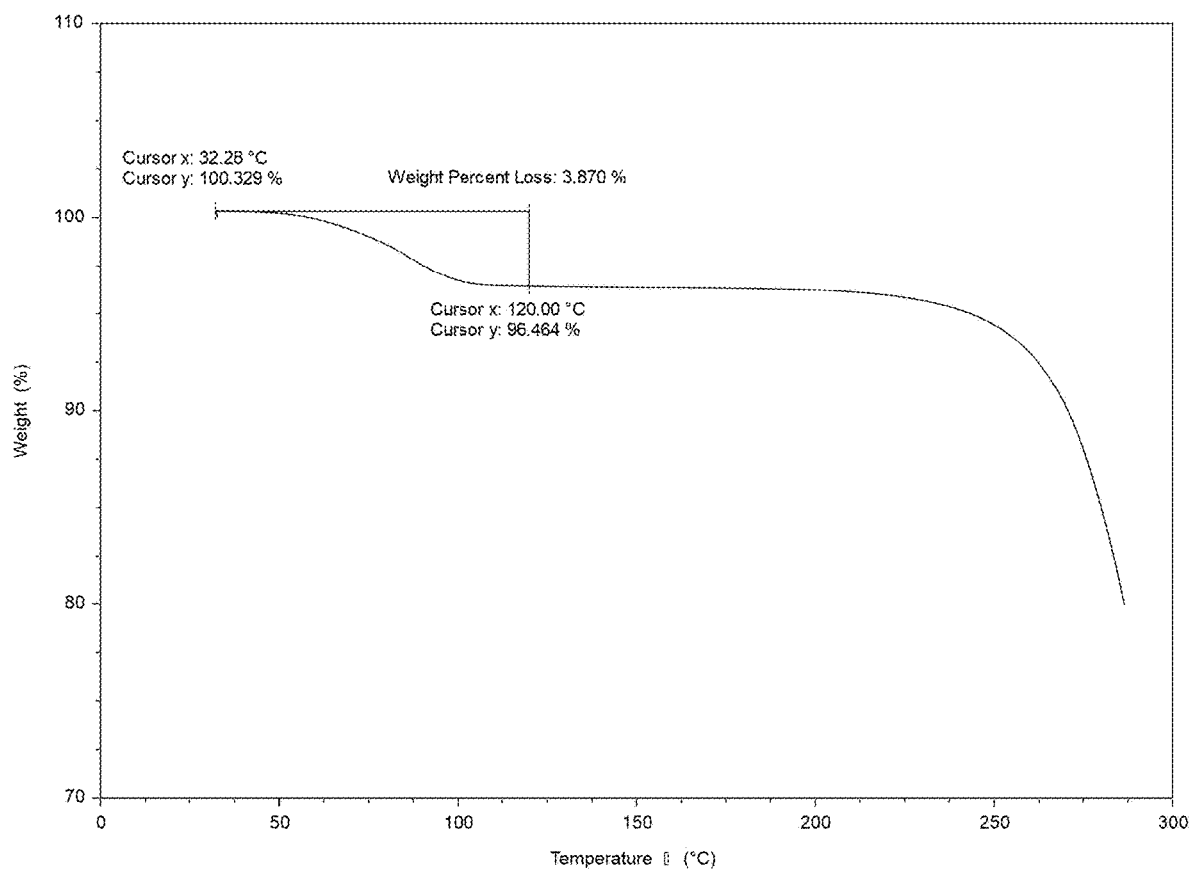
FIG. 43 depicts the thermogravimetric analysis (TGA) profile of Form N.

The contemplated crystalline Form N of 5-(3,4-dichlorophenyl)-N-((1R,2R)-2-hydroxycyclohexyl)-6-(2,2,2-trifluoroethoxy)nicotinamide, hydrate, may be characterized by a thermogravimetric analysis (TGA) profile showing a mass loss of about 3.9 wt. % up to about 120° C. (FIG. 43). In some embodiments, crystalline Form N may be characterized by Karl Fischer (KF) analysis showing 4.2% water by weight (1.13 equivalent by molar ratio).

In another embodiment, disclosed herein is a crystalline form of 5-(3,4-dichlorophenyl)-N-((1R,2R)-2-hydroxycyclohexyl)-6-(2,2,2-trifluoroethoxy)nicotinamide, hydrate, characterized by a powder X-ray diffraction pattern having a characteristic peak in degrees 2θ at about 7.6 (referred to herein as "Form O").

In one embodiment, the crystalline Form O of 5-(3,4-dichlorophenyl)-N-((1R,2R)-2-hydroxycyclohexyl)-6-(2,2,2-trifluoroethoxy)nicotinamide, hydrate, is characterized by a powder X-ray diffraction pattern that has a characteristic peak in degrees 2θ at about 7.6, is characterized by a powder X-ray diffraction pattern that has a characteristic peak in degrees 2θ at about 11.9, is characterized by a powder X-ray diffraction pattern that has a characteristic peak in degrees 2θ at about 12.7, is characterized by a powder X-ray diffraction pattern that has a characteristic peak in degrees 2θ at about 15.1, is characterized by a powder X-ray diffraction pattern that has a characteristic peak in degrees 2θ at about 17.7, is characterized by a powder X-ray diffraction pattern that has a characteristic peak in degrees 2θ at about 19.2, is characterized by a powder X-ray diffraction pattern that has a characteristic peak in degrees 2θ at about 22.0, is characterized by a powder X-ray diffraction pattern that has a characteristic peak in degrees 2θ at about 22.7, is characterized by a powder X-ray diffraction pattern that has a characteristic peak in degrees 2θ at about 24.4, is characterized by a powder X-ray diffraction pattern that has a characteristic peak in degrees 2θ at about 25.2, is characterized by a powder X-ray diffraction pattern that has a characteristic peak in degrees 2θ at about 29.8, and/or is characterized by a powder X-ray diffraction pattern that has a characteristic peak in degrees 2θ at about 39.0. In another embodiment, crystalline Form O is characterized by a powder X-ray diffraction pattern having at least one or more characteristic peaks in degrees 2θ at about 7.6, 11.9, 12.7, 15.1, 17.7, 19.2, 22.0, 22.7, 24.4, 25.2, 29.8, and 39.0. For example, a contemplated crystalline form has a powder X-ray diffraction pattern shown in FIG. 44. In one embodiment, the powder X-ray diffraction pattern of the crystalline form was obtained using Cu Kα radiation.

Figure 45:
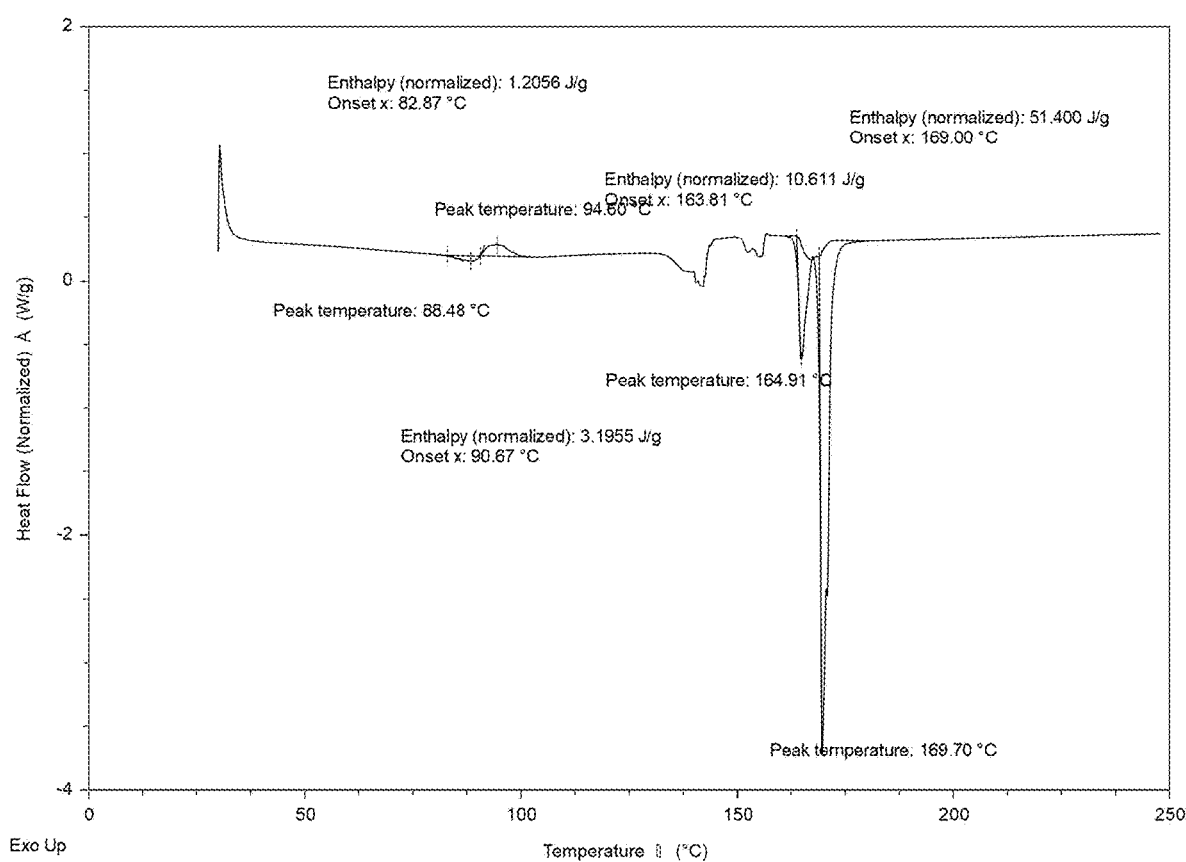
FIG. 45 depicts the characterization of Form O by differential scanning calorimetry (DSC).

The contemplated crystalline Form O of 5-(3,4-dichlorophenyl)-N-((1R,2R)-2-hydroxycyclohexyl)-6-(2,2,2-trifluoroethoxy)nicotinamide, hydrate, may be characterized by a differential scanning calorimetry (DSC) profile showing a characteristic endotherm with an onset of about 83° C. and a peak of about 88° C.; a characteristic exotherm with an onset of about 91° C. and a peak of about 95° C.; a characteristic endotherm with an onset of about 164° C. and a peak of about 165° C.; and a characteristic endotherm with an onset of about 169° C. and a peak of about 170° C. Form O, for example, may be characterized by the differential scanning calorimetry profile shown in FIG. 45.

Figure 46:
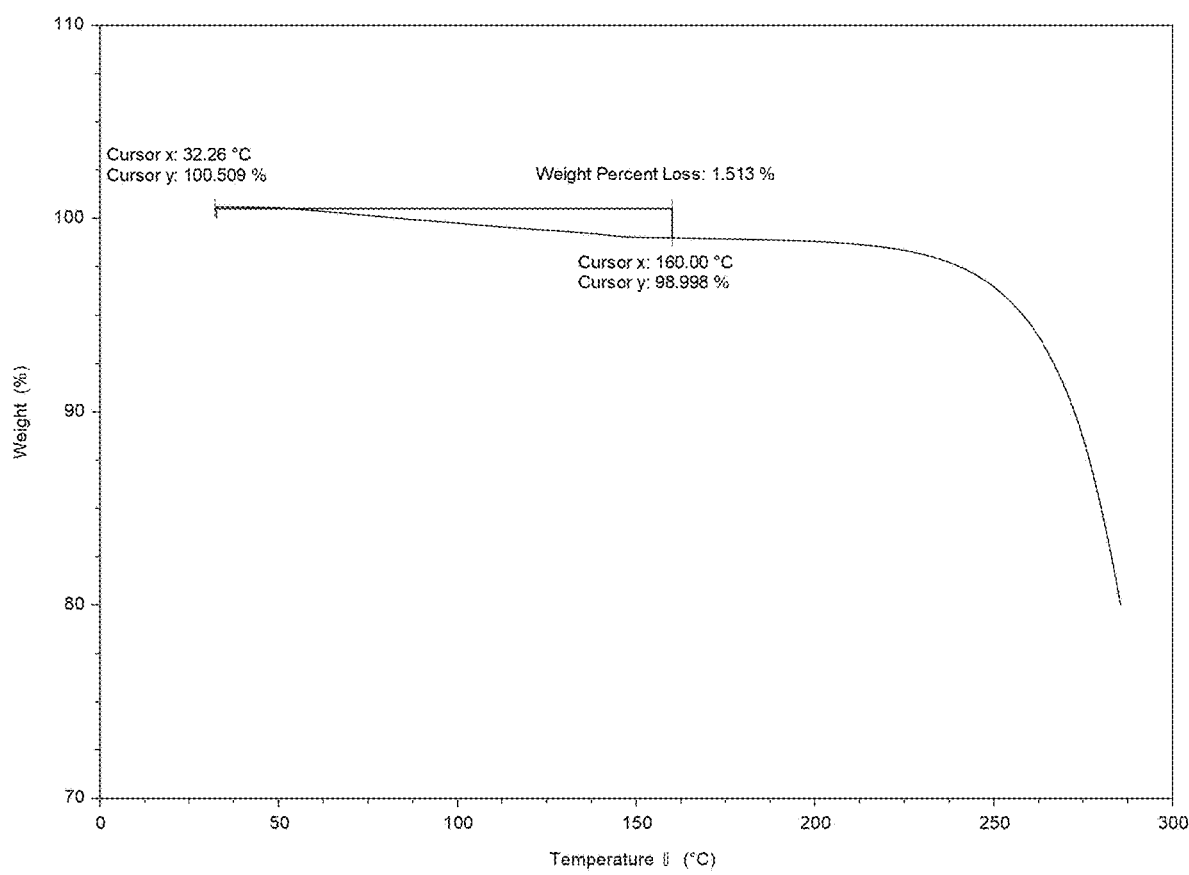
FIG. 46 depicts the thermogravimetric analysis (TGA) profile of Form O.

The contemplated crystalline Form O of 5-(3,4-dichlorophenyl)-N-((1R,2R)-2-hydroxycyclohexyl)-6-(2,2,2-trifluoroethoxy)nicotinamide, hydrate, may be characterized by a thermogravimetric analysis (TGA) profile showing a mass loss of about 1.5 wt. % up to about 160° C. (FIG. 46). In some embodiments, crystalline Form O may be characterized by Karl Fischer (KF) analysis showing 3.2% water by weight (0.85 equivalent by molar ratio).

In another embodiment, disclosed herein is a crystalline form of 5-(3,4-dichlorophenyl)-N-((1R,2R)-2-hydroxycyclohexyl)-6-(2,2,2-trifluoroethoxy)nicotinamide, methanol solvate, characterized by a powder X-ray diffraction pattern having a characteristic peak in degrees 2θ at about 6.3 (referred to herein as "Form P").

In one embodiment, the crystalline Form P of 5-(3,4-dichlorophenyl)-N-((1R,2R)-2-hydroxycyclohexyl)-6-(2,2,2-trifluoroethoxy)nicotinamide, methanol solvate, is characterized by a powder X-ray diffraction pattern that has a characteristic peak in degrees 2θ at about 6.3, is characterized by a powder X-ray diffraction pattern that has a characteristic peak in degrees 2θ at about 12.1 is characterized by a powder X-ray diffraction pattern that has a characteristic peak in degrees 2θ at about 12.5, is characterized by a powder X-ray diffraction pattern that has a characteristic peak in degrees 2θ at about 12.7, is characterized by a powder X-ray diffraction pattern that has a characteristic peak in degrees 2θ at about 18.9, is characterized by a powder X-ray diffraction pattern that has a characteristic peak in degrees 2θ at about 19.6, is characterized by a powder X-ray diffraction pattern that has a characteristic peak in degrees 2θ at about 19.7, is characterized by a powder X-ray diffraction pattern that has a characteristic peak in degrees 2θ at about 25.0, is characterized by a powder X-ray diffraction pattern that has a characteristic peak in degrees 2θ at about 25.5, is characterized by a powder X-ray diffraction pattern that has a characteristic peak in degrees 2θ at about 27.3 is characterized by a powder X-ray diffraction pattern that has a characteristic peak in degrees 2θ at about 27.7, and/or is characterized by a powder X-ray diffraction pattern that has a characteristic peak in degrees 2θ at about 38.8. In another embodiment, crystalline Form P is characterized by a powder X-ray diffraction pattern having at least one or more characteristic peaks in degrees 2θ at about 6.3, 12.1, 12.5, 12.7, 18.9, 19.6, 19.7, 25.0, 25.5, 27.3, 27.7, and 38.8. For example, a contemplated crystalline form has a powder X-ray diffraction pattern shown in FIG. 47. In one embodiment, the powder X-ray diffraction pattern of the crystalline form was obtained using Cu Kα radiation.

In another embodiment, disclosed herein is a crystalline form of 5-(3,4-dichlorophenyl)-N-((1R,2R)-2-hydroxycyclohexyl)-6-(2,2,2-trifluoroethoxy)nicotinamide, acetonitrile solvate, characterized by a powder X-ray diffraction pattern having a characteristic peak in degrees 2θ at about 23.8 (referred to herein as "Form Q").

In one embodiment, the crystalline Form Q of 5-(3,4-dichlorophenyl)-N-((1R,2R)-2-hydroxycyclohexyl)-6-(2,2,2-trifluoroethoxy)nicotinamide, acetonitrile solvate, is characterized by a powder X-ray diffraction pattern that has a characteristic peak in degrees 2θ at about 6.6, is characterized by a powder X-ray diffraction pattern that has a characteristic peak in degrees 2θ at about 8.4, is characterized by a powder X-ray diffraction pattern that has a characteristic peak in degrees 2θ at about 14.4, is characterized by a powder X-ray diffraction pattern that has a characteristic peak in degrees 2θ at about 18.6, is characterized by a powder X-ray diffraction pattern that has a characteristic peak in degrees 2θ at about 19.9, is characterized by a powder X-ray diffraction pattern that has a characteristic peak in degrees 2θ at about 20.9, is characterized by a powder X-ray diffraction pattern that has a characteristic peak in degrees 2θ at about 21.1, is characterized by a powder X-ray diffraction pattern that has a characteristic peak in degrees 2θ at about 22.7, is characterized by a powder X-ray diffraction pattern that has a characteristic peak in degrees 2θ at about 23.6, is characterized by a powder X-ray diffraction pattern that has a characteristic peak in degrees 2θ at about 23.8 is characterized by a powder X-ray diffraction pattern that has a characteristic peak in degrees 2θ at about 24.5, and/or is characterized by a powder X-ray diffraction pattern that has a characteristic peak in degrees 2θ at about 26.4. In another embodiment, crystalline Form Q is characterized by a powder X-ray diffraction pattern having at least one or more characteristic peaks in degrees 2θ at about 6.6, 8.4, 14.4, 18.6, 19.9, 20.9, 21.1, 22.7, 23.6, 23.8, 24.5, and 26.4. For example, a contemplated crystalline form has a powder X-ray diffraction pattern shown in FIG. 48. In one embodiment, the powder X-ray diffraction pattern of the crystalline form was obtained using Cu Kα radiation.

In another embodiment, disclosed herein is a crystalline form of 5-(3,4-dichlorophenyl)-N-((1R,2R)-2-hydroxycyclohexyl)-6-(2,2,2-trifluoroethoxy)nicotinamide, 1,4-dioxane solvate, characterized by a powder X-ray diffraction pattern having a characteristic peak in degrees 2θ at about 22.4 (referred to herein as "Form R").

In one embodiment, the crystalline Form R of 5-(3,4-dichlorophenyl)-N-((1R,2R)-2-hydroxycyclohexyl)-6-(2,2,2-trifluoroethoxy)nicotinamide, 1,4-dioxane solvate, is characterized by a powder X-ray diffraction pattern that has a characteristic peak in degrees 2θ at about 11.1, is characterized by a powder X-ray diffraction pattern that has a characteristic peak in degrees 2θ at about 17.3, is characterized by a powder X-ray diffraction pattern that has a characteristic peak in degrees 2θ at about 17.5, is characterized by a powder X-ray diffraction pattern that has a characteristic peak in degrees 2θ at about 17.9, is characterized by a powder X-ray diffraction pattern that has a characteristic peak in degrees 2θ at about 18.2, is characterized by a powder X-ray diffraction pattern that has a characteristic peak in degrees 2θ at about 22.4, is characterized by a powder X-ray diffraction pattern that has a characteristic peak in degrees 2θ at about 23.3, is characterized by a powder X-ray diffraction pattern that has a characteristic peak in degrees 2θ at about 28.4, is characterized by a powder X-ray diffraction pattern that has a characteristic peak in degrees 2θ at about 29.1, is characterized by a powder X-ray diffraction pattern that has a characteristic peak in degrees 2θ at about 33.8 is characterized by a powder X-ray diffraction pattern that has a characteristic peak in degrees 2θ at about 34.5, and/or is characterized by a powder X-ray diffraction pattern that has a characteristic peak in degrees 2θ at about 39.7. In another embodiment, crystalline Form R is characterized by a powder X-ray diffraction pattern having at least one or more characteristic peaks in degrees 2θ at about 11.1, 17.3, 17.5, 17.9, 18.2, 22.4, 23.3, 28.4, 29.1, 33.8, 34.5, and 39.7. For example, a contemplated crystalline form has a powder X-ray diffraction pattern shown in FIG. 49. In one embodiment, the powder X-ray diffraction pattern of the crystalline form was obtained using Cu Kα radiation.

In another embodiment, disclosed herein is a crystalline form of 5-(3,4-dichlorophenyl)-N-((1R,2R)-2-hydroxycyclohexyl)-6-(2,2,2-trifluoroethoxy)nicotinamide, trifluoroethanol solvate, characterized by a powder X-ray diffraction pattern having a characteristic peak in degrees 2θ at about 22.8 (referred to herein as "Form S").

In one embodiment, the crystalline Form S of 5-(3,4-dichlorophenyl)-N-((1R,2R)-2-hydroxycyclohexyl)-6-(2,2,2-trifluoroethoxy)nicotinamide, trifluoroethanol solvate, is characterized by a powder X-ray diffraction pattern that has a characteristic peak in degrees 2θ at about 7.5, is characterized by a powder X-ray diffraction pattern that has a characteristic peak in degrees 2θ at about 12.0, is characterized by a powder X-ray diffraction pattern that has a characteristic peak in degrees 2θ at about 17.7, is characterized by a powder X-ray diffraction pattern that has a characteristic peak in degrees 2θ at about 19.2, is characterized by a powder X-ray diffraction pattern that has a characteristic peak in degrees 2θ at about 21.6, is characterized by a powder X-ray diffraction pattern that has a characteristic peak in degrees 2θ at about 22.8, is characterized by a powder X-ray diffraction pattern that has a characteristic peak in degrees 2θ at about 23.5, is characterized by a powder X-ray diffraction pattern that has a characteristic peak in degrees 2θ at about 24.4, is characterized by a powder X-ray diffraction pattern that has a characteristic peak in degrees 2θ at about 25.3, is characterized by a powder X-ray diffraction pattern that has a characteristic peak in degrees 2θ at about 30.0, is characterized by a powder X-ray diffraction pattern that has a characteristic peak in degrees 2θ at about 31.6, and/or is characterized by a powder X-ray diffraction pattern that has a characteristic peak in degrees 2θ at about 34.3. In another embodiment, crystalline Form S is characterized by a powder X-ray diffraction pattern having at least one or more characteristic peaks in degrees 2θ at about 7.5, 12.0, 17.7, 19.2, 21.6, 22.8, 23.5, 24.4, 25.3, 30.0, 31.6, and 34.3. For example, a contemplated crystalline form has a powder X-ray diffraction pattern shown in FIG. 50. In one embodiment, the powder X-ray diffraction pattern of the crystalline form was obtained using Cu Kα radiation.

In another embodiment, disclosed herein is a crystalline form of 5-(3,4-dichlorophenyl)-N-((1R,2R)-2-hydroxycyclohexyl)-6-(2,2,2-trifluoroethoxy)nicotinamide, hydrate, characterized by a powder X-ray diffraction pattern having a characteristic peak in degrees 2θ at about 12.2 (referred to herein as "Form T").

In one embodiment, the crystalline Form T of 5-(3,4-dichlorophenyl)-N-((1R,2R)-2-hydroxycyclohexyl)-6-(2,2,2-trifluoroethoxy)nicotinamide, hydrate, is characterized by a powder X-ray diffraction pattern that has a characteristic peak in degrees 2θ at about 5.4, is characterized by a powder X-ray diffraction pattern that has a characteristic peak in degrees 2θ at about 7.0, is characterized by a powder X-ray diffraction pattern that has a characteristic peak in degrees 2θ at about 9.0, is characterized by a powder X-ray diffraction pattern that has a characteristic peak in degrees 2θ at about 10.8, is characterized by a powder X-ray diffraction pattern that has a characteristic peak in degrees 2θ at about 12.2, is characterized by a powder X-ray diffraction pattern that has a characteristic peak in degrees 2θ at about 13.0, is characterized by a powder X-ray diffraction pattern that has a characteristic peak in degrees 2θ at about 16.1, is characterized by a powder X-ray diffraction pattern that has a characteristic peak in degrees 2θ at about 19.4, is characterized by a powder X-ray diffraction pattern that has a characteristic peak in degrees 2θ at about 19.7, is characterized by a powder X-ray diffraction pattern that has a characteristic peak in degrees 2θ at about 20.9, is characterized by a powder X-ray diffraction pattern that has a characteristic peak in degrees 2θ at about 22.5, and/or is characterized by a powder X-ray diffraction pattern that has a characteristic peak in degrees 2θ at about 28.3. In another embodiment, crystalline Form T is characterized by a powder X-ray diffraction pattern having at least one or more characteristic peaks in degrees 2θ at about 5.4, 7.0, 9.0, 10.8, 12.2, 13.0, 16.1, 19.4, 19.7, 20.9, 22.5, and 28.3. For example, a contemplated crystalline form has a powder X-ray diffraction pattern shown in FIG. 51. In one embodiment, the powder X-ray diffraction pattern of the crystalline form was obtained using Cu Kα radiation.

The contemplated crystalline Form T of 5-(3,4-dichlorophenyl)-N-((1R,2R)-2-hydroxycyclohexyl)-6-(2,2,2-trifluoroethoxy)nicotinamide, hydrate, may be characterized by a differential scanning calorimetry (DSC) profile showing a characteristic endotherm with an onset of about 55° C.; a characteristic endotherm with an onset of about 89° C. and a peak of about 98° C.; a characteristic endotherm with an onset of about 163° C. and a peak of about 164° C.; and a characteristic endotherm with an onset and a peak of about 169° C. Form T, for example, may be characterized by the differential scanning calorimetry profile shown in FIG. 52.

Figure 53:
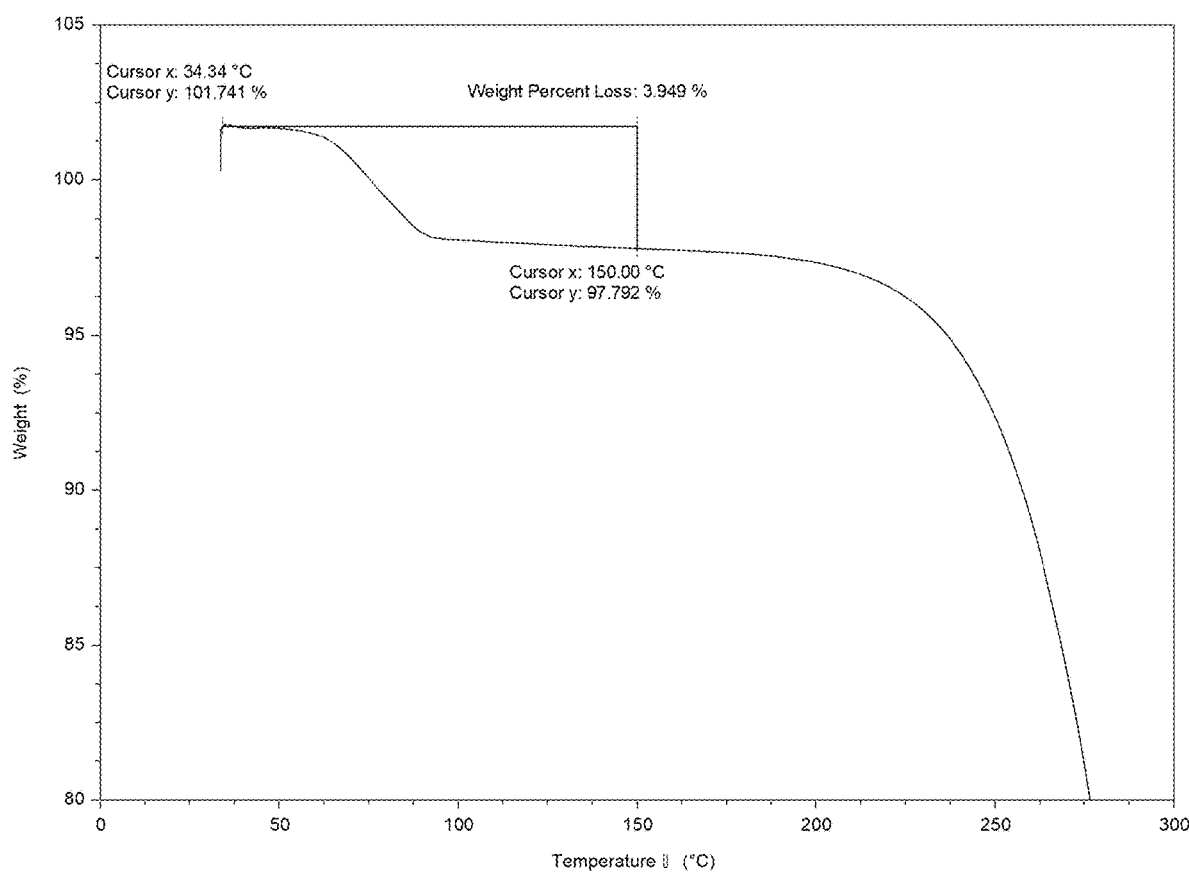
FIG. 53 depicts the thermogravimetric analysis (TGA) profile of Form T.

The contemplated crystalline Form T of 5-(3,4-dichlorophenyl)-N-((1R,2R)-2-hydroxycyclohexyl)-6-(2,2,2-trifluoroethoxy)nicotinamide, hydrate, may be characterized by a thermogravimetric analysis (TGA) profile showing a mass loss of about 3.9 wt. % up to about 150° C. (FIG. 53). In some embodiments, crystalline Form T may be characterized by Karl Fischer (KF) analysis showing 6.7% water by weight (1.85 equivalent by molar ratio).

In another embodiment, disclosed herein is a crystalline form of 5-(3,4-dichlorophenyl)-N-((1R,2R)-2-hydroxycyclohexyl)-6-(2,2,2-trifluoroethoxy)nicotinamide, hydrate, characterized by a powder X-ray diffraction pattern having a characteristic peak in degrees 2θ at about 6.0 (referred to herein as "Form U").

In one embodiment, the crystalline Form U of 5-(3,4-dichlorophenyl)-N-((1R,2R)-2-hydroxycyclohexyl)-6-(2,2,2-trifluoroethoxy)nicotinamide, hydrate, is characterized by a powder X-ray diffraction pattern that has a characteristic peak in degrees 2θ at about 6.0, is characterized by a powder X-ray diffraction pattern that has a characteristic peak in degrees 2θ at about 12.0, is characterized by a powder X-ray diffraction pattern that has a characteristic peak in degrees 2θ at about 13.3, is characterized by a powder X-ray diffraction pattern that has a characteristic peak in degrees 2θ at about 17.9, is characterized by a powder X-ray diffraction pattern that has a characteristic peak in degrees 2θ at about 18.9, is characterized by a powder X-ray diffraction pattern that has a characteristic peak in degrees 2θ at about 21.4, is characterized by a powder X-ray diffraction pattern that has a characteristic peak in degrees 2θ at about 22.0, is characterized by a powder X-ray diffraction pattern that has a characteristic peak in degrees 2θ at about 24.0, is characterized by a powder X-ray diffraction pattern that has a characteristic peak in degrees 2θ at about 24.3, is characterized by a powder X-ray diffraction pattern that has a characteristic peak in degrees 2θ at about 26.3, is characterized by a powder X-ray diffraction pattern that has a characteristic peak in degrees 2θ at about 32.3, and/or is characterized by a powder X-ray diffraction pattern that has a characteristic peak in degrees 2θ at about 36.3. In another embodiment, crystalline Form U is characterized by a powder X-ray diffraction pattern having at least one or more characteristic peaks in degrees 2θ at about 6.0, 12.0, 13.3, 17.9, 18.9, 21.4, 22.0, 24.0, 24.3, 26.3, 32.3, and 36.3. For example, a contemplated crystalline form has a powder X-ray diffraction pattern shown in FIG. 54. In one embodiment, the powder X-ray diffraction pattern of the crystalline form was obtained using Cu Kα radiation.

The contemplated crystalline Form U of 5-(3,4-dichlorophenyl)-N-((1R,2R)-2-hydroxycyclohexyl)-6-(2,2,2-trifluoroethoxy)nicotinamide, hydrate, may be characterized by a differential scanning calorimetry (DSC) profile showing a characteristic endotherm with an onset of about 33° C.; a characteristic endotherm with an onset of about 92° C. and a peak of about 99° C.; a characteristic endotherm with an onset of about 164° C. and a peak of about 165° C.; and a characteristic endotherm with an onset and a peak of about 169° C. Form U, for example, may be characterized by the differential scanning calorimetry profile shown in FIG. 55.

Figure 56:
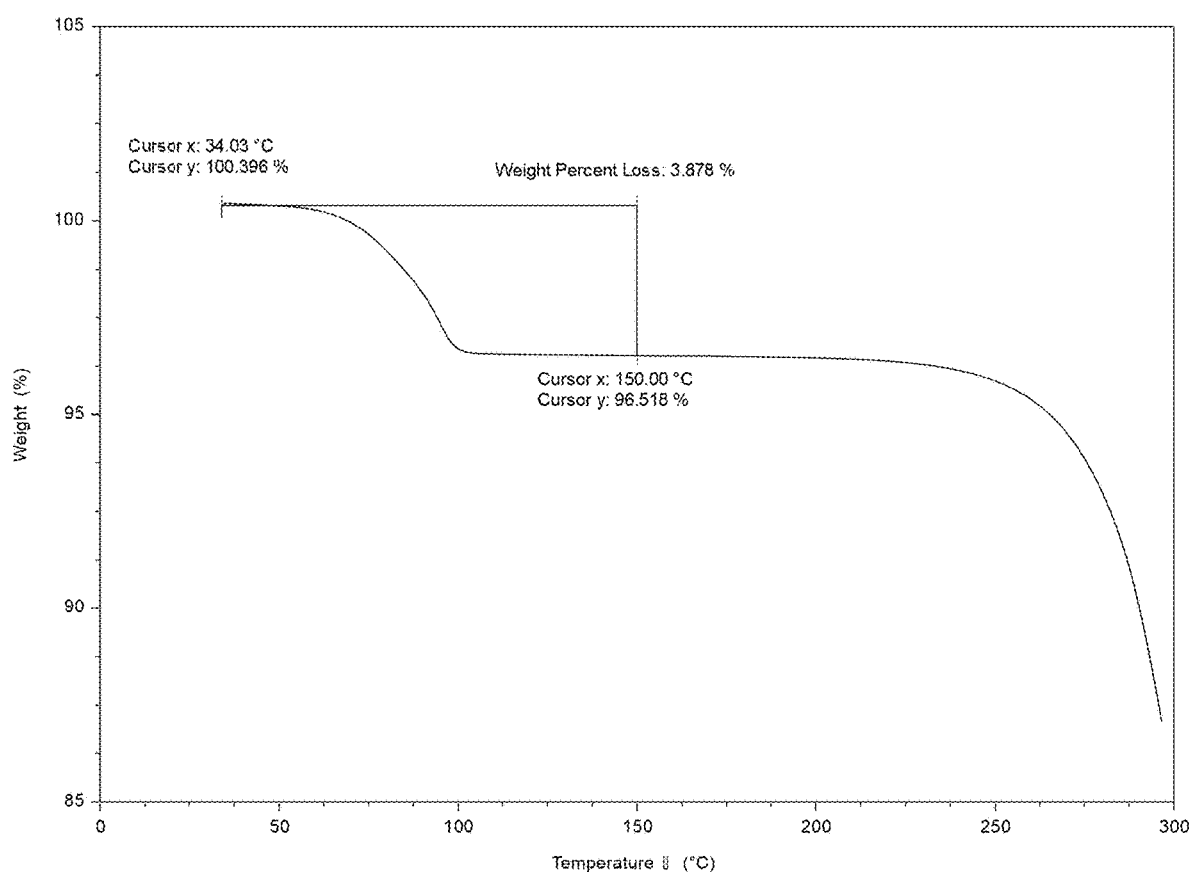
FIG. 56 depicts the thermogravimetric analysis (TGA) profile of Form U.

The contemplated crystalline Form U of 5-(3,4-dichlorophenyl)-N-((1R,2R)-2-hydroxycyclohexyl)-6-(2,2,2-trifluoroethoxy)nicotinamide, hydrate, may be characterized by a thermogravimetric analysis (TGA) profile showing a mass loss of about 3.9 wt. % up to about 150° C. (FIG. 56). In some embodiments, crystalline Form U may be characterized by Karl Fischer (KF) analysis showing 5.1% water by weight (1.38 equivalent by molar ratio).

In another embodiment, disclosed herein is a crystalline form of 5-(3,4-dichlorophenyl)-N-((1R,2R)-2-hydroxycyclohexyl)-6-(2,2,2-trifluoroethoxy)nicotinamide, hydrate, characterized by a powder X-ray diffraction pattern having a characteristic peak in degrees 2θ at about 19.4 (referred to herein as "Form V").

In one embodiment, the crystalline Form V of 5-(3,4-dichlorophenyl)-N-((1R,2R)-2-hydroxycyclohexyl)-6-(2,2,2-trifluoroethoxy)nicotinamide, hydrate, is characterized by a powder X-ray diffraction pattern that has a characteristic peak in degrees 2θ at about 6.5, is characterized by a powder X-ray diffraction pattern that has a characteristic peak in degrees 2θ at about 13.0, is characterized by a powder X-ray diffraction pattern that has a characteristic peak in degrees 2θ at about 17.1, is characterized by a powder X-ray diffraction pattern that has a characteristic peak in degrees 2θ at about 17.4, is characterized by a powder X-ray diffraction pattern that has a characteristic peak in degrees 2θ at about 19.4, is characterized by a powder X-ray diffraction pattern that has a characteristic peak in degrees 2θ at about 23.4, is characterized by a powder X-ray diffraction pattern that has a characteristic peak in degrees 2θ at about 23.7, is characterized by a powder X-ray diffraction pattern that has a characteristic peak in degrees 2θ at about 26.0, is characterized by a powder X-ray diffraction pattern that has a characteristic peak in degrees 2θ at about 28.3, is characterized by a powder X-ray diffraction pattern that has a characteristic peak in degrees 2θ at about 29.2, is characterized by a powder X-ray diffraction pattern that has a characteristic peak in degrees 2θ at about 32.7, and/or is characterized by a powder X-ray diffraction pattern that has a characteristic peak in degrees 2θ at about 34.4. In another embodiment, crystalline Form V is characterized by a powder X-ray diffraction pattern having at least one or more characteristic peaks in degrees 2θ at about 6.5, 13.0, 17.1, 17.4, 19.4, 23.4, 23.7, 26.0, 28.3, 29.2, 32.7, and 34.4. For example, a contemplated crystalline form has a powder X-ray diffraction pattern shown in FIG. 57. In one embodiment, the powder X-ray diffraction pattern of the crystalline form was obtained using Cu Kα radiation.

The contemplated crystalline Form V of 5-(3,4-dichlorophenyl)-N-((1R,2R)-2-hydroxycyclohexyl)-6-(2,2,2-trifluoroethoxy)nicotinamide, hydrate, may be characterized by a differential scanning calorimetry (DSC) profile showing a characteristic endotherm with an onset of about 48° C.; a characteristic endotherm with a peak of about 90° C. and a peak of about 96° C.; a characteristic endotherm with an onset of about 163° C. and a peak of about 165° C.; and a characteristic endotherm with an onset and a peak of about 169° C. Form V, for example, may be characterized by the differential scanning calorimetry profile shown in FIG. 58.

Figure 59:
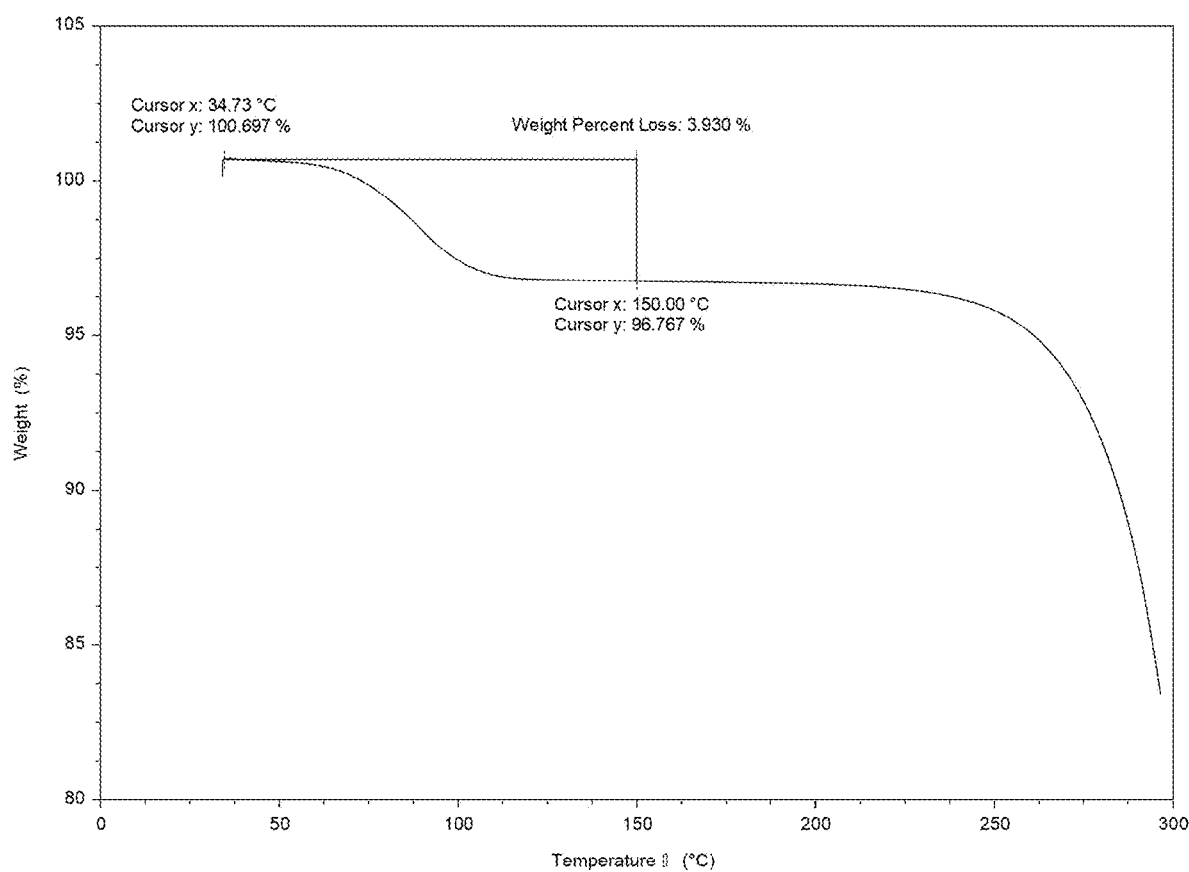
FIG. 59 depicts the thermogravimetric analysis (TGA) profile of Form V.

The contemplated crystalline Form V of 5-(3,4-dichlorophenyl)-N-((1R,2R)-2-hydroxycyclohexyl)-6-(2,2,2-trifluoroethoxy)nicotinamide, hydrate, may be characterized by a thermogravimetric analysis (TGA) profile showing a mass loss of about 3.9 wt. % up to about 150° C. (FIG. 59). In some embodiments, crystalline Form V may be characterized by Karl Fischer (KF) analysis showing 7.1% water by weight (1.97 equivalent by molar ratio).

In another embodiment, disclosed herein is a crystalline form of 5-(3,4-dichlorophenyl)-N-((1R,2R)-2-hydroxycyclohexyl)-6-(2,2,2-trifluoroethoxy)nicotinamide, hydrate, characterized by a powder X-ray diffraction pattern having a characteristic peak in degrees 2θ at about 25.5 (referred to herein as "Form W").

In one embodiment, the crystalline Form W of 5-(3,4-dichlorophenyl)-N-((1R,2R)-2-hydroxycyclohexyl)-6-(2,2,2-trifluoroethoxy)nicotinamide, hydrate, is characterized by a powder X-ray diffraction pattern that has a characteristic peak in degrees 2θ at about 6.2, is characterized by a powder X-ray diffraction pattern that has a characteristic peak in degrees 2θ at about 12.4, is characterized by a powder X-ray diffraction pattern that has a characteristic peak in degrees 2θ at about 13.8, is characterized by a powder X-ray diffraction pattern that has a characteristic peak in degrees 2θ at about 18.9, is characterized by a powder X-ray diffraction pattern that has a characteristic peak in degrees 2θ at about 19.5, is characterized by a powder X-ray diffraction pattern that has a characteristic peak in degrees 2θ at about 20.6, is characterized by a powder X-ray diffraction pattern that has a characteristic peak in degrees 2θ at about 21.8, is characterized by a powder X-ray diffraction pattern that has a characteristic peak in degrees 2θ at about 24.8, is characterized by a powder X-ray diffraction pattern that has a characteristic peak in degrees 2θ at about 25.5, is characterized by a powder X-ray diffraction pattern that has a characteristic peak in degrees 2θ at about 26.4, is characterized by a powder X-ray diffraction pattern that has a characteristic peak in degrees 2θ at about 27.7, and/or is characterized by a powder X-ray diffraction pattern that has a characteristic peak in degrees 2θ at about 28.1. In another embodiment, crystalline Form W is characterized by a powder X-ray diffraction pattern having at least one or more characteristic peaks in degrees 2θ at about 6.2, 12.4, 13.8, 18.9, 19.5, 20.6, 21.8, 24.8, 25.5, 26.4, 27.7, and 28.1. For example, a contemplated crystalline form has a powder X-ray diffraction pattern shown in FIG. 60. In one embodiment, the powder X-ray diffraction pattern of the crystalline form was obtained using Cu Kα radiation.

The contemplated crystalline Form W of 5-(3,4-dichlorophenyl)-N-((1R,2R)-2-hydroxycyclohexyl)-6-(2,2,2-trifluoroethoxy)nicotinamide, hydrate, may be characterized by a differential scanning calorimetry (DSC) profile showing a characteristic endotherm with an onset of about 50° C.; a characteristic endotherm with an onset of about 98° C. and a peak of about 99° C.; a characteristic endotherm with an onset and a peak of about 164° C.; and a characteristic endotherm with an onset and a peak of about 169° C. Form W, for example, may be characterized by the differential scanning calorimetry profile shown in FIG. 61.

Figure 62:
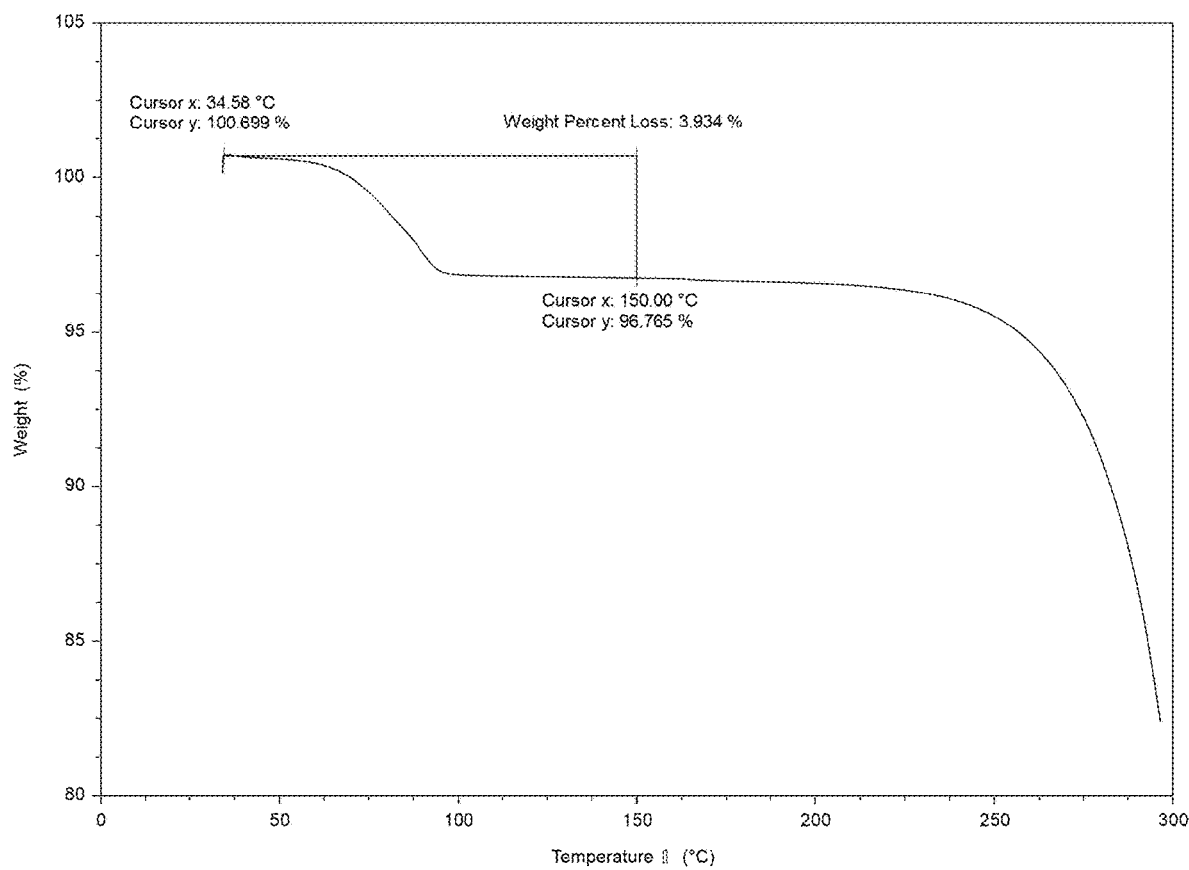
FIG. 62 depicts the thermogravimetric analysis (TGA) profile of Form W.

The contemplated crystalline Form W of 5-(3,4-dichlorophenyl)-N-((1R,2R)-2-hydroxycyclohexyl)-6-(2,2,2-trifluoroethoxy)nicotinamide, hydrate, may be characterized by a thermogravimetric analysis (TGA) profile showing a mass loss of about 3.9 wt. % up to about 150° C. (FIG. 62). In some embodiments, crystalline Form W may be characterized by Karl Fischer (KF) analysis showing 4.5% water by weight (1.21 equivalent by molar ratio).

In another embodiment, disclosed herein is a crystalline form of 5-(3,4-dichlorophenyl)-N-((1R,2R)-2-hydroxycyclohexyl)-6-(2,2,2-trifluoroethoxy)nicotinamide, 1,4-dioxane solvate, characterized by a powder X-ray diffraction pattern having a characteristic peak in degrees 2θ at about 20.5 (referred to herein as "Form X").

In one embodiment, the crystalline Form X of 5-(3,4-dichlorophenyl)-N-((1R,2R)-2-hydroxycyclohexyl)-6-(2,2,2-trifluoroethoxy)nicotinamide, 1,4-dioxane solvate, is characterized by a powder X-ray diffraction pattern that has a characteristic peak in degrees 2θ at about 8.1, is characterized by a powder X-ray diffraction pattern that has a characteristic peak in degrees 2θ at about 17.3, is characterized by a powder X-ray diffraction pattern that has a characteristic peak in degrees 2θ at about 17.5, is characterized by a powder X-ray diffraction pattern that has a characteristic peak in degrees 2θ at about 18.3, is characterized by a powder X-ray diffraction pattern that has a characteristic peak in degrees 2θ at about 18.8, is characterized by a powder X-ray diffraction pattern that has a characteristic peak in degrees 2θ at about 20.5, is characterized by a powder X-ray diffraction pattern that has a characteristic peak in degrees 2θ at about 22.0, is characterized by a powder X-ray diffraction pattern that has a characteristic peak in degrees 2θ at about 23.3, is characterized by a powder X-ray diffraction pattern that has a characteristic peak in degrees 2θ at about 23.7, is characterized by a powder X-ray diffraction pattern that has a characteristic peak in degrees 2θ at about 24.6, is characterized by a powder X-ray diffraction pattern that has a characteristic peak in degrees 2θ at about 24.9, and/or is characterized by a powder X-ray diffraction pattern that has a characteristic peak in degrees 2θ at about 31.7. In another embodiment, crystalline Form X is characterized by a powder X-ray diffraction pattern having at least one or more characteristic peaks in degrees 2θ at about 8.1, 17.3, 17.5, 18.3, 18.8, 20.5, 22.0, 23.3, 23.7, 24.6, 24.9, and 31.7. For example, a contemplated crystalline form has a powder X-ray diffraction pattern shown in FIG. 63. In one embodiment, the powder X-ray diffraction pattern of the crystalline form was obtained using Cu Kα radiation.

In another embodiment, disclosed herein is a crystalline form of 5-(3,4-dichlorophenyl)-N-((1R,2R)-2-hydroxycyclohexyl)-6-(2,2,2-trifluoroethoxy)nicotinamide, ethanol solvate, characterized by a powder X-ray diffraction pattern having a characteristic peak in degrees 2θ at about 6.2 (referred to herein as "Form Y").

In one embodiment, the crystalline Form Y of 5-(3,4-dichlorophenyl)-N-((1R,2R)-2-hydroxycyclohexyl)-6-(2,2,2-trifluoroethoxy)nicotinamide, ethanol solvate, is characterized by a powder X-ray diffraction pattern that has a characteristic peak in degrees 2θ at about 6.2, is characterized by a powder X-ray diffraction pattern that has a characteristic peak in degrees 2θ at about 12.3, is characterized by a powder X-ray diffraction pattern that has a characteristic peak in degrees 2θ at about 18.0, is characterized by a powder X-ray diffraction pattern that has a characteristic peak in degrees 2θ at about 18.8, is characterized by a powder X-ray diffraction pattern that has a characteristic peak in degrees 2θ at about 19.4, is characterized by a powder X-ray diffraction pattern that has a characteristic peak in degrees 2θ at about 20.5, is characterized by a powder X-ray diffraction pattern that has a characteristic peak in degrees 2θ at about 24.1, is characterized by a powder X-ray diffraction pattern that has a characteristic peak in degrees 2θ at about 24.8, is characterized by a powder X-ray diffraction pattern that has a characteristic peak in degrees 2θ at about 25.5, is characterized by a powder X-ray diffraction pattern that has a characteristic peak in degrees 2θ at about 26.3, is characterized by a powder X-ray diffraction pattern that has a characteristic peak in degrees 2θ at about 27.7, and/or is characterized by a powder X-ray diffraction pattern that has a characteristic peak in degrees 2θ at about 28.0. In another embodiment, crystalline Form Y is characterized by a powder X-ray diffraction pattern having at least one or more characteristic peaks in degrees 2θ at about 6.2, 12.3, 18.0, 18.8, 19.4, 20.5, 24.1, 24.8, 25.5, 26.3, 27.7, and 28.0. For example, a contemplated crystalline form has a powder X-ray diffraction pattern shown in FIG. 64. In one embodiment, the powder X-ray diffraction pattern of the crystalline form was obtained using Cu Kα radiation.

In another embodiment, disclosed herein is a crystalline form of 5-(3,4-dichlorophenyl)-N-((1R,2R)-2-hydroxycyclohexyl)-6-(2,2,2-trifluoroethoxy)nicotinamide, isopropanol solvate, characterized by a powder X-ray diffraction pattern having a characteristic peak in degrees 2θ at about 19.4 (referred to herein as "Form Z").

In one embodiment, the crystalline Form Z of 5-(3,4-dichlorophenyl)-N-((1R,2R)-2-hydroxycyclohexyl)-6-(2,2,2-trifluoroethoxy)nicotinamide, isopropanol solvate, is characterized by a powder X-ray diffraction pattern that has a characteristic peak in degrees 2θ at about 6.5, is characterized by a powder X-ray diffraction pattern that has a characteristic peak in degrees 2θ at about 12.9, is characterized by a powder X-ray diffraction pattern that has a characteristic peak in degrees 2θ at about 17.1, is characterized by a powder X-ray diffraction pattern that has a characteristic peak in degrees 2θ at about 19.4, is characterized by a powder X-ray diffraction pattern that has a characteristic peak in degrees 2θ at about 22.5, is characterized by a powder X-ray diffraction pattern that has a characteristic peak in degrees 2θ at about 23.4, is characterized by a powder X-ray diffraction pattern that has a characteristic peak in degrees 2θ at about 26.0, is characterized by a powder X-ray diffraction pattern that has a characteristic peak in degrees 2θ at about 29.7, is characterized by a powder X-ray diffraction pattern that has a characteristic peak in degrees 2θ at about 29.8, is characterized by a powder X-ray diffraction pattern that has a characteristic peak in degrees 2θ at about 32.7, is characterized by a powder X-ray diffraction pattern that has a characteristic peak in degrees 2θ at about 34.0, and/or is characterized by a powder X-ray diffraction pattern that has a characteristic peak in degrees 2θ at about 34.4. In another embodiment, crystalline Form Z is characterized by a powder X-ray diffraction pattern having at least one or more characteristic peaks in degrees 2θ at about 6.5, 12.9, 17.1, 19.4, 22.5, 23.4, 26.0, 29.7, 29.8, 32.7, 34.0, and 34.4. For example, a contemplated crystalline form has a powder X-ray diffraction pattern shown in FIG. 65. In one embodiment, the powder X-ray diffraction pattern of the crystalline form was obtained using Cu Kα radiation.

In another embodiment, disclosed herein is a crystalline form of 5-(3,4-dichlorophenyl)-N-((1R,2R)-2-hydroxycyclohexyl)-6-(2,2,2-trifluoroethoxy)nicotinamide, tetrahydrofuran solvate, characterized by a powder X-ray diffraction pattern having a characteristic peak in degrees 2θ at about 13.0 (referred to herein as "Form AA").

In one embodiment, the crystalline Form AA of 5-(3,4-dichlorophenyl)-N-((1R,2R)-2-hydroxycyclohexyl)-6-(2,2,2-trifluoroethoxy)nicotinamide, tetrahydrofuran solvate, is characterized by a powder X-ray diffraction pattern that has a characteristic peak in degrees 2θ at about 6.5, is characterized by a powder X-ray diffraction pattern that has a characteristic peak in degrees 2θ at about 13.0, is characterized by a powder X-ray diffraction pattern that has a characteristic peak in degrees 2θ at about 17.1, is characterized by a powder X-ray diffraction pattern that has a characteristic peak in degrees 2θ at about 19.4, is characterized by a powder X-ray diffraction pattern that has a characteristic peak in degrees 2θ at about 22.5, is characterized by a powder X-ray diffraction pattern that has a characteristic peak in degrees 2θ at about 23.4, is characterized by a powder X-ray diffraction pattern that has a characteristic peak in degrees 2θ at about 26.0, is characterized by a powder X-ray diffraction pattern that has a characteristic peak in degrees 2θ at about 28.3, is characterized by a powder X-ray diffraction pattern that has a characteristic peak in degrees 2θ at about 29.9, is characterized by a powder X-ray diffraction pattern that has a characteristic peak in degrees 2θ at about 32.7, is characterized by a powder X-ray diffraction pattern that has a characteristic peak in degrees 2θ at about 34.0, and/or is characterized by a powder X-ray diffraction pattern that has a characteristic peak in degrees 2θ at about 34.6. In another embodiment, crystalline Form AA is characterized by a powder X-ray diffraction pattern having at least one or more characteristic peaks in degrees 2θ at about 6.5, 13.0, 17.1, 19.4, 22.5, 23.4, 26.0, 28.3, 29.9, 32.7, 34.0, and 34.6. For example, a contemplated crystalline form has a powder X-ray diffraction pattern shown in FIG. 66. In one embodiment, the powder X-ray diffraction pattern of the crystalline form was obtained using Cu Kα radiation.

In another embodiment, disclosed herein is a crystalline form of 5-(3,4-dichlorophenyl)-N-((1R,2R)-2-hydroxycyclohexyl)-6-(2,2,2-trifluoroethoxy)nicotinamide, anhydrate, characterized by a powder X-ray diffraction pattern having a characteristic peak in degrees 2θ at about 18.7 (referred to herein as "Form 2").

In one embodiment, the crystalline Form 2 of 5-(3,4-dichlorophenyl)-N-((1R,2R)-2-hydroxycyclohexyl)-6-(2,2,2-trifluoroethoxy)nicotinamide, anhydrate, is characterized by a powder X-ray diffraction pattern that has a characteristic peak in degrees 2θ at about 6.3, is characterized by a powder X-ray diffraction pattern that has a characteristic peak in degrees 2θ at about 6.5, is characterized by a powder X-ray diffraction pattern that has a characteristic peak in degrees 2θ at about 12.4, is characterized by a powder X-ray diffraction pattern that has a characteristic peak in degrees 2θ at about 13.0, is characterized by a powder X-ray diffraction pattern that has a characteristic peak in degrees 2θ at about 16.0, is characterized by a powder X-ray diffraction pattern that has a characteristic peak in degrees 2θ at about 16.6, is characterized by a powder X-ray diffraction pattern that has a characteristic peak in degrees 2θ at about 18.1, is characterized by a powder X-ray diffraction pattern that has a characteristic peak in degrees 2θ at about 18.7, is characterized by a powder X-ray diffraction pattern that has a characteristic peak in degrees 2θ at about 19.4, is characterized by a powder X-ray diffraction pattern that has a characteristic peak in degrees 2θ at about 19.9, is characterized by a powder X-ray diffraction pattern that has a characteristic peak in degrees 2θ at about 25.0, and/or is characterized by a powder X-ray diffraction pattern that has a characteristic peak in degrees 2θ at about 26.0. In another embodiment, crystalline Form 2 is characterized by a powder X-ray diffraction pattern having at least one or more characteristic peaks in degrees 2θ at about 6.3, 6.5, 12.4, 13.0, 16.0, 16.6, 18.1, 18.7, 19.4, 19.9, 25.0, and 26.0. For example, a contemplated crystalline form has a powder X-ray diffraction pattern shown in FIG. 67. In one embodiment, the powder X-ray diffraction pattern of the crystalline form was obtained using Cu Kα radiation.

The contemplated crystalline Form 2 of 5-(3,4-dichlorophenyl)-N-((1R,2R)-2-hydroxycyclohexyl)-6-(2,2,2-trifluoroethoxy)nicotinamide, anhydrate, may be characterized by a differential scanning calorimetry (DSC) profile showing a characteristic endotherm with an onset of about 94° C.; a characteristic exotherm with an onset of about 98° C.; a characteristic endotherm with an onset of about 165° C.; and a characteristic endotherm with an onset and a peak of about 169° C. Form 2, for example, may be characterized by the differential scanning calorimetry profile shown in FIG. 68.

Figure 69:
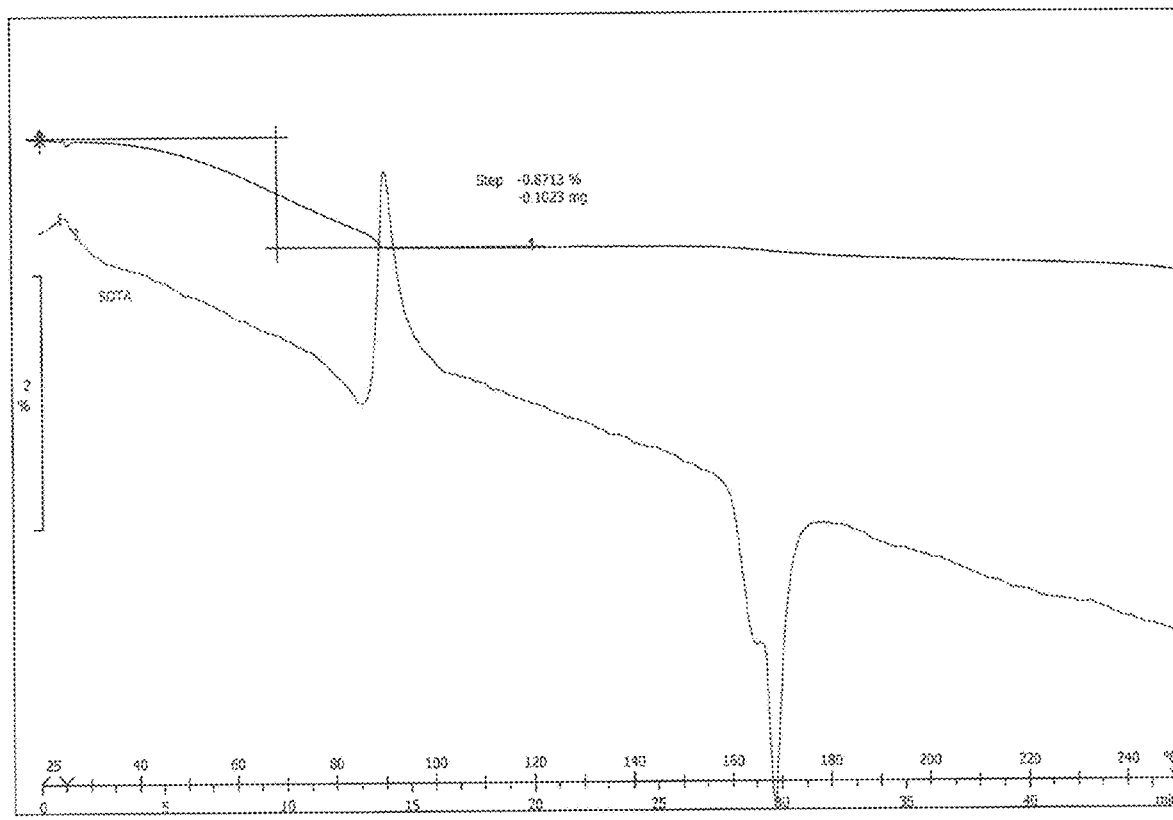
FIG. 69 depicts the thermogravimetric analysis (TGA) profile of Form 2.
Figure 70:
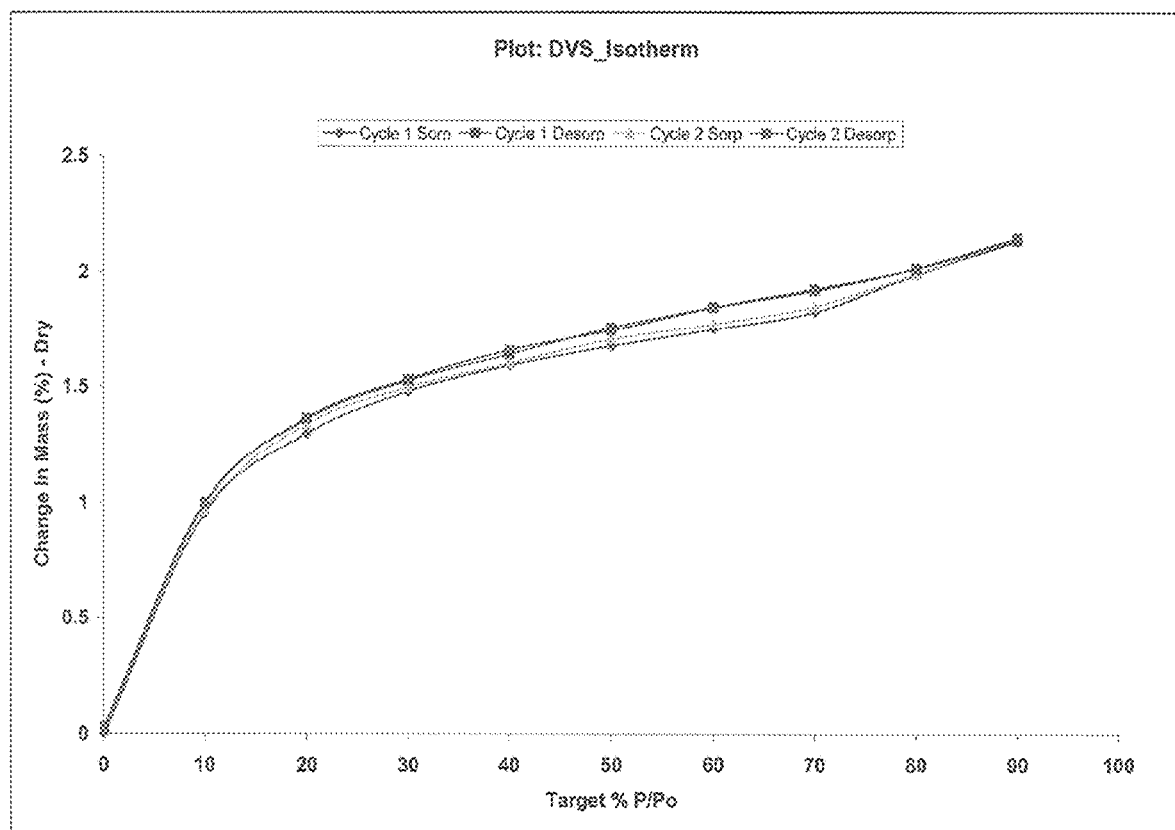
FIG. 70 depicts the dynamic vapor sorption (DVS) profile of Form 2.

The contemplated crystalline Form 2 of 5-(3,4-dichlorophenyl)-N-((1R,2R)-2-hydroxycyclohexyl)-6-(2,2,2-trifluoroethoxy)nicotinamide, anhydrate, may be characterized by a thermogravimetric analysis (TGA) profile showing a mass loss of about 0.9 wt. % up to about 120° C. (FIG. 69). In some embodiments, crystalline Form 2 may be characterized by a dynamic vapor sorption (DVS) profile showing a reversable total mass change of about 2.1 wt. % between about 0 to about 90% relative humidity (RH) at 25° C. (FIG. 70).

In another embodiment, a substantially amorphous form of 5-(3,4-dichlorophenyl)-N-((1R,2R)-2-hydroxycyclohexyl)-6-(2,2,2-trifluoroethoxy)nicotinamide is disclosed herein.

In a further embodiment, a pharmaceutical composition comprising a disclosed crystalline form of 5-(3,4-dichlorophenyl)-N-((1R,2R)-2-hydroxycyclohexyl)-6-(2,2,2-trifluoroethoxy)nicotinamide and a pharmaceutically acceptable excipient is disclosed herein. For example, a pharmaceutical composition comprising the crystalline Form E of 5-(3,4-dichlorophenyl)-N-((1R,2R)-2-hydroxycyclohexyl)-6-(2,2,2-trifluoroethoxy)nicotinamide, anhydrate, and a pharmaceutically acceptable excipient is disclosed herein. In another embodiment, a pharmaceutical composition formed from a disclosed crystalline form of 5-(3,4-dichlorophenyl)-N-((1R,2R)-2-hydroxycyclohexyl)-6-(2,2,2-trifluoroethoxy)nicotinamide is disclosed herein. For example, a pharmaceutical composition formed from the crystalline Form E of 5-(3,4-dichlorophenyl)-N-((1R,2R)-2-hydroxycyclohexyl)-6-(2,2,2-trifluoroethoxy)nicotinamide, anhydrate, is disclosed herein. In some embodiments, a disclosed pharmaceutical composition may be a formulation for oral administration.

In yet another embodiment, a pharmaceutical composition comprising a disclosed amorphous form of 5-(3,4-dichlorophenyl)-N-((1R,2R)-2-hydroxycyclohexyl)-6-(2,2,2-trifluoroethoxy)nicotinamide, and a pharmaceutically acceptable excipient is disclosed herein.

In an embodiment, a drug substance comprising at least a detectable amount of a disclosed crystalline form of 5-(3,4-dichlorophenyl)-N-((1R,2R)-2-hydroxycyclohexyl)-6-(2,2,2-trifluoroethoxy)nicotinamide is disclosed herein. In another embodiment, a drug substance comprising a substantially pure crystalline form of 5-(3,4-dichlorophenyl)-N-((1R,2R)-2-hydroxycyclohexyl)-6-(2,2,2-trifluoroethoxy)nicotinamide is disclosed herein. For example, a drug substance comprising a substantially pure crystalline Form E of 5-(3,4-dichlorophenyl)-N-((1R,2R)-2-hydroxycyclohexyl)-6-(2,2,2-trifluoroethoxy)nicotinamide, anhydrate, is disclosed herein.

Compositions

Another aspect of the disclosure provides pharmaceutical compositions comprising crystalline compounds as disclosed herein formulated together with a pharmaceutically acceptable excipient. In particular, the present disclosure provides pharmaceutical compositions comprising crystalline compounds as disclosed herein formulated together with one or more pharmaceutically acceptable excipients. These formulations include those suitable for oral, topical (e.g., transdermal), buccal, ocular, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral, subcutaneous or intravenous administration.

Exemplary pharmaceutical compositions of this disclosure may be used in the form of a pharmaceutical preparation, for example, in solid, semisolid or liquid form, which contains one or more of the compound of the disclosure, as an active ingredient, in admixture with an organic or inorganic excipient or excipient suitable for external, enteral or parenteral applications. The active ingredient may be compounded, for example, with the usual non-toxic, pharmaceutically acceptable excipients for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical excipient, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the disclosure, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable excipients, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, nano-suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or excipients comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition includes powders, sprays, ointments, pastes, creams, lotions, gels, solutions, patches and inhalants. The active component may be mixed under sterile conditions with a pharmaceutically acceptable excipient, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present disclosure may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable excipients and stabilizers. The excipients and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this disclosure suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous excipients which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants. For example, crystalline forms provided herein may be milled to obtain a particular particle size, and in at least some embodiments, such crystalline forms may remain substantially stable upon milling.

Amounts of a crystalline compound as described herein in a formulation may vary according to factors such as the disease state, age, sex, and weight of the individual. Dosage regimens can be adjusted to provide the optimum therapeutic response. For example, a single bolus can be administered, several divided doses may be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active crystalline compound calculated to produce the desired therapeutic effect in association with the required pharmaceutical carrier.

The specifications for the dosage unit forms of the disclosure are dictated by and directly dependent on (a) the unique characteristics of the crystalline compound selected and the particular therapeutic effect to be achieved, and (b) the limitations inherent in the art of compounding such an active crystalline compound for the treatment of sensitivity in individuals.

Disclosed compositions can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it is suitable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin.

A disclosed crystalline compound can be administered in a time release formulation, for example in a composition which includes a slow release polymer. The crystalline compound can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are generally known to those skilled in the art.

In accordance with an alternative aspect of the disclosure, a disclosed crystalline compound can be formulated with one or more additional compounds that enhance the solubility of the compound.

Methods

In some embodiments, the disclosure provides a method of treating a kidney disease, a cancer, a blood disorder, or other disorder in a patient in need thereof, comprising administering to the patient an effective amount of a disclosed crystalline compound, for example, a disclosed crystalline form of 5-(3,4-dichlorophenyl)-N-((1R,2R)-2-hydroxycyclohexyl)-6-(2,2,2-trifluoroethoxy)nicotinamide. In other embodiments, the disclosure provides a method of treating a kidney disease in a patient in need thereof, comprising administering to the patient an effective amount of a pharmaceutical composition comprising a disclosed crystalline compound, for example, a disclosed crystalline form of 5-(3,4-dichlorophenyl)-N-((1R,2R)-2-hydroxycyclohexyl)-6-(2,2,2-trifluoroethoxy)nicotinamide.

In some embodiments, the kidney disease or disorder may be a chronic kidney disease, a glomerular disease, or a proteinuric kidney disease. In certain embodiments, the disclosure provides a method of treating a chronic kidney disease, a glomerular disease, or a proteinuric kidney disease in a patient in need thereof, comprising administering to the patient an effective amount of a disclosed crystalline compound, for example, a disclosed crystalline form of 5-(3,4-dichlorophenyl)-N-((1R,2R)-2-hydroxycyclohexyl)-6-(2,2,2-trifluoroethoxy)nicotinamide. In other embodiments, the disclosure provides a method of treating a chronic kidney disease, a glomerular disease, or a proteinuric kidney disease in a patient in need thereof, comprising administering to the patient an effective amount of a pharmaceutical composition comprising a disclosed crystalline compound, for example, a disclosed crystalline form of 5-(3,4-dichlorophenyl)-N-((1R,2R)-2-hydroxycyclohexyl)-6-(2,2,2-trifluoroethoxy)nicotinamide.

In certain embodiments, the kidney disease may be selected from the group consisting of, for example, Alport syndrome, focal segmental glomerulosclerosis, and diabetic kidney disease. In certain embodiments, the disclosure provides a method of treating Alport syndrome, focal segmental glomerulosclerosis, or diabetic kidney disease in a patient in need thereof, comprising administering to the patient an effective amount of a disclosed crystalline compound, for example, a disclosed crystalline form of 5-(3,4-dichlorophenyl)-N-((1R,2R)-2-hydroxycyclohexyl)-6-(2,2,2-trifluoroethoxy)nicotinamide. In other embodiments, the disclosure provides a method of treating Alport syndrome, focal segmental glomerulosclerosis, or diabetic kidney disease in a patient in need thereof, comprising administering to the patient an effective amount of a pharmaceutical composition comprising a disclosed crystalline compound, for example, a disclosed crystalline form of 5-(3,4-dichlorophenyl)-N-((1R,2R)-2-hydroxycyclohexyl)-6-(2,2,2-trifluoroethoxy)nicotinamide.

In particular, in certain embodiments, the disclosure provides a method of treating the above medical indications comprising administering to a patient in need thereof an effective amount of a crystalline compound disclosed herein. In certain other embodiments, the disclosure provides a method of treating the above medical conditions in a patient in need thereof, comprising orally, subcutaneously, or intravenously administering to the patient a composition comprising a disclosed crystalline form.

The crystalline compounds disclosed herein can be used as a medicament or pharmaceutically acceptable composition, e.g., in the form of pharmaceutical preparations for oral, enteral, parenteral, or topical administration, and the contemplated methods disclosed herein may include administering orally, enterally, parenterally, or topically a disclosed crystalline compound, or a composition comprising or formed from such a disclosed crystalline compound. For example, a disclosed crystalline form may be capable of controlling one or more pharmacokinetic properties (e.g., a longer or shorter release profile) when administered by a certain route (e.g., oral) or in a certain formulation, as compared to a different route (e.g., subcutaneous) or other formulation e.g., a formulation having the amorphous form. In one embodiment, a disclosed crystalline form may afford substantial reproducibility from one formulation to another.

EXAMPLES

The compounds described herein can be prepared in a number of ways based on the teachings contained herein and synthetic procedures known in the art. The following non-limiting examples illustrate the disclosure.

X-ray powder diffraction was performed using a Bruker D8 Advance according to the parameters listed in Table 1.

TABLE 1

| | |
|---|---|
| Detector | LYNXEYE_XE_T(1D mode) |
| Open angle | 2.94° |
| Radiation | Cu/K-Alpha1 (λ = 1.5406 Å) |
| X-ray generator power | 40 kV, 40 mA |
| Primary beam path slits | Twin_Primary motorized slit 10.0 mm by sample length; SollerMount axial soller 2.5° |
| Secondary beam path slits | Detector OpticsMount soller slit 2.5°; Twin_Secondary motorized slit 5.2 mm |
| Scan mode | Continuous scan |
| Scan type | Locked coupled |
| Step size | 0.02° |
| Time per step | 0.3 second per step |
| Scan range | 2° to 40° |
| Sample rotation speed | 15 rpm |
| Sample holder | Monocrystalline silicon, with cavity |

Differential scanning calorimetry (DSC) was performed according to the parameters listed in Table 2.

TABLE 2

| | |
|---|---|
| Instrument | TA Discovery 2500 or Q2000 |
| Sample pan | Tzero pan and Tzero hermetic lid with a pin hole of 0.7 mm in diameter |
| Temperature range | 30 to 250° C. or before decomposition |
| Heating rate | 10° C./min |
| Nitrogen flow | 50 mL/min |
| Sample mass | About 1-2 mg |

Thermal gravimetric analysis (TGA) was performed according to the parameters listed in Table 3.

TABLE 3

| | |
|---|---|
| Instrument | Discovery 5500 or Q5000 |
| Sample pan | Aluminum, open |
| Start temperature | Ambient condition (below 35° C.) |
| Final temperature | 300° C. or abort next segment if weight <80% (w/w) (The weight loss of the compound is no more than 20% (w/w)) |
| Heating rate | 10° C./min |
| Nitrogen flow | Balance 10 mL/min; sample chamber 25 mL/min |
| Sample mass | About 2-10 mg |

Dynamic vapor sorption (DVS) analysis was performed according to the parameters listed in Table 4. Karl Fischer analysis was performed using a Mettler Toledo Coulometric KF Titrator C30.

TABLE 4

| Method 1 (for anhydrates) | |
|---|---|
| Instrument | Intrinsic, Advantage or Adventure |

TABLE 4-continued

| | |
|---|---|
| Total gas flow | 200 sccm |
| Oven temperature | 25° C. |
| Solvent | Water |
| Method | Cycle: 40-0-95-0-40% RH |
| | Stage Step: 10% |
| | Equilibrium: 0.002 dm/dt (%/min) |
| | Minimum dm/dt stability duration: 60 min |
| | Maximum dm/dt stage time: 360 min |

| Method 2 (for hydrates) | |
|---|---|
| Instrument | Intrinsic, Advantage or Adventure |
| Total gas flow | 200 sccm |
| Oven temperature | 25° C. |
| Solvent | Water |
| Method | Cycle: 40-95-0-95-40% RH |
| | Stage Step: 10% |
| | Equilibrium: 0.002 dm/dt (%/min ) |
| | Minimum dm/dt stability duration: 60 min |
| | Maximum dm/dt stage time: 360 min |

Example 1

An XRPD pattern of crystalline Form E is shown in FIG. 1. Characteristic peaks include one or more of the peaks shown in Table 5.

TABLE 5

| Angle | d Value | Rel. Intensity |
|---|---|---|
| 6.297 | 14.02545 | 2.70% |
| 7.205 | 12.25889 | 2.00% |
| 8.857 | 9.97625 | 2.50% |
| 10.297 | 8.58412 | 100.00% |
| 11.957 | 7.39548 | 1.80% |
| 14.395 | 6.14824 | 2.30% |
| 14.915 | 5.93492 | 12.80% |
| 15.285 | 5.79228 | 1.20% |
| 15.856 | 5.58487 | 60.40% |
| 17.705 | 5.00545 | 17.40% |
| 18.852 | 4.70345 | 7.80% |
| 20.614 | 4.30524 | 30.70% |
| 20.926 | 4.24164 | 2.80% |
| 21.143 | 4.19871 | 25.50% |
| 21.85 | 4.06442 | 9.50% |
| 23.305 | 3.81381 | 6.80% |
| 23.773 | 3.73987 | 2.10% |
| 24.052 | 3.69699 | 1.20% |
| 25.206 | 3.53032 | 5.60% |
| 26.086 | 3.41316 | 15.00% |
| 26.661 | 3.34084 | 5.20% |
| 27.477 | 3.24344 | 1.10% |
| 28.048 | 3.17874 | 4.80% |
| 29.712 | 3.00436 | 9.90% |
| 30.025 | 2.97376 | 2.00% |
| 31.108 | 2.87264 | 1.10% |
| 31.641 | 2.82552 | 1.80% |
| 32.983 | 2.71352 | 8.10% |
| 33.899 | 2.64229 | 3.00% |
| 36.132 | 2.48396 | 6.70% |
| 37.178 | 2.41645 | 5.30% |
| 38.167 | 2.35606 | 1.20% |
| 38.91 | 2.31273 | 1.00% |
| 39.345 | 2.28819 | 7.30% |

Figure 1A:
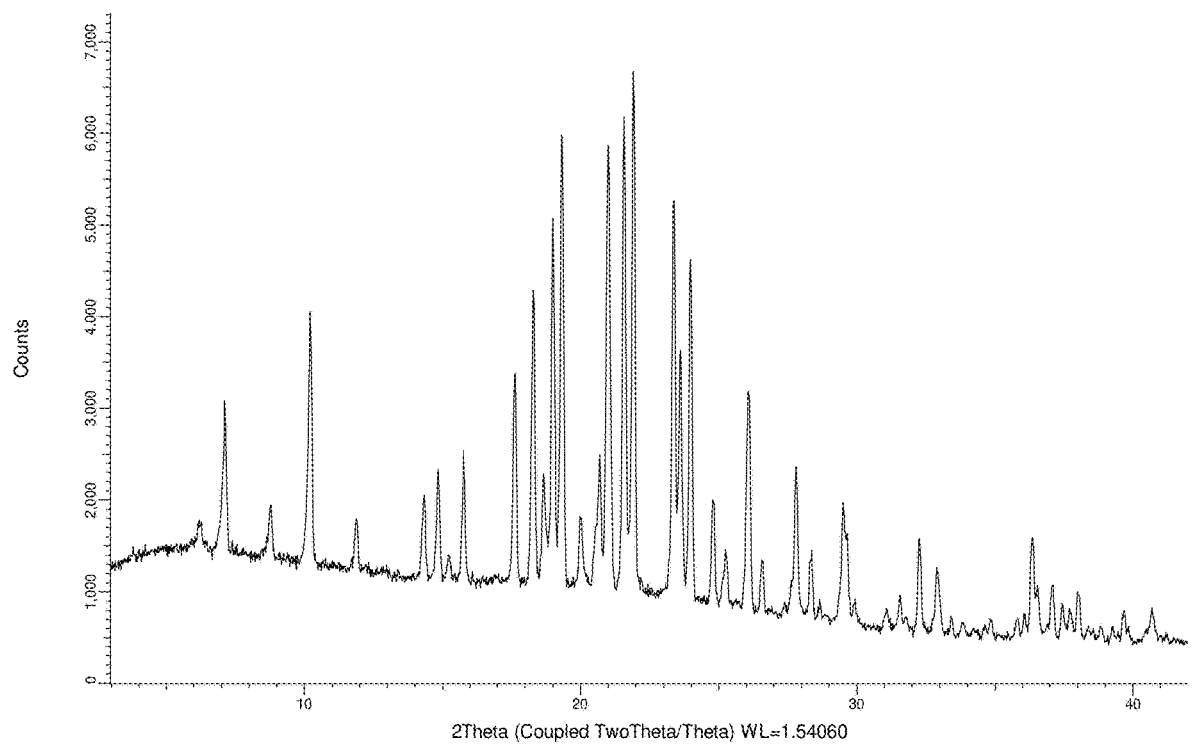
FIG. 1A depicts an X-ray powder diffraction (XRPD) pattern of 5-(3,4-dichlorophenyl)-N-((1R,2R)-2-hydroxycyclohexyl)-6-(2,2,2-trifluoroethoxy)nicotinamide, anhydrate (Form E).

An XRPD pattern of crystalline Form E is shown in FIG. 1A. Characteristic peaks include one or more of the peaks shown in Table 6.

TABLE 6

| Angle | d Value | Rel. Intensity |
|---|---|---|
| 6.22 | 14.19853 | 4.90% |
| 7.126 | 12.39581 | 26.70% |
| 8.788 | 10.05442 | 9.40% |
| 10.22 | 8.64837 | 45.40% |
| 11.889 | 7.43763 | 8.80% |
| 14.33 | 6.17571 | 15.10% |
| 14.842 | 5.96383 | 20.20% |
| 15.228 | 5.81353 | 4.80% |
| 15.776 | 5.61308 | 23.70% |
| 17.632 | 5.02595 | 39.20% |
| 18.3 | 4.84396 | 53.40% |
| 18.677 | 4.74701 | 19.30% |
| 19.015 | 4.66359 | 66.70% |
| 19.336 | 4.58674 | 83.10% |
| 20.019 | 4.43181 | 12.20% |
| 20.835 | 4.26011 | 8.70% |
| 20.697 | 4.28819 | 24.80% |
| 21.005 | 4.22601 | 81.80% |
| 21.583 | 4.11413 | 90.50% |
| 21.922 | 4.05118 | 100.00% |
| 23.374 | 3.8028 | 76.50% |
| 23.614 | 3.76466 | 47.90% |
| 23.981 | 3.70783 | 68.20% |
| 24.798 | 3.58751 | 20.00% |
| 25.261 | 3.52279 | 11.40% |
| 26.078 | 3.41425 | 40.20% |
| 26.601 | 3.34834 | 9.60% |
| 27.819 | 3.20434 | 30.50% |
| 28.367 | 3.14377 | 11.40% |
| 28.687 | 3.10934 | 3.30% |
| 29.523 | 3.02315 | 24.70% |
| 29.933 | 2.9827 | 4.70% |
| 31.096 | 2.87376 | 3.50% |
| 31.571 | 2.83159 | 7.50% |
| 31.76 | 2.81519 | 3.60% |
| 32.272 | 2.77167 | 20.30% |
| 32.914 | 2.71908 | 13.00% |
| 33.428 | 2.67845 | 4.60% |
| 33.837 | 2.64694 | 2.70% |
| 34.645 | 2.58708 | 2.40% |
| 34.855 | 2.57197 | 3.90% |
| 35.806 | 2.50577 | 3.90% |
| 36.086 | 2.48698 | 4.30% |
| 36.351 | 2.46945 | 21.40% |
| 36.539 | 2.45718 | 12.60% |
| 37.101 | 2.42124 | 11.30% |
| 37.465 | 2.39856 | 7.30% |
| 37.731 | 2.38224 | 6.20% |
| 38.031 | 2.36415 | 10.30% |
| 38.398 | 2.3424 | 2.80% |
| 38.86 | 2.31558 | 3.20% |
| 39.261 | 2.29288 | 2.60% |
| 39.686 | 2.26928 | 7.40% |
| 40.698 | 2.21519 | 7.40% |
| 41.208 | 2.18892 | 2.10% |

Figure 2:
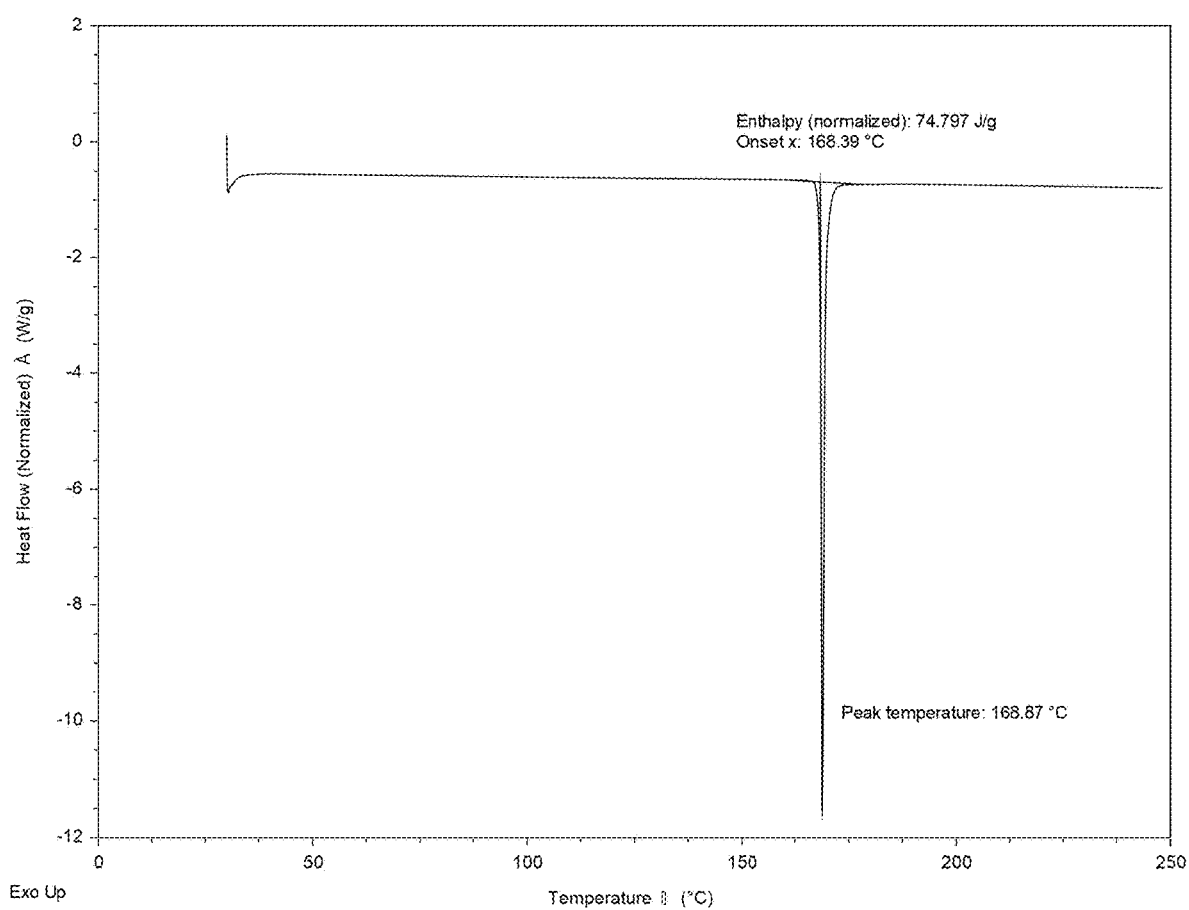
FIG. 2 depicts the characterization of Form E by differential scanning calorimetry (DSC).

FIG. 2 depicts the differential scanning calorimetry (DSC) profile of crystalline Form E. As shown in FIG. 2, crystalline Form E shows a characteristic endotherm with an onset of about 168° C. and a peak of about 169° C.

Crystalline Form E of 5-(3,4-dichlorophenyl)-N-((1R,2R)-2-hydroxycyclohexyl)-6-(2,2,2-trifluoroethoxy)nicotinamide, anhydrate, displayed a thermogravimetric analysis (TGA) profile showing a mass loss of about 0.6 wt. % up to about 150° C. Crystalline Form E displayed a dynamic vapor sorption (DVS) profile showing a reversable total mass change of about 0.3 wt. % between about 0 to about 90% relative humidity (RH) at 25° C. Crystalline Form E displayed a needle-like morphology by polarized light microscopy.

About 5 mg of crystalline Form E was weighed in 2 mL glass vials. 20 μL aliquots of each solvent were added to dissolve the compound at 25° C. Vortex and sonication were applied to assist dissolution. The maximum volume of each solvent added was 1 mL. Approximate solubility was determined by visual observation and shown in Table 7.

TABLE 7

| Solvent | Solubility (mg/mL) |
|---|---|
| Water | <5 |
| Methanol | >250 |
| Ethanol | >250 |
| 2-Propanol | 125-250 |
| Acetone | >250 |
| Methyl ethyl ketone | >250 |
| Acetonitrile | 50-62.5 |
| Ethyl acetate | >250 |
| Isopropyl acetate | 125-250 |
| t-Butyl methyl ether | 8.3-12.5 |
| 1,4-Dioxane | 50-62.5 |
| Tetrahydrofuran | >250 |
| Toluene | <5 |
| Dichloromethane | <5 |
| Heptane | <5 |
| TFE | 83.3-125 |
| DMF | >250 |

Example 2

Crystalline, Form A material of 5-(3,4-dichlorophenyl)-N-((1R,2R)-2-hydroxycyclohexyl)-6-(2,2,2-trifluoroethoxy)nicotinamide, anhydrate, was prepared as follows. A sample of crystalline Form N material of 5-(3,4-dichlorophenyl)-N-((1R,2R)-2-hydroxycyclohexyl)-6-(2,2,2-trifluoroethoxy)nicotinamide, hydrate, was further dried by heating at 150° C. XRPD analysis indicated that the dried material was crystalline with a pattern consistent with Form A.

Figure 5:
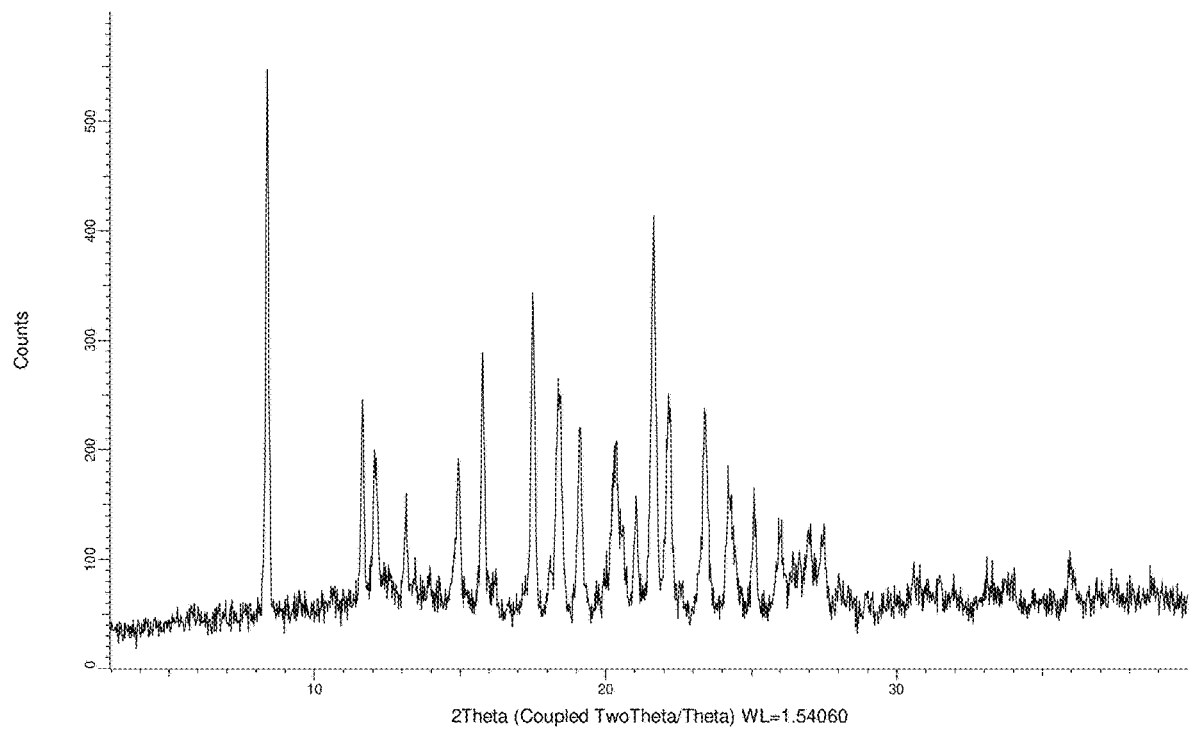
FIG. 5 depicts an X-ray powder diffraction (XRPD) pattern of 5-(3,4-dichlorophenyl)-N-((1R,2R)-2-hydroxycyclohexyl)-6-(2,2,2-trifluoroethoxy)nicotinamide, anhydrate (Form A).

An XRPD pattern of crystalline Form A is shown in FIG. 5. Characteristic peaks include one or more of the peaks shown in Table 8.

TABLE 8

| Angle | d Value | Rel. Intensity |
|---|---|---|
| 8.392 | 10.52812 | 100.00% |
| 11.657 | 7.58552 | 34.90% |
| 12.1 | 7.30833 | 20.00% |
| 13.146 | 6.72951 | 18.20% |
| 13.482 | 6.56216 | 6.30% |
| 13.963 | 6.33747 | 4.90% |
| 14.938 | 5.92571 | 23.70% |
| 15.796 | 5.60584 | 44.60% |
| 16.202 | 5.46619 | 5.70% |
| 17.516 | 5.05904 | 56.00% |
| 18.116 | 4.89284 | 8.80% |
| 18.406 | 4.81628 | 32.10% |
| 19.125 | 4.63682 | 32.50% |
| 20.37 | 4.35613 | 29.20% |
| 20.591 | 4.31003 | 13.60% |
| 21.053 | 4.21636 | 18.80% |
| 21.65 | 4.10143 | 69.00% |
| 22.187 | 4.00345 | 33.00% |
| 23.416 | 3.79605 | 33.20% |
| 24.232 | 3.67005 | 20.40% |
| 25.117 | 3.54264 | 21.30% |
| 26.015 | 3.42235 | 11.30% |
| 26.992 | 3.3007 | 13.40% |
| 27.504 | 3.24041 | 13.70% |
| 28.076 | 3.17568 | 6.90% |
| 28.972 | 3.07944 | 4.20% |
| 30.571 | 2.92187 | 9.80% |
| 31.469 | 2.84058 | 5.70% |
| 33.097 | 2.70448 | 11.30% |
| 34.007 | 2.63414 | 3.70% |

TABLE 8-continued

| Angle | d Value | Rel. Intensity |
|---|---|---|
| 35.982 | 2.49396 | 8.70% |
| 37.413 | 2.40178 | 5.70% |

Figure 5A:
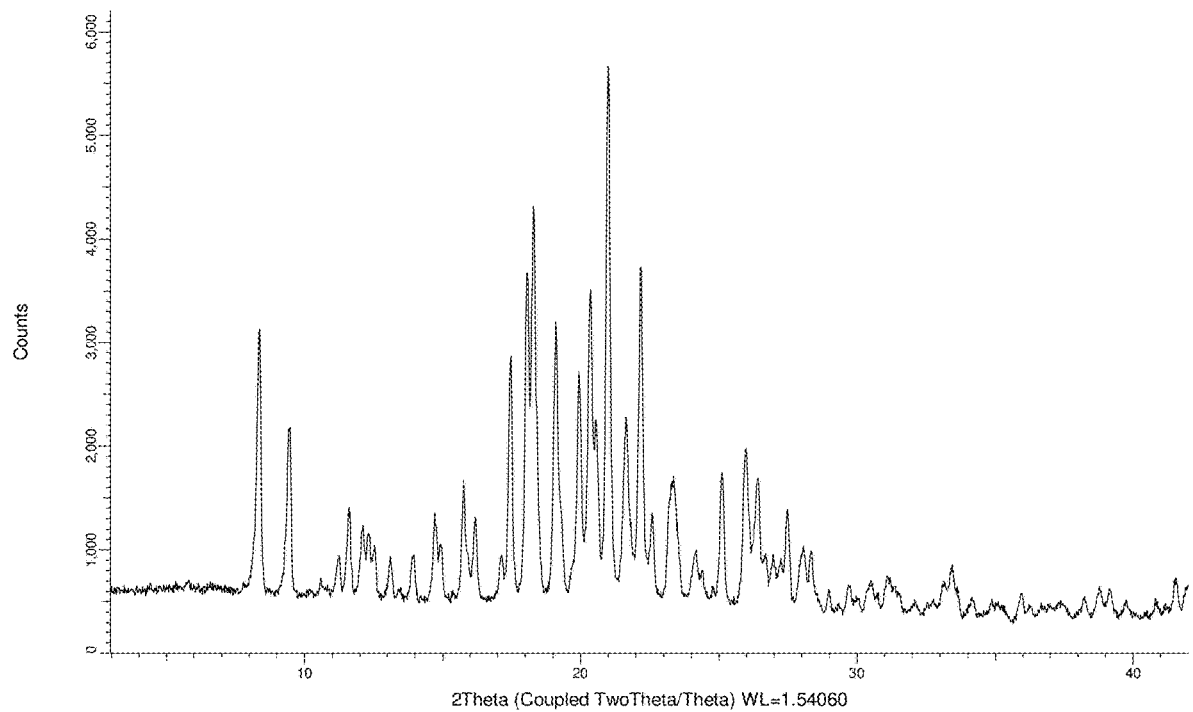
FIG. 5A depicts an X-ray powder diffraction (XRPD) pattern of 5-(3,4-dichlorophenyl)-N-((1R,2R)-2-hydroxycyclohexyl)-6-(2,2,2-trifluoroethoxy)nicotinamide, anhydrate (Form A).

An XRPD pattern of crystalline Form A is shown in FIG. 5A. Characteristic peaks include one or more of the peaks shown in Table 9.

TABLE 9

| Angle | d Value | Rel. Intensity |
|---|---|---|
| 8.371 | 10.55378 | 48.80% |
| 9.459 | 9.34247 | 30.30% |
| 10.663 | 8.29041 | 1.30% |
| 11.248 | 7.86022 | 6.90% |
| 11.626 | 7.60529 | 15.20% |
| 12.114 | 7.29998 | 12.60% |
| 12.536 | 7.05564 | 9.30% |
| 13.116 | 6.74444 | 7.80% |
| 13.941 | 6.34753 | 8.10% |
| 14.772 | 5.99199 | 11.40% |
| 14.931 | 5.92856 | 9.40% |
| 15.768 | 5.61579 | 22.10% |
| 16.201 | 5.46658 | 15.60% |
| 17.151 | 5.16602 | 7.40% |
| 17.474 | 5.07114 | 45.00% |
| 18.077 | 4.90319 | 60.10% |
| 18.304 | 4.84287 | 73.00% |
| 19.108 | 4.64111 | 52.00% |
| 19.953 | 4.44626 | 41.00% |
| 20.356 | 4.35926 | 57.30% |
| 20.555 | 4.31748 | 32.50% |
| 21.002 | 4.22652 | 100.00% |
| 21.654 | 4.10081 | 31.50% |
| 22.182 | 4.00424 | 61.80% |
| 22.591 | 3.93267 | 16.40% |
| 23.302 | 3.8143 | 22.30% |
| 24.163 | 3.68032 | 8.30% |
| 24.399 | 3.64518 | 5.30% |
| 25.111 | 3.54347 | 24.60% |
| 25.97 | 3.4282 | 29.10% |
| 26.43 | 3.36959 | 23.60% |
| 26.666 | 3.34021 | 12.20% |
| 26.985 | 3.30149 | 9.20% |
| 27.499 | 3.24094 | 18.50% |
| 28.074 | 3.1759 | 11.60% |
| 28.356 | 3.14489 | 11.20% |
| 28.997 | 3.07684 | 4.90% |
| 29.706 | 3.00497 | 5.10% |
| 29.983 | 2.97783 | 2.50% |
| 30.509 | 2.92773 | 5.70% |
| 31.118 | 2.87182 | 7.00% |
| 31.51 | 2.83693 | 3.80% |
| 32.114 | 2.78495 | 1.90% |
| 32.544 | 2.7491 | 3.00% |
| 32.792 | 2.72891 | 4.50% |
| 33.132 | 2.70166 | 7.70% |
| 33.187 | 2.69729 | 4.80% |
| 33.442 | 2.67735 | 9.60% |
| 34.148 | 2.62356 | 3.30% |
| 34.865 | 2.57127 | 4.30% |
| 35.945 | 2.49644 | 4.90% |
| 36.241 | 2.47675 | 1.90% |
| 37.413 | 2.40177 | 2.20% |
| 38.23 | 2.35231 | 4.60% |
| 38.789 | 2.31966 | 6.30% |
| 39.163 | 2.29839 | 5.60% |
| 39.76 | 2.26525 | 4.00% |
| 40.87 | 2.20624 | 2.60% |
| 41.56 | 2.17119 | 6.90% |

Figure 6:
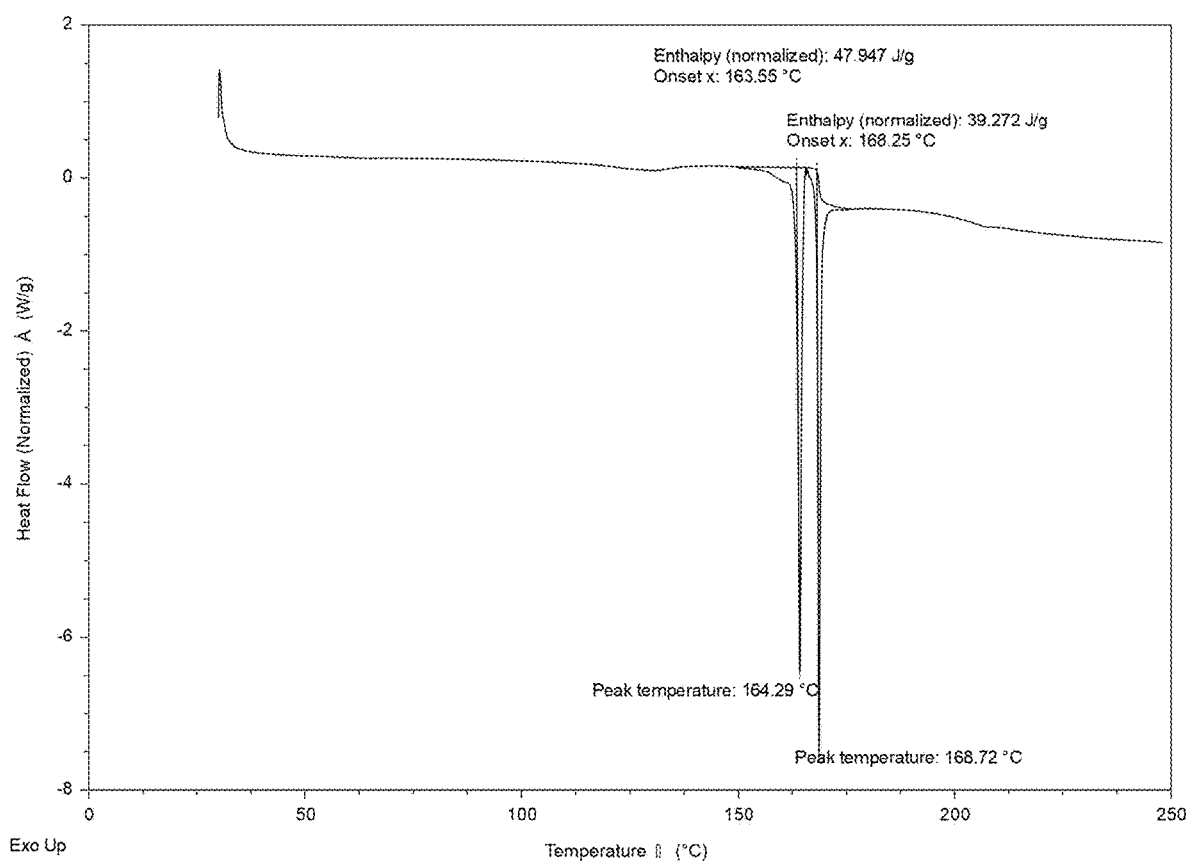
FIG. 6 depicts the characterization of Form A by differential scanning calorimetry (DSC).

FIG. 6 depicts the differential scanning calorimetry (DSC) profile of crystalline Form A. As shown in FIG. 6, crystalline Form A shows a characteristic endotherm with an onset and a peak of about 164° C.; and a characteristic endotherm with an onset of about 168° C. and a peak of about 169° C. Crystalline Form A displayed a thermogravimetric analysis (TGA) profile showing a mass loss of about 0.33 wt. % up to about 180° C. Crystalline Form A displayed a dynamic vapor sorption (DVS) profile showing a reversable total mass change of about 1.8 wt. % between about 0 to about 90% relative humidity (RH) at 25° C.

Example 3

Crystalline, Form B material of 5-(3,4-dichlorophenyl)-N-((1R,2R)-2-hydroxycyclohexyl)-6-(2,2,2-trifluoroethoxy)nicotinamide, monohydrate was prepared as follows. About 50 mg of crystalline Form E material of 5-(3,4-dichlorophenyl)-N-((1R,2R)-2-hydroxycyclohexyl)-6-(2,2,2-trifluoroethoxy)nicotinamide, anhydrate, was equilibrated in water at 50° C. for 1 week with stirring at 400 rpm. The obtained suspension was filtered through a 0.45 μm nylon membrane filter by centrifugation at 14,000 rpm. XRPD analysis of the material was crystalline with a pattern consistent with Form B.

Figure 9:
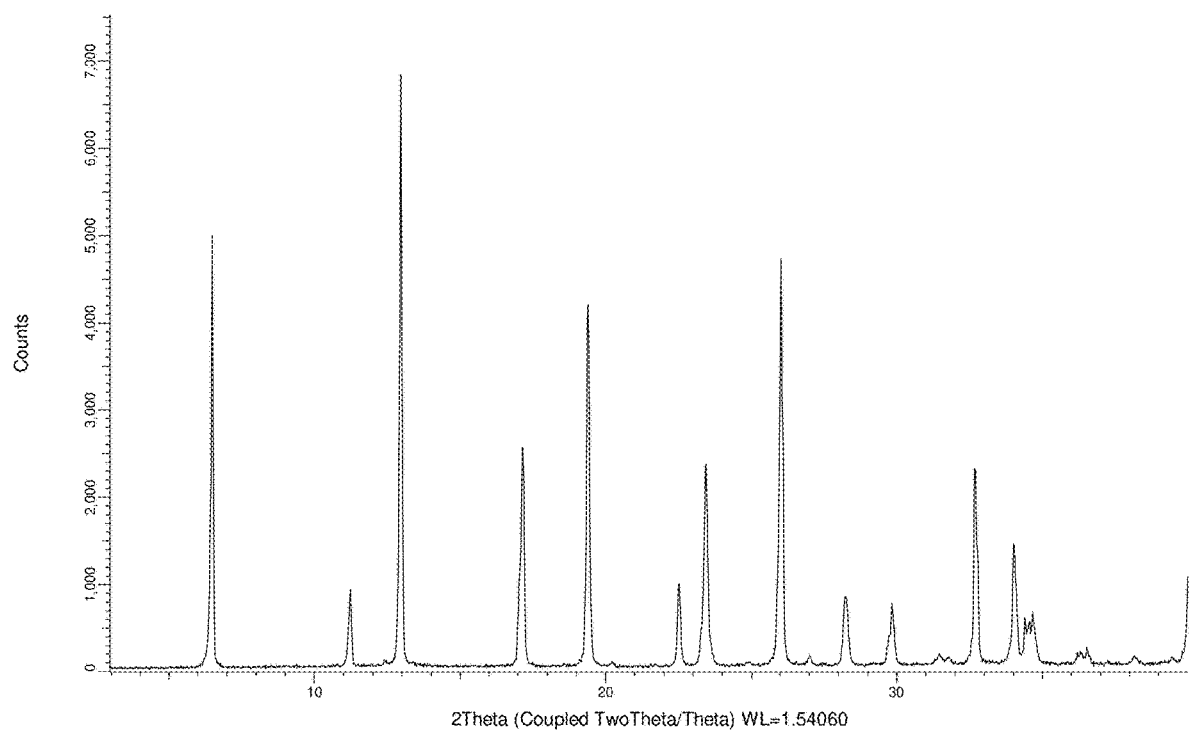
FIG. 9 depicts an X-ray powder diffraction (XRPD) pattern of 5-(3,4-dichlorophenyl)-N-((1R,2R)-2-hydroxycyclohexyl)-6-(2,2,2-trifluoroethoxy)nicotinamide, monohydrate (Form B).

An XRPD pattern of crystalline Form B is shown in FIG. 9. Characteristic peaks include one or more of the peaks shown in Table 10.

TABLE 10

| Angle | d Value | Rel. Intensity |
|---|---|---|
| 8.392 | 10.52812 | 100.00% |
| 11.657 | 7.58552 | 34.90% |
| 12.1 | 7.30833 | 20.00% |
| 13.146 | 6.72951 | 18.20% |
| 13.482 | 6.56216 | 6.30% |
| 13.963 | 6.33747 | 4.90% |
| 14.938 | 5.92571 | 23.70% |
| 15.796 | 5.60584 | 44.60% |
| 16.202 | 5.46619 | 5.70% |
| 17.516 | 5.05904 | 56.00% |
| 18.116 | 4.89284 | 8.80% |
| 18.406 | 4.81628 | 32.10% |
| 19.125 | 4.63682 | 32.50% |
| 20.37 | 4.35613 | 29.20% |
| 20.591 | 4.31003 | 13.60% |
| 21.053 | 4.21636 | 18.80% |
| 21.65 | 4.10143 | 69.00% |
| 22.187 | 4.00345 | 33.00% |
| 23.416 | 3.79605 | 33.20% |
| 24.232 | 3.67005 | 20.40% |
| 25.117 | 3.54264 | 21.30% |
| 26.015 | 3.42235 | 11.30% |
| 26.992 | 3.3007 | 13.40% |
| 27.504 | 3.24041 | 13.70% |
| 28.076 | 3.17568 | 6.90% |
| 28.972 | 3.07944 | 4.20% |
| 30.571 | 2.92187 | 9.80% |
| 31.469 | 2.84058 | 5.70% |
| 33.097 | 2.70448 | 11.30% |
| 34.007 | 2.63414 | 3.70% |
| 35.982 | 2.49396 | 8.70% |
| 37.413 | 2.40178 | 5.70% |

Figure 9A:
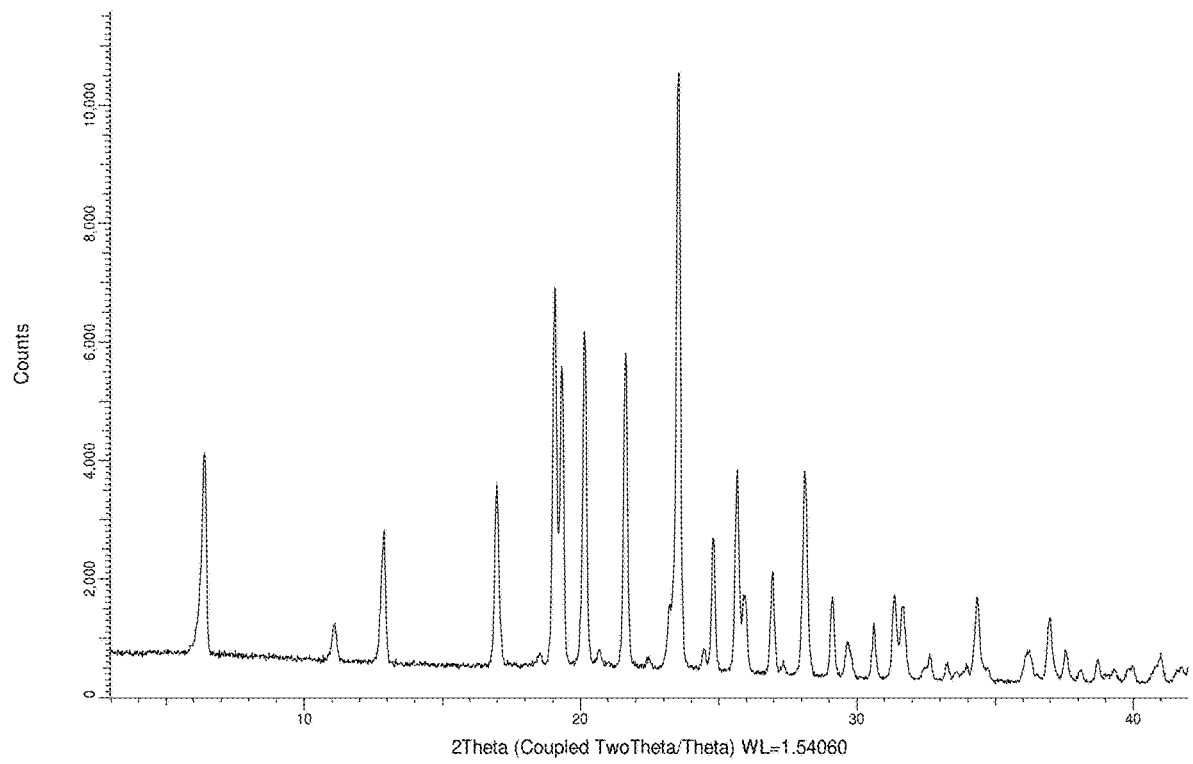
FIG. 9A depicts an X-ray powder diffraction (XRPD) pattern of 5-(3,4-dichlorophenyl)-N-((1R,2R)-2-hydroxycyclohexyl)-6-(2,2,2-trifluoroethoxy)nicotinamide, monohydrate (Form B).

An XRPD pattern of crystalline Form B is shown in FIG. 9A. Characteristic peaks include one or more of the peaks shown in Table 11.

TABLE 11

| Angle | d Value | Rel. Intensity |
|---|---|---|
| 6.412 | 1377.25% | 30.50% |
| 11.09 | 797.17% | 5.70% |
| 12.89 | 686.26% | 21.80% |
| 16.984 | 521.64% | 29.70% |

TABLE 11-continued

| Angle | d Value | Rel. Intensity |
| --- | --- | --- |
| 18.541 | 478.15% | 2.20% |
| 19.083 | 464.71% | 62.20% |
| 19.338 | 458.63% | 49.00% |
| 20.158 | 440.16% | 56.00% |
| 20.689 | 428.98% | 2.60% |
| 21.637 | 410.38% | 52.90% |
| 22.475 | 395.28% | 1.50% |
| 23.55 | 377.48% | 100.00% |
| 24.477 | 363.38% | 3.00% |
| 24.804 | 358.66% | 23.20% |
| 25.668 | 346.78% | 34.70% |
| 25.922 | 343.44% | 11.90% |
| 26.968 | 330.35% | 17.50% |
| 27.356 | 325.75% | 2.30% |
| 28.13 | 316.97% | 35.70% |
| 29.123 | 306.38% | 13.90% |
| 29.703 | 300.53% | 4.60% |
| 30.621 | 291.72% | 10.30% |
| 31.365 | 284.97% | 14.60% |
| 31.665 | 282.35% | 12.00% |
| 32.468 | 275.54% | 1.70% |
| 32.641 | 274.12% | 4.70% |
| 33.271 | 269.07% | 2.90% |
| 33.596 | 266.54% | 1.20% |
| 33.963 | 263.75% | 3.00% |
| 34.352 | 260.85% | 14.70% |
| 34.742 | 258.01% | 2.30% |
| 36.195 | 247.97% | 4.60% |
| 36.988 | 242.84% | 11.40% |
| 37.574 | 239.19% | 5.60% |
| 38.104 | 235.98% | 2.30% |
| 38.74 | 232.25% | 4.00% |
| 39.308 | 229.03% | 2.20% |
| 39.948 | 225.50% | 1.80% |
| 40.996 | 219.97% | 5.20% |
| 41.715 | 216.35% | 1.40% |

Figure 10:
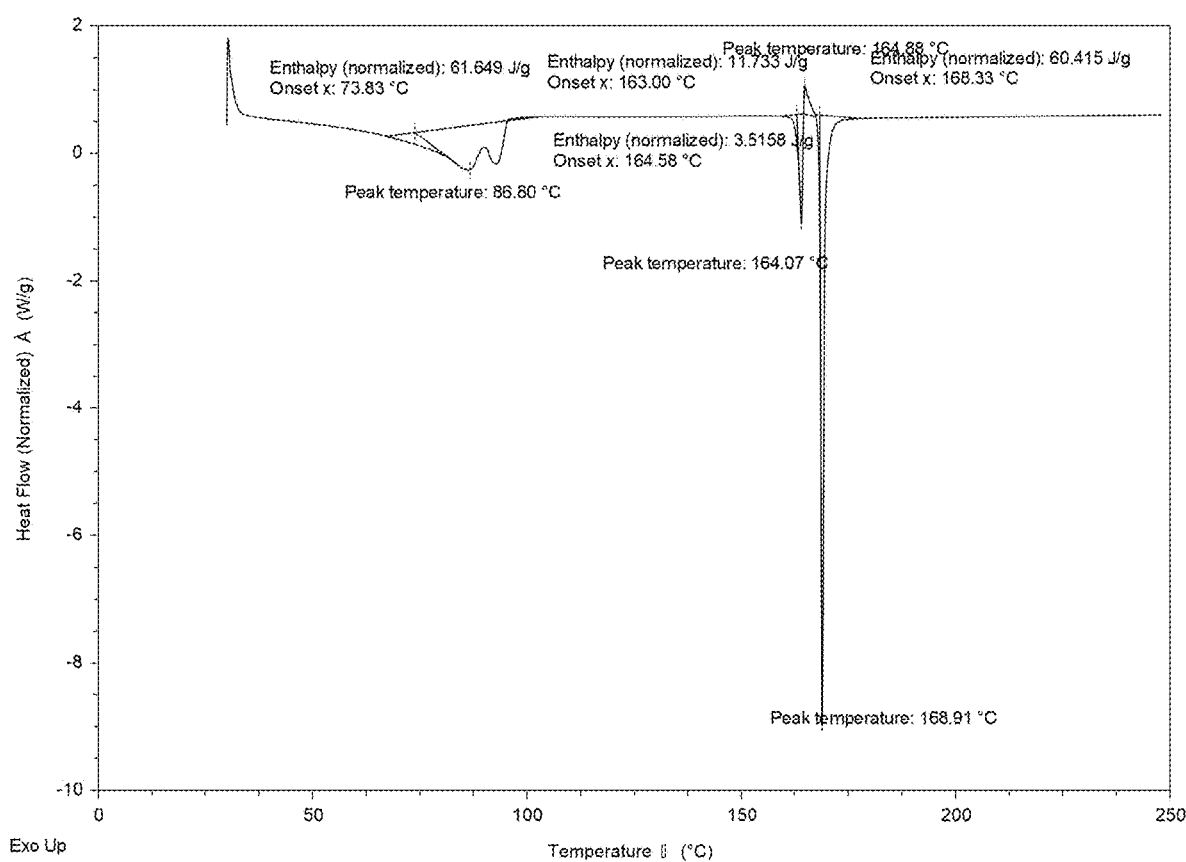
FIG. 10 depicts the characterization of Form B by differential scanning calorimetry (DSC).

FIG. 10 depicts the differential scanning calorimetry (DSC) profile of crystalline Form B. As shown in FIG. 10, crystalline Form B shows a characteristic endotherm with an onset of about 74° C. and a peak of about 87° C.; a characteristic endotherm with an onset of about 163° C. and a peak of about 164° C.; a characteristic exotherm with an onset and a peak of about 165° C.; and a characteristic endotherm with an onset of about 168° C. and a peak of about 169° C. Crystalline Form B displayed a thermogravimetric analysis (TGA) profile showing a mass loss of about 3.5 wt. % up to about 120° C. Crystalline Form B displayed a dynamic vapor sorption (DVS) profile showing a reversable total mass change of about 0.3 wt. % between about 0 to about 90% relative humidity (RH) at 25° C. Karl Fischer (KF) analysis showed 3.8% water by weight (1.02 equivalent by molar ratio).

Example 4

Figure 12:
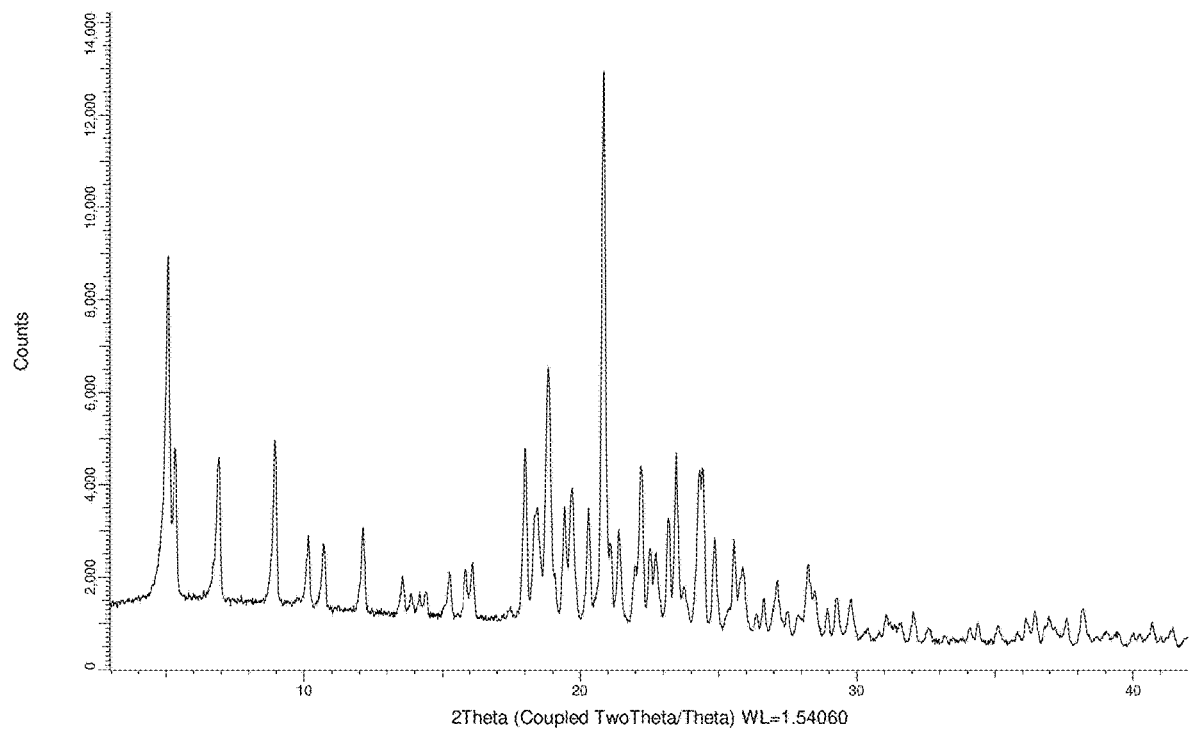
FIG. 12 depicts the X-ray powder diffraction (XRPD) pattern of 5-(3,4-dichlorophenyl)-N-((1R,2R)-2-hydroxycyclohexyl)-6-(2,2,2-trifluoroethoxy)nicotinamide, anhydrate (Form C).

The XRPD pattern of crystalline Form C material of 5-(3,4-dichlorophenyl)-N-((1R,2R)-2-hydroxycyclohexyl)-6-(2,2,2-trifluoroethoxy)nicotinamide, anhydrate, is shown in FIG. 12. Characteristic peaks include one or more of the peaks shown in Table 12.

TABLE 12

| Angle | d Value | Rel. Intensity |
| --- | --- | --- |
| 5.077 | 17.39208 | 54.50% |
| 5.348 | 16.51019 | 23.90% |
| 6.927 | 12.74992 | 24.00% |
| 8.964 | 9.85765 | 28.50% |
| 10.163 | 8.69671 | 12.80% |
| 10.722 | 8.24428 | 11.90% |
| 12.14 | 7.28445 | 15.40% |
| 13.564 | 6.52276 | 7.20% |
| 13.887 | 6.37188 | 3.50% |
| 14.193 | 6.23518 | 3.60% |
| 14.407 | 6.14295 | 3.90% |
| 15.269 | 5.79794 | 7.50% |
| 15.861 | 5.58314 | 8.60% |
| 16.112 | 5.49646 | 9.90% |
| 17.475 | 5.07095 | 2.20% |
| 18.01 | 4.9214 | 31.30% |
| 18.449 | 4.80527 | 19.70% |
| 18.85 | 4.70393 | 44.30% |
| 19.481 | 4.55289 | 12.30% |
| 19.701 | 4.50252 | 23.00% |
| 20.304 | 4.3702 | 20.00% |
| 20.852 | 4.2566 | 100.00% |
| 21.399 | 4.149 | 17.10% |
| 21.994 | 4.03818 | 9.70% |
| 22.199 | 4.00128 | 28.10% |
| 22.528 | 3.94351 | 13.30% |
| 22.734 | 3.90835 | 12.60% |
| 23.19 | 3.83246 | 19.30% |
| 23.476 | 3.78646 | 31.30% |
| 23.755 | 3.74266 | 6.70% |
| 24.364 | 3.6504 | 21.40% |
| 24.86 | 3.57864 | 16.30% |
| 25.357 | 3.5096 | 3.40% |
| 25.563 | 3.48189 | 16.40% |
| 25.877 | 3.44032 | 10.90% |
| 26.392 | 3.37431 | 2.90% |
| 26.655 | 3.34162 | 6.20% |
| 27.14 | 3.28302 | 9.20% |
| 27.516 | 3.23903 | 3.80% |
| 27.949 | 3.18976 | 2.50% |
| 28.257 | 3.1557 | 13.10% |
| 28.49 | 3.13042 | 8.20% |
| 28.958 | 3.0809 | 5.50% |
| 29.286 | 3.04712 | 7.50% |
| 29.797 | 2.99601 | 7.60% |
| 30.37 | 2.94082 | 1.20% |
| 30.823 | 2.89863 | 1.90% |
| 31.064 | 2.87666 | 5.40% |
| 31.572 | 2.83149 | 3.20% |
| 32.05 | 2.79035 | 5.80% |
| 32.598 | 2.74467 | 2.60% |
| 33.179 | 2.69795 | 1.30% |
| 34.099 | 2.62723 | 3.20% |
| 34.392 | 2.60554 | 4.20% |
| 35.108 | 2.55398 | 3.30% |
| 35.813 | 2.50535 | 2.50% |
| 36.131 | 2.48403 | 5.20% |
| 36.445 | 2.46332 | 6.70% |
| 36.972 | 2.42938 | 5.00% |
| 37.611 | 2.38957 | 5.30% |
| 38.198 | 2.3542 | 6.60% |
| 39.037 | 2.30554 | 2.20% |
| 39.402 | 2.28502 | 2.40% |
| 40.013 | 2.2515 | 2.30% |
| 40.274 | 2.23752 | 2.10% |
| 40.7 | 2.2151 | 4.70% |
| 41.447 | 2.17686 | 3.10% |

FIG. 3 depicts the differential scanning calorimetry (DSC) profile of crystalline Form C. As shown in FIG. 3, crystalline Form C shows a characteristic endotherm with an onset of about 144° C.; a characteristic endotherm with an onset of about 164° C.; and a characteristic endotherm with an onset of about 168° C. Crystalline Form C displayed a thermogravimetric analysis (TGA) profile showing a mass loss of about 0.1 wt. % up to about 130° C.

Example 5

The XRPD pattern of crystalline Form D material of 5-(3,4-dichlorophenyl)-N-((1R,2R)-2-hydroxycyclohexyl)-

Figure 15:
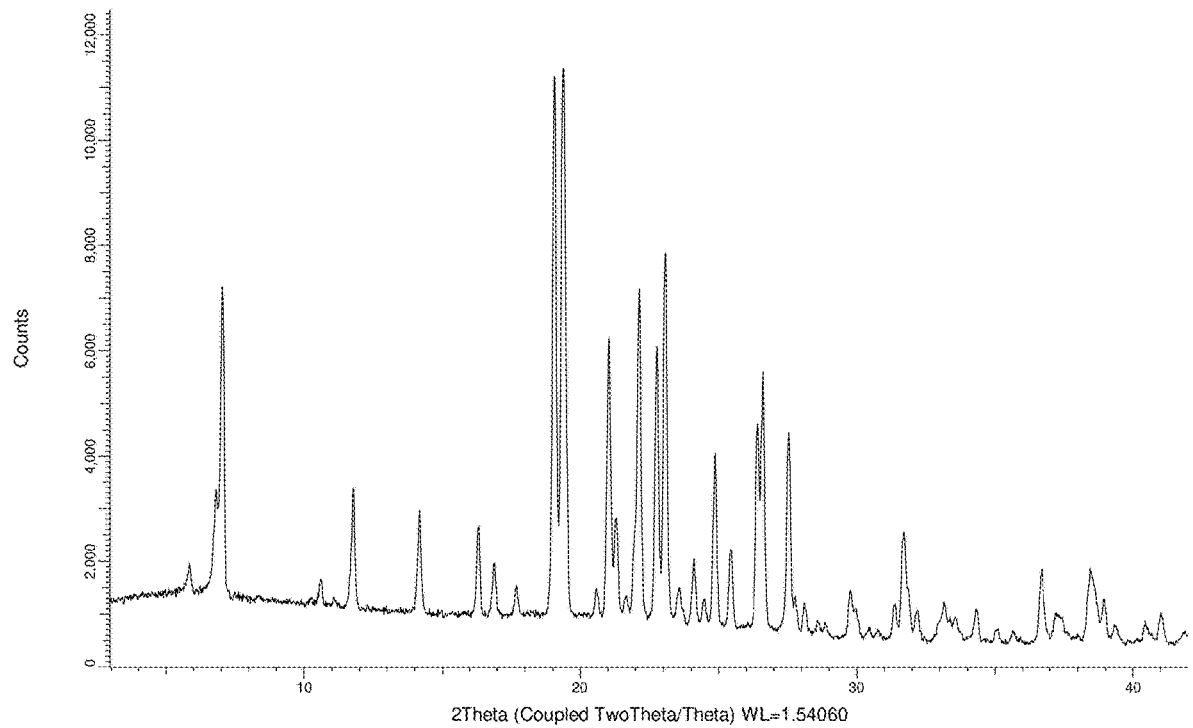
FIG. 15 depicts the X-ray powder diffraction (XRPD) pattern of 5-(3,4-dichlorophenyl)-N-((1R,2R)-2-hydroxycyclohexyl)-6-(2,2,2-trifluoroethoxy)nicotinamide, anhydrate (Form D).

6-(2,2,2-trifluoroethoxy)nicotinamide, anhydrate, is shown in FIG. 15. Characteristic peaks include one or more of the peaks shown in Table 13.

TABLE 13

| Angle | d Value | Rel. Intensity |
|---|---|---|
| 5.077 | 17.39208 | 54.50% |
| 5.348 | 16.51019 | 23.90% |
| 6.927 | 12.74992 | 24.00% |
| 8.964 | 9.85765 | 28.50% |
| 10.163 | 8.69671 | 12.80% |
| 10.722 | 8.24428 | 11.90% |
| 12.14 | 7.28445 | 15.40% |
| 13.564 | 6.52276 | 7.20% |
| 13.887 | 6.37188 | 3.50% |
| 14.193 | 6.23518 | 3.60% |
| 14.407 | 6.14295 | 3.90% |
| 15.269 | 5.79794 | 7.50% |
| 15.861 | 5.58314 | 8.60% |
| 16.112 | 5.49646 | 9.90% |
| 17.475 | 5.07095 | 2.20% |
| 18.01 | 4.9214 | 31.30% |
| 18.449 | 4.80527 | 19.70% |
| 18.85 | 4.70393 | 44.30% |
| 19.481 | 4.55289 | 12.30% |
| 19.701 | 4.50252 | 23.00% |
| 20.304 | 4.3702 | 20.00% |
| 20.852 | 4.2566 | 100.00% |
| 21.399 | 4.149 | 17.10% |
| 21.994 | 4.03818 | 9.70% |
| 22.199 | 4.00128 | 28.10% |
| 22.528 | 3.94351 | 13.30% |
| 22.734 | 3.90835 | 12.60% |
| 23.19 | 3.83246 | 19.30% |
| 23.476 | 3.78646 | 31.30% |
| 23.755 | 3.74266 | 6.70% |
| 24.364 | 3.6504 | 21.40% |
| 24.86 | 3.57864 | 16.30% |
| 25.357 | 3.5096 | 3.40% |
| 25.563 | 3.48189 | 16.40% |
| 25.877 | 3.44032 | 10.90% |
| 26.392 | 3.37431 | 2.90% |
| 26.655 | 3.34162 | 6.20% |
| 27.14 | 3.28302 | 9.20% |
| 27.516 | 3.23903 | 3.80% |
| 27.949 | 3.18976 | 2.50% |
| 28.257 | 3.1557 | 13.10% |
| 28.49 | 3.13042 | 8.20% |
| 28.958 | 3.0809 | 5.50% |
| 29.286 | 3.04712 | 7.50% |
| 29.797 | 2.99601 | 7.60% |
| 30.37 | 2.94082 | 1.20% |
| 30.823 | 2.89863 | 1.90% |
| 31.064 | 2.87666 | 5.40% |
| 31.572 | 2.83149 | 3.20% |
| 32.05 | 2.79035 | 5.80% |
| 32.598 | 2.74467 | 2.60% |
| 33.179 | 2.69795 | 1.30% |
| 34.099 | 2.62723 | 3.20% |
| 34.392 | 2.60554 | 4.20% |
| 35.108 | 2.55398 | 3.30% |
| 35.813 | 2.50535 | 2.50% |
| 36.131 | 2.48403 | 5.20% |
| 36.445 | 2.46332 | 6.70% |
| 36.972 | 2.42938 | 5.00% |
| 37.611 | 2.38957 | 5.30% |
| 38.198 | 2.3542 | 6.60% |
| 39.037 | 2.30554 | 2.20% |
| 39.402 | 2.28502 | 2.40% |
| 40.013 | 2.2515 | 2.30% |
| 40.274 | 2.23752 | 2.10% |
| 40.7 | 2.2151 | 4.70% |
| 41.447 | 2.17686 | 3.10% |

Figure 16:
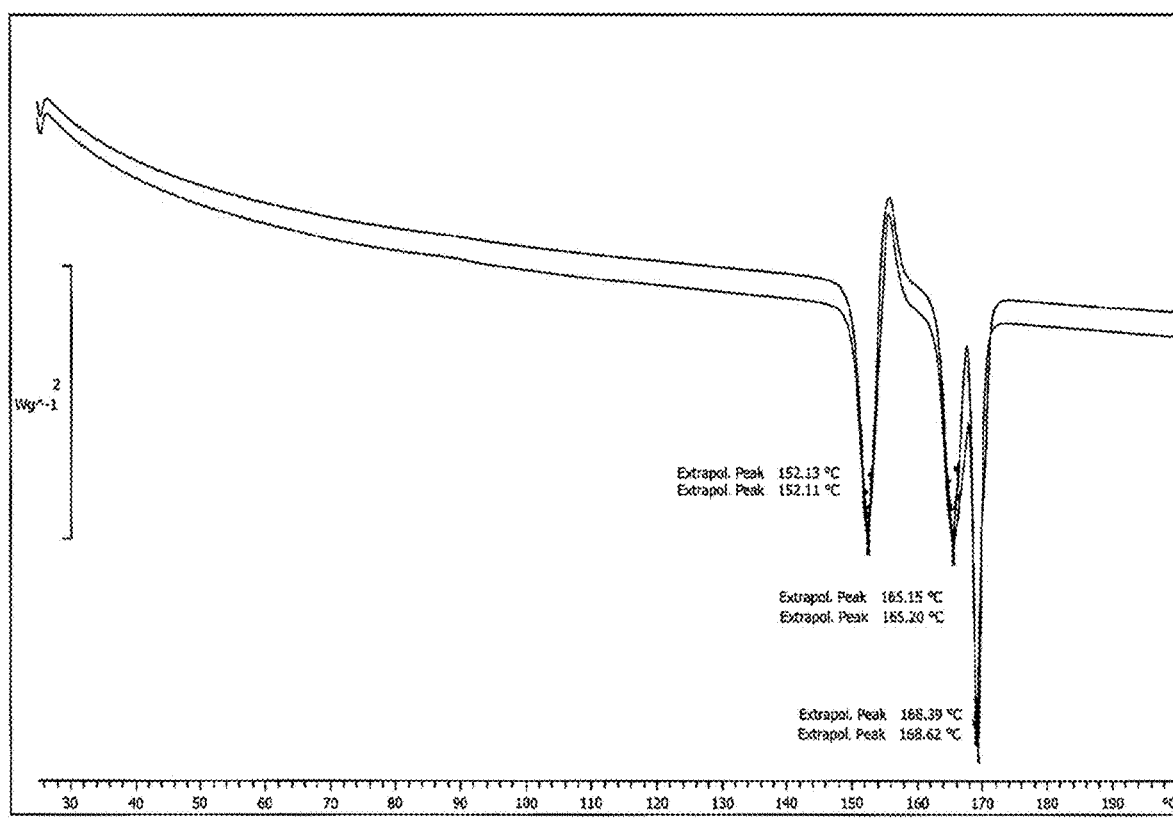
FIG. 16 depicts the characterization of Form D by differential scanning calorimetry (DSC).

FIG. 16 depicts the differential scanning calorimetry (DSC) profile of crystalline Form D. As shown in FIG. 16, crystalline Form D shows a characteristic endotherm with an onset of about 152° C.; a characteristic endotherm with an onset of about 165° C.; and a characteristic endotherm with an onset of about 168° C. Crystalline Form D displayed a thermogravimetric analysis (TGA) profile showing a mass loss of about 0.6 wt. % up to about 150° C. Crystalline Form D displayed a dynamic vapor sorption (DVS) profile showing a reversable total mass change of about 20 wt. % between about 0 to about 90% relative humidity (RH) at 25° C.

Example 6

Crystalline, Form F material of 5-(3,4-dichlorophenyl)-N-((1R,2R)-2-hydroxycyclohexyl)-6-(2,2,2-trifluoroethoxy)nicotinamide, hydrate, was prepared as follows. About 50 mg of crystalline Form E material of 5-(3,4-dichlorophenyl)-N-((1R,2R)-2-hydroxycyclohexyl)-6-(2,2,2-trifluoroethoxy)nicotinamide, anhydrate, was equilibrated in isopropanol under a temperature cycle between 5° C. to 50° C. at a heating/cooling rate of 0.2° C./min for 10 cycles with stirring at 400 rpm. XRPD analysis of the wet cake material indicated that the material was crystalline with a pattern consistent with Form Z. XRPD analysis of the dried material indicated that the material was crystalline with a pattern consistent with Form F.

Figure 19:
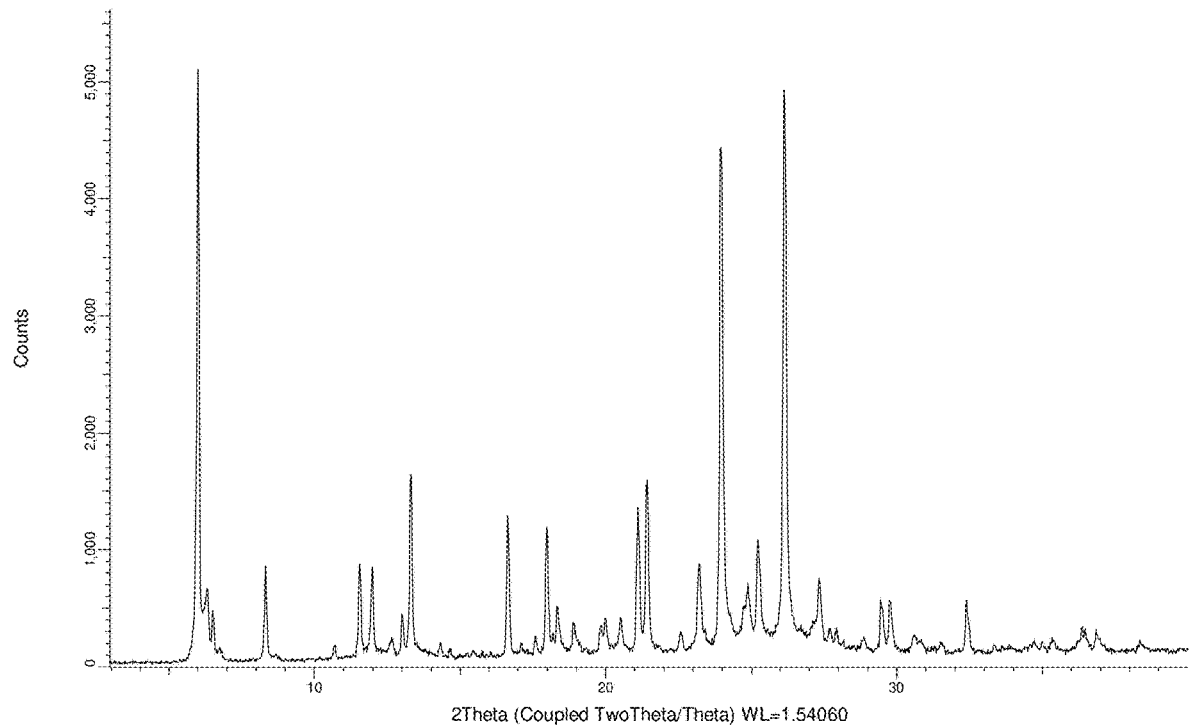
FIG. 19 depicts an X-ray powder diffraction (XRPD) pattern of 5-(3,4-dichlorophenyl)-N-((1R,2R)-2-hydroxycyclohexyl)-6-(2,2,2-trifluoroethoxy)nicotinamide, hydrate (Form F).

An XRPD pattern of crystalline Form F is shown in FIG. 19. Characteristic peaks include one or more of the peaks shown in Table 14.

TABLE 14

| Angle | d Value | Rel. Intensity |
|---|---|---|
| 5.077 | 17.39208 | 54.50% |
| 5.348 | 16.51019 | 23.90% |
| 6.927 | 12.74992 | 24.00% |
| 8.964 | 9.85765 | 28.50% |
| 10.163 | 8.69671 | 12.80% |
| 10.722 | 8.24428 | 11.90% |
| 12.14 | 7.28445 | 15.40% |
| 13.564 | 6.52276 | 7.20% |
| 13.887 | 6.37188 | 3.50% |
| 14.193 | 6.23518 | 3.60% |
| 14.407 | 6.14295 | 3.90% |
| 15.269 | 5.79794 | 7.50% |
| 15.861 | 5.58314 | 8.60% |
| 16.112 | 5.49646 | 9.90% |
| 17.475 | 5.07095 | 2.20% |
| 18.01 | 4.9214 | 31.30% |
| 18.449 | 4.80527 | 19.70% |
| 18.85 | 4.70393 | 44.30% |
| 19.481 | 4.55289 | 12.30% |
| 19.701 | 4.50252 | 23.00% |
| 20.304 | 4.3702 | 20.00% |
| 20.852 | 4.2566 | 100.00% |
| 21.399 | 4.149 | 17.10% |
| 21.994 | 4.03818 | 9.70% |
| 22.199 | 4.00128 | 28.10% |
| 22.528 | 3.94351 | 13.30% |
| 22.734 | 3.90835 | 12.60% |
| 23.19 | 3.83246 | 19.30% |
| 23.476 | 3.78646 | 31.30% |
| 23.755 | 3.74266 | 6.70% |
| 24.364 | 3.6504 | 21.40% |
| 24.86 | 3.57864 | 16.30% |
| 25.357 | 3.5096 | 3.40% |
| 25.563 | 3.48189 | 16.40% |
| 25.877 | 3.44032 | 10.90% |
| 26.392 | 3.37431 | 2.90% |
| 26.655 | 3.34162 | 6.20% |
| 27.14 | 3.28302 | 9.20% |
| 27.516 | 3.23903 | 3.80% |
| 27.949 | 3.18976 | 2.50% |
| 28.257 | 3.1557 | 13.10% |
| 28.49 | 3.13042 | 8.20% |
| 28.958 | 3.0809 | 5.50% |

TABLE 14-continued

| Angle | d Value | Rel. Intensity |
|---|---|---|
| 29.286 | 3.04712 | 7.50% |
| 29.797 | 2.99601 | 7.60% |
| 30.37 | 2.94082 | 1.20% |
| 30.823 | 2.89863 | 1.90% |
| 31.064 | 2.87666 | 5.40% |
| 31.572 | 2.83149 | 3.20% |
| 32.05 | 2.79035 | 5.80% |
| 32.598 | 2.74467 | 2.60% |
| 33.179 | 2.69795 | 1.30% |
| 34.099 | 2.62723 | 3.20% |
| 34.392 | 2.60554 | 4.20% |
| 35.108 | 2.55398 | 3.30% |
| 35.813 | 2.50535 | 2.50% |
| 36.131 | 2.48403 | 5.20% |
| 36.445 | 2.46332 | 6.70% |
| 36.972 | 2.42938 | 5.00% |
| 37.611 | 2.38957 | 5.30% |
| 38.198 | 2.3542 | 6.60% |
| 39.037 | 2.30554 | 2.20% |
| 39.402 | 2.28502 | 2.40% |
| 40.013 | 2.2515 | 2.30% |
| 40.274 | 2.23752 | 2.10% |
| 40.7 | 2.2151 | 4.70% |
| 41.447 | 2.17686 | 3.10% |

Figure 19A:
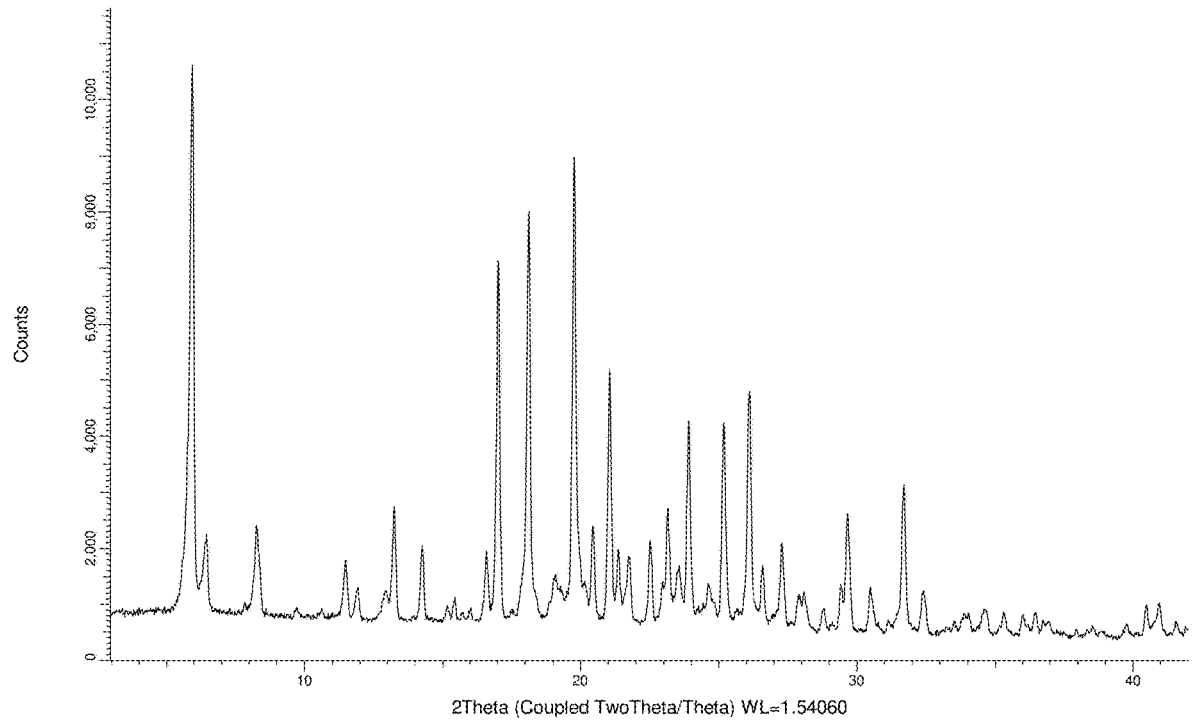
FIG. 19A depicts an X-ray powder diffraction (XRPD) pattern of 5-(3,4-dichlorophenyl)-N-((1R,2R)-2-hydroxycyclohexyl)-6-(2,2,2-trifluoroethoxy)nicotinamide, hydrate (Form F).

An XRPD pattern of crystalline Form F is shown in FIG. 19A. Characteristic peaks include one or more of the peaks shown in Table 15.

TABLE 15

| Angle | d Value | Rel. Intensity |
|---|---|---|
| 5.956 | 14.82812 | 100.00% |
| 6.454 | 13.68395 | 14.00% |
| 8.284 | 10.66438 | 17.10% |
| 9.727 | 9.08602 | 2.10% |
| 10.623 | 8.3214 | 1.90% |
| 11.5 | 7.68846 | 11.40% |
| 11.93 | 7.41261 | 6.30% |
| 12.942 | 6.83481 | 5.50% |
| 13.248 | 6.67774 | 21.70% |
| 14.261 | 6.20562 | 14.90% |
| 15.17 | 5.8359 | 2.90% |
| 15.437 | 5.73547 | 4.90% |
| 15.764 | 5.61718 | 1.50% |
| 16.039 | 5.52151 | 2.70% |
| 16.605 | 5.3345 | 14.20% |
| 17.029 | 5.2027 | 72.80% |
| 17.556 | 5.04755 | 1.70% |
| 18.133 | 4.88834 | 80.70% |
| 19.096 | 4.64388 | 8.50% |
| 19.776 | 4.48582 | 93.40% |
| 20.454 | 4.3386 | 18.60% |
| 21.056 | 4.21584 | 50.50% |
| 21.374 | 4.15388 | 14.60% |
| 21.755 | 4.08194 | 13.40% |
| 22.524 | 3.94419 | 17.00% |
| 23.164 | 3.83677 | 23.50% |
| 23.555 | 3.77397 | 10.40% |
| 23.908 | 3.71905 | 42.20% |
| 24.628 | 3.6118 | 7.50% |
| 25.18 | 3.53389 | 41.50% |
| 25.68 | 3.46628 | 1.60% |
| 26.103 | 3.41097 | 48.50% |
| 26.604 | 3.34789 | 12.90% |
| 27.304 | 3.26366 | 17.70% |
| 27.957 | 3.18892 | 6.10% |
| 28.102 | 3.17279 | 8.70% |
| 28.8 | 3.09746 | 4.80% |
| 29.436 | 3.03195 | 10.40% |
| 29.675 | 3.00803 | 25.20% |
| 30.497 | 2.92878 | 10.20% |
| 31.16 | 2.86798 | 2.30% |
| 31.699 | 2.82044 | 33.00% |
| 32.402 | 2.76086 | 9.40% |

TABLE 15-continued

| Angle | d Value | Rel. Intensity |
|---|---|---|
| 33.526 | 2.67085 | 3.00% |
| 33.94 | 2.63921 | 3.10% |
| 34.624 | 2.58862 | 4.60% |
| 35.319 | 2.53925 | 5.90% |
| 36.007 | 2.4923 | 4.80% |
| 36.454 | 2.46274 | 5.20% |
| 36.765 | 2.44263 | 3.40% |
| 36.973 | 2.42935 | 3.00% |
| 37.956 | 2.36867 | 1.80% |
| 38.545 | 2.33383 | 2.80% |
| 38.855 | 2.31587 | 1.20% |
| 39.771 | 2.26467 | 2.90% |
| 40.497 | 2.22573 | 7.70% |
| 40.952 | 2.20202 | 7.50% |
| 41.541 | 2.17217 | 3.60% |

Figure 20:
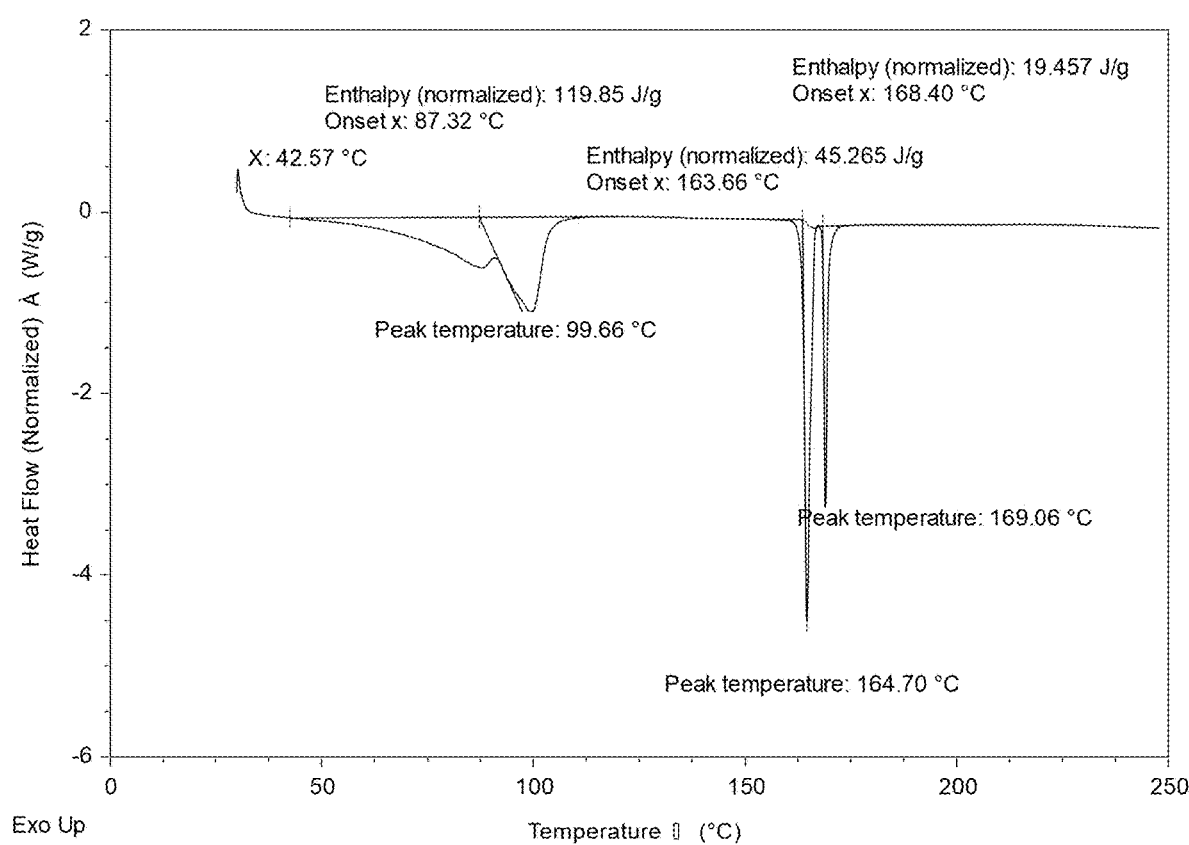
FIG. 20 depicts the characterization of Form F by differential scanning calorimetry (DSC).

FIG. 20 depicts the differential scanning calorimetry (DSC) profile of crystalline Form F. As shown in FIG. 20, crystalline Form F shows a characteristic endotherm with an onset of about 87° C. and a peak of about 100° C.; and a characteristic endotherm with an onset of about 164° C. and a peak of about 165° C.; and a characteristic endotherm with an onset of about 168° C. and a peak of about 169° C. Crystalline Form F displayed a thermogravimetric analysis (TGA) profile showing a mass loss of about 4.1 wt. % up to about 150° C. Karl Fischer (KF) analysis showed 5.0% water by weight (1.35 equivalent by molar ratio).

Example 7

Crystalline, Form G material of 5-(3,4-dichlorophenyl)-N-((1R,2R)-2-hydroxycyclohexyl)-6-(2,2,2-trifluoroethoxy)nicotinamide, diisopropylamine monosolvate, was prepared as follows. About 50 mg of crystalline Form E material of 5-(3,4-dichlorophenyl)-N-((1R,2R)-2-hydroxycyclohexyl)-6-(2,2,2-trifluoroethoxy)nicotinamide, anhydrate, was equilibrated in diisopropylamine at 25° C. for 2 weeks with stirring at 400 rpm. The obtained suspension was filtered through a 0.45 μm nylon membrane filter by centrifugation at 14,000 rpm. XRPD analysis indicated that the material was crystalline with a pattern consistent with Form G.

Figure 22:
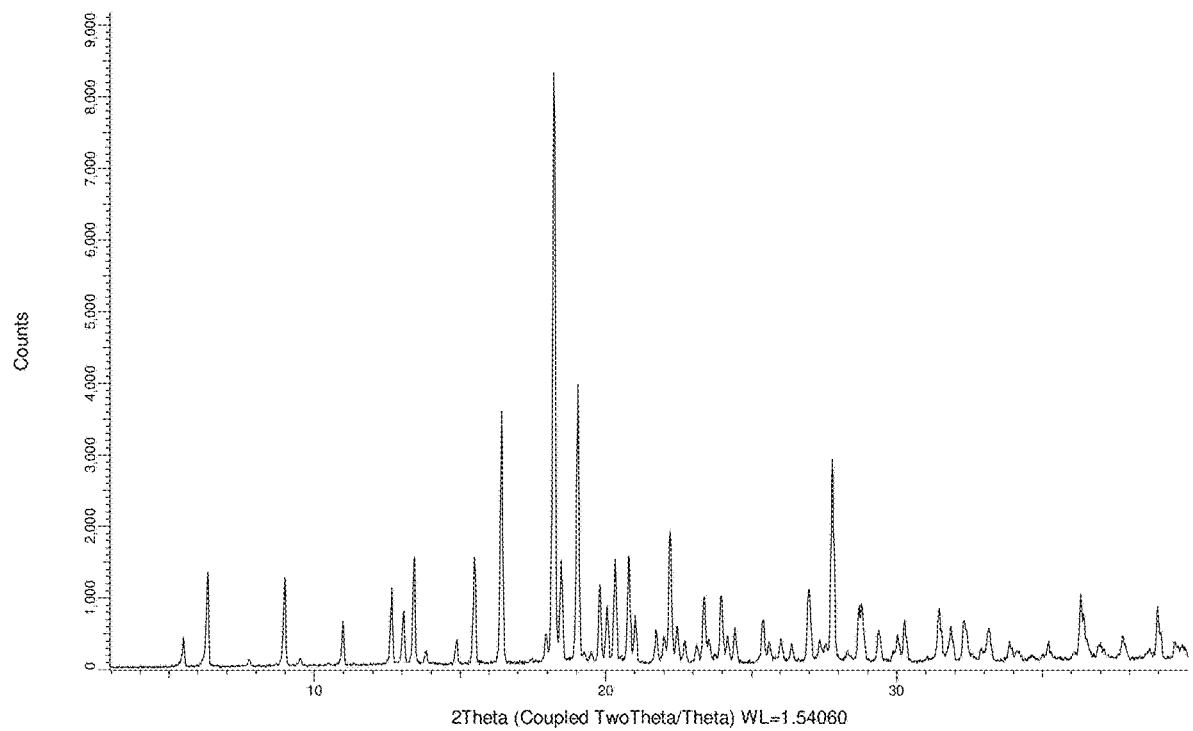
FIG. 22 depicts an X-ray powder diffraction (XRPD) pattern of 5-(3,4-dichlorophenyl)-N-((1R,2R)-2-hydroxycyclohexyl)-6-(2,2,2-trifluoroethoxy)nicotinamide, diisopropylamine monosolvate (Form G).

An XRPD pattern of crystalline Form G is shown in FIG. 22. Characteristic peaks include one or more of the peaks shown in Table 16.

TABLE 16

| Angle | d Value | Rel. Intensity |
|---|---|---|
| 5.077 | 17.39208 | 54.50% |
| 5.348 | 16.51019 | 23.90% |
| 6.927 | 12.74992 | 24.00% |
| 8.964 | 9.85765 | 28.50% |
| 10.163 | 8.69671 | 12.80% |
| 10.722 | 8.24428 | 11.90% |
| 12.14 | 7.28445 | 15.40% |
| 13.564 | 6.52276 | 7.20% |
| 13.887 | 6.37188 | 3.50% |
| 14.193 | 6.23518 | 3.60% |
| 14.407 | 6.14295 | 3.90% |
| 15.269 | 5.79794 | 7.50% |
| 15.861 | 5.58314 | 8.60% |
| 16.112 | 5.49646 | 9.90% |
| 17.475 | 5.07095 | 2.20% |
| 18.01 | 4.9214 | 31.30% |
| 18.449 | 4.80527 | 19.70% |
| 18.85 | 4.70393 | 44.30% |
| 19.481 | 4.55289 | 12.30% |

TABLE 16-continued

| Angle | d Value | Rel. Intensity |
|---|---|---|
| 19.701 | 4.50252 | 23.00% |
| 20.304 | 4.3702 | 20.00% |
| 20.852 | 4.2566 | 100.00% |
| 21.399 | 4.149 | 17.10% |
| 21.994 | 4.03818 | 9.70% |
| 22.199 | 4.00128 | 28.10% |
| 22.528 | 3.94351 | 13.30% |
| 22.734 | 3.90835 | 12.60% |
| 23.19 | 3.83246 | 19.30% |
| 23.476 | 3.78646 | 31.30% |
| 23.755 | 3.74266 | 6.70% |
| 24.364 | 3.6504 | 21.40% |
| 24.86 | 3.57864 | 16.30% |
| 25.357 | 3.5096 | 3.40% |
| 25.563 | 3.48189 | 16.40% |
| 25.877 | 3.44032 | 10.90% |
| 26.392 | 3.37431 | 2.90% |
| 26.655 | 3.34162 | 6.20% |
| 27.14 | 3.28302 | 9.20% |
| 27.516 | 3.23903 | 3.80% |
| 27.949 | 3.18976 | 2.50% |
| 28.257 | 3.1557 | 13.10% |
| 28.49 | 3.13042 | 8.20% |
| 28.958 | 3.0809 | 5.50% |
| 29.286 | 3.04712 | 7.50% |
| 29.797 | 2.99601 | 7.60% |
| 30.37 | 2.94082 | 1.20% |
| 30.823 | 2.89863 | 1.90% |
| 31.064 | 2.87666 | 5.40% |
| 31.572 | 2.83149 | 3.20% |
| 32.05 | 2.79035 | 5.80% |
| 32.598 | 2.74467 | 2.60% |
| 33.179 | 2.69795 | 1.30% |
| 34.099 | 2.62723 | 3.20% |
| 34.392 | 2.60554 | 4.20% |
| 35.108 | 2.55398 | 3.30% |
| 35.813 | 2.50535 | 2.50% |
| 36.131 | 2.48403 | 5.20% |
| 36.445 | 2.46332 | 6.70% |
| 36.972 | 2.42938 | 5.00% |
| 37.611 | 2.38957 | 5.30% |
| 38.198 | 2.3542 | 6.60% |
| 39.037 | 2.30554 | 2.20% |
| 39.402 | 2.28502 | 2.40% |
| 40.013 | 2.2515 | 2.30% |
| 40.274 | 2.23752 | 2.10% |
| 40.7 | 2.2151 | 4.70% |
| 41.447 | 2.17686 | 3.10% |

Figure 22A:
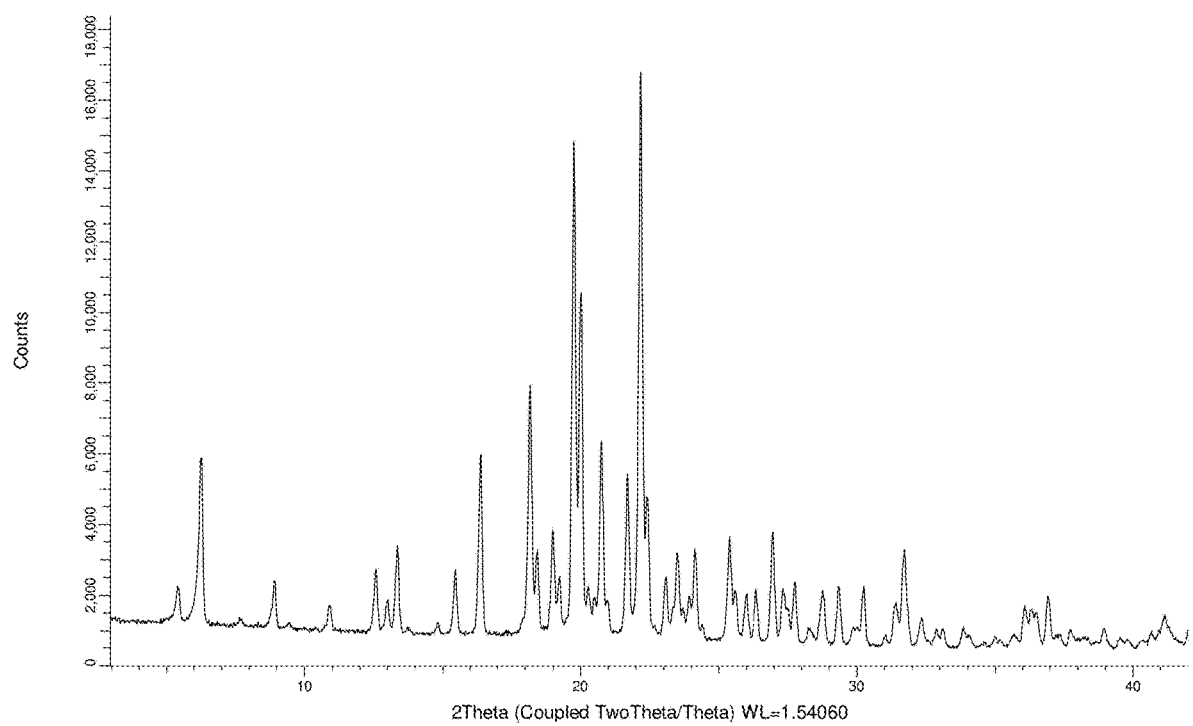
FIG. 22A depicts an X-ray powder diffraction (XRPD) pattern of 5-(3,4-dichlorophenyl)-N-((1R,2R)-2-hydroxycyclohexyl)-6-(2,2,2-trifluoroethoxy)nicotinamide, diisopropylamine monosolvate (Form G).

An XRPD pattern of crystalline Form G is shown in FIG. 22A. Characteristic peaks include one or more of the peaks shown in Table 17.

TABLE 17

| Angle | d Value | Rel. Intensity |
|---|---|---|
| 5.44 | 16.23308 | 5.20% |
| 6.27 | 14.08626 | 26.90% |
| 7.677 | 11.5069 | 1.20% |
| 8.924 | 9.90138 | 7.70% |
| 10.919 | 8.0966 | 4.40% |
| 12.59 | 7.02546 | 10.80% |
| 13 | 6.80458 | 5.70% |
| 13.366 | 6.61908 | 15.10% |
| 14.818 | 5.97356 | 1.90% |
| 15.458 | 5.72769 | 10.80% |
| 16.393 | 5.4029 | 31.20% |
| 18.181 | 4.87537 | 43.30% |
| 18.437 | 4.80849 | 14.60% |
| 19.007 | 4.66555 | 17.80% |
| 19.241 | 4.6092 | 10.00% |
| 19.763 | 4.48866 | 88.20% |
| 20.015 | 4.43275 | 60.30% |
| 20.281 | 4.37513 | 7.80% |
| 20.76 | 4.27534 | 34.30% |

TABLE 17-continued

| Angle | d Value | Rel. Intensity |
|---|---|---|
| 21.707 | 4.09078 | 28.00% |
| 22.175 | 4.00559 | 100.00% |
| 22.408 | 3.96435 | 25.00% |
| 23.087 | 3.84928 | 10.50% |
| 23.502 | 3.78236 | 15.50% |
| 23.932 | 3.71525 | 7.20% |
| 24.138 | 3.68403 | 17.20% |
| 24.395 | 3.64585 | 2.80% |
| 25.393 | 3.50478 | 18.40% |
| 25.592 | 3.47798 | 9.20% |
| 25.995 | 3.42497 | 8.20% |
| 26.359 | 3.37841 | 10.10% |
| 26.968 | 3.30359 | 20.50% |
| 27.351 | 3.25816 | 9.20% |
| 27.766 | 3.21042 | 11.00% |
| 28.305 | 3.15043 | 2.30% |
| 28.779 | 3.09966 | 9.80% |
| 29.352 | 3.0404 | 10.80% |
| 29.958 | 2.98029 | 2.80% |
| 30.252 | 2.95196 | 10.80% |
| 31.036 | 2.87918 | 2.10% |
| 31.415 | 2.84528 | 7.60% |
| 31.72 | 2.81863 | 18.10% |
| 32.347 | 2.76545 | 5.20% |
| 32.882 | 2.7216 | 3.40% |
| 33.101 | 2.70416 | 4.10% |
| 33.856 | 2.64552 | 4.00% |
| 34.062 | 2.62999 | 2.00% |
| 35.004 | 2.56137 | 2.10% |
| 35.188 | 2.54837 | 1.70% |
| 35.693 | 2.51345 | 2.00% |
| 36.079 | 2.48745 | 7.50% |
| 36.329 | 2.47091 | 6.80% |
| 36.437 | 2.46387 | 4.30% |
| 36.945 | 2.43109 | 9.40% |
| 37.307 | 2.40836 | 1.20% |
| 37.751 | 2.38103 | 3.30% |
| 38.278 | 2.34947 | 1.40% |
| 38.961 | 2.30986 | 3.60% |
| 39.55 | 2.27678 | 2.00% |
| 39.814 | 2.26232 | 1.90% |
| 40.369 | 2.23246 | 1.10% |
| 40.679 | 2.21618 | 3.20% |
| 41.15 | 2.19187 | 5.60% |

Figure 23:
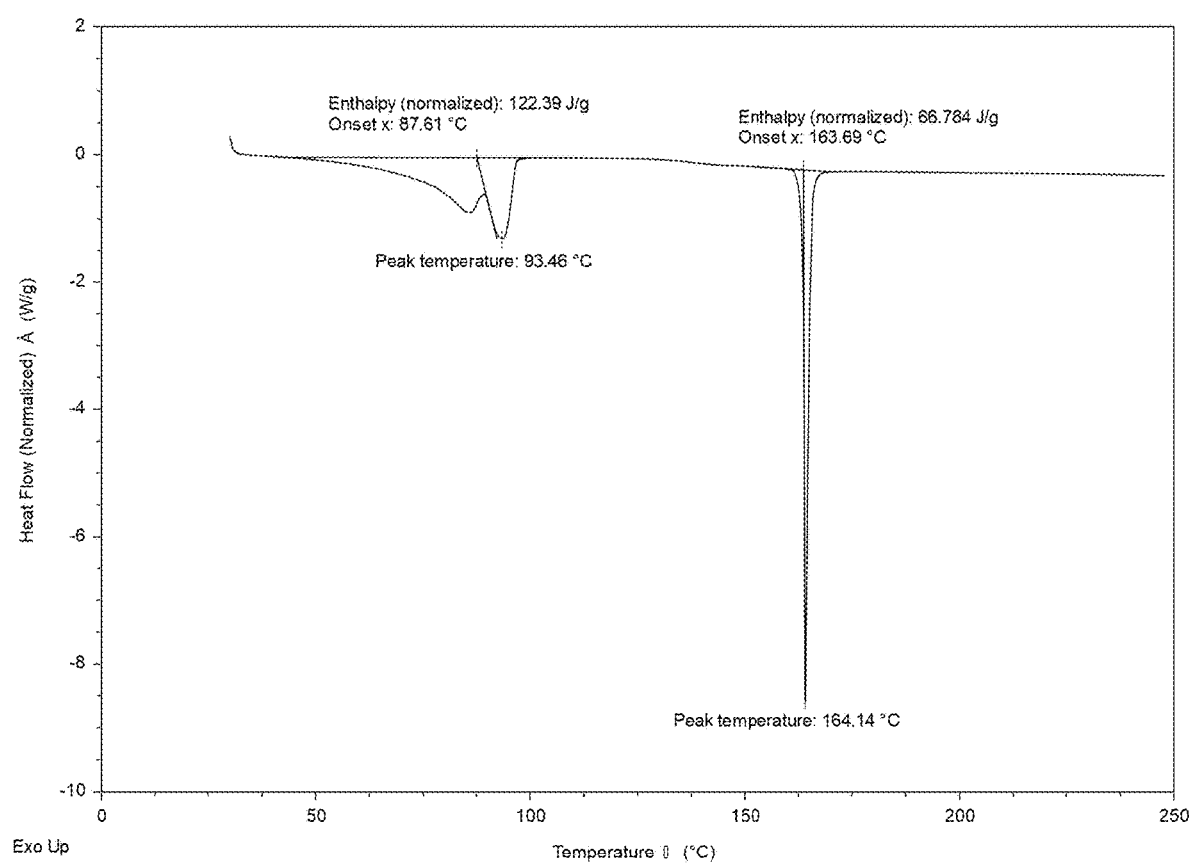
FIG. 23 depicts the characterization of Form G by differential scanning calorimetry (DSC).
Figure 24:
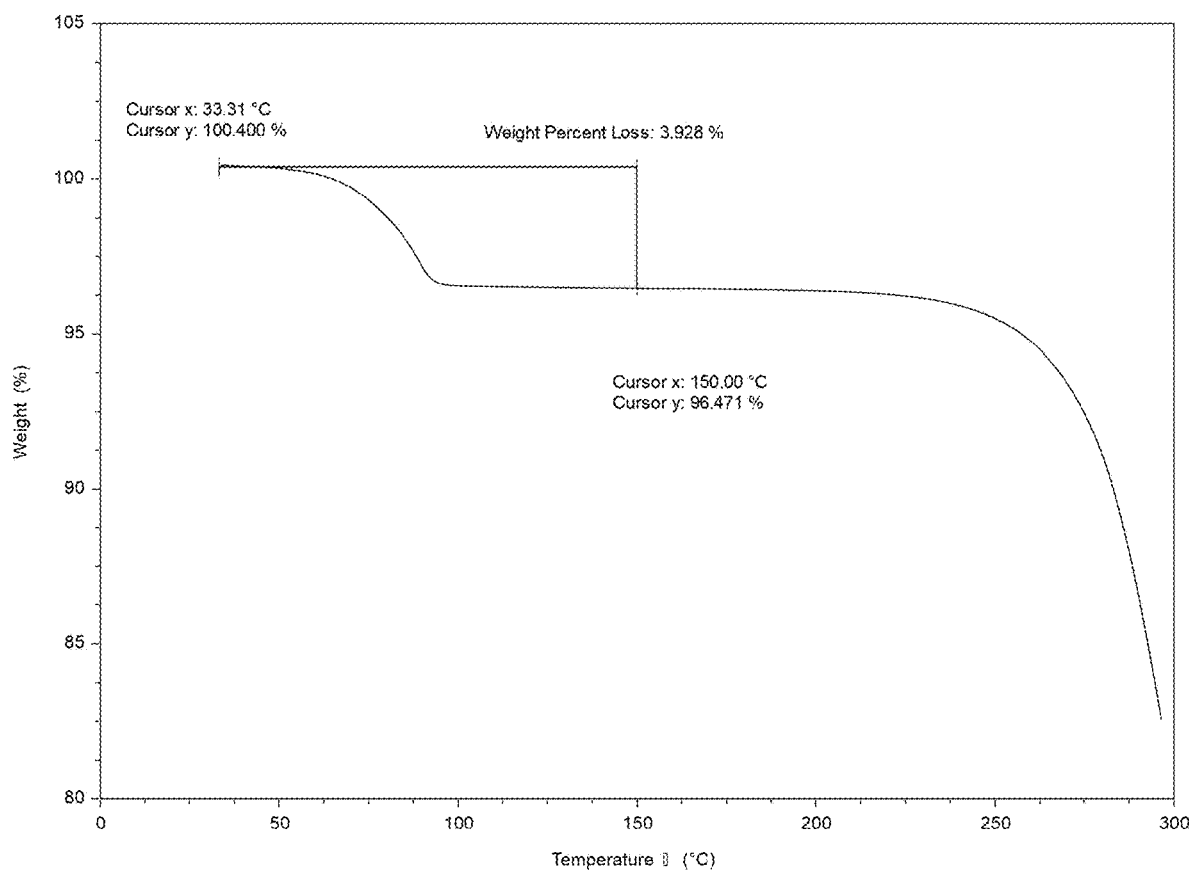
FIG. 24 depicts the thermogravimetric analysis (TGA) profile of Form G.

FIG. 23 depicts the differential scanning calorimetry (DSC) profile of crystalline Form G. As shown in FIG. 23, crystalline Form G shows a characteristic endotherm with an onset of about 88° C. and a peak of about 93° C.; and a characteristic endotherm with an onset and a peak of about 164° C. Crystalline Form G displayed a thermogravimetric analysis (TGA) profile showing a mass loss of about 3.9 wt. % up to about 150° C.

Example 8

Figure 25:
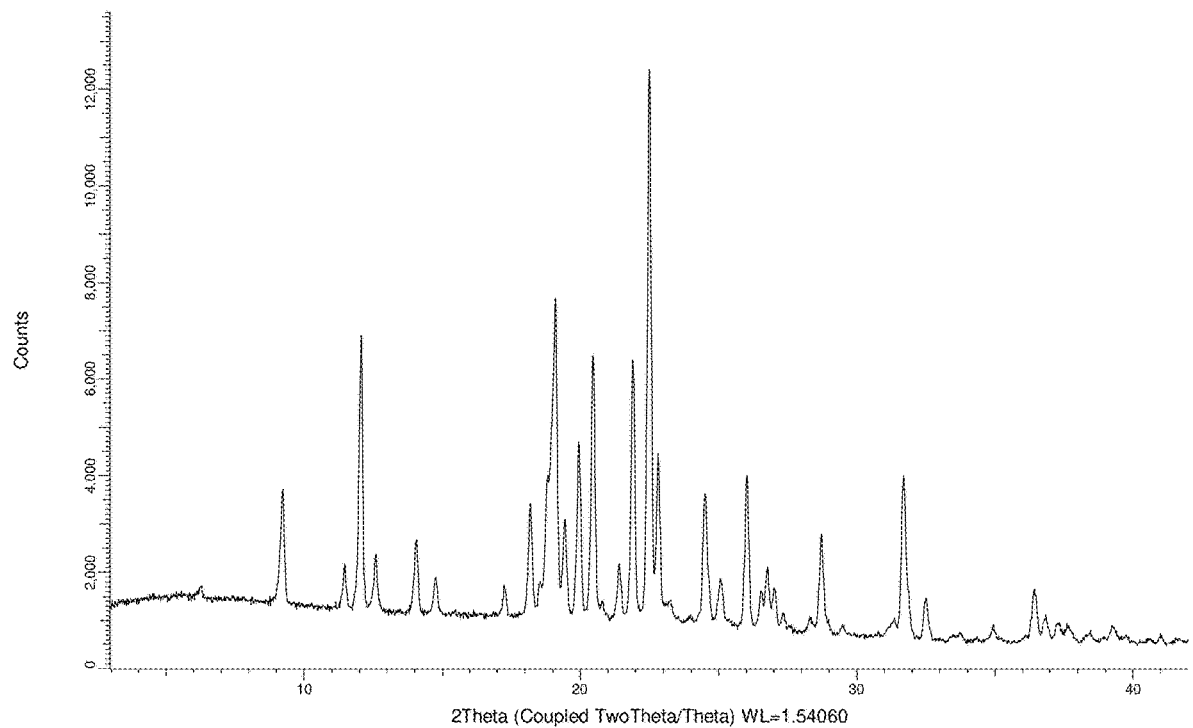
FIG. 25 depicts the X-ray powder diffraction (XRPD) pattern of 5-(3,4-dichlorophenyl)-N-((1R,2R)-2-hydroxycyclohexyl)-6-(2,2,2-trifluoroethoxy)nicotinamide, anhydrate (Form H).

The XRPD pattern of crystalline Form H material of 5-(3,4-dichlorophenyl)-N-((1R,2R)-2-hydroxycyclohexyl)-6-(2,2,2-trifluoroethoxy)nicotinamide, anhydrate, is shown in FIG. 25. Characteristic peaks include one or more of the peaks shown in Table 18.

TABLE 18

| Angle | d Value | Rel. Intensity |
|---|---|---|
| 5.077 | 17.39208 | 54.50% |
| 5.348 | 16.51019 | 23.90% |
| 6.927 | 12.74992 | 24.00% |
| 8.964 | 9.85765 | 28.50% |
| 10.163 | 8.69671 | 12.80% |
| 10.722 | 8.24428 | 11.90% |
| 12.14 | 7.28445 | 15.40% |

TABLE 18-continued

| Angle | d Value | Rel. Intensity |
| --- | --- | --- |
| 13.564 | 6.52276 | 7.20% |
| 13.887 | 6.37188 | 3.50% |
| 14.193 | 6.23518 | 3.60% |
| 14.407 | 6.14295 | 3.90% |
| 15.269 | 5.79794 | 7.50% |
| 15.861 | 5.58314 | 8.60% |
| 16.112 | 5.49646 | 9.90% |
| 17.475 | 5.07095 | 2.20% |
| 18.01 | 4.9214 | 31.30% |
| 18.449 | 4.80527 | 19.70% |
| 18.85 | 4.70393 | 44.30% |
| 19.481 | 4.55289 | 12.30% |
| 19.701 | 4.50252 | 23.00% |
| 20.304 | 4.3702 | 20.00% |
| 20.852 | 4.2566 | 100.00% |
| 21.399 | 4.149 | 17.10% |
| 21.994 | 4.03818 | 9.70% |
| 22.199 | 4.00128 | 28.10% |
| 22.528 | 3.94351 | 13.30% |
| 22.734 | 3.90835 | 12.60% |
| 23.19 | 3.83246 | 19.30% |
| 23.476 | 3.78646 | 31.30% |
| 23.755 | 3.74266 | 6.70% |
| 24.364 | 3.6504 | 21.40% |
| 24.86 | 3.57864 | 16.30% |
| 25.357 | 3.5096 | 3.40% |
| 25.563 | 3.48189 | 16.40% |
| 25.877 | 3.44032 | 10.90% |
| 26.392 | 3.37431 | 2.90% |
| 26.655 | 3.34162 | 6.20% |
| 27.14 | 3.28302 | 9.20% |
| 27.516 | 3.23903 | 3.80% |
| 27.949 | 3.18976 | 2.50% |
| 28.257 | 3.1557 | 13.10% |
| 28.49 | 3.13042 | 8.20% |
| 28.958 | 3.0809 | 5.50% |
| 29.286 | 3.04712 | 7.50% |
| 29.797 | 2.99601 | 7.60% |
| 30.37 | 2.94082 | 1.20% |
| 30.823 | 2.89863 | 1.90% |
| 31.064 | 2.87666 | 5.40% |
| 31.572 | 2.83149 | 3.20% |
| 32.05 | 2.79035 | 5.80% |
| 32.598 | 2.74467 | 2.60% |
| 33.179 | 2.69795 | 1.30% |
| 34.099 | 2.62723 | 3.20% |
| 34.392 | 2.60554 | 4.20% |
| 35.108 | 2.55398 | 3.30% |
| 35.813 | 2.50535 | 2.50% |
| 36.131 | 2.48403 | 5.20% |
| 36.445 | 2.46332 | 6.70% |
| 36.972 | 2.42938 | 5.00% |
| 37.611 | 2.38957 | 5.30% |
| 38.198 | 2.3542 | 6.60% |
| 39.037 | 2.30554 | 2.20% |
| 39.402 | 2.28502 | 2.40% |
| 40.013 | 2.2515 | 2.30% |
| 40.274 | 2.23752 | 2.10% |
| 40.7 | 2.2151 | 4.70% |
| 41.447 | 2.17686 | 3.10% |

Figure 26:
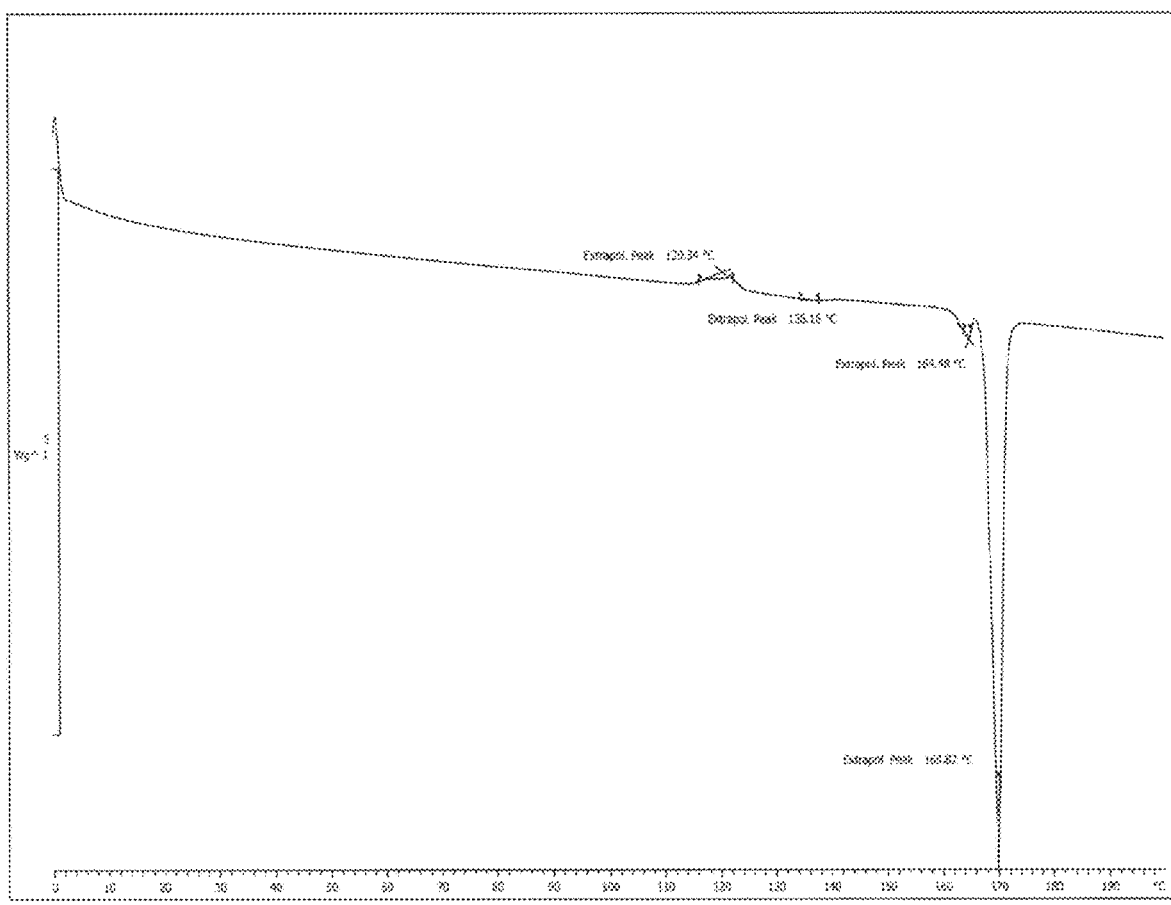
FIG. 26 depicts the characterization of Form H by differential scanning calorimetry (DSC).

FIG. 26 depicts the differential scanning calorimetry (DSC) profile of crystalline Form H. As shown in FIG. 26, crystalline Form H shows a characteristic exotherm with an onset of about 120° C.; a characteristic endotherm with an onset of about 136° C.; a characteristic endotherm with an onset of about 164° C.; and a characteristic endotherm with an onset of about 169° C. Crystalline Form H displayed a thermogravimetric analysis (TGA) profile showing a mass loss of about 0.11 wt. % up to about 152° C. Crystalline Form H displayed a dynamic vapor sorption (DVS) profile showing a total mass change of about 2.5 wt. % between about 0 to about 70% relative humidity (RH) at 25° C., and a total mass change of about 25 wt. % between about 70 to about 90% relative humidity (RH) at 25° C.

Example 9

Crystalline, Form I material of 5-(3,4-dichlorophenyl)-N-((1R,2R)-2-hydroxycyclohexyl)-6-(2,2,2-trifluoroethoxy) nicotinamide, anhydrate, was prepared as follows. About 50 mg of crystalline Form E material of 5-(3,4-dichlorophenyl)-N-((1R,2R)-2-hydroxycyclohexyl)-6-(2,2,2-trifluoroethoxy)nicotinamide, anhydrate, was equilibrated in toluene at 50° C. for 1 week with stirring at 400 rpm. The obtained suspension was filtered through a 0.45 μm nylon membrane filter by centrifugation at 14,000 rpm. XRPD analysis indicated that the material was crystalline with a pattern consistent with Form I.

Figure 29:
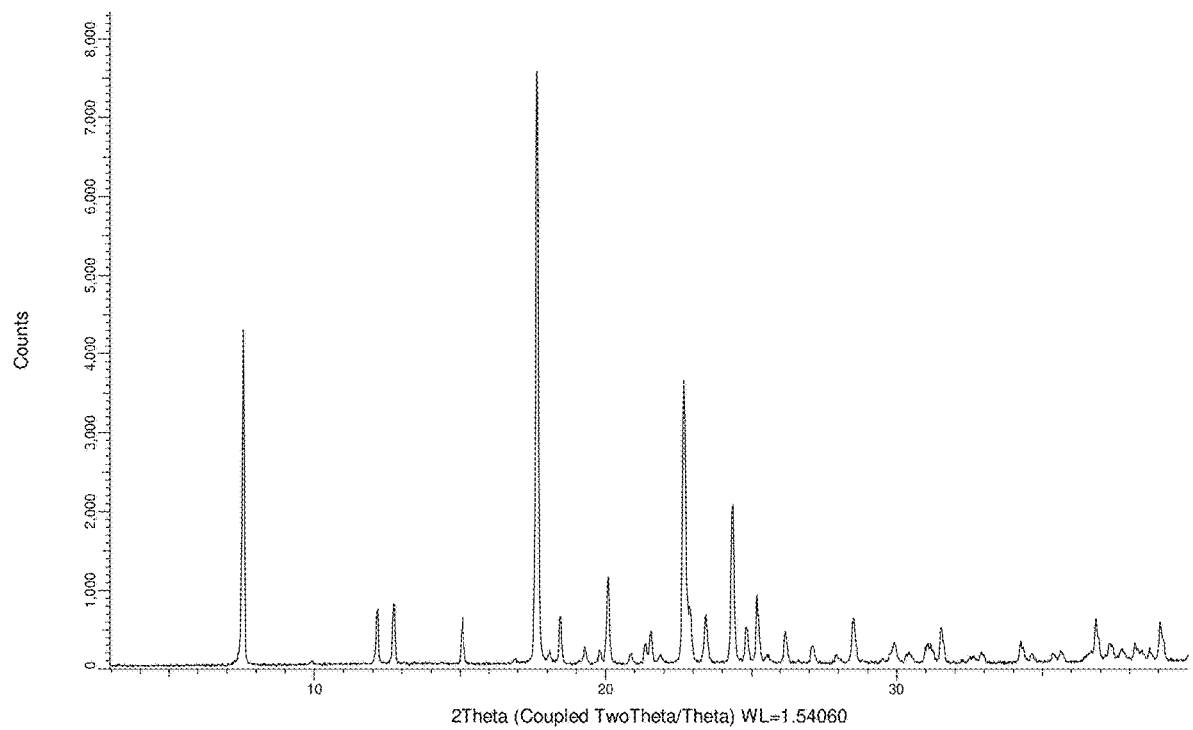
FIG. 29 depicts an X-ray powder diffraction (XRPD) pattern of 5-(3,4-dichlorophenyl)-N-((1R,2R)-2-hydroxycyclohexyl)-6-(2,2,2-trifluoroethoxy)nicotinamide, anhydrate (Form I).

An XRPD pattern of crystalline Form I is shown in FIG. 29. Characteristic peaks include one or more of the peaks shown in Table 19.

TABLE 19

| Angle | d Value | Rel. Intensity |
| --- | --- | --- |
| 5.077 | 17.39208 | 54.50% |
| 5.348 | 16.51019 | 23.90% |
| 6.927 | 12.74992 | 24.00% |
| 8.964 | 9.85765 | 28.50% |
| 10.163 | 8.69671 | 12.80% |
| 10.722 | 8.24428 | 11.90% |
| 12.14 | 7.28445 | 15.40% |
| 13.564 | 6.52276 | 7.20% |
| 13.887 | 6.37188 | 3.50% |
| 14.193 | 6.23518 | 3.60% |
| 14.407 | 6.14295 | 3.90% |
| 15.269 | 5.79794 | 7.50% |
| 15.861 | 5.58314 | 8.60% |
| 16.112 | 5.49646 | 9.90% |
| 17.475 | 5.07095 | 2.20% |
| 18.01 | 4.9214 | 31.30% |
| 18.449 | 4.80527 | 19.70% |
| 18.85 | 4.70393 | 44.30% |
| 19.481 | 4.55289 | 12.30% |
| 19.701 | 4.50252 | 23.00% |
| 20.304 | 4.3702 | 20.00% |
| 20.852 | 4.2566 | 100.00% |
| 21.399 | 4.149 | 17.10% |
| 21.994 | 4.03818 | 9.70% |
| 22.199 | 4.00128 | 28.10% |
| 22.528 | 3.94351 | 13.30% |
| 22.734 | 3.90835 | 12.60% |
| 23.19 | 3.83246 | 19.30% |
| 23.476 | 3.78646 | 31.30% |
| 23.755 | 3.74266 | 6.70% |
| 24.364 | 3.6504 | 21.40% |
| 24.86 | 3.57864 | 16.30% |
| 25.357 | 3.5096 | 3.40% |
| 25.563 | 3.48189 | 16.40% |
| 25.877 | 3.44032 | 10.90% |
| 26.392 | 3.37431 | 2.90% |
| 26.655 | 3.34162 | 6.20% |
| 27.14 | 3.28302 | 9.20% |
| 27.516 | 3.23903 | 3.80% |
| 27.949 | 3.18976 | 2.50% |
| 28.257 | 3.1557 | 13.10% |
| 28.49 | 3.13042 | 8.20% |
| 28.958 | 3.0809 | 5.50% |
| 29.286 | 3.04712 | 7.50% |
| 29.797 | 2.99601 | 7.60% |
| 30.37 | 2.94082 | 1.20% |
| 30.823 | 2.89863 | 1.90% |
| 31.064 | 2.87666 | 5.40% |
| 31.572 | 2.83149 | 3.20% |
| 32.05 | 2.79035 | 5.80% |
| 32.598 | 2.74467 | 2.60% |
| 33.179 | 2.69795 | 1.30% |
| 34.099 | 2.62723 | 3.20% |
| 34.392 | 2.60554 | 4.20% |
| 35.108 | 2.55398 | 3.30% |
| 35.813 | 2.50535 | 2.50% |
| 36.131 | 2.48403 | 5.20% |

TABLE 19-continued

| Angle | d Value | Rel. Intensity |
|---|---|---|
| 36.445 | 2.46332 | 6.70% |
| 36.972 | 2.42938 | 5.00% |
| 37.611 | 2.38957 | 5.30% |
| 38.198 | 2.3542 | 6.60% |
| 39.037 | 2.30554 | 2.20% |
| 39.402 | 2.28502 | 2.40% |
| 40.013 | 2.2515 | 2.30% |
| 40.274 | 2.23752 | 2.10% |
| 40.7 | 2.2151 | 4.70% |
| 41.447 | 2.17686 | 3.10% |

Figure 29A:
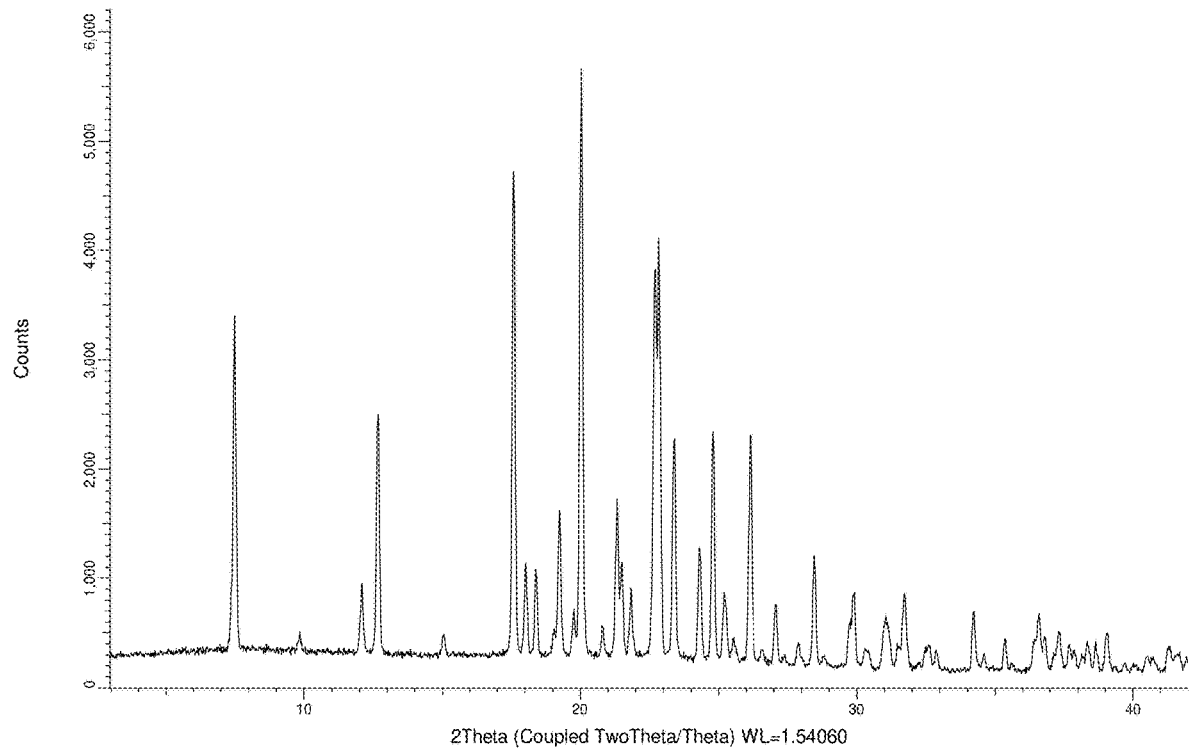
FIG. 29A depicts an X-ray powder diffraction (XRPD) pattern of 5-(3,4-dichlorophenyl)-N-((1R,2R)-2-hydroxycyclohexyl)-6-(2,2,2-trifluoroethoxy)nicotinamide, anhydrate (Form I).

An XRPD pattern of crystalline Form I is shown in FIG. 29A. Characteristic peaks include one or more of the peaks shown in Table 20.

TABLE 20

| Angle | d Value | Rel. Intensity |
|---|---|---|
| 7.502 | 11.774 | 52.90% |
| 9.855 | 8.96794 | 3.10% |
| 12.096 | 7.31096 | 11.30% |
| 12.68 | 6.97563 | 38.20% |
| 15.046 | 5.88338 | 3.30% |
| 17.6 | 5.03502 | 80.20% |
| 18.035 | 4.91452 | 15.20% |
| 18.405 | 4.81654 | 14.30% |
| 19.254 | 4.60614 | 23.90% |
| 19.769 | 4.48733 | 7.20% |
| 20.039 | 4.42736 | 100.00% |
| 20.808 | 4.2655 | 5.50% |
| 21.334 | 4.16146 | 25.70% |
| 21.502 | 4.12942 | 16.00% |
| 21.838 | 4.06665 | 11.30% |
| 22.841 | 3.89027 | 75.50% |
| 23.393 | 3.79969 | 37.50% |
| 24.316 | 3.65753 | 19.70% |
| 24.8 | 3.58725 | 39.90% |
| 25.21 | 3.52975 | 11.20% |
| 25.546 | 3.48415 | 3.00% |
| 26.15 | 3.40505 | 40.40% |
| 26.584 | 3.35033 | 2.20% |
| 27.087 | 3.2893 | 10.50% |
| 27.393 | 3.25323 | 1.00% |
| 27.907 | 3.19449 | 3.50% |
| 28.479 | 3.13158 | 20.50% |
| 28.814 | 3.09597 | 1.90% |
| 29.901 | 2.98585 | 13.60% |
| 30.332 | 2.94438 | 2.50% |
| 31.058 | 2.87722 | 8.50% |
| 31.494 | 2.83835 | 4.10% |
| 31.731 | 2.81767 | 13.00% |
| 32.621 | 2.74285 | 4.10% |
| 32.872 | 2.72243 | 3.70% |
| 34.232 | 2.6173 | 11.60% |
| 34.608 | 2.58974 | 3.20% |
| 35.358 | 2.53651 | 6.40% |
| 35.605 | 2.51947 | 1.20% |
| 36.589 | 2.45396 | 10.30% |
| 36.822 | 2.43895 | 6.50% |
| 37.34 | 2.40631 | 6.50% |
| 37.71 | 2.38351 | 4.90% |
| 37.863 | 2.37424 | 3.40% |
| 38.17 | 2.35585 | 2.30% |
| 38.366 | 2.3443 | 5.80% |
| 38.662 | 2.32699 | 6.10% |
| 39.065 | 2.30391 | 7.60% |
| 39.711 | 2.26793 | 1.50% |
| 40.524 | 2.2243 | 2.60% |
| 40.728 | 2.21362 | 2.80% |
| 41.317 | 2.18338 | 3.50% |
| 41.61 | 2.1687 | 2.10% |

Figure 30:
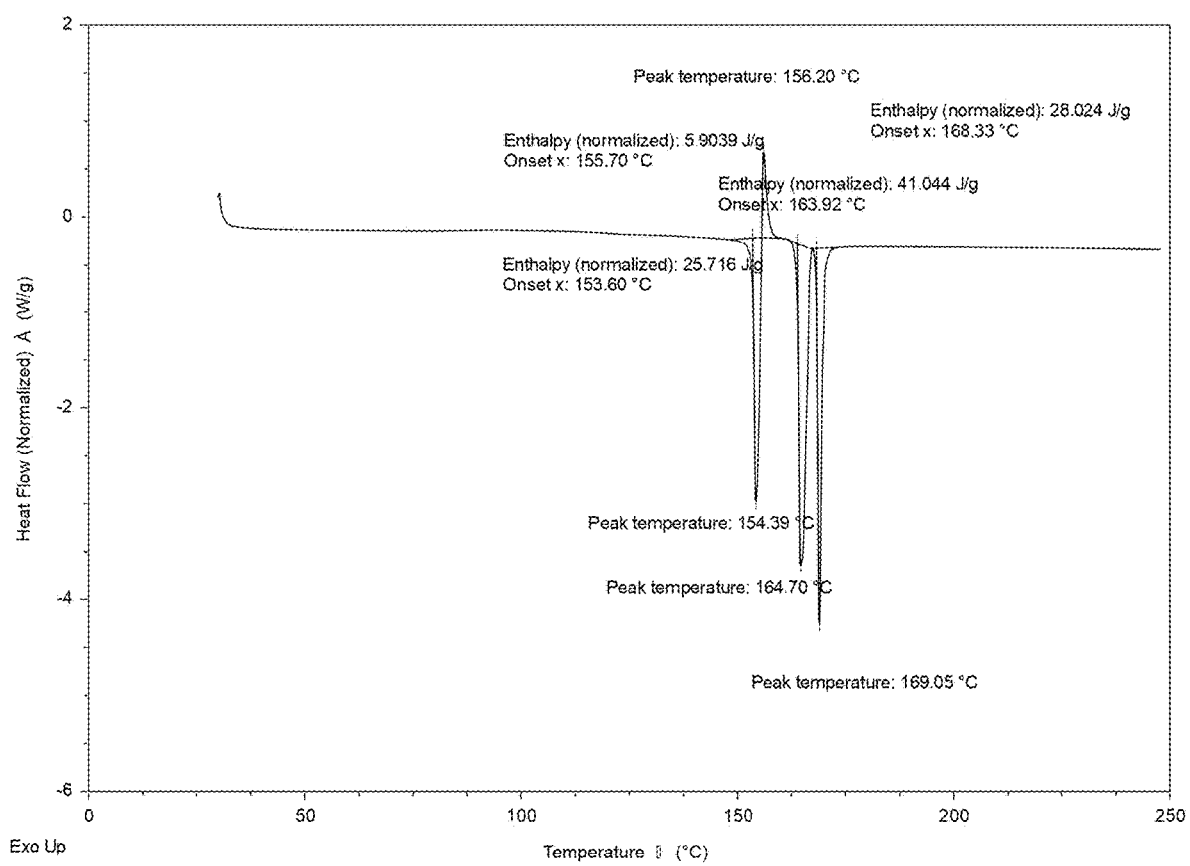
FIG. 30 depicts the characterization of Form I by differential scanning calorimetry (DSC).

FIG. 30 depicts the differential scanning calorimetry (DSC) profile of crystalline Form I. As shown in FIG. 30, crystalline Form I shows a characteristic endotherm with an onset of about 154° C.; a characteristic exotherm with an onset of about 156° C.; a characteristic endotherm with an onset of about 164° C.; and a characteristic endotherm with an onset of about 168° C. Crystalline Form I displayed a thermogravimetric analysis (TGA) profile showing a mass loss of about 0.1 wt. % up to about 120° C. Crystalline Form I displayed a dynamic vapor sorption (DVS) profile showing a total mass change of about 10 wt. % between about 0 to about 90% relative humidity (RH) at 25° C.

Example 10

Figure 33:
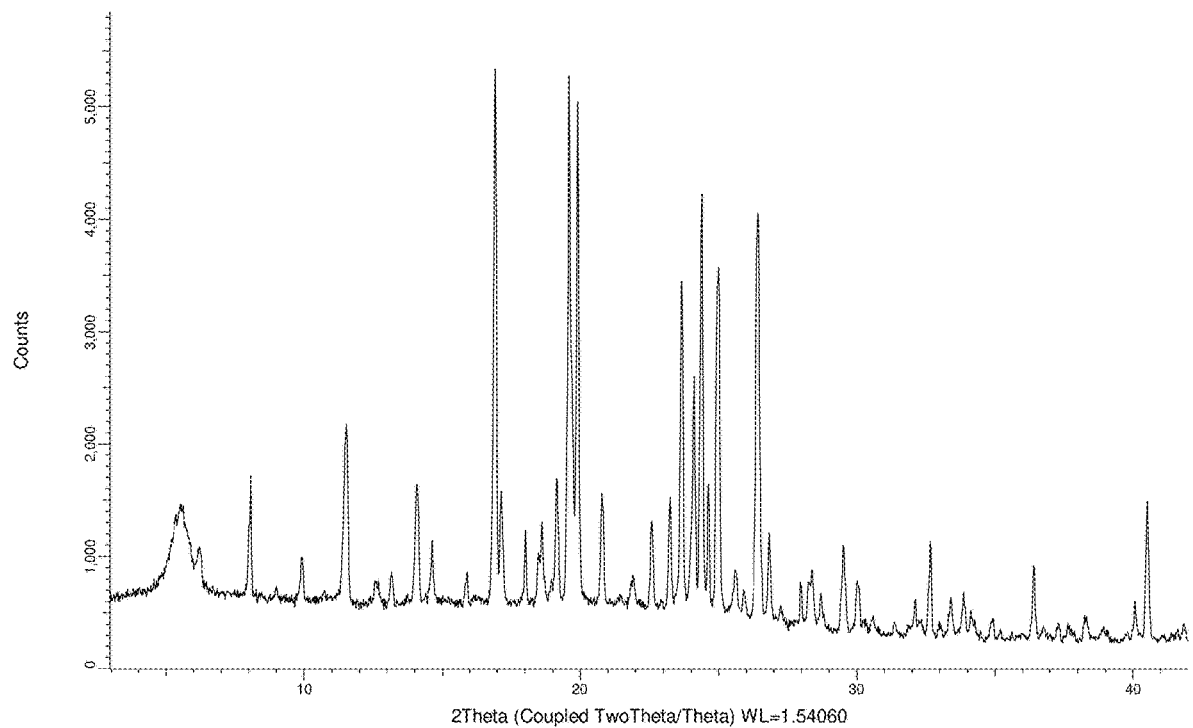
FIG. 33 depicts the X-ray powder diffraction (XRPD) pattern of 5-(3,4-dichlorophenyl)-N-((1R,2R)-2-hydroxycyclohexyl)-6-(2,2,2-trifluoroethoxy)nicotinamide, ethanol solvate (Form J).

The XRPD pattern of crystalline Form J material of 5-(3,4-dichlorophenyl)-N-((1R,2R)-2-hydroxycyclohexyl)-6-(2,2,2-trifluoroethoxy)nicotinamide, ethanol solvate, is shown in FIG. 33. Characteristic peaks include one or more of the peaks shown in Table 21.

TABLE 21

| Angle | d Value | Rel. Intensity |
|---|---|---|
| 5.077 | 17.39208 | 54.50% |
| 5.348 | 16.51019 | 23.90% |
| 6.927 | 12.74992 | 24.00% |
| 8.964 | 9.85765 | 28.50% |
| 10.163 | 8.69671 | 12.80% |
| 10.722 | 8.24428 | 11.90% |
| 12.14 | 7.28445 | 15.40% |
| 13.564 | 6.52276 | 7.20% |
| 13.887 | 6.37188 | 3.50% |
| 14.193 | 6.23518 | 3.60% |
| 14.407 | 6.14295 | 3.90% |
| 15.269 | 5.79794 | 7.50% |
| 15.861 | 5.58314 | 8.60% |
| 16.112 | 5.49646 | 9.90% |
| 17.475 | 5.07095 | 2.20% |
| 18.01 | 4.9214 | 31.30% |
| 18.449 | 4.80527 | 19.70% |
| 18.85 | 4.70393 | 44.30% |
| 19.481 | 4.55289 | 12.30% |
| 19.701 | 4.50252 | 23.00% |
| 20.304 | 4.3702 | 20.00% |
| 20.852 | 4.2566 | 100.00% |
| 21.399 | 4.149 | 17.10% |
| 21.994 | 4.03818 | 9.70% |
| 22.199 | 4.00128 | 28.10% |
| 22.528 | 3.94351 | 13.30% |
| 22.734 | 3.90835 | 12.60% |
| 23.19 | 3.83246 | 19.30% |
| 23.476 | 3.78646 | 31.30% |
| 23.755 | 3.74266 | 6.70% |
| 24.364 | 3.6504 | 21.40% |
| 24.86 | 3.57864 | 16.30% |
| 25.357 | 3.5096 | 3.40% |
| 25.563 | 3.48189 | 16.40% |
| 25.877 | 3.44032 | 10.90% |
| 26.392 | 3.37431 | 2.90% |
| 26.655 | 3.34162 | 6.20% |
| 27.14 | 3.28302 | 9.20% |
| 27.516 | 3.23903 | 3.80% |
| 27.949 | 3.18976 | 2.50% |
| 28.257 | 3.1557 | 13.10% |
| 28.49 | 3.13042 | 8.20% |
| 28.958 | 3.0809 | 5.50% |
| 29.286 | 3.04712 | 7.50% |
| 29.797 | 2.99601 | 7.60% |
| 30.37 | 2.94082 | 1.20% |
| 30.823 | 2.89863 | 1.90% |
| 31.064 | 2.87666 | 5.40% |
| 31.572 | 2.83149 | 3.20% |
| 32.05 | 2.79035 | 5.80% |
| 32.598 | 2.74467 | 2.60% |
| 33.179 | 2.69795 | 1.30% |
| 34.099 | 2.62723 | 3.20% |
| 34.392 | 2.60554 | 4.20% |
| 35.108 | 2.55398 | 3.30% |

TABLE 21-continued

| Angle | d Value | Rel. Intensity |
|---|---|---|
| 35.813 | 2.50535 | 2.50% |
| 36.131 | 2.48403 | 5.20% |
| 36.445 | 2.46332 | 6.70% |
| 36.972 | 2.42938 | 5.00% |
| 37.611 | 2.38957 | 5.30% |
| 38.198 | 2.3542 | 6.60% |
| 39.037 | 2.30554 | 2.20% |
| 39.402 | 2.28502 | 2.40% |
| 40.013 | 2.2515 | 2.30% |
| 40.274 | 2.23752 | 2.10% |
| 40.7 | 2.2151 | 4.70% |
| 41.447 | 2.17686 | 3.10% |

Example 11

Figure 34:
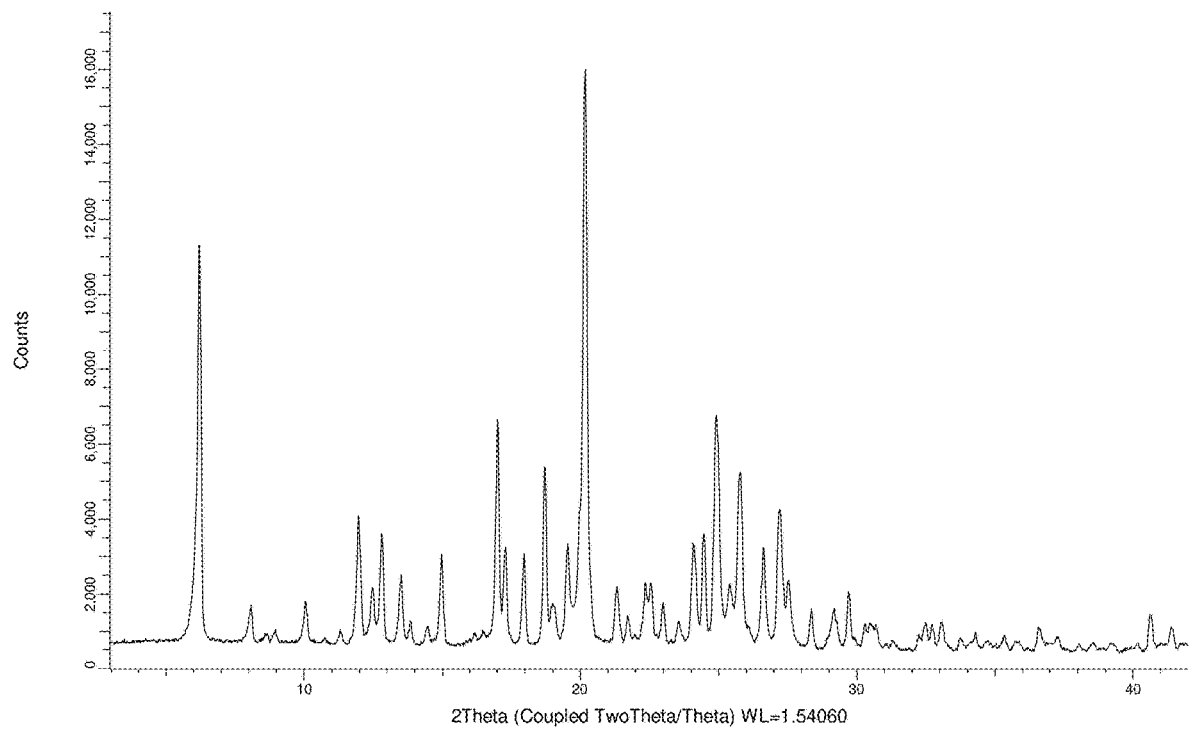
FIG. 34 depicts the X-ray powder diffraction (XRPD) pattern of 5-(3,4-dichlorophenyl)-N-((1R,2R)-2-hydroxycyclohexyl)-6-(2,2,2-trifluoroethoxy)nicotinamide, methanol solvate (Form K).

The XRPD pattern of crystalline Form K material of 5-(3,4-dichlorophenyl)-N-((1R,2R)-2-hydroxycyclohexyl)-6-(2,2,2-trifluoroethoxy)nicotinamide, methanol solvate, is shown in FIG. 34. Characteristic peaks include one or more of the peaks shown in Table 22.

TABLE 22

| Angle | d Value | Rel. Intensity |
|---|---|---|
| 5.077 | 17.39208 | 54.50% |
| 5.348 | 16.51019 | 23.90% |
| 6.927 | 12.74992 | 24.00% |
| 8.964 | 9.85765 | 28.50% |
| 10.163 | 8.69671 | 12.80% |
| 10.722 | 8.24428 | 11.90% |
| 12.14 | 7.28445 | 15.40% |
| 13.564 | 6.52276 | 7.20% |
| 13.887 | 6.37188 | 3.50% |
| 14.193 | 6.23518 | 3.60% |
| 14.407 | 6.14295 | 3.90% |
| 15.269 | 5.79794 | 7.50% |
| 15.861 | 5.58314 | 8.60% |
| 16.112 | 5.49646 | 9.90% |
| 17.475 | 5.07095 | 2.20% |
| 18.01 | 4.9214 | 31.30% |
| 18.449 | 4.80527 | 19.70% |
| 18.85 | 4.70393 | 44.30% |
| 19.481 | 4.55289 | 12.30% |
| 19.701 | 4.50252 | 23.00% |
| 20.304 | 4.3702 | 20.00% |
| 20.852 | 4.2566 | 100.00% |
| 21.399 | 4.149 | 17.10% |
| 21.994 | 4.03818 | 9.70% |
| 22.199 | 4.00128 | 28.10% |
| 22.528 | 3.94351 | 13.30% |
| 22.734 | 3.90835 | 12.60% |
| 23.19 | 3.83246 | 19.30% |
| 23.476 | 3.78646 | 31.30% |
| 23.755 | 3.74266 | 6.70% |
| 24.364 | 3.6504 | 21.40% |
| 24.86 | 3.57864 | 16.30% |
| 25.357 | 3.5096 | 3.40% |
| 25.563 | 3.48189 | 16.40% |
| 25.877 | 3.44032 | 10.90% |
| 26.392 | 3.37431 | 2.90% |
| 26.655 | 3.34162 | 6.20% |
| 27.14 | 3.28302 | 9.20% |
| 27.516 | 3.23903 | 3.80% |
| 27.949 | 3.18976 | 2.50% |
| 28.257 | 3.1557 | 13.10% |
| 28.49 | 3.13042 | 8.20% |
| 28.958 | 3.0809 | 5.50% |
| 29.286 | 3.04712 | 7.50% |
| 29.797 | 2.99601 | 7.60% |
| 30.37 | 2.94082 | 1.20% |
| 30.823 | 2.89863 | 1.90% |
| 31.064 | 2.87666 | 5.40% |
| 31.572 | 2.83149 | 3.20% |

TABLE 22-continued

| Angle | d Value | Rel. Intensity |
|---|---|---|
| 32.05 | 2.79035 | 5.80% |
| 32.598 | 2.74467 | 2.60% |
| 33.179 | 2.69795 | 1.30% |
| 34.099 | 2.62723 | 3.20% |
| 34.392 | 2.60554 | 4.20% |
| 35.108 | 2.55398 | 3.30% |
| 35.813 | 2.50535 | 2.50% |
| 36.131 | 2.48403 | 5.20% |
| 36.445 | 2.46332 | 6.70% |
| 36.972 | 2.42938 | 5.00% |
| 37.611 | 2.38957 | 5.30% |
| 38.198 | 2.3542 | 6.60% |
| 39.037 | 2.30554 | 2.20% |
| 39.402 | 2.28502 | 2.40% |
| 40.013 | 2.2515 | 2.30% |
| 40.274 | 2.23752 | 2.10% |
| 40.7 | 2.2151 | 4.70% |
| 41.447 | 2.17686 | 3.10% |

Example 12

Crystalline, Form L material of 5-(3,4-dichlorophenyl)-N-((1R,2R)-2-hydroxycyclohexyl)-6-(2,2,2-trifluoroethoxy)nicotinamide, hydrate, was prepared as follows. About 50 mg of crystalline Form E material of 5-(3,4-dichlorophenyl)-N-((1R,2R)-2-hydroxycyclohexyl)-6-(2,2,2-trifluoroethoxy)nicotinamide, anhydrate, was equilibrated in methanol at 50° C. for 1 week with stirring at 400 rpm. The obtained suspension was filtered through a 0.45 μm nylon membrane filter by centrifugation at 14,000 rpm. XRPD analysis of the wet cake material indicated that the material was crystalline with a pattern consistent with Form P. XRPD analysis of the dried material indicated that the material was crystalline with a pattern consistent with Form L.

Figure 35:
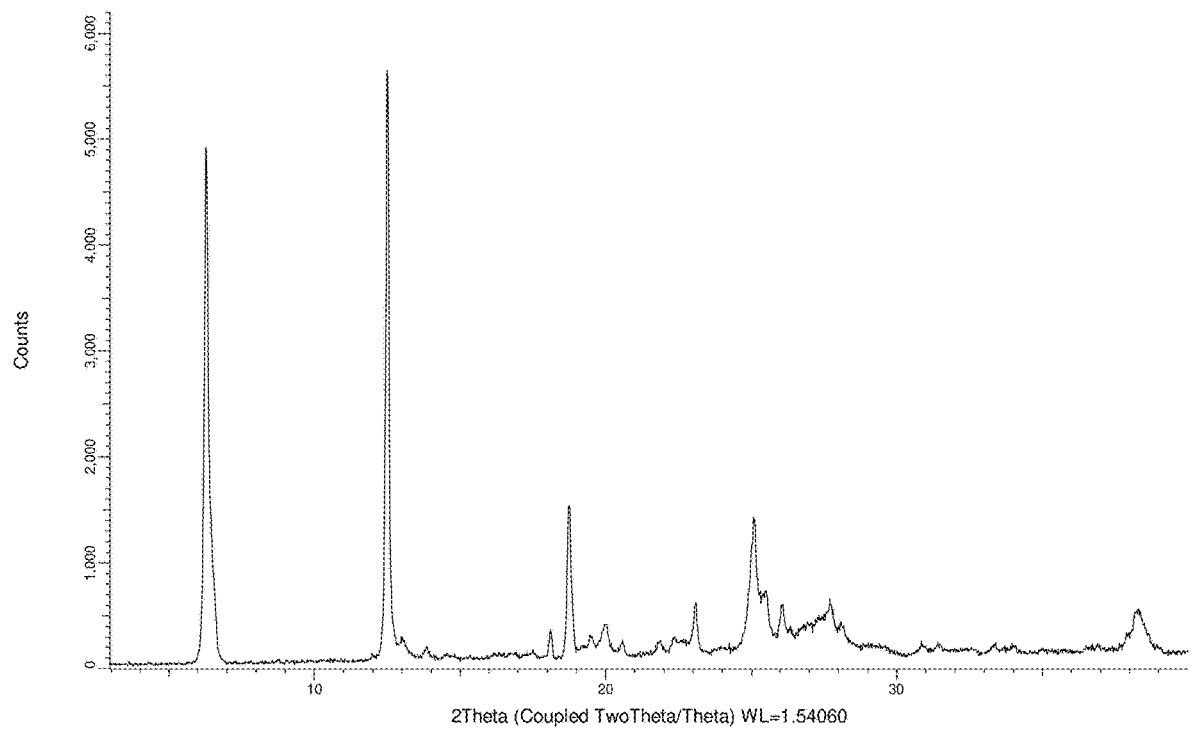
FIG. 35 depicts the X-ray powder diffraction (XRPD) pattern of 5-(3,4-dichlorophenyl)-N-((1R,2R)-2-hydroxycyclohexyl)-6-(2,2,2-trifluoroethoxy)nicotinamide, hydrate (Form L).

The XRPD pattern of crystalline Form L is shown in FIG. 35. Characteristic peaks include one or more of the peaks shown in Table 23.

TABLE 23

| Angle | d Value | Rel. Intensity |
|---|---|---|
| 5.077 | 17.39208 | 54.50% |
| 5.348 | 16.51019 | 23.90% |
| 6.927 | 12.74992 | 24.00% |
| 8.964 | 9.85765 | 28.50% |
| 10.163 | 8.69671 | 12.80% |
| 10.722 | 8.24428 | 11.90% |
| 12.14 | 7.28445 | 15.40% |
| 13.564 | 6.52276 | 7.20% |
| 13.887 | 6.37188 | 3.50% |
| 14.193 | 6.23518 | 3.60% |
| 14.407 | 6.14295 | 3.90% |
| 15.269 | 5.79794 | 7.50% |
| 15.861 | 5.58314 | 8.60% |
| 16.112 | 5.49646 | 9.90% |
| 17.475 | 5.07095 | 2.20% |
| 18.01 | 4.9214 | 31.30% |
| 18.449 | 4.80527 | 19.70% |
| 18.85 | 4.70393 | 44.30% |
| 19.481 | 4.55289 | 12.30% |
| 19.701 | 4.50252 | 23.00% |
| 20.304 | 4.3702 | 20.00% |
| 20.852 | 4.2566 | 100.00% |
| 21.399 | 4.149 | 17.10% |
| 21.994 | 4.03818 | 9.70% |
| 22.199 | 4.00128 | 28.10% |
| 22.528 | 3.94351 | 13.30% |
| 22.734 | 3.90835 | 12.60% |
| 23.19 | 3.83246 | 19.30% |
| 23.476 | 3.78646 | 31.30% |

TABLE 23-continued

| Angle | d Value | Rel. Intensity |
|---|---|---|
| 23.755 | 3.74266 | 6.70% |
| 24.364 | 3.6504 | 21.40% |
| 24.86 | 3.57864 | 16.30% |
| 25.357 | 3.5096 | 3.40% |
| 25.563 | 3.48189 | 16.40% |
| 25.877 | 3.44032 | 10.90% |
| 26.392 | 3.37431 | 2.90% |
| 26.655 | 3.34162 | 6.20% |
| 27.14 | 3.28302 | 9.20% |
| 27.516 | 3.23903 | 3.80% |
| 27.949 | 3.18976 | 2.50% |
| 28.257 | 3.1557 | 13.10% |
| 28.49 | 3.13042 | 8.20% |
| 28.958 | 3.0809 | 5.50% |
| 29.286 | 3.04712 | 7.50% |
| 29.797 | 2.99601 | 7.60% |
| 30.37 | 2.94082 | 1.20% |
| 30.823 | 2.89863 | 1.90% |
| 31.064 | 2.87666 | 5.40% |
| 31.572 | 2.83149 | 3.20% |
| 32.05 | 2.79035 | 5.80% |
| 32.598 | 2.74467 | 2.60% |
| 33.179 | 2.69795 | 1.30% |
| 34.099 | 2.62723 | 3.20% |
| 34.392 | 2.60554 | 4.20% |
| 35.108 | 2.55398 | 3.30% |
| 35.813 | 2.50535 | 2.50% |
| 36.131 | 2.48403 | 5.20% |
| 36.445 | 2.46332 | 6.70% |
| 36.972 | 2.42938 | 5.00% |
| 37.611 | 2.38957 | 5.30% |
| 38.198 | 2.3542 | 6.60% |
| 39.037 | 2.30554 | 2.20% |
| 39.402 | 2.28502 | 2.40% |
| 40.013 | 2.2515 | 2.30% |
| 40.274 | 2.23752 | 2.10% |
| 40.7 | 2.2151 | 4.70% |
| 41.447 | 2.17686 | 3.10% |

Figure 36:
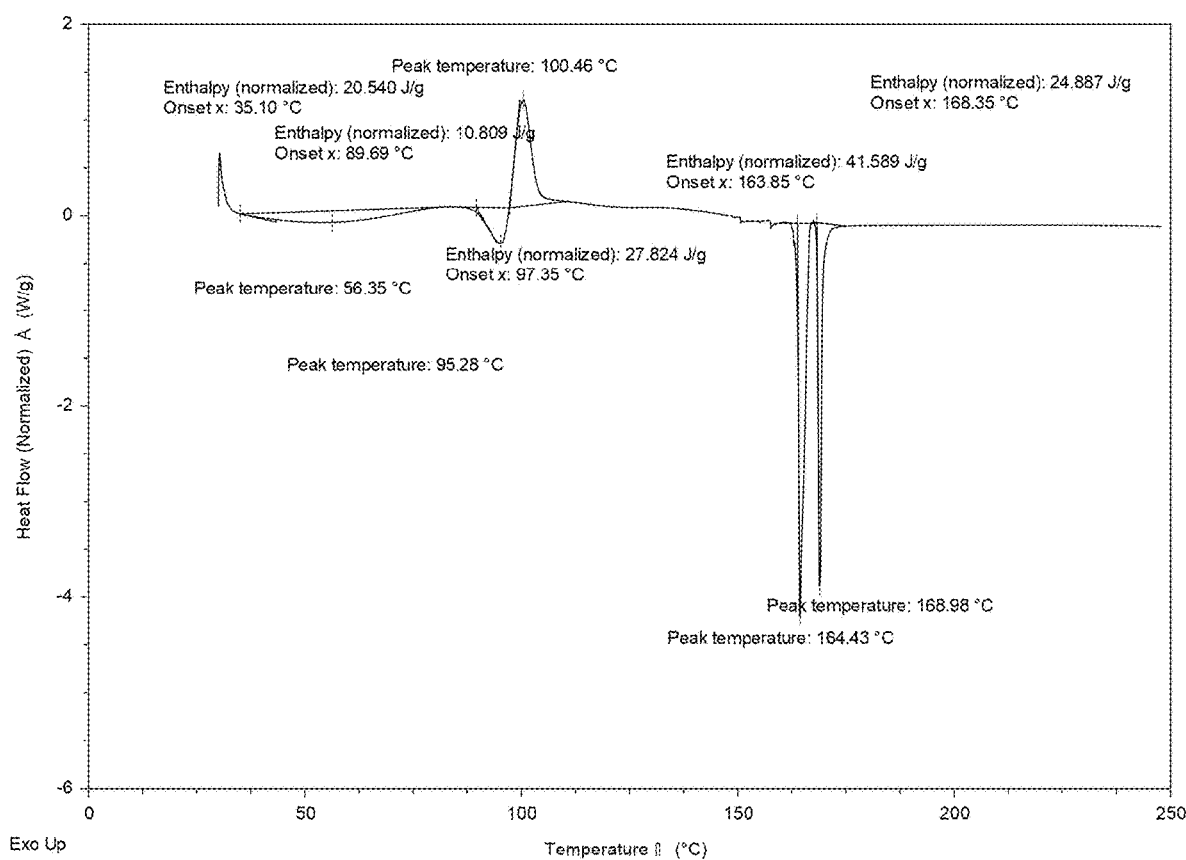
FIG. 36 depicts the characterization of Form L by differential scanning calorimetry (DSC).

FIG. 36 depicts the differential scanning calorimetry (DSC) profile of crystalline Form L. As shown in FIG. 36, crystalline Form L shows a characteristic endotherm with an onset of about 35° C. and a peak of about 56° C.; a characteristic endotherm with an onset of about 90° C. and a peak of about 95° C.; a characteristic exotherm with an onset of about 97° C. and a peak of about 100° C.; a characteristic endotherm with an onset and a peak of about 164° C.; and a characteristic endotherm with an onset of about 168° C. and a peak of about 169° C. Crystalline Form L displayed a thermogravimetric analysis (TGA) profile showing a mass loss of about 2.2 wt. % up to about 120° C. Karl Fischer (KF) analysis showed 4.4% water by weight (1.18 equivalent by molar ratio).

Example 13

Crystalline, Form M material of 5-(3,4-dichlorophenyl)-N-((1R,2R)-2-hydroxycyclohexyl)-6-(2,2,2-trifluoroethoxy)nicotinamide, hydrate, was prepared as follows. About 50 mg of crystalline Form E material of 5-(3,4-dichlorophenyl)-N-((1R,2R)-2-hydroxycyclohexyl)-6-(2,2,2-trifluoroethoxy)nicotinamide, anhydrate, was dissolved in a minimal amount of acetonitrile at 50° C., and the solution filtered through a 0.45 μm nylon membrane filter by centrifugation at 14,000 rpm. The clear solution was cooled to 5° C. at 0.1° C./min, and the precipitate collected by centrifugation filtration through a 0.45 μm nylon membrane filter at 14,000 rpm. XRPD analysis of the wet cake material indicated that the material was crystalline with a pattern consistent with Form Q. XRPD analysis of the dried material indicated that the material was crystalline with a pattern consistent with Form M.

Figure 38:
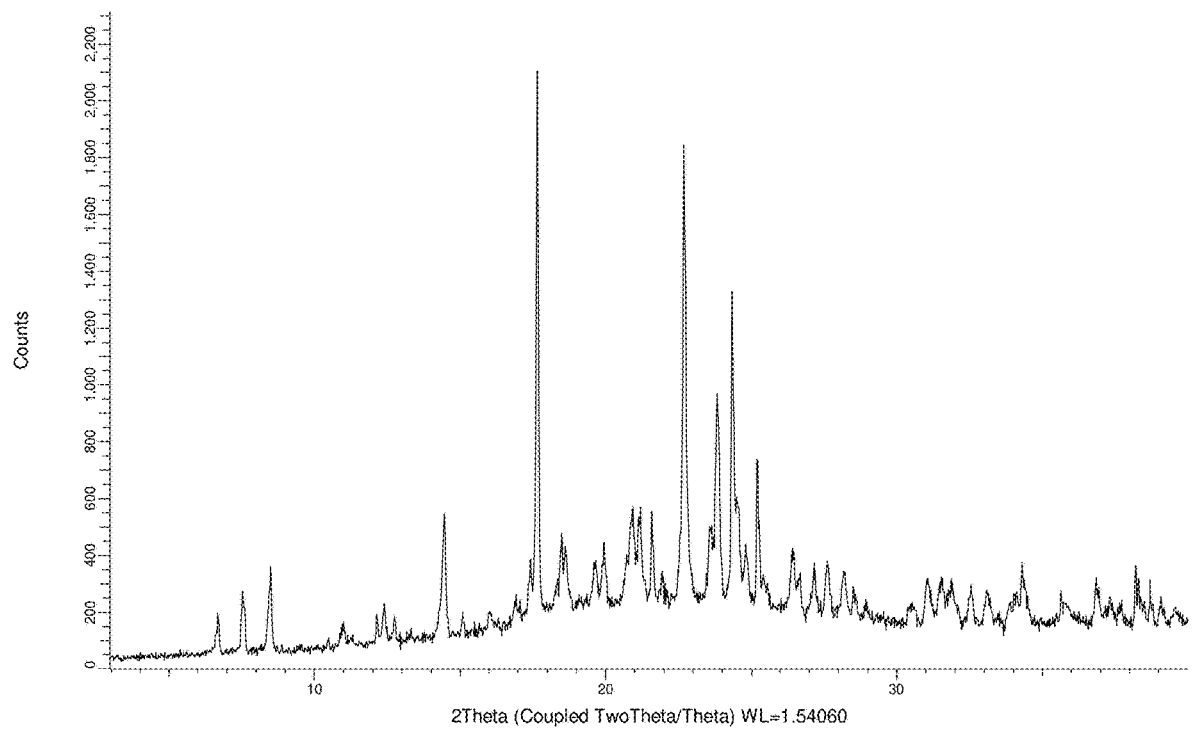
FIG. 38 depicts the X-ray powder diffraction (XRPD) pattern of 5-(3,4-dichlorophenyl)-N-((1R,2R)-2-hydroxycyclohexyl)-6-(2,2,2-trifluoroethoxy)nicotinamide, hydrate (Form M).

The XRPD pattern of crystalline Form M is shown in FIG. 38. Characteristic peaks include one or more of the peaks shown in Table 24.

TABLE 24

| Angle | d Value | Rel. Intensity |
|---|---|---|
| 5.077 | 17.39208 | 54.50% |
| 5.348 | 16.51019 | 23.90% |
| 6.927 | 12.74992 | 24.00% |
| 8.964 | 9.85765 | 28.50% |
| 10.163 | 8.69671 | 12.80% |
| 10.722 | 8.24428 | 11.90% |
| 12.14 | 7.28445 | 15.40% |
| 13.564 | 6.52276 | 7.20% |
| 13.887 | 6.37188 | 3.50% |
| 14.193 | 6.23518 | 3.60% |
| 14.407 | 6.14295 | 3.90% |
| 15.269 | 5.79794 | 7.50% |
| 15.861 | 5.58314 | 8.60% |
| 16.112 | 5.49646 | 9.90% |
| 17.475 | 5.07095 | 2.20% |
| 18.01 | 4.9214 | 31.30% |
| 18.449 | 4.80527 | 19.70% |
| 18.85 | 4.70393 | 44.30% |
| 19.481 | 4.55289 | 12.30% |
| 19.701 | 4.50252 | 23.00% |
| 20.304 | 4.3702 | 20.00% |
| 20.852 | 4.2566 | 100.00% |
| 21.399 | 4.149 | 17.10% |
| 21.994 | 4.03818 | 9.70% |
| 22.199 | 4.00128 | 28.10% |
| 22.528 | 3.94351 | 13.30% |
| 22.734 | 3.90835 | 12.60% |
| 23.19 | 3.83246 | 19.30% |
| 23.476 | 3.78646 | 31.30% |
| 23.755 | 3.74266 | 6.70% |
| 24.364 | 3.6504 | 21.40% |
| 24.86 | 3.57864 | 16.30% |
| 25.357 | 3.5096 | 3.40% |
| 25.563 | 3.48189 | 16.40% |
| 25.877 | 3.44032 | 10.90% |
| 26.392 | 3.37431 | 2.90% |
| 26.655 | 3.34162 | 6.20% |
| 27.14 | 3.28302 | 9.20% |
| 27.516 | 3.23903 | 3.80% |
| 27.949 | 3.18976 | 2.50% |
| 28.257 | 3.1557 | 13.10% |
| 28.49 | 3.13042 | 8.20% |
| 28.958 | 3.0809 | 5.50% |
| 29.286 | 3.04712 | 7.50% |
| 29.797 | 2.99601 | 7.60% |
| 30.37 | 2.94082 | 1.20% |
| 30.823 | 2.89863 | 1.90% |
| 31.064 | 2.87666 | 5.40% |
| 31.572 | 2.83149 | 3.20% |
| 32.05 | 2.79035 | 5.80% |
| 32.598 | 2.74467 | 2.60% |
| 33.179 | 2.69795 | 1.30% |
| 34.099 | 2.62723 | 3.20% |
| 34.392 | 2.60554 | 4.20% |
| 35.108 | 2.55398 | 3.30% |
| 35.813 | 2.50535 | 2.50% |
| 36.131 | 2.48403 | 5.20% |
| 36.445 | 2.46332 | 6.70% |
| 36.972 | 2.42938 | 5.00% |
| 37.611 | 2.38957 | 5.30% |
| 38.198 | 2.3542 | 6.60% |
| 39.037 | 2.30554 | 2.20% |
| 39.402 | 2.28502 | 2.40% |
| 40.013 | 2.2515 | 2.30% |
| 40.274 | 2.23752 | 2.10% |
| 40.7 | 2.2151 | 4.70% |
| 41.447 | 2.17686 | 3.10% |

Figure 39:
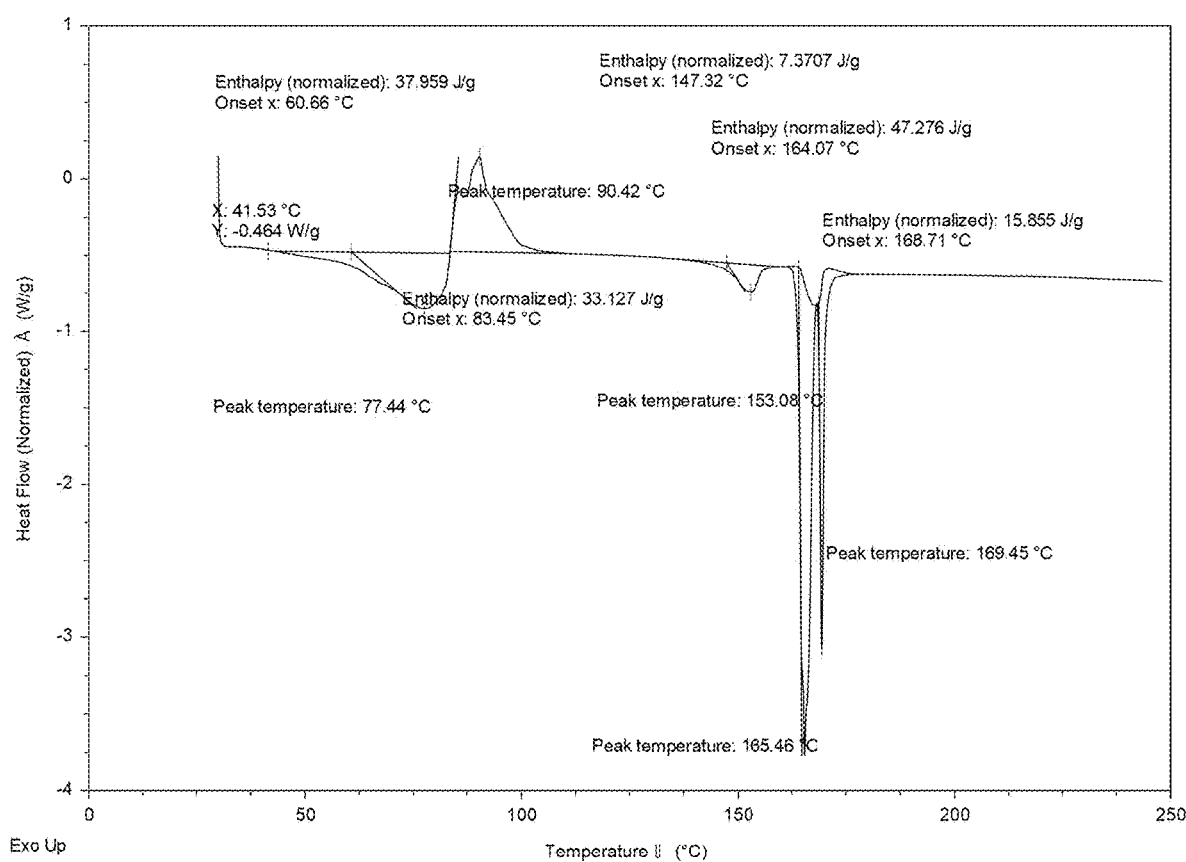
FIG. 39 depicts the characterization of Form M by differential scanning calorimetry (DSC).

FIG. 39 depicts the differential scanning calorimetry (DSC) profile of crystalline Form M. As shown in FIG. 39, crystalline Form M shows a characteristic endotherm with an onset of about 61° C. and a peak of about 77° C.; a characteristic exotherm with an onset of about 83° C. and a peak of about 90° C.; a characteristic endotherm with an onset of about 147° C. and a peak of about 153° C.; a characteristic endotherm with an onset of about 164° C. and a peak of about 165; and a characteristic endotherm with an onset and a peak of about 169° C. Crystalline Form M displayed a thermogravimetric analysis (TGA) profile showing a mass loss of about 3.4 wt. % up to about 120° C. Karl Fischer (KF) analysis showed 3.5% water by weight (0.93 equivalent by molar ratio).

Example 14

Crystalline, Form N material of 5-(3,4-dichlorophenyl)-N-((1R,2R)-2-hydroxycyclohexyl)-6-(2,2,2-trifluoroethoxy)nicotinamide, hydrate, was prepared as follows. About 50 mg of crystalline Form E material of 5-(3,4-dichlorophenyl)-N-((1R,2R)-2-hydroxycyclohexyl)-6-(2,2,2-trifluoroethoxy)nicotinamide, anhydrate, was equilibrated in 1,4-dioxane at 50° C. for 1 week with stirring at 400 rpm. The obtained suspension was filtered through a 0.45 μm nylon membrane filter by centrifugation at 14,000 rpm. XRPD analysis of the wet cake material indicated that the material was crystalline with a pattern consistent with Form R. XRPD analysis of the dried material indicated that the material was crystalline with a pattern consistent with Form N.

Figure 41:
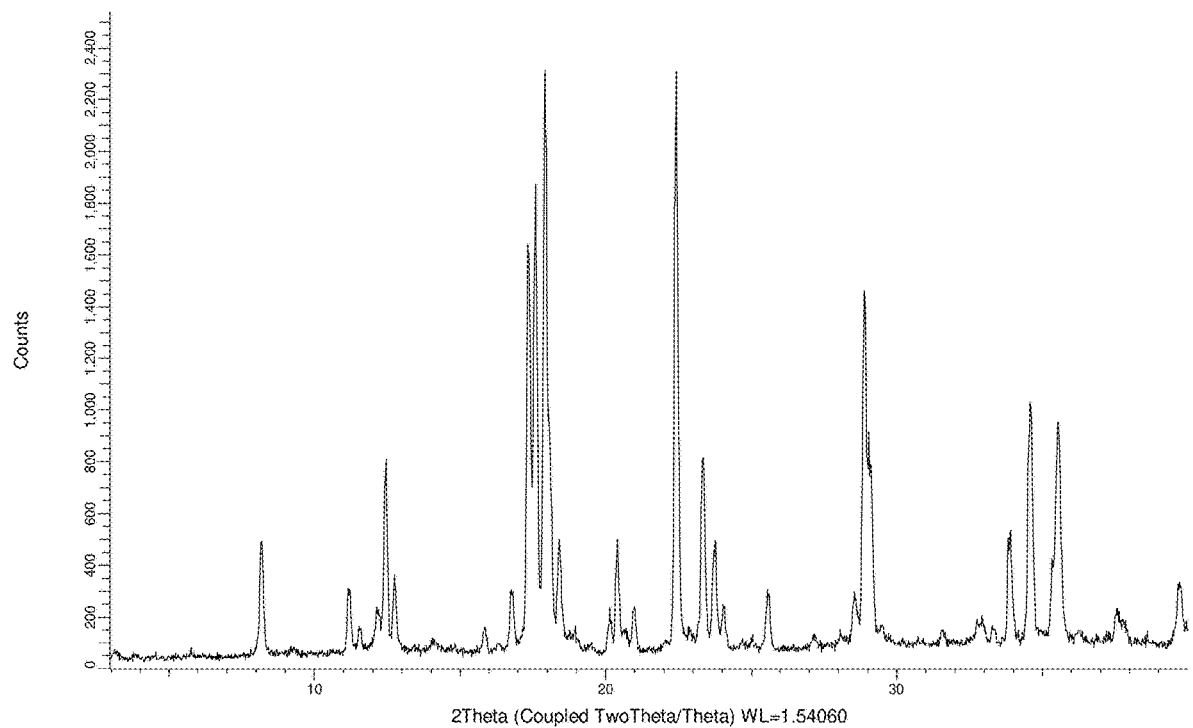
FIG. 41 depicts the X-ray powder diffraction (XRPD) pattern of 5-(3,4-dichlorophenyl)-N-((1R,2R)-2-hydroxycyclohexyl)-6-(2,2,2-trifluoroethoxy)nicotinamide, hydrate (Form N).

The XRPD pattern of crystalline Form N is shown in FIG. 41. Characteristic peaks include one or more of the peaks shown in Table 25.

TABLE 25

| Angle | d Value | Rel. Intensity |
|---|---|---|
| 5.077 | 17.39208 | 54.50% |
| 5.348 | 16.51019 | 23.90% |
| 6.927 | 12.74992 | 24.00% |
| 8.964 | 9.85765 | 28.50% |
| 10.163 | 8.69671 | 12.80% |
| 10.722 | 8.24428 | 11.90% |
| 12.14 | 7.28445 | 15.40% |
| 13.564 | 6.52276 | 7.20% |
| 13.887 | 6.37188 | 3.50% |
| 14.193 | 6.23518 | 3.60% |
| 14.407 | 6.14295 | 3.90% |
| 15.269 | 5.79794 | 7.50% |
| 15.861 | 5.58314 | 8.60% |
| 16.112 | 5.49646 | 9.90% |
| 17.475 | 5.07095 | 2.20% |
| 18.01 | 4.9214 | 31.30% |
| 18.449 | 4.80527 | 19.70% |
| 18.85 | 4.70393 | 44.30% |
| 19.481 | 4.55289 | 12.30% |
| 19.701 | 4.50252 | 23.00% |
| 20.304 | 4.3702 | 20.00% |
| 20.852 | 4.2566 | 100.00% |
| 21.399 | 4.149 | 17.10% |
| 21.994 | 4.03818 | 9.70% |
| 22.199 | 4.00128 | 28.10% |
| 22.528 | 3.94351 | 13.30% |
| 22.734 | 3.90835 | 12.60% |
| 23.19 | 3.83246 | 19.30% |
| 23.476 | 3.78646 | 31.30% |
| 23.755 | 3.74266 | 6.70% |
| 24.364 | 3.6504 | 21.40% |
| 24.86 | 3.57864 | 16.30% |
| 25.357 | 3.5096 | 3.40% |
| 25.563 | 3.48189 | 16.40% |
| 25.877 | 3.44032 | 10.90% |
| 26.392 | 3.37431 | 2.90% |
| 26.655 | 3.34162 | 6.20% |
| 27.14 | 3.28302 | 9.20% |
| 27.516 | 3.23903 | 3.80% |

TABLE 25-continued

| Angle | d Value | Rel. Intensity |
|---|---|---|
| 27.949 | 3.18976 | 2.50% |
| 28.257 | 3.1557 | 13.10% |
| 28.49 | 3.13042 | 8.20% |
| 28.958 | 3.0809 | 5.50% |
| 29.286 | 3.04712 | 7.50% |
| 29.797 | 2.99601 | 7.60% |
| 30.37 | 2.94082 | 1.20% |
| 30.823 | 2.89863 | 1.90% |
| 31.064 | 2.87666 | 5.40% |
| 31.572 | 2.83149 | 3.20% |
| 32.05 | 2.79035 | 5.80% |
| 32.598 | 2.74467 | 2.60% |
| 33.179 | 2.69795 | 1.30% |
| 34.099 | 2.62723 | 3.20% |
| 34.392 | 2.60554 | 4.20% |
| 35.108 | 2.55398 | 3.30% |
| 35.813 | 2.50535 | 2.50% |
| 36.131 | 2.48403 | 5.20% |
| 36.445 | 2.46332 | 6.70% |
| 36.972 | 2.42938 | 5.00% |
| 37.611 | 2.38957 | 5.30% |
| 38.198 | 2.3542 | 6.60% |
| 39.037 | 2.30554 | 2.20% |
| 39.402 | 2.28502 | 2.40% |
| 40.013 | 2.2515 | 2.30% |
| 40.274 | 2.23752 | 2.10% |
| 40.7 | 2.2151 | 4.70% |
| 41.447 | 2.17686 | 3.10% |

Figure 42:
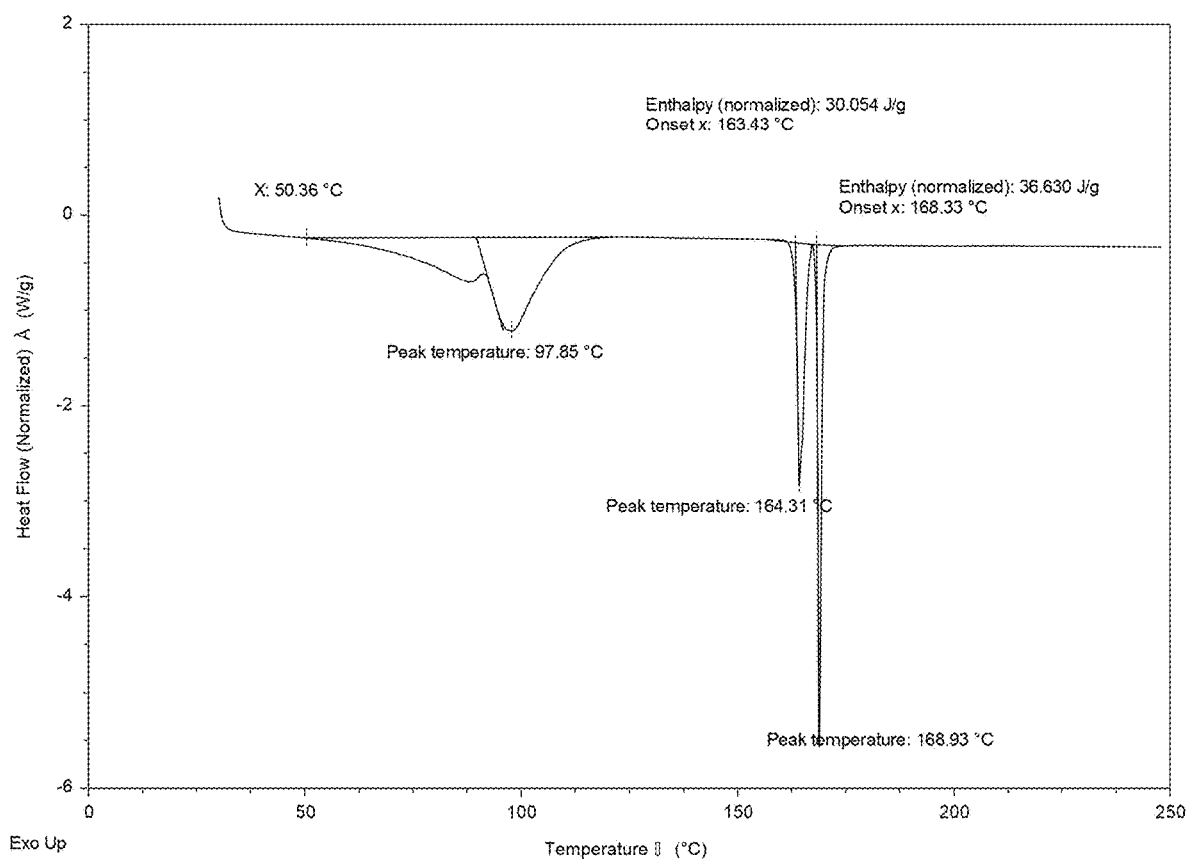
FIG. 42 depicts the characterization of Form N by differential scanning calorimetry (DSC).

FIG. 42 depicts the differential scanning calorimetry (DSC) profile of crystalline Form N. As shown in FIG. 42, crystalline Form N shows a characteristic endotherm with an onset of about 50° C. and a peak of about 98° C.; a characteristic endotherm with an onset of about 163° C. and a peak of about 164° C.; and a characteristic endotherm with an onset of about 168° C. and a peak of about 169° C. Crystalline Form N displayed a thermogravimetric analysis (TGA) profile showing a mass loss of about 3.9 wt. % up to about 120° C. Karl Fischer (KF) analysis showed 4.2% water by weight (1.13 equivalent by molar ratio).

Example 15

Crystalline, Form O material of 5-(3,4-dichlorophenyl)-N-((1R,2R)-2-hydroxycyclohexyl)-6-(2,2,2-trifluoroethoxy)nicotinamide, hydrate, was prepared as follows. About 50 mg of crystalline Form E material of 5-(3,4-dichlorophenyl)-N-((1R,2R)-2-hydroxycyclohexyl)-6-(2,2,2-trifluoroethoxy)nicotinamide, anhydrate, was equilibrated in trifluoroethanol at 50° C. for 1 week with stirring at 400 rpm. The obtained suspension was filtered through a 0.45 μm nylon membrane filter by centrifugation at 14,000 rpm. XRPD analysis of the wet cake material indicated that the material was crystalline with a pattern consistent with Form S. XRPD analysis of the dried material indicated that the material was crystalline with a pattern consistent with Form O.

Figure 44:
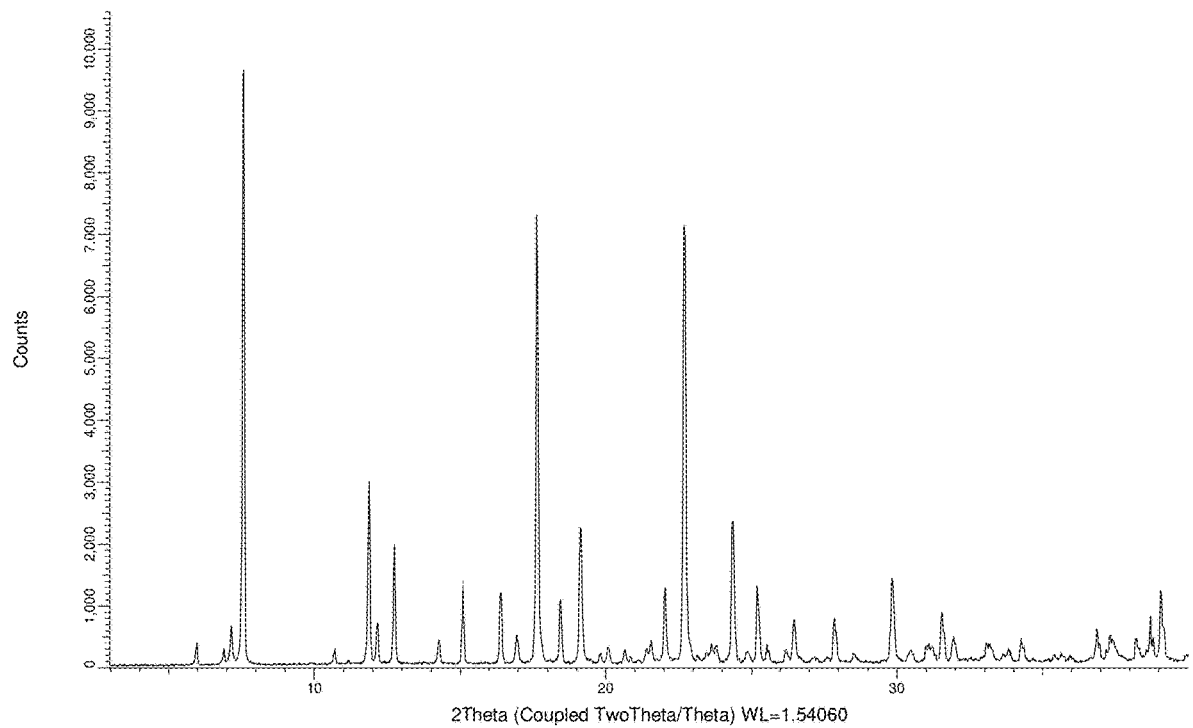
FIG. 44 depicts the X-ray powder diffraction (XRPD) pattern of 5-(3,4-dichlorophenyl)-N-((1R,2R)-2-hydroxycyclohexyl)-6-(2,2,2-trifluoroethoxy)nicotinamide, hydrate (Form O).

The XRPD pattern of crystalline Form O is shown in FIG. 44. Characteristic peaks include one or more of the peaks shown in Table 26.

TABLE 26

| Angle | d Value | Rel. Intensity |
|---|---|---|
| 5.077 | 17.39208 | 54.50% |
| 5.348 | 16.51019 | 23.90% |
| 6.927 | 12.74992 | 24.00% |
| 8.964 | 9.85765 | 28.50% |
| 10.163 | 8.69671 | 12.80% |

TABLE 26-continued

| Angle | d Value | Rel. Intensity |
|---|---|---|
| 10.722 | 8.24428 | 11.90% |
| 12.14 | 7.28445 | 15.40% |
| 13.564 | 6.52276 | 7.20% |
| 13.887 | 6.37188 | 3.50% |
| 14.193 | 6.23518 | 3.60% |
| 14.407 | 6.14295 | 3.90% |
| 15.269 | 5.79794 | 7.50% |
| 15.861 | 5.58314 | 8.60% |
| 16.112 | 5.49646 | 9.90% |
| 17.475 | 5.07095 | 2.20% |
| 18.01 | 4.9214 | 31.30% |
| 18.449 | 4.80527 | 19.70% |
| 18.85 | 4.70393 | 44.30% |
| 19.481 | 4.55289 | 12.30% |
| 19.701 | 4.50252 | 23.00% |
| 20.304 | 4.3702 | 20.00% |
| 20.852 | 4.2566 | 100.00% |
| 21.399 | 4.149 | 17.10% |
| 21.994 | 4.03818 | 9.70% |
| 22.199 | 4.00128 | 28.10% |
| 22.528 | 3.94351 | 13.30% |
| 22.734 | 3.90835 | 12.60% |
| 23.19 | 3.83246 | 19.30% |
| 23.476 | 3.78646 | 31.30% |
| 23.755 | 3.74266 | 6.70% |
| 24.364 | 3.6504 | 21.40% |
| 24.86 | 3.57864 | 16.30% |
| 25.357 | 3.5096 | 3.40% |
| 25.563 | 3.48189 | 16.40% |
| 25.877 | 3.44032 | 10.90% |
| 26.392 | 3.37431 | 2.90% |
| 26.655 | 3.34162 | 6.20% |
| 27.14 | 3.28302 | 9.20% |
| 27.516 | 3.23903 | 3.80% |
| 27.949 | 3.18976 | 2.50% |
| 28.257 | 3.1557 | 13.10% |
| 28.49 | 3.13042 | 8.20% |
| 28.958 | 3.0809 | 5.50% |
| 29.286 | 3.04712 | 7.50% |
| 29.797 | 2.99601 | 7.60% |
| 30.37 | 2.94082 | 1.20% |
| 30.823 | 2.89863 | 1.90% |
| 31.064 | 2.87666 | 5.40% |
| 31.572 | 2.83149 | 3.20% |
| 32.05 | 2.79035 | 5.80% |
| 32.598 | 2.74467 | 2.60% |
| 33.179 | 2.69795 | 1.30% |
| 34.099 | 2.62723 | 3.20% |
| 34.392 | 2.60554 | 4.20% |
| 35.108 | 2.55398 | 3.30% |
| 35.813 | 2.50535 | 2.50% |
| 36.131 | 2.48403 | 5.20% |
| 36.445 | 2.46332 | 6.70% |
| 36.972 | 2.42938 | 5.00% |
| 37.611 | 2.38957 | 5.30% |
| 38.198 | 2.3542 | 6.60% |
| 39.037 | 2.30554 | 2.20% |
| 39.402 | 2.28502 | 2.40% |
| 40.013 | 2.2515 | 2.30% |
| 40.274 | 2.23752 | 2.10% |
| 40.7 | 2.2151 | 4.70% |
| 41.447 | 2.17686 | 3.10% |

FIG. 44 depicts the differential scanning calorimetry (DSC) profile of crystalline Form O. As shown in FIG. 44, crystalline Form O shows a characteristic endotherm with an onset of about 83° C. and a peak of about 88° C.; a characteristic exotherm with an onset of about 91° C. and a peak of about 95° C.; a characteristic endotherm with an onset of about 164° C. and a peak of about 165° C.; and a characteristic endotherm with an onset of about 169° C. and a peak of about 170° C. Crystalline Form O displayed a thermogravimetric analysis (TGA) profile showing a mass loss of about 1.5 wt. % up to about 160¹° C. Karl Fischer (KF) analysis showed 3.2% water by weight (0.85 equivalent by molar ratio).

Example 16

Figure 47:
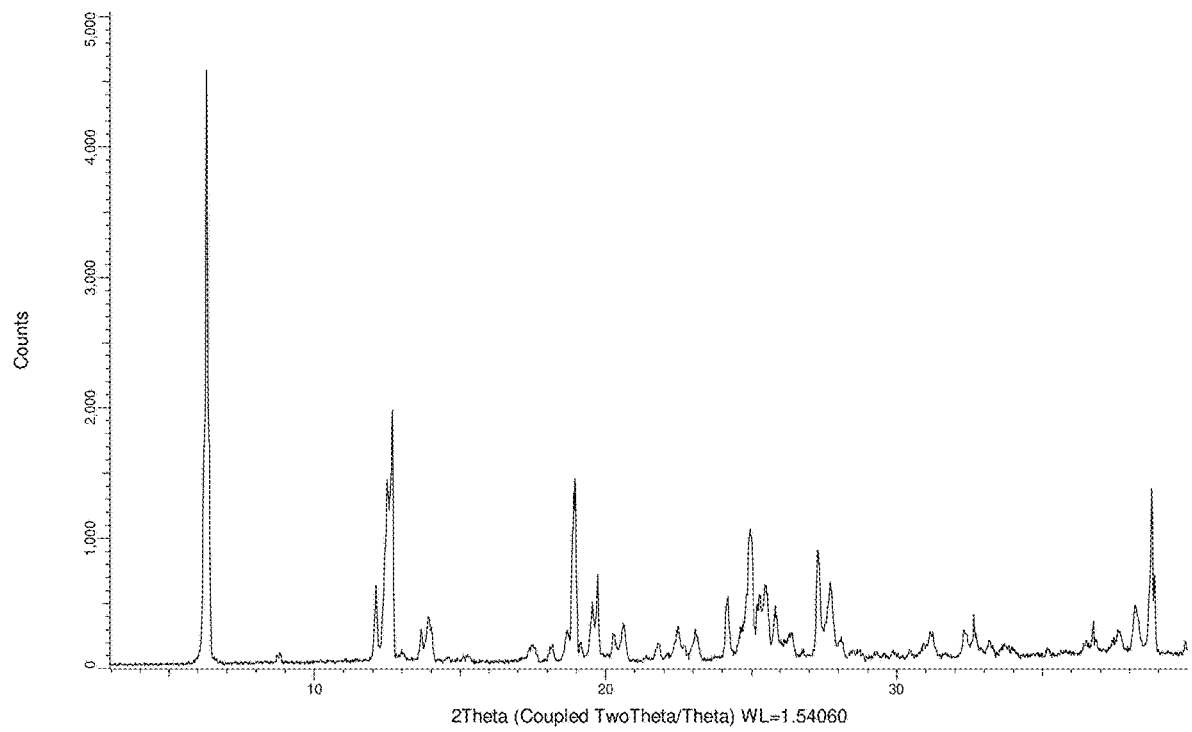
FIG. 47 depicts the X-ray powder diffraction (XRPD) pattern of 5-(3,4-dichlorophenyl)-N-((1R,2R)-2-hydroxycyclohexyl)-6-(2,2,2-trifluoroethoxy)nicotinamide, methanol solvate (Form P).

The XRPD pattern of crystalline Form P material of 5-(3,4-dichlorophenyl)-N-((1R,2R)-2-hydroxycyclohexyl)-6-(2,2,2-trifluoroethoxy)nicotinamide, methanol solvate, prepared according to the procedure in Example 12, is shown in FIG. 47. Characteristic peaks include one or more of the peaks shown in Table 27.

TABLE 27

| Angle | d Value | Rel. Intensity |
|---|---|---|
| 5.077 | 17.39208 | 54.50% |
| 5.348 | 16.51019 | 23.90% |
| 6.927 | 12.74992 | 24.00% |
| 8.964 | 9.85765 | 28.50% |
| 10.163 | 8.69671 | 12.80% |
| 10.722 | 8.24428 | 11.90% |
| 12.14 | 7.28445 | 15.40% |
| 13.564 | 6.52276 | 7.20% |
| 13.887 | 6.37188 | 3.50% |
| 14.193 | 6.23518 | 3.60% |
| 14.407 | 6.14295 | 3.90% |
| 15.269 | 5.79794 | 7.50% |
| 15.861 | 5.58314 | 8.60% |
| 16.112 | 5.49646 | 9.90% |
| 17.475 | 5.07095 | 2.20% |
| 18.01 | 4.9214 | 31.30% |
| 18.449 | 4.80527 | 19.70% |
| 18.85 | 4.70393 | 44.30% |
| 19.481 | 4.55289 | 12.30% |
| 19.701 | 4.50252 | 23.00% |
| 20.304 | 4.3702 | 20.00% |
| 20.852 | 4.2566 | 100.00% |
| 21.399 | 4.149 | 17.10% |
| 21.994 | 4.03818 | 9.70% |
| 22.199 | 4.00128 | 28.10% |
| 22.528 | 3.94351 | 13.30% |
| 22.734 | 3.90835 | 12.60% |
| 23.19 | 3.83246 | 19.30% |
| 23.476 | 3.78646 | 31.30% |
| 23.755 | 3.74266 | 6.70% |
| 24.364 | 3.6504 | 21.40% |
| 24.86 | 3.57864 | 16.30% |
| 25.357 | 3.5096 | 3.40% |
| 25.563 | 3.48189 | 16.40% |
| 25.877 | 3.44032 | 10.90% |
| 26.392 | 3.37431 | 2.90% |
| 26.655 | 3.34162 | 6.20% |
| 27.14 | 3.28302 | 9.20% |
| 27.516 | 3.23903 | 3.80% |
| 27.949 | 3.18976 | 2.50% |
| 28.257 | 3.1557 | 13.10% |
| 28.49 | 3.13042 | 8.20% |
| 28.958 | 3.0809 | 5.50% |
| 29.286 | 3.04712 | 7.50% |
| 29.797 | 2.99601 | 7.60% |
| 30.37 | 2.94082 | 1.20% |
| 30.823 | 2.89863 | 1.90% |
| 31.064 | 2.87666 | 5.40% |
| 31.572 | 2.83149 | 3.20% |
| 32.05 | 2.79035 | 5.80% |
| 32.598 | 2.74467 | 2.60% |
| 33.179 | 2.69795 | 1.30% |
| 34.099 | 2.62723 | 3.20% |
| 34.392 | 2.60554 | 4.20% |
| 35.108 | 2.55398 | 3.30% |
| 35.813 | 2.50535 | 2.50% |
| 36.131 | 2.48403 | 5.20% |
| 36.445 | 2.46332 | 6.70% |
| 36.972 | 2.42938 | 5.00% |
| 37.611 | 2.38957 | 5.30% |
| 38.198 | 2.3542 | 6.60% |
| 39.037 | 2.30554 | 2.20% |

TABLE 27-continued

| Angle | d Value | Rel. Intensity |
|---|---|---|
| 39.402 | 2.28502 | 2.40% |
| 40.013 | 2.2515 | 2.30% |
| 40.274 | 2.23752 | 2.10% |
| 40.7 | 2.2151 | 4.70% |
| 41.447 | 2.17686 | 3.10% |

Example 17

Figure 48:
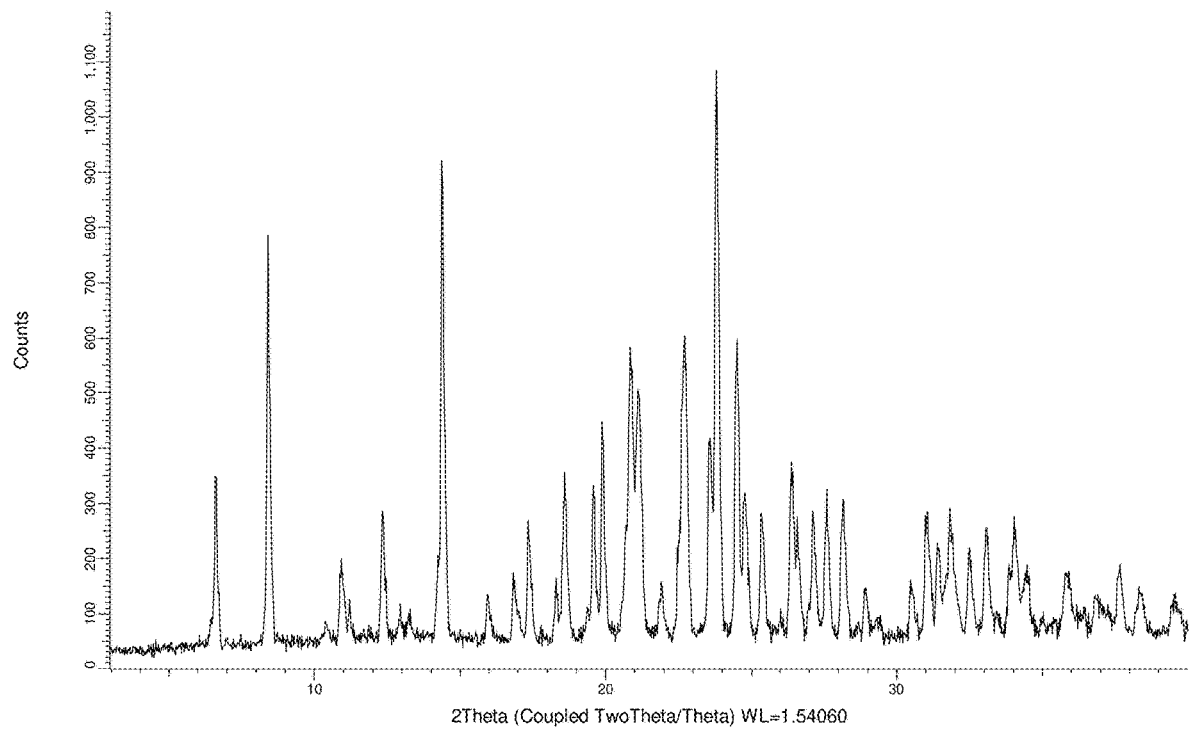
FIG. 48 depicts the X-ray powder diffraction (XRPD) pattern of 5-(3,4-dichlorophenyl)-N-((1R,2R)-2-hydroxycyclohexyl)-6-(2,2,2-trifluoroethoxy)nicotinamide, acetonitrile solvate (Form Q).

The XRPD pattern of crystalline Form Q material of 5-(3,4-dichlorophenyl)-N-((1R,2R)-2-hydroxycyclohexyl)-6-(2,2,2-trifluoroethoxy)nicotinamide, acetonitrile solvate, prepared according to the procedure in Example 13, is shown in FIG. 48. Characteristic peaks include one or more of the peaks shown in Table 28.

TABLE 28

| Angle | d Value | Rel. Intensity |
|---|---|---|
| 5.077 | 17.39208 | 54.50% |
| 5.348 | 16.51019 | 23.90% |
| 6.927 | 12.74992 | 24.00% |
| 8.964 | 9.85765 | 28.50% |
| 10.163 | 8.69671 | 12.80% |
| 10.722 | 8.24428 | 11.90% |
| 12.14 | 7.28445 | 15.40% |
| 13.564 | 6.52276 | 7.20% |
| 13.887 | 6.37188 | 3.50% |
| 14.193 | 6.23518 | 3.60% |
| 14.407 | 6.14295 | 3.90% |
| 15.269 | 5.79794 | 7.50% |
| 15.861 | 5.58314 | 8.60% |
| 16.112 | 5.49646 | 9.90% |
| 17.475 | 5.07095 | 2.20% |
| 18.01 | 4.9214 | 31.30% |
| 18.449 | 4.80527 | 19.70% |
| 18.85 | 4.70393 | 44.30% |
| 19.481 | 4.55289 | 12.30% |
| 19.701 | 4.50252 | 23.00% |
| 20.304 | 4.3702 | 20.00% |
| 20.852 | 4.2566 | 100.00% |
| 21.399 | 4.149 | 17.10% |
| 21.994 | 4.03818 | 9.70% |
| 22.199 | 4.00128 | 28.10% |
| 22.528 | 3.94351 | 13.30% |
| 22.734 | 3.90835 | 12.60% |
| 23.19 | 3.83246 | 19.30% |
| 23.476 | 3.78646 | 31.30% |
| 23.755 | 3.74266 | 6.70% |
| 24.364 | 3.6504 | 21.40% |
| 24.86 | 3.57864 | 16.30% |
| 25.357 | 3.5096 | 3.40% |
| 25.563 | 3.48189 | 16.40% |
| 25.877 | 3.44032 | 10.90% |
| 26.392 | 3.37431 | 2.90% |
| 26.655 | 3.34162 | 6.20% |
| 27.14 | 3.28302 | 9.20% |
| 27.516 | 3.23903 | 3.80% |
| 27.949 | 3.18976 | 2.50% |
| 28.257 | 3.1557 | 13.10% |
| 28.49 | 3.13042 | 8.20% |
| 28.958 | 3.0809 | 5.50% |
| 29.286 | 3.04712 | 7.50% |
| 29.797 | 2.99601 | 7.60% |
| 30.37 | 2.94082 | 1.20% |
| 30.823 | 2.89863 | 1.90% |
| 31.064 | 2.87666 | 5.40% |
| 31.572 | 2.83149 | 3.20% |
| 32.05 | 2.79035 | 5.80% |
| 32.598 | 2.74467 | 2.60% |
| 33.179 | 2.69795 | 1.30% |
| 34.099 | 2.62723 | 3.20% |
| 34.392 | 2.60554 | 4.20% |
| 35.108 | 2.55398 | 3.30% |

TABLE 28-continued

| Angle | d Value | Rel. Intensity |
|---|---|---|
| 35.813 | 2.50535 | 2.50% |
| 36.131 | 2.48403 | 5.20% |
| 36.445 | 2.46332 | 6.70% |
| 36.972 | 2.42938 | 5.00% |
| 37.611 | 2.38957 | 5.30% |
| 38.198 | 2.3542 | 6.60% |
| 39.037 | 2.30554 | 2.20% |
| 39.402 | 2.28502 | 2.40% |
| 40.013 | 2.2515 | 2.30% |
| 40.274 | 2.23752 | 2.10% |
| 40.7 | 2.2151 | 4.70% |
| 41.447 | 2.17686 | 3.10% |

Example 18

Figure 49:
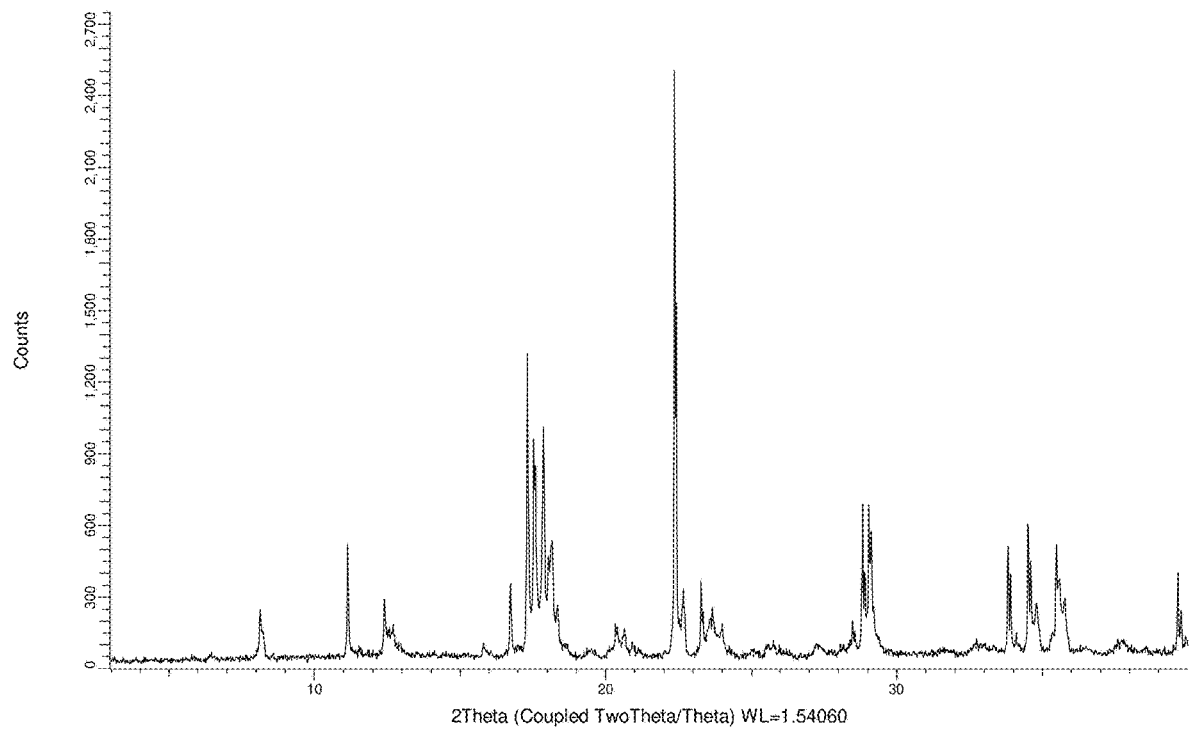
FIG. 49 depicts the X-ray powder diffraction (XRPD) pattern of 5-(3,4-dichlorophenyl)-N-((1R,2R)-2-hydroxycyclohexyl)-6-(2,2,2-trifluoroethoxy)nicotinamide, 1,4-dioxane solvate (Form R).

The XRPD pattern of crystalline Form R material of 5-(3,4-dichlorophenyl)-N-((1R,2R)-2-hydroxycyclohexyl)-6-(2,2,2-trifluoroethoxy)nicotinamide, 1,4-dioxane solvate, ill prepared according to the procedure in Example 14, is shown in FIG. 49. Characteristic peaks include one or more of the peaks shown in Table 29.

TABLE 29

| Angle | d Value | Rel. Intensity |
|---|---|---|
| 5.077 | 17.39208 | 54.50% |
| 5.348 | 16.51019 | 23.90% |
| 6.927 | 12.74992 | 24.00% |
| 8.964 | 9.85765 | 28.50% |
| 10.163 | 8.69671 | 12.80% |
| 10.722 | 8.24428 | 11.90% |
| 12.14 | 7.28445 | 15.40% |
| 13.564 | 6.52276 | 7.20% |
| 13.887 | 6.37188 | 3.50% |
| 14.193 | 6.23518 | 3.60% |
| 14.407 | 6.14295 | 3.90% |
| 15.269 | 5.79794 | 7.50% |
| 15.861 | 5.58314 | 8.60% |
| 16.112 | 5.49646 | 9.90% |
| 17.475 | 5.07095 | 2.20% |
| 18.01 | 4.9214 | 31.30% |
| 18.449 | 4.80527 | 19.70% |
| 18.85 | 4.70393 | 44.30% |
| 19.481 | 4.55289 | 12.30% |
| 19.701 | 4.50252 | 23.00% |
| 20.304 | 4.3702 | 20.00% |
| 20.852 | 4.2566 | 100.00% |
| 21.399 | 4.149 | 17.10% |
| 21.994 | 4.03818 | 9.70% |
| 22.199 | 4.00128 | 28.10% |
| 22.528 | 3.94351 | 13.30% |
| 22.734 | 3.90835 | 12.60% |
| 23.19 | 3.83246 | 19.30% |
| 23.476 | 3.78646 | 31.30% |
| 23.755 | 3.74266 | 6.70% |
| 24.364 | 3.6504 | 21.40% |
| 24.86 | 3.57864 | 16.30% |
| 25.357 | 3.5096 | 3.40% |
| 25.563 | 3.48189 | 16.40% |
| 25.877 | 3.44032 | 10.90% |
| 26.392 | 3.37431 | 2.90% |
| 26.655 | 3.34162 | 6.20% |
| 27.14 | 3.28302 | 9.20% |
| 27.516 | 3.23903 | 3.80% |
| 27.949 | 3.18976 | 2.50% |
| 28.257 | 3.1557 | 13.10% |
| 28.49 | 3.13042 | 8.20% |
| 28.958 | 3.0809 | 5.50% |
| 29.286 | 3.04712 | 7.50% |
| 29.797 | 2.99601 | 7.60% |
| 30.37 | 2.94082 | 1.20% |
| 30.823 | 2.89863 | 1.90% |
| 31.064 | 2.87666 | 5.40% |

TABLE 29-continued

| Angle | d Value | Rel. Intensity |
|---|---|---|
| 31.572 | 2.83149 | 3.20% |
| 32.05 | 2.79035 | 5.80% |
| 32.598 | 2.74467 | 2.60% |
| 33.179 | 2.69795 | 1.30% |
| 34.099 | 2.62723 | 3.20% |
| 34.392 | 2.60554 | 4.20% |
| 35.108 | 2.55398 | 3.30% |
| 35.813 | 2.50535 | 2.50% |
| 36.131 | 2.48403 | 5.20% |
| 36.445 | 2.46332 | 6.70% |
| 36.972 | 2.42938 | 5.00% |
| 37.611 | 2.38957 | 5.30% |
| 38.198 | 2.3542 | 6.60% |
| 39.037 | 2.30554 | 2.20% |
| 39.402 | 2.28502 | 2.40% |
| 40.013 | 2.2515 | 2.30% |
| 40.274 | 2.23752 | 2.10% |
| 40.7 | 2.2151 | 4.70% |
| 41.447 | 2.17686 | 3.10% |

Example 19

Figure 50:
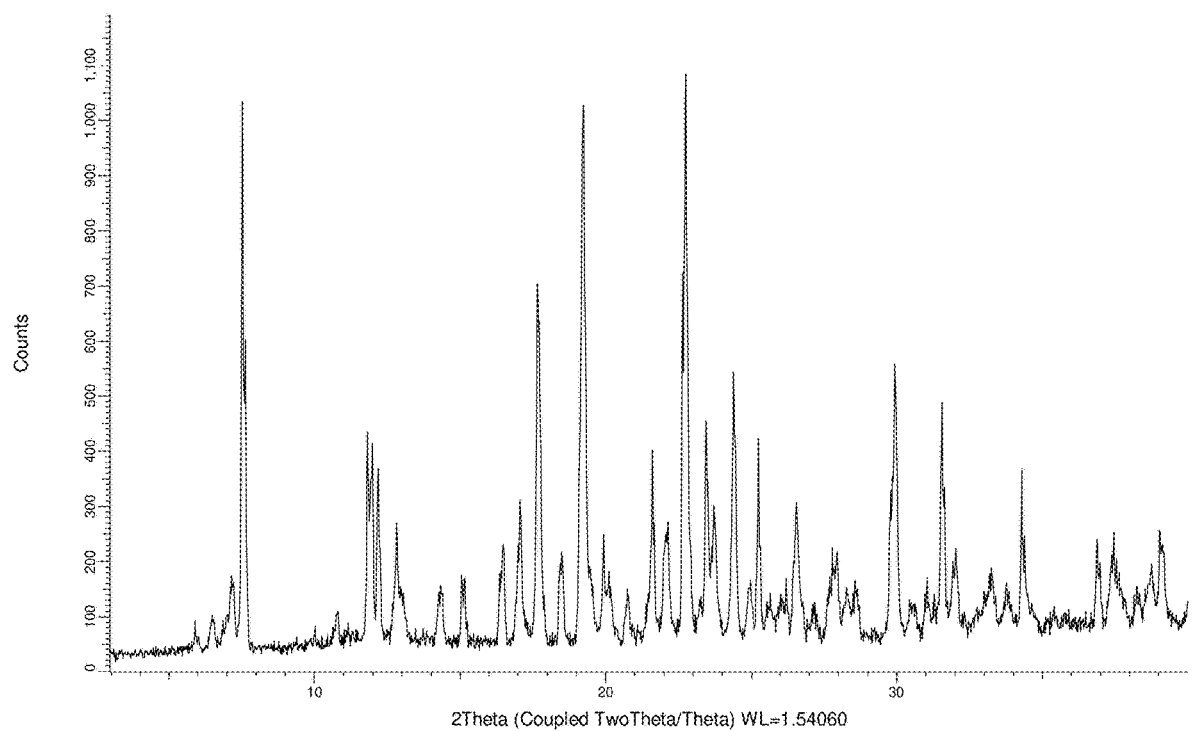
FIG. 50 depicts the X-ray powder diffraction (XRPD) pattern of 5-(3,4-dichlorophenyl)-N-((1R,2R)-2-hydroxycyclohexyl)-6-(2,2,2-trifluoroethoxy)nicotinamide, trifluoroethanol solvate (Form S).

The XRPD pattern of crystalline Form S material of 5-(3,4-dichlorophenyl)-N-((1R,2R)-2-hydroxycyclohexyl)-6-(2,2,2-trifluoroethoxy)nicotinamide, trifluoroethanol solvate, prepared according to the procedure in Example 15, is shown in FIG. 50. Characteristic peaks include one or more of the peaks shown in Table 30.

TABLE 30

| Angle | d Value | Rel. Intensity |
|---|---|---|
| 5.077 | 17.39208 | 54.50% |
| 5.348 | 16.51019 | 23.90% |
| 6.927 | 12.74992 | 24.00% |
| 8.964 | 9.85765 | 28.50% |
| 10.163 | 8.69671 | 12.80% |
| 10.722 | 8.24428 | 11.90% |
| 12.14 | 7.28445 | 15.40% |
| 13.564 | 6.52276 | 7.20% |
| 13.887 | 6.37188 | 3.50% |
| 14.193 | 6.23518 | 3.60% |
| 14.407 | 6.14295 | 3.90% |
| 15.269 | 5.79794 | 7.50% |
| 15.861 | 5.58314 | 8.60% |
| 16.112 | 5.49646 | 9.90% |
| 17.475 | 5.07095 | 2.20% |
| 18.01 | 4.9214 | 31.30% |
| 18.449 | 4.80527 | 19.70% |
| 18.85 | 4.70393 | 44.30% |
| 19.481 | 4.55289 | 12.30% |
| 19.701 | 4.50252 | 23.00% |
| 20.304 | 4.3702 | 20.00% |
| 20.852 | 4.2566 | 100.00% |
| 21.399 | 4.149 | 17.10% |
| 21.994 | 4.03818 | 9.70% |
| 22.199 | 4.00128 | 28.10% |
| 22.528 | 3.94351 | 13.30% |
| 22.734 | 3.90835 | 12.60% |
| 23.19 | 3.83246 | 19.30% |
| 23.476 | 3.78646 | 31.30% |
| 23.755 | 3.74266 | 6.70% |
| 24.364 | 3.6504 | 21.40% |
| 24.86 | 3.57864 | 16.30% |
| 25.357 | 3.5096 | 3.40% |
| 25.563 | 3.48189 | 16.40% |
| 25.877 | 3.44032 | 10.90% |
| 26.392 | 3.37431 | 2.90% |
| 26.655 | 3.34162 | 6.20% |
| 27.14 | 3.28302 | 9.20% |
| 27.516 | 3.23903 | 3.80% |
| 27.949 | 3.18976 | 2.50% |
| 28.257 | 3.1557 | 13.10% |

TABLE 30-continued

| Angle | d Value | Rel. Intensity |
|---|---|---|
| 28.49 | 3.13042 | 8.20% |
| 28.958 | 3.0809 | 5.50% |
| 29.286 | 3.04712 | 7.50% |
| 29.797 | 2.99601 | 7.60% |
| 30.37 | 2.94082 | 1.20% |
| 30.823 | 2.89863 | 1.90% |
| 31.064 | 2.87666 | 5.40% |
| 31.572 | 2.83149 | 3.20% |
| 32.05 | 2.79035 | 5.80% |
| 32.598 | 2.74467 | 2.60% |
| 33.179 | 2.69795 | 1.30% |
| 34.099 | 2.62723 | 3.20% |
| 34.392 | 2.60554 | 4.20% |
| 35.108 | 2.55398 | 3.30% |
| 35.813 | 2.50535 | 2.50% |
| 36.131 | 2.48403 | 5.20% |
| 36.445 | 2.46332 | 6.70% |
| 36.972 | 2.42938 | 5.00% |
| 37.611 | 2.38957 | 5.30% |
| 38.198 | 2.3542 | 6.60% |
| 39.037 | 2.30554 | 2.20% |
| 39.402 | 2.28502 | 2.40% |
| 40.013 | 2.2515 | 2.30% |
| 40.274 | 2.23752 | 2.10% |
| 40.7 | 2.2151 | 4.70% |
| 41.447 | 2.17686 | 3.10% |

Example 20

Crystalline, Form T material of 5-(3,4-dichlorophenyl)-N-((1R,2R)-2-hydroxycyclohexyl)-6-(2,2,2-trifluoroethoxy)nicotinamide, hydrate, was prepared as follows. About 50 mg of crystalline Form E material of 5-(3,4-dichlorophenyl)-N-((1R,2R)-2-hydroxycyclohexyl)-6-(2,2,2-trifluoroethoxy)nicotinamide, anhydrate, was equilibrated in acetone at 25° C. for 2 weeks with stirring at 400 rpm. The obtained suspension was filtered through a 0.45 μm nylon membrane filter by centrifugation at 14,000 rpm. XRPD analysis of the material indicated that the material was crystalline with a pattern consistent with Form T.

Figure 51:
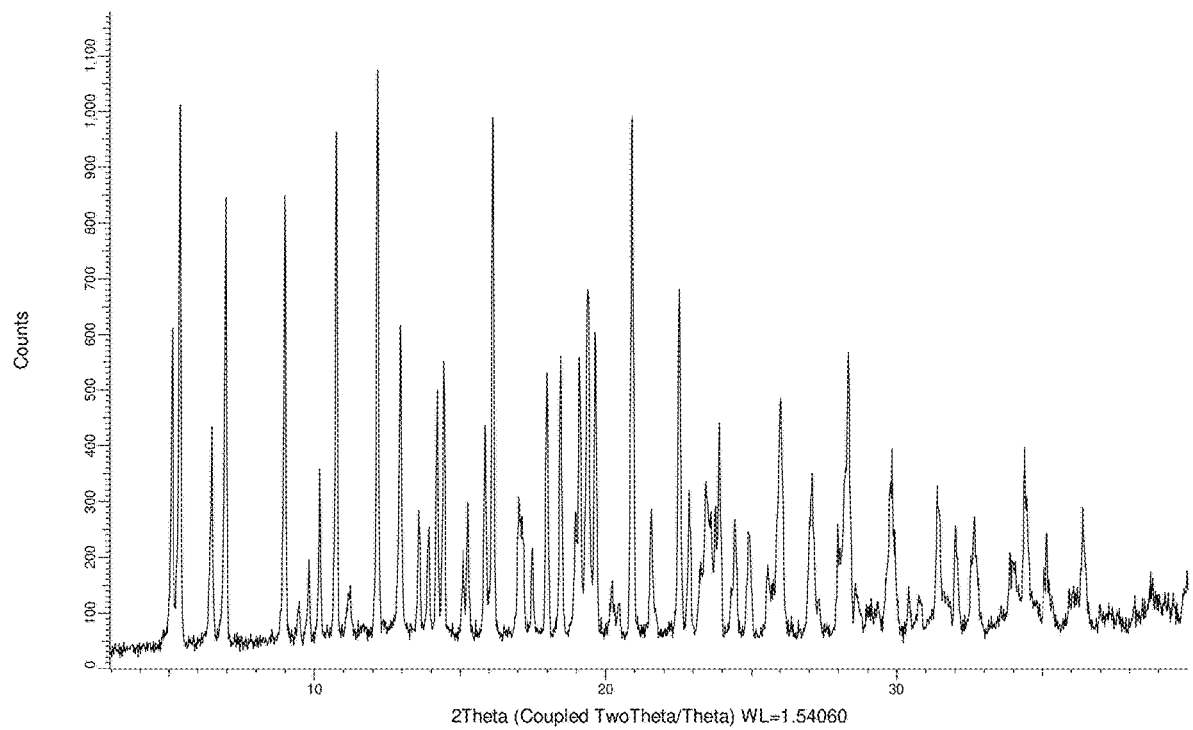
FIG. 51 depicts the X-ray powder diffraction (XRPD) pattern of 5-(3,4-dichlorophenyl)-N-((1R,2R)-2-hydroxycyclohexyl)-6-(2,2,2-trifluoroethoxy)nicotinamide, hydrate (Form T).

The XRPD pattern of crystalline Form T is shown in FIG. 51. Characteristic peaks include one or more of the peaks shown in Table 31.

TABLE 31

| Angle | d Value | Rel. Intensity |
|---|---|---|
| 5.077 | 17.39208 | 54.50% |
| 5.348 | 16.51019 | 23.90% |
| 6.927 | 12.74992 | 24.00% |
| 8.964 | 9.85765 | 28.50% |
| 10.163 | 8.69671 | 12.80% |
| 10.722 | 8.24428 | 11.90% |
| 12.14 | 7.28445 | 15.40% |
| 13.564 | 6.52276 | 7.20% |
| 13.887 | 6.37188 | 3.50% |
| 14.193 | 6.23518 | 3.60% |
| 14.407 | 6.14295 | 3.90% |
| 15.269 | 5.79794 | 7.50% |
| 15.861 | 5.58314 | 8.60% |
| 16.112 | 5.49646 | 9.90% |
| 17.475 | 5.07095 | 2.20% |
| 18.01 | 4.9214 | 31.30% |
| 18.449 | 4.80527 | 19.70% |
| 18.85 | 4.70393 | 44.30% |
| 19.481 | 4.55289 | 12.30% |
| 19.701 | 4.50252 | 23.00% |
| 20.304 | 4.3702 | 20.00% |
| 20.852 | 4.2566 | 100.00% |
| 21.399 | 4.149 | 17.10% |

TABLE 31-continued

| Angle | d Value | Rel. Intensity |
|---|---|---|
| 21.994 | 4.03818 | 9.70% |
| 22.199 | 4.00128 | 28.10% |
| 22.528 | 3.94351 | 13.30% |
| 22.734 | 3.90835 | 12.60% |
| 23.19 | 3.83246 | 19.30% |
| 23.476 | 3.78646 | 31.30% |
| 23.755 | 3.74266 | 6.70% |
| 24.364 | 3.6504 | 21.40% |
| 24.86 | 3.57864 | 16.30% |
| 25.357 | 3.5096 | 3.40% |
| 25.563 | 3.48189 | 16.40% |
| 25.877 | 3.44032 | 10.90% |
| 26.392 | 3.37431 | 2.90% |
| 26.655 | 3.34162 | 6.20% |
| 27.14 | 3.28302 | 9.20% |
| 27.516 | 3.23903 | 3.80% |
| 27.949 | 3.18976 | 2.50% |
| 28.257 | 3.1557 | 13.10% |
| 28.49 | 3.13042 | 8.20% |
| 28.958 | 3.0809 | 5.50% |
| 29.286 | 3.04712 | 7.50% |
| 29.797 | 2.99601 | 7.60% |
| 30.37 | 2.94082 | 1.20% |
| 30.823 | 2.89863 | 1.90% |
| 31.064 | 2.87666 | 5.40% |
| 31.572 | 2.83149 | 3.20% |
| 32.05 | 2.79035 | 5.80% |
| 32.598 | 2.74467 | 2.60% |
| 33.179 | 2.69795 | 1.30% |
| 34.099 | 2.62723 | 3.20% |
| 34.392 | 2.60554 | 4.20% |
| 35.108 | 2.55398 | 3.30% |
| 35.813 | 2.50535 | 2.50% |
| 36.131 | 2.48403 | 5.20% |
| 36.445 | 2.46332 | 6.70% |
| 36.972 | 2.42938 | 5.00% |
| 37.611 | 2.38957 | 5.30% |
| 38.198 | 2.3542 | 6.60% |
| 39.037 | 2.30554 | 2.20% |
| 39.402 | 2.28502 | 2.40% |
| 40.013 | 2.2515 | 2.30% |
| 40.274 | 2.23752 | 2.10% |
| 40.7 | 2.2151 | 4.70% |
| 41.447 | 2.17686 | 3.10% |

Figure 52:
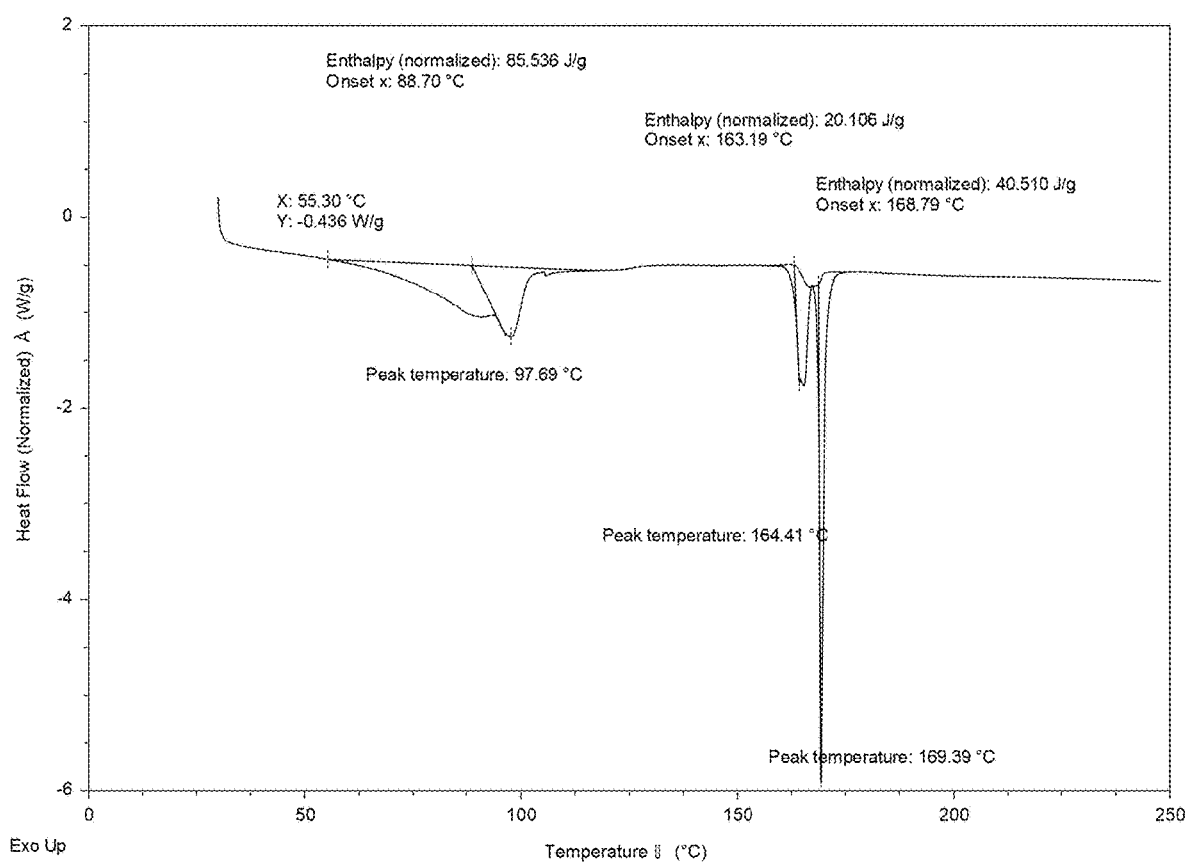
FIG. 52 depicts the characterization of Form T by differential scanning calorimetry (DSC).

FIG. 52 depicts the differential scanning calorimetry (DSC) profile of crystalline Form T. As shown in FIG. 52, crystalline Form T shows a characteristic endotherm with an onset of about 55° C.; a characteristic endotherm with an onset of about 89° C. and a peak of about 98° C.; a characteristic endotherm with an onset of about 163° C. and a peak of about 164° C.; and a characteristic endotherm with an onset and a peak of about 169° C. Crystalline Form T displayed a thermogravimetric analysis (TGA) profile showing a mass loss of about 3.9 wt. % up to about 150° C. Karl Fischer (KF) analysis showed 6.7% water by weight (1.85 equivalent by molar ratio).

Example 21

Crystalline, Form U material of 5-(3,4-dichlorophenyl)-N-((1R,2R)-2-hydroxycyclohexyl)-6-(2,2,2-trifluoroethoxy)nicotinamide, hydrate, was prepared as follows. About 50 mg of crystalline Form E material of 5-(3,4-dichlorophenyl)-N-((1R,2R)-2-hydroxycyclohexyl)-6-(2,2,2-trifluoroethoxy)nicotinamide, anhydrate, was dissolved in a minimal amount of isopropanol at 50° C., and the solution filtered through a 0.45 μm nylon membrane filter by centrifugation at 14,000 rpm. The clear solution was cooled to 5° C. at 0.1° C./min, and the precipitate collected by centrifugation filtration through a 0.45 μm nylon membrane filter at 14,000 rpm. XRPD analysis of the material indicated that the material was crystalline with a pattern consistent with Form U.

Figure 54:
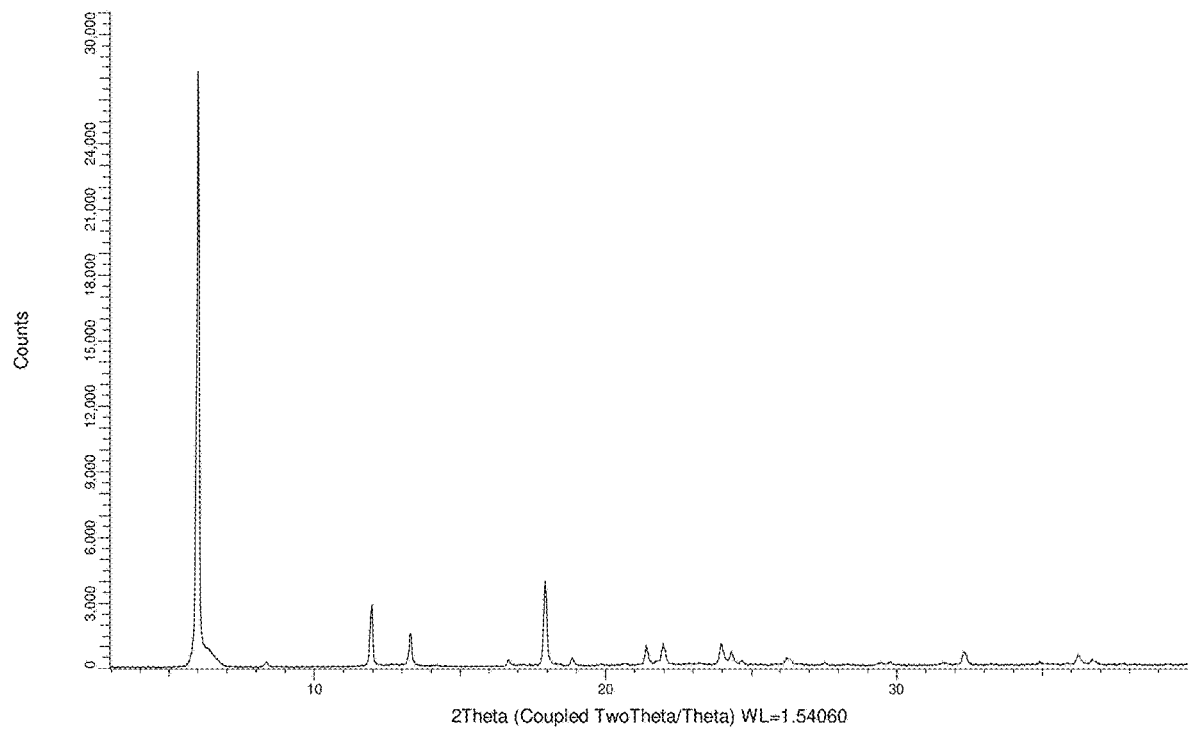
FIG. 54 depicts the X-ray powder diffraction (XRPD) pattern of 5-(3,4-dichlorophenyl)-N-((1R,2R)-2-hydroxycyclohexyl)-6-(2,2,2-trifluoroethoxy)nicotinamide, hydrate (Form U).

The XRPD pattern of crystalline Form U is shown in FIG. 54. Characteristic peaks include one or more of the peaks shown in Table 32.

TABLE 32

| Angle | d Value | Rel. Intensity |
|---|---|---|
| 5.077 | 17.39208 | 54.50% |
| 5.348 | 16.51019 | 23.90% |
| 6.927 | 12.74992 | 24.00% |
| 8.964 | 9.85765 | 28.50% |
| 10.163 | 8.69671 | 12.80% |
| 10.722 | 8.24428 | 11.90% |
| 12.14 | 7.28445 | 15.40% |
| 13.564 | 6.52276 | 7.20% |
| 13.887 | 6.37188 | 3.50% |
| 14.193 | 6.23518 | 3.60% |
| 14.407 | 6.14295 | 3.90% |
| 15.269 | 5.79794 | 7.50% |
| 15.861 | 5.58314 | 8.60% |
| 16.112 | 5.49646 | 9.90% |
| 17.475 | 5.07095 | 2.20% |
| 18.01 | 4.9214 | 31.30% |
| 18.449 | 4.80527 | 19.70% |
| 18.85 | 4.70393 | 44.30% |
| 19.481 | 4.55289 | 12.30% |
| 19.701 | 4.50252 | 23.00% |
| 20.304 | 4.3702 | 20.00% |
| 20.852 | 4.2566 | 100.00% |
| 21.399 | 4.149 | 17.10% |
| 21.994 | 4.03818 | 9.70% |
| 22.199 | 4.00128 | 28.10% |
| 22.528 | 3.94351 | 13.30% |
| 22.734 | 3.90835 | 12.60% |
| 23.19 | 3.83246 | 19.30% |
| 23.476 | 3.78646 | 31.30% |
| 23.755 | 3.74266 | 6.70% |
| 24.364 | 3.6504 | 21.40% |
| 24.86 | 3.57864 | 16.30% |
| 25.357 | 3.5096 | 3.40% |
| 25.563 | 3.48189 | 16.40% |
| 25.877 | 3.44032 | 10.90% |
| 26.392 | 3.37431 | 2.90% |
| 26.655 | 3.34162 | 6.20% |
| 27.14 | 3.28302 | 9.20% |
| 27.516 | 3.23903 | 3.80% |
| 27.949 | 3.18976 | 2.50% |
| 28.257 | 3.1557 | 13.10% |
| 28.49 | 3.13042 | 8.20% |
| 28.958 | 3.0809 | 5.50% |
| 29.286 | 3.04712 | 7.50% |
| 29.797 | 2.99601 | 7.60% |
| 30.37 | 2.94082 | 1.20% |
| 30.823 | 2.89863 | 1.90% |
| 31.064 | 2.87666 | 5.40% |
| 31.572 | 2.83149 | 3.20% |
| 32.05 | 2.79035 | 5.80% |
| 32.598 | 2.74467 | 2.60% |
| 33.179 | 2.69795 | 1.30% |
| 34.099 | 2.62723 | 3.20% |
| 34.392 | 2.60554 | 4.20% |
| 35.108 | 2.55398 | 3.30% |
| 35.813 | 2.50535 | 2.50% |
| 36.131 | 2.48403 | 5.20% |
| 36.445 | 2.46332 | 6.70% |
| 36.972 | 2.42938 | 5.00% |
| 37.611 | 2.38957 | 5.30% |
| 38.198 | 2.3542 | 6.60% |
| 39.037 | 2.30554 | 2.20% |
| 39.402 | 2.28502 | 2.40% |
| 40.013 | 2.2515 | 2.30% |
| 40.274 | 2.23752 | 2.10% |
| 40.7 | 2.2151 | 4.70% |
| 41.447 | 2.17686 | 3.10% |

Figure 55:
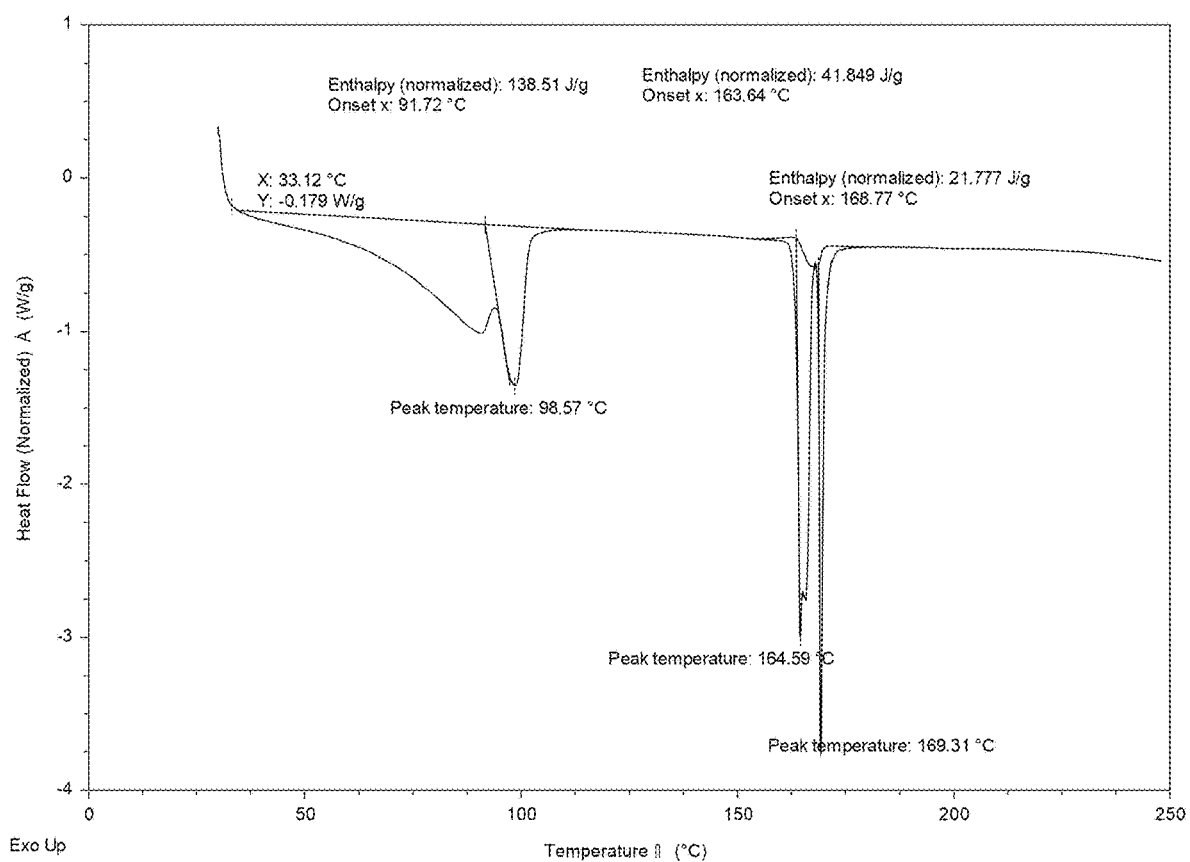
FIG. 55 depicts the characterization of Form U by differential scanning calorimetry (DSC).

FIG. 55 depicts the differential scanning calorimetry (DSC) profile of crystalline Form U. As shown in FIG. 55, crystalline Form U shows a characteristic endotherm with an onset of about 33° C.; a characteristic endotherm with an onset of about 92° C. and a peak of about 99° C.; a characteristic endotherm with an onset of about 164° C. and a peak of about 165° C.; and a characteristic endotherm with an onset and a peak of about 169° C. Crystalline Form U displayed a thermogravimetric analysis (TGA) profile showing a mass loss of about 3.9 wt. % up to about 150° C. Karl Fischer (KF) analysis showed 5.1% water by weight (1.38 equivalent by molar ratio).

Example 22

Crystalline, Form V material of 5-(3,4-dichlorophenyl)-N-((1R,2R)-2-hydroxycyclohexyl)-6-(2,2,2-trifluoroethoxy)nicotinamide, hydrate, was prepared as follows. About 50 mg of crystalline Form E material of 5-(3,4-dichlorophenyl)-N-((1R,2R)-2-hydroxycyclohexyl)-6-(2,2,2-trifluoroethoxy)nicotinamide, anhydrate, was dissolved in a minimal amount of tetrahydrofuran at 50° C. The solution was filtered through a 0.45 µm nylon membrane filter by centrifugation at 14,000 rpm, placed into a 0° C. ice bath, and agitated. The precipitate was collected by centrifugation filtration through a 0.45 µm nylon membrane filter at 14,000 rpm. XRPD analysis of the wet cake material indicated that the material was crystalline with a pattern consistent with Form AA. XRPD analysis of the dried material indicated that the material was crystalline with a pattern consistent with Form V.

Figure 57:
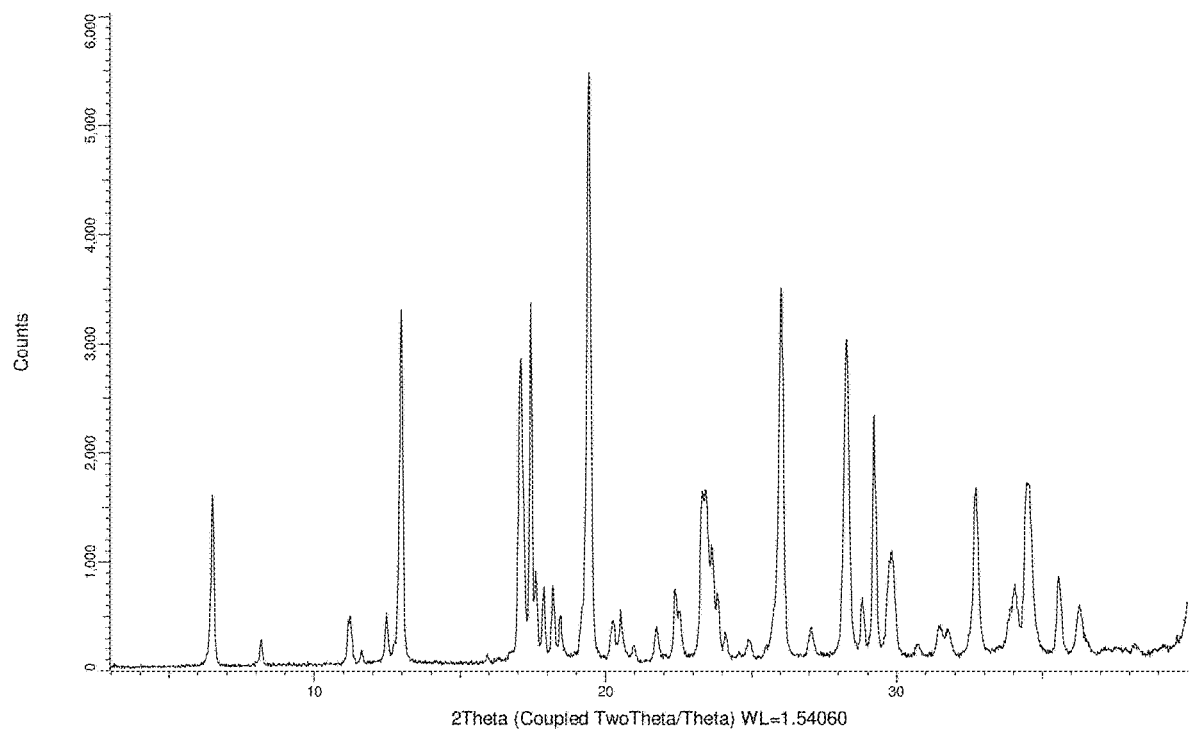
FIG. 57 depicts the X-ray powder diffraction (XRPD) pattern of 5-(3,4-dichlorophenyl)-N-((1R,2R)-2-hydroxycyclohexyl)-6-(2,2,2-trifluoroethoxy)nicotinamide, hydrate (Form V).

The XRPD pattern of crystalline Form V is shown in FIG. 57. Characteristic peaks include one or more of the peaks shown in Table 33.

TABLE 33

| Angle | d Value | Rel. Intensity |
|---|---|---|
| 5.077 | 17.39208 | 54.50% |
| 5.348 | 16.51019 | 23.90% |
| 6.927 | 12.74992 | 24.00% |
| 8.964 | 9.85765 | 28.50% |
| 10.163 | 8.69671 | 12.80% |
| 10.722 | 8.24428 | 11.90% |
| 12.14 | 7.28445 | 15.40% |
| 13.564 | 6.52276 | 7.20% |
| 13.887 | 6.37188 | 3.50% |
| 14.193 | 6.23518 | 3.60% |
| 14.407 | 6.14295 | 3.90% |
| 15.269 | 5.79794 | 7.50% |
| 15.861 | 5.58314 | 8.60% |
| 16.112 | 5.49646 | 9.90% |
| 17.475 | 5.07095 | 2.20% |
| 18.01 | 4.9214 | 31.30% |
| 18.449 | 4.80527 | 19.70% |
| 18.85 | 4.70393 | 44.30% |
| 19.481 | 4.55289 | 12.30% |
| 19.701 | 4.50252 | 23.00% |
| 20.304 | 4.3702 | 20.00% |
| 20.852 | 4.2566 | 100.00% |
| 21.399 | 4.149 | 17.10% |
| 21.994 | 4.03818 | 9.70% |
| 22.199 | 4.00128 | 28.10% |
| 22.528 | 3.94351 | 13.30% |
| 22.734 | 3.90835 | 12.60% |
| 23.19 | 3.83246 | 19.30% |
| 23.476 | 3.78646 | 31.30% |
| 23.755 | 3.74266 | 6.70% |
| 24.364 | 3.6504 | 21.40% |
| 24.86 | 3.57864 | 16.30% |
| 25.357 | 3.5096 | 3.40% |
| 25.563 | 3.48189 | 16.40% |

TABLE 33-continued

| Angle | d Value | Rel. Intensity |
|---|---|---|
| 25.877 | 3.44032 | 10.90% |
| 26.392 | 3.37431 | 2.90% |
| 26.655 | 3.34162 | 6.20% |
| 27.14 | 3.28302 | 9.20% |
| 27.516 | 3.23903 | 3.80% |
| 27.949 | 3.18976 | 2.50% |
| 28.257 | 3.1557 | 13.10% |
| 28.49 | 3.13042 | 8.20% |
| 28.958 | 3.0809 | 5.50% |
| 29.286 | 3.04712 | 7.50% |
| 29.797 | 2.99601 | 7.60% |
| 30.37 | 2.94082 | 1.20% |
| 30.823 | 2.89863 | 1.90% |
| 31.064 | 2.87666 | 5.40% |
| 31.572 | 2.83149 | 3.20% |
| 32.05 | 2.79035 | 5.80% |
| 32.598 | 2.74467 | 2.60% |
| 33.179 | 2.69795 | 1.30% |
| 34.099 | 2.62723 | 3.20% |
| 34.392 | 2.60554 | 4.20% |
| 35.108 | 2.55398 | 3.30% |
| 35.813 | 2.50535 | 2.50% |
| 36.131 | 2.48403 | 5.20% |
| 36.445 | 2.46332 | 6.70% |
| 36.972 | 2.42938 | 5.00% |
| 37.611 | 2.38957 | 5.30% |
| 38.198 | 2.3542 | 6.60% |
| 39.037 | 2.30554 | 2.20% |
| 39.402 | 2.28502 | 2.40% |
| 40.013 | 2.2515 | 2.30% |
| 40.274 | 2.23752 | 2.10% |
| 40.7 | 2.2151 | 4.70% |
| 41.447 | 2.17686 | 3.10% |

Figure 58:
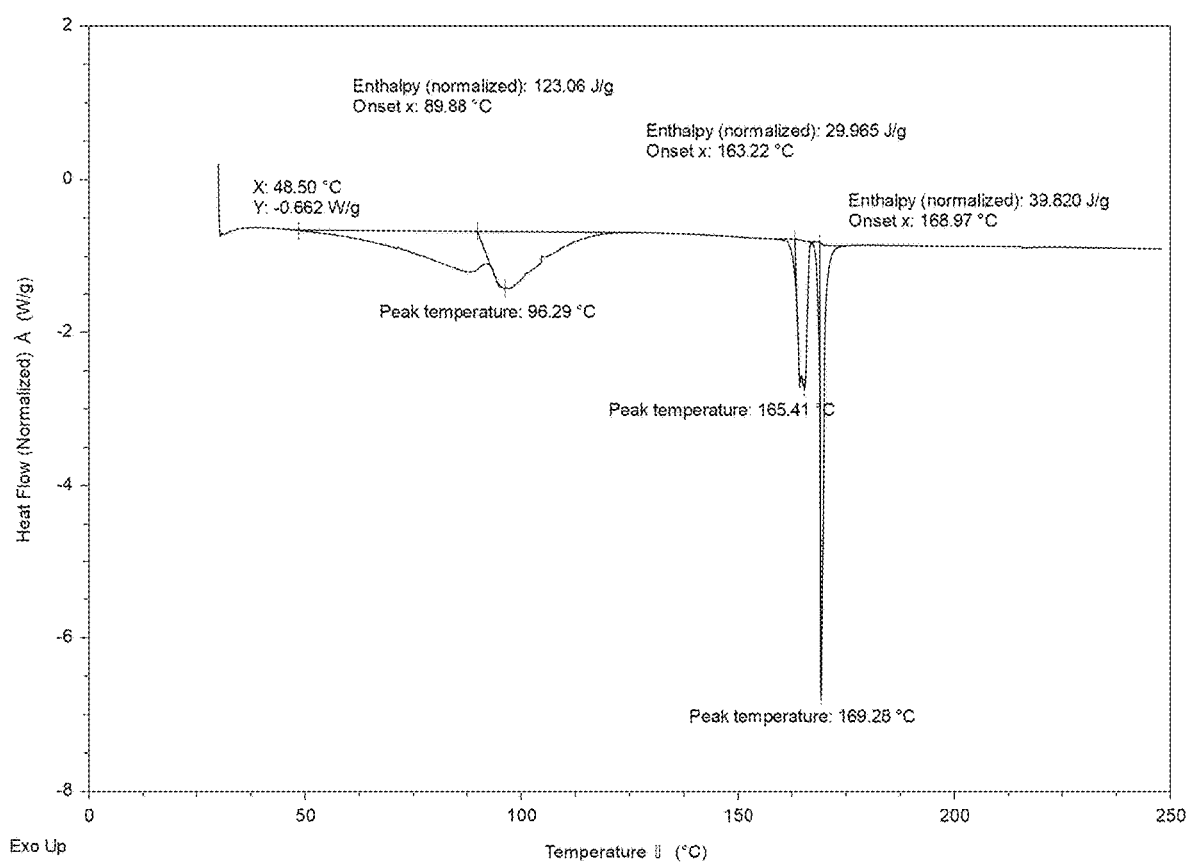
FIG. 58 depicts the characterization of Form V by differential scanning calorimetry (DSC).

FIG. 58 depicts the differential scanning calorimetry (DSC) profile of crystalline Form V. As shown in FIG. 58, crystalline Form V shows a characteristic endotherm with an onset of about 48° C.; a characteristic endotherm with a peak of about 90° C. and a peak of about 96° C.; a characteristic endotherm with an onset of about 163° C. and a peak of about 165° C.; and a characteristic endotherm with an onset and a peak of about 169° C. Crystalline Form V displayed a thermogravimetric analysis (TGA) profile showing a mass loss of about 3.9 wt. % up to about 150° C. Karl Fischer (KF) analysis showed 7.1% water by weight (1.97 equivalent by molar ratio).

Example 23

Crystalline, Form W material of 5-(3,4-dichlorophenyl)-N-((1R,2R)-2-hydroxycyclohexyl)-6-(2,2,2-trifluoroethoxy)nicotinamide, hydrate, was prepared as follows. About 50 mg of crystalline Form E material of 5-(3,4-dichlorophenyl)-N-((1R,2R)-2-hydroxycyclohexyl)-6-(2,2,2-trifluoroethoxy)nicotinamide, anhydrate, was dissolved in a minimal amount of ethanol at 50° C. The solution was filtered through a 0.45 µm nylon membrane filter by centrifugation at 14,000 rpm, placed into a 0° C. ice bath, and agitated. The precipitate was collected by centrifugation filtration through a 0.45 µm nylon membrane filter at 14,000 rpm. XRPD analysis of the wet cake material indicated that the material was crystalline with a pattern consistent with Form Y. XRPD analysis of the dried material indicated that the material was crystalline with a pattern consistent with Form W.

Figure 60:
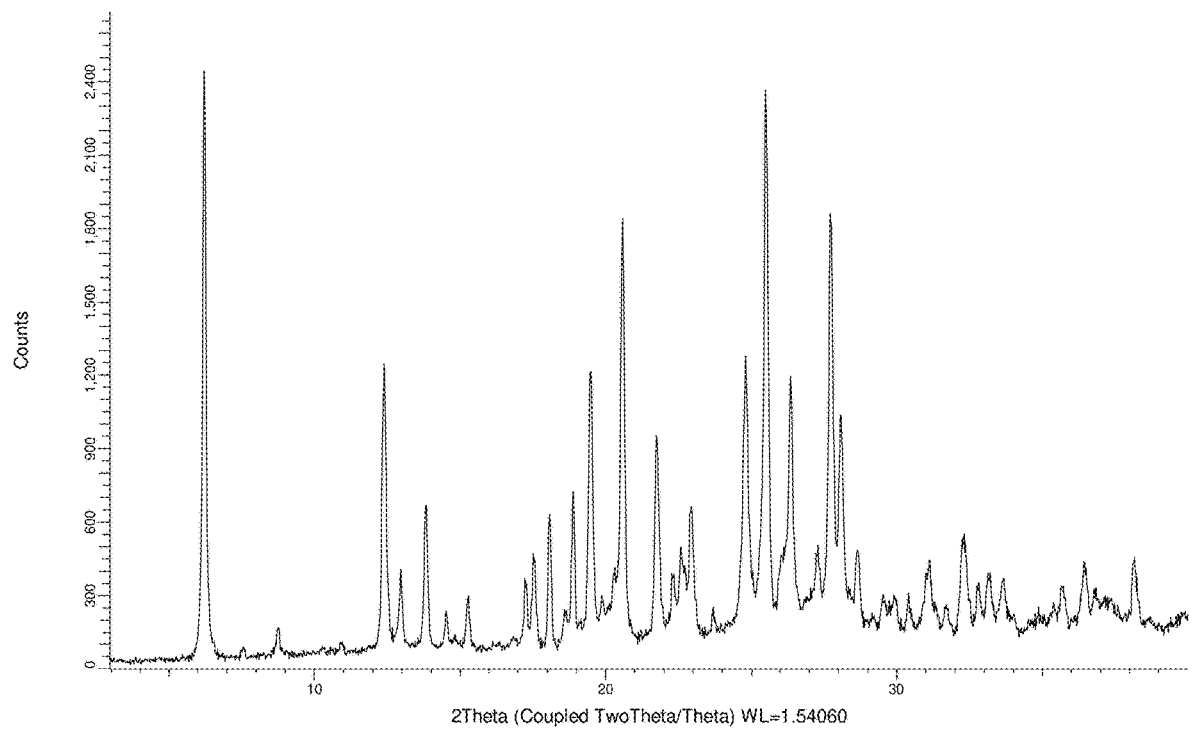
FIG. 60 depicts the X-ray powder diffraction (XRPD) pattern of 5-(3,4-dichlorophenyl)-N-((1R,2R)-2-hydroxycyclohexyl)-6-(2,2,2-trifluoroethoxy)nicotinamide, hydrate (Form W).

The XRPD pattern of crystalline Form W is shown in FIG. 60. Characteristic peaks include one or more of the peaks shown in Table 34.

TABLE 34

| Angle | d Value | Rel. Intensity |
|---|---|---|
| 5.077 | 17.39208 | 54.50% |
| 5.348 | 16.51019 | 23.90% |
| 6.927 | 12.74992 | 24.00% |
| 8.964 | 9.85765 | 28.50% |
| 10.163 | 8.69671 | 12.80% |
| 10.722 | 8.24428 | 11.90% |
| 12.14 | 7.28445 | 15.40% |
| 13.564 | 6.52276 | 7.20% |
| 13.887 | 6.37188 | 3.50% |
| 14.193 | 6.23518 | 3.60% |
| 14.407 | 6.14295 | 3.90% |
| 15.269 | 5.79794 | 7.50% |
| 15.861 | 5.58314 | 8.60% |
| 16.112 | 5.49646 | 9.90% |
| 17.475 | 5.07095 | 2.20% |
| 18.01 | 4.9214 | 31.30% |
| 18.449 | 4.80527 | 19.70% |
| 18.85 | 4.70393 | 44.30% |
| 19.481 | 4.55289 | 12.30% |
| 19.701 | 4.50252 | 23.00% |
| 20.304 | 4.3702 | 20.00% |
| 20.852 | 4.2566 | 100.00% |
| 21.399 | 4.149 | 17.10% |
| 21.994 | 4.03818 | 9.70% |
| 22.199 | 4.00128 | 28.10% |
| 22.528 | 3.94351 | 13.30% |
| 22.734 | 3.90835 | 12.60% |
| 23.19 | 3.83246 | 19.30% |
| 23.476 | 3.78646 | 31.30% |
| 23.755 | 3.74266 | 6.70% |
| 24.364 | 3.6504 | 21.40% |
| 24.86 | 3.57864 | 16.30% |
| 25.357 | 3.5096 | 3.40% |
| 25.563 | 3.48189 | 16.40% |
| 25.877 | 3.44032 | 10.90% |
| 26.392 | 3.37431 | 2.90% |
| 26.655 | 3.34162 | 6.20% |
| 27.14 | 3.28302 | 9.20% |
| 27.516 | 3.23903 | 3.80% |
| 27.949 | 3.18976 | 2.50% |
| 28.257 | 3.1557 | 13.10% |
| 28.49 | 3.13042 | 8.20% |
| 28.958 | 3.0809 | 5.50% |
| 29.286 | 3.04712 | 7.50% |
| 29.797 | 2.99601 | 7.60% |
| 30.37 | 2.94082 | 1.20% |
| 30.823 | 2.89863 | 1.90% |
| 31.064 | 2.87666 | 5.40% |
| 31.572 | 2.83149 | 3.20% |
| 32.05 | 2.79035 | 5.80% |
| 32.598 | 2.74467 | 2.60% |
| 33.179 | 2.69795 | 1.30% |
| 34.099 | 2.62723 | 3.20% |
| 34.392 | 2.60554 | 4.20% |
| 35.108 | 2.55398 | 3.30% |
| 35.813 | 2.50535 | 2.50% |
| 36.131 | 2.48403 | 5.20% |
| 36.445 | 2.46332 | 6.70% |
| 36.972 | 2.42938 | 5.00% |
| 37.611 | 2.38957 | 5.30% |
| 38.198 | 2.3542 | 6.60% |
| 39.037 | 2.30554 | 2.20% |
| 39.402 | 2.28502 | 2.40% |
| 40.013 | 2.2515 | 2.30% |
| 40.274 | 2.23752 | 2.10% |
| 40.7 | 2.2151 | 4.70% |
| 41.447 | 2.17686 | 3.10% |

Figure 61:
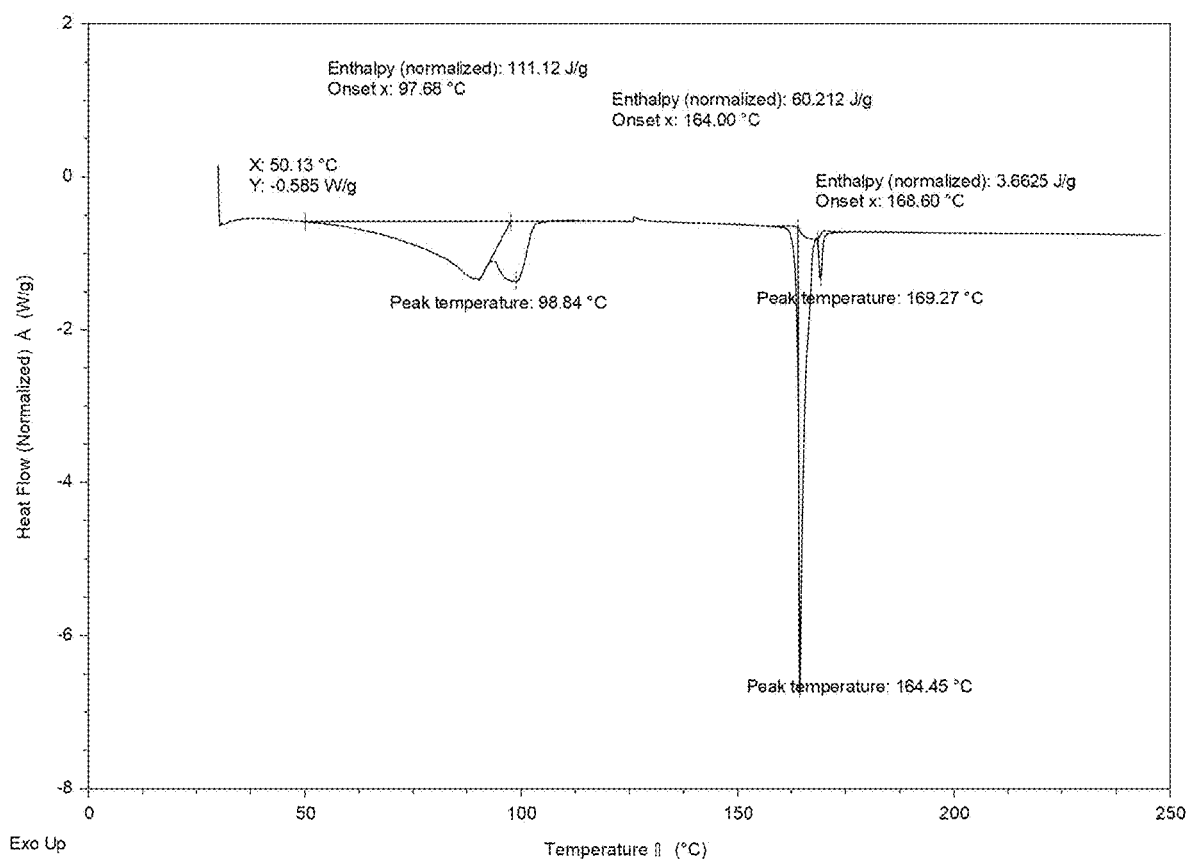
FIG. 61 depicts the characterization of Form W by differential scanning calorimetry (DSC).

FIG. 61 depicts the differential scanning calorimetry (DSC) profile of crystalline Form W. As shown in FIG. 61, crystalline Form W shows a characteristic endotherm with an onset of about 50° C.; a characteristic endotherm with an onset of about 98° C. and a peak of about 99° C.; a characteristic endotherm with an onset and a peak of about 164° C.; and a characteristic endotherm with an onset and a peak of about 169° C. Crystalline Form W displayed a thermogravimetric analysis (TGA) profile showing a mass loss of about 3.9 wt. % up to about 150° C. Karl Fischer (KF) analysis showed 4.5% water by weight (1.21 equivalent by molar ratio).

Example 24

Figure 63:
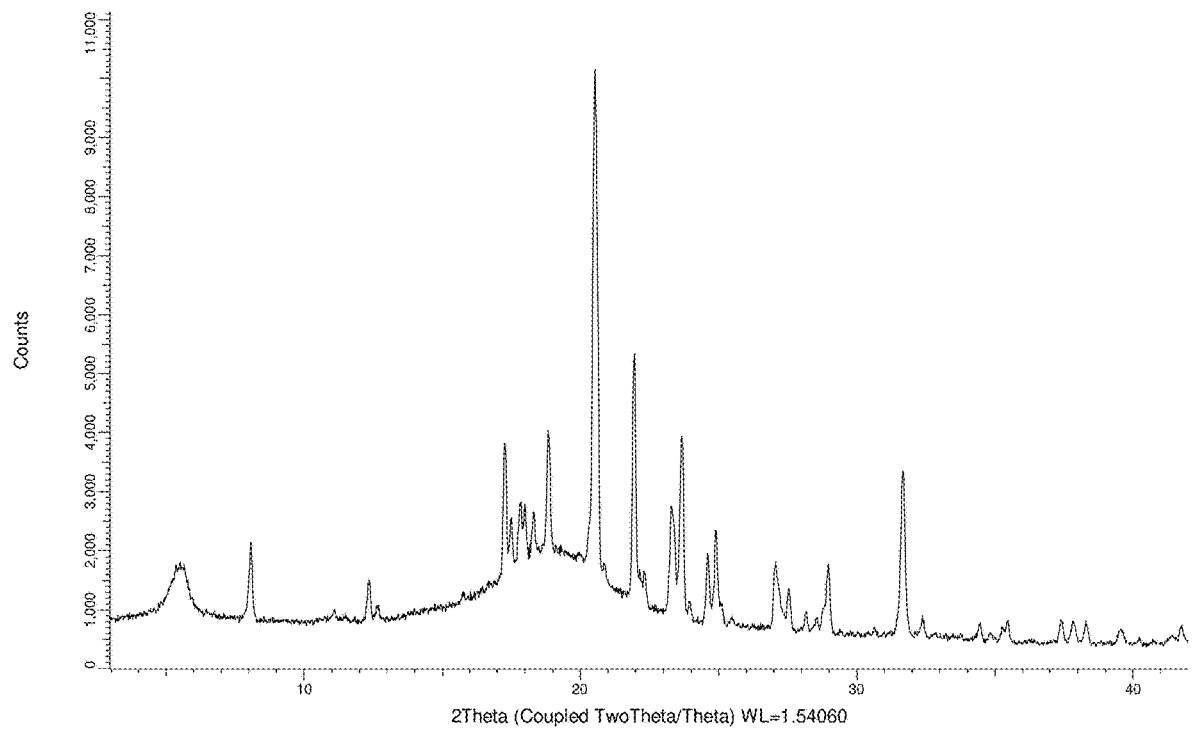
FIG. 63 depicts the X-ray powder diffraction (XRPD) pattern of 5-(3,4-dichlorophenyl)-N-((1R,2R)-2-hydroxycyclohexyl)-6-(2,2,2-trifluoroethoxy)nicotinamide, dioxane solvate (Form X).

The XRPD pattern of crystalline Form X material of 5-(3,4-dichlorophenyl)-N-((1R,2R)-2-hydroxycyclohexyl)-6-(2,2,2-trifluoroethoxy)nicotinamide, 1,4-dioxane solvate, is shown in FIG. 63. Characteristic peaks include one or more of the peaks shown in Table 35.

TABLE 35

| Angle | d Value | Rel. Intensity |
|---|---|---|
| 5.077 | 17.39208 | 54.50% |
| 5.348 | 16.51019 | 23.90% |
| 6.927 | 12.74992 | 24.00% |
| 8.964 | 9.85765 | 28.50% |
| 10.163 | 8.69671 | 12.80% |
| 10.722 | 8.24428 | 11.90% |
| 12.14 | 7.28445 | 15.40% |
| 13.564 | 6.52276 | 7.20% |
| 13.887 | 6.37188 | 3.50% |
| 14.193 | 6.23518 | 3.60% |
| 14.407 | 6.14295 | 3.90% |
| 15.269 | 5.79794 | 7.50% |
| 15.861 | 5.58314 | 8.60% |
| 16.112 | 5.49646 | 9.90% |
| 17.475 | 5.07095 | 2.20% |
| 18.01 | 4.9214 | 31.30% |
| 18.449 | 4.80527 | 19.70% |
| 18.85 | 4.70393 | 44.30% |
| 19.481 | 4.55289 | 12.30% |
| 19.701 | 4.50252 | 23.00% |
| 20.304 | 4.3702 | 20.00% |
| 20.852 | 4.2566 | 100.00% |
| 21.399 | 4.149 | 17.10% |
| 21.994 | 4.03818 | 9.70% |
| 22.199 | 4.00128 | 28.10% |
| 22.528 | 3.94351 | 13.30% |
| 22.734 | 3.90835 | 12.60% |
| 23.19 | 3.83246 | 19.30% |
| 23.476 | 3.78646 | 31.30% |
| 23.755 | 3.74266 | 6.70% |
| 24.364 | 3.6504 | 21.40% |
| 24.86 | 3.57864 | 16.30% |
| 25.357 | 3.5096 | 3.40% |
| 25.563 | 3.48189 | 16.40% |
| 25.877 | 3.44032 | 10.90% |
| 26.392 | 3.37431 | 2.90% |
| 26.655 | 3.34162 | 6.20% |
| 27.14 | 3.28302 | 9.20% |
| 27.516 | 3.23903 | 3.80% |
| 27.949 | 3.18976 | 2.50% |
| 28.257 | 3.1557 | 13.10% |
| 28.49 | 3.13042 | 8.20% |
| 28.958 | 3.0809 | 5.50% |
| 29.286 | 3.04712 | 7.50% |
| 29.797 | 2.99601 | 7.60% |
| 30.37 | 2.94082 | 1.20% |
| 30.823 | 2.89863 | 1.90% |
| 31.064 | 2.87666 | 5.40% |
| 31.572 | 2.83149 | 3.20% |
| 32.05 | 2.79035 | 5.80% |
| 32.598 | 2.74467 | 2.60% |
| 33.179 | 2.69795 | 1.30% |
| 34.099 | 2.62723 | 3.20% |
| 34.392 | 2.60554 | 4.20% |
| 35.108 | 2.55398 | 3.30% |
| 35.813 | 2.50535 | 2.50% |
| 36.131 | 2.48403 | 5.20% |
| 36.445 | 2.46332 | 6.70% |
| 36.972 | 2.42938 | 5.00% |
| 37.611 | 2.38957 | 5.30% |
| 38.198 | 2.3542 | 6.60% |
| 39.037 | 2.30554 | 2.20% |

TABLE 35-continued

| Angle | d Value | Rel. Intensity |
|---|---|---|
| 39.402 | 2.28502 | 2.40% |
| 40.013 | 2.2515 | 2.30% |
| 40.274 | 2.23752 | 2.10% |
| 40.7 | 2.2151 | 4.70% |
| 41.447 | 2.17686 | 3.10% |

Example 25

Figure 64:
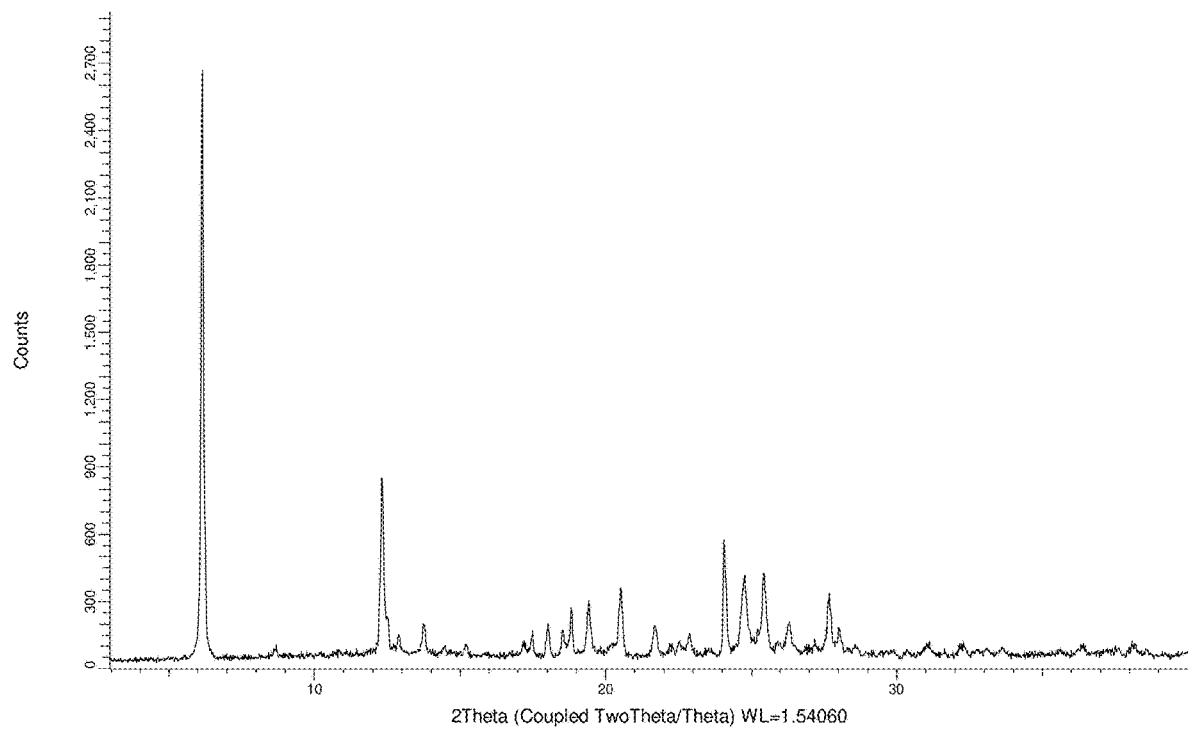
FIG. 64 depicts the X-ray powder diffraction (XRPD) pattern of 5-(3,4-dichlorophenyl)-N-((1R,2R)-2-hydroxycyclohexyl)-6-(2,2,2-trifluoroethoxy)nicotinamide, ethanol solvate (Form Y).

The XRPD pattern of crystalline Form Y material of 5-(3,4-dichlorophenyl)-N-((1R,2R)-2-hydroxycyclohexyl)-6-(2,2,2-trifluoroethoxy)nicotinamide, ethanol solvate, prepared according to the procedure in Example 23, is shown in FIG. 64. Characteristic peaks include one or more of the peaks shown in Table 36.

TABLE 36

| Angle | d Value | Rel. Intensity |
|---|---|---|
| 5.077 | 17.39208 | 54.50% |
| 5.348 | 16.51019 | 23.90% |
| 6.927 | 12.74992 | 24.00% |
| 8.964 | 9.85765 | 28.50% |
| 10.163 | 8.69671 | 12.80% |
| 10.722 | 8.24428 | 11.90% |
| 12.14 | 7.28445 | 15.40% |
| 13.564 | 6.52276 | 7.20% |
| 13.887 | 6.37188 | 3.50% |
| 14.193 | 6.23518 | 3.60% |
| 14.407 | 6.14295 | 3.90% |
| 15.269 | 5.79794 | 7.50% |
| 15.861 | 5.58314 | 8.60% |
| 16.112 | 5.49646 | 9.90% |
| 17.475 | 5.07095 | 2.20% |
| 18.01 | 4.9214 | 31.30% |
| 18.449 | 4.80527 | 19.70% |
| 18.85 | 4.70393 | 44.30% |
| 19.481 | 4.55289 | 12.30% |
| 19.701 | 4.50252 | 23.00% |
| 20.304 | 4.3702 | 20.00% |
| 20.852 | 4.2566 | 100.00% |
| 21.399 | 4.149 | 17.10% |
| 21.994 | 4.03818 | 9.70% |
| 22.199 | 4.00128 | 28.10% |
| 22.528 | 3.94351 | 13.30% |
| 22.734 | 3.90835 | 12.60% |
| 23.19 | 3.83246 | 19.30% |
| 23.476 | 3.78646 | 31.30% |
| 23.755 | 3.74266 | 6.70% |
| 24.364 | 3.6504 | 21.40% |
| 24.86 | 3.57864 | 16.30% |
| 25.357 | 3.5096 | 3.40% |
| 25.563 | 3.48189 | 16.40% |
| 25.877 | 3.44032 | 10.90% |
| 26.392 | 3.37431 | 2.90% |
| 26.655 | 3.34162 | 6.20% |
| 27.14 | 3.28302 | 9.20% |
| 27.516 | 3.23903 | 3.80% |
| 27.949 | 3.18976 | 2.50% |
| 28.257 | 3.1557 | 13.10% |
| 28.49 | 3.13042 | 8.20% |
| 28.958 | 3.0809 | 5.50% |
| 29.286 | 3.04712 | 7.50% |
| 29.797 | 2.99601 | 7.60% |
| 30.37 | 2.94082 | 1.20% |
| 30.823 | 2.89863 | 1.90% |
| 31.064 | 2.87666 | 5.40% |
| 31.572 | 2.83149 | 3.20% |
| 32.05 | 2.79035 | 5.80% |
| 32.598 | 2.74467 | 2.60% |
| 33.179 | 2.69795 | 1.30% |
| 34.099 | 2.62723 | 3.20% |
| 34.392 | 2.60554 | 4.20% |
| 35.108 | 2.55398 | 3.30% |

TABLE 36-continued

| Angle | d Value | Rel. Intensity |
|---|---|---|
| 35.813 | 2.50535 | 2.50% |
| 36.131 | 2.48403 | 5.20% |
| 36.445 | 2.46332 | 6.70% |
| 36.972 | 2.42938 | 5.00% |
| 37.611 | 2.38957 | 5.30% |
| 38.198 | 2.3542 | 6.60% |
| 39.037 | 2.30554 | 2.20% |
| 39.402 | 2.28502 | 2.40% |
| 40.013 | 2.2515 | 2.30% |
| 40.274 | 2.23752 | 2.10% |
| 40.7 | 2.2151 | 4.70% |
| 41.447 | 2.17686 | 3.10% |

Example 26

Figure 65:
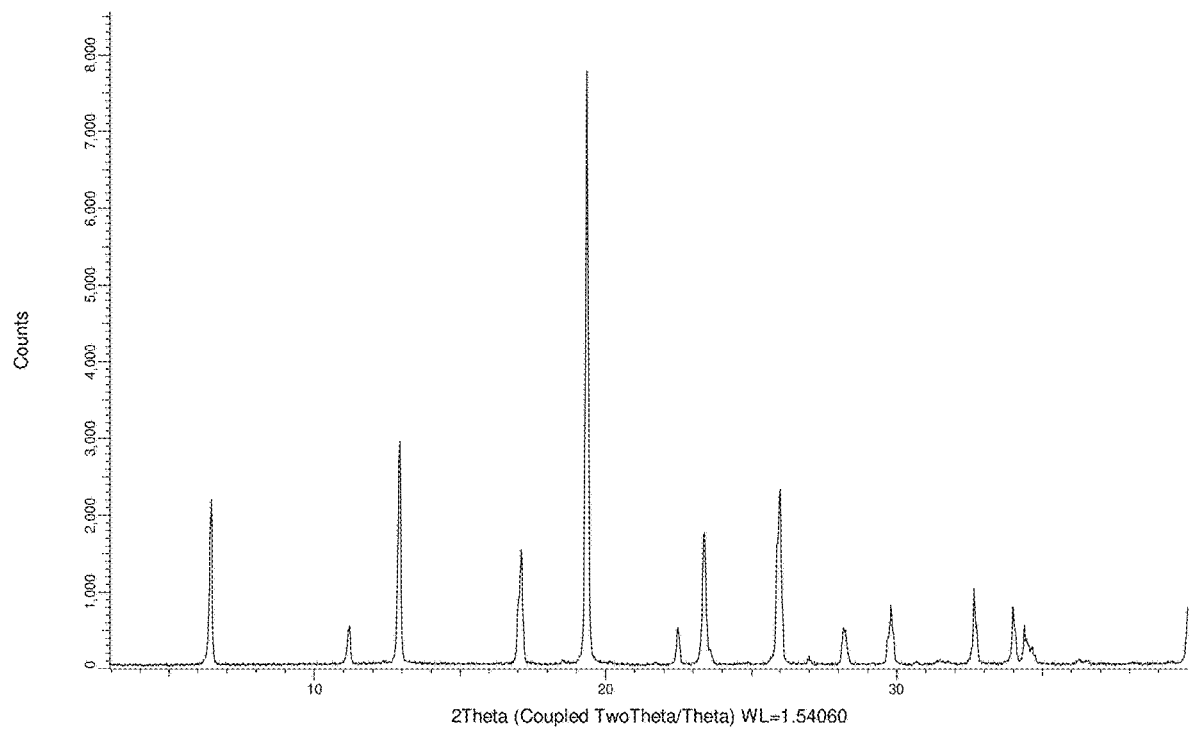
FIG. 65 depicts the X-ray powder diffraction (XRPD) pattern of 5-(3,4-dichlorophenyl)-N-((1R,2R)-2-hydroxycyclohexyl)-6-(2,2,2-trifluoroethoxy)nicotinamide, isopropanol solvate (Form Z).

The XRPD pattern of crystalline Form Z material of 5-(3,4-dichlorophenyl)-N-((1R,2R)-2-hydroxycyclohexyl)-6-(2,2,2-trifluoroethoxy)nicotinamide, isopropanol solvate, prepared according to the procedure in Example 6, is shown in FIG. 65. Characteristic peaks include one or more of the peaks shown in Table 37.

TABLE 37

| Angle | d Value | Rel. Intensity |
|---|---|---|
| 5.077 | 17.39208 | 54.50% |
| 5.348 | 16.51019 | 23.90% |
| 6.927 | 12.74992 | 24.00% |
| 8.964 | 9.85765 | 28.50% |
| 10.163 | 8.69671 | 12.80% |
| 10.722 | 8.24428 | 11.90% |
| 12.14 | 7.28445 | 15.40% |
| 13.564 | 6.52276 | 7.20% |
| 13.887 | 6.37188 | 3.50% |
| 14.193 | 6.23518 | 3.60% |
| 14.407 | 6.14295 | 3.90% |
| 15.269 | 5.79794 | 7.50% |
| 15.861 | 5.58314 | 8.60% |
| 16.112 | 5.49646 | 9.90% |
| 17.475 | 5.07095 | 2.20% |
| 18.01 | 4.9214 | 31.30% |
| 18.449 | 4.80527 | 19.70% |
| 18.85 | 4.70393 | 44.30% |
| 19.481 | 4.55289 | 12.30% |
| 19.701 | 4.50252 | 23.00% |
| 20.304 | 4.3702 | 20.00% |
| 20.852 | 4.2566 | 100.00% |
| 21.399 | 4.149 | 17.10% |
| 21.994 | 4.03818 | 9.70% |
| 22.199 | 4.00128 | 28.10% |
| 22.528 | 3.94351 | 13.30% |
| 22.734 | 3.90835 | 12.60% |
| 23.19 | 3.83246 | 19.30% |
| 23.476 | 3.78646 | 31.30% |
| 23.755 | 3.74266 | 6.70% |
| 24.364 | 3.6504 | 21.40% |
| 24.86 | 3.57864 | 16.30% |
| 25.357 | 3.5096 | 3.40% |
| 25.563 | 3.48189 | 16.40% |
| 25.877 | 3.44032 | 10.90% |
| 26.392 | 3.37431 | 2.90% |
| 26.655 | 3.34162 | 6.20% |
| 27.14 | 3.28302 | 9.20% |
| 27.516 | 3.23903 | 3.80% |
| 27.949 | 3.18976 | 2.50% |
| 28.257 | 3.1557 | 13.10% |
| 28.49 | 3.13042 | 8.20% |
| 28.958 | 3.0809 | 5.50% |
| 29.286 | 3.04712 | 7.50% |
| 29.797 | 2.99601 | 7.60% |
| 30.37 | 2.94082 | 1.20% |
| 30.823 | 2.89863 | 1.90% |
| 31.064 | 2.87666 | 5.40% |

TABLE 37-continued

| Angle | d Value | Rel. Intensity |
|---|---|---|
| 31.572 | 2.83149 | 3.20% |
| 32.05 | 2.79035 | 5.80% |
| 32.598 | 2.74467 | 2.60% |
| 33.179 | 2.69795 | 1.30% |
| 34.099 | 2.62723 | 3.20% |
| 34.392 | 2.60554 | 4.20% |
| 35.108 | 2.55398 | 3.30% |
| 35.813 | 2.50535 | 2.50% |
| 36.131 | 2.48403 | 5.20% |
| 36.445 | 2.46332 | 6.70% |
| 36.972 | 2.42938 | 5.00% |
| 37.611 | 2.38957 | 5.30% |
| 38.198 | 2.3542 | 6.60% |
| 39.037 | 2.30554 | 2.20% |
| 39.402 | 2.28502 | 2.40% |
| 40.013 | 2.2515 | 2.30% |
| 40.274 | 2.23752 | 2.10% |
| 40.7 | 2.2151 | 4.70% |
| 41.447 | 2.17686 | 3.10% |

Example 27

Figure 66:
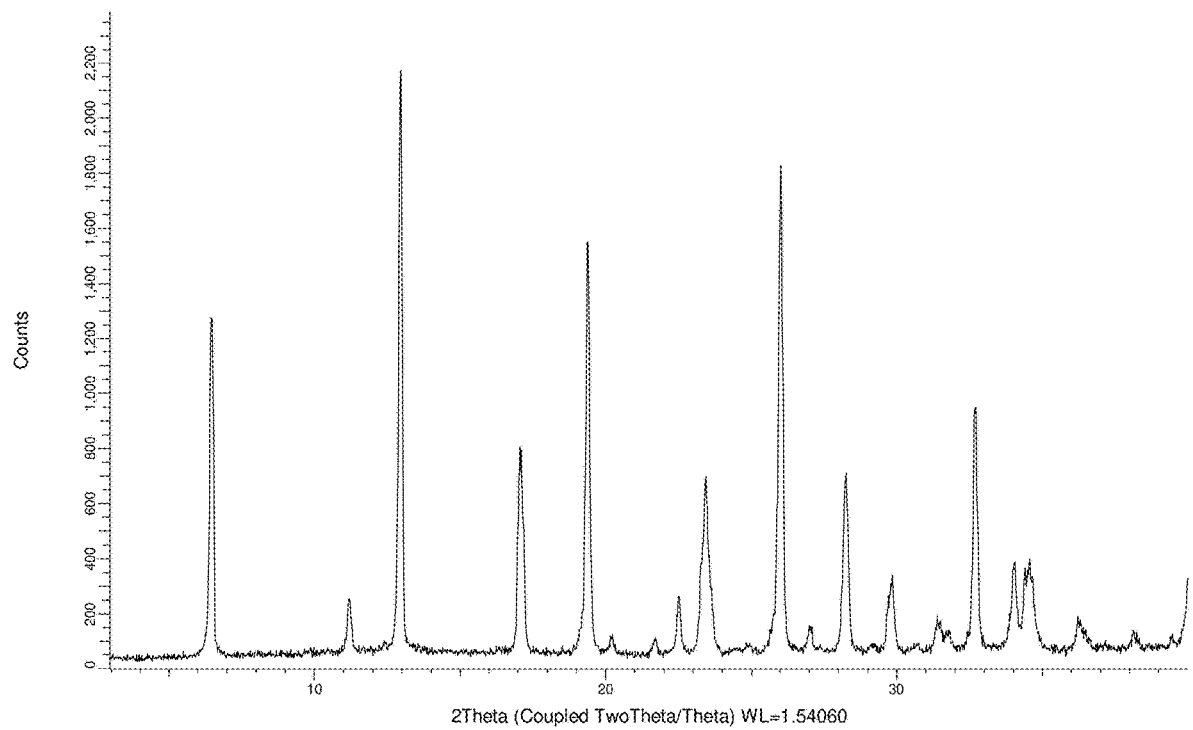
FIG. 66 depicts the X-ray powder diffraction (XRPD) pattern of 5-(3,4-dichlorophenyl)-N-((1R,2R)-2-hydroxycyclohexyl)-6-(2,2,2-trifluoroethoxy)nicotinamide, tetrahydrofuran solvate (Form AA).

The XRPD pattern of crystalline Form AA material of 5-(3,4-dichlorophenyl)-N-((1R,2R)-2-hydroxycyclohexyl)-6-(2,2,2-trifluoroethoxy)nicotinamide, tetrahydrofuran solvate, prepared according to the procedure in Example 22, is shown in FIG. 66. Characteristic peaks include one or more of the peaks shown in Table 38.

TABLE 38

| Angle | d Value | Rel. Intensity |
|---|---|---|
| 5.077 | 17.39208 | 54.50% |
| 5.348 | 16.51019 | 23.90% |
| 6.927 | 12.74992 | 24.00% |
| 8.964 | 9.85765 | 28.50% |
| 10.163 | 8.69671 | 12.80% |
| 10.722 | 8.24428 | 11.90% |
| 12.14 | 7.28445 | 15.40% |
| 13.564 | 6.52276 | 7.20% |
| 13.887 | 6.37188 | 3.50% |
| 14.193 | 6.23518 | 3.60% |
| 14.407 | 6.14295 | 3.90% |
| 15.269 | 5.79794 | 7.50% |
| 15.861 | 5.58314 | 8.60% |
| 16.112 | 5.49646 | 9.90% |
| 17.475 | 5.07095 | 2.20% |
| 18.01 | 4.9214 | 31.30% |
| 18.449 | 4.80527 | 19.70% |
| 18.85 | 4.70393 | 44.30% |
| 19.481 | 4.55289 | 12.30% |
| 19.701 | 4.50252 | 23.00% |
| 20.304 | 4.3702 | 20.00% |
| 20.852 | 4.2566 | 100.00% |
| 21.399 | 4.149 | 17.10% |
| 21.994 | 4.03818 | 9.70% |
| 22.199 | 4.00128 | 28.10% |
| 22.528 | 3.94351 | 13.30% |
| 22.734 | 3.90835 | 12.60% |
| 23.19 | 3.83246 | 19.30% |
| 23.476 | 3.78646 | 31.30% |
| 23.755 | 3.74266 | 6.70% |
| 24.364 | 3.6504 | 21.40% |
| 24.86 | 3.57864 | 16.30% |
| 25.357 | 3.5096 | 3.40% |
| 25.563 | 3.48189 | 16.40% |
| 25.877 | 3.44032 | 10.90% |
| 26.392 | 3.37431 | 2.90% |
| 26.655 | 3.34162 | 6.20% |
| 27.14 | 3.28302 | 9.20% |
| 27.516 | 3.23903 | 3.80% |
| 27.949 | 3.18976 | 2.50% |
| 28.257 | 3.1557 | 13.10% |

TABLE 38-continued

| Angle | d Value | Rel. Intensity |
|---|---|---|
| 28.49 | 3.13042 | 8.20% |
| 28.958 | 3.0809 | 5.50% |
| 29.286 | 3.04712 | 7.50% |
| 29.797 | 2.99601 | 7.60% |
| 30.37 | 2.94082 | 1.20% |
| 30.823 | 2.89863 | 1.90% |
| 31.064 | 2.87666 | 5.40% |
| 31.572 | 2.83149 | 3.20% |
| 32.05 | 2.79035 | 5.80% |
| 32.598 | 2.74467 | 2.60% |
| 33.179 | 2.69795 | 1.30% |
| 34.099 | 2.62723 | 3.20% |
| 34.392 | 2.60554 | 4.20% |
| 35.108 | 2.55398 | 3.30% |
| 35.813 | 2.50535 | 2.50% |
| 36.131 | 2.48403 | 5.20% |
| 36.445 | 2.46332 | 6.70% |
| 36.972 | 2.42938 | 5.00% |
| 37.611 | 2.38957 | 5.30% |
| 38.198 | 2.3542 | 6.60% |
| 39.037 | 2.30554 | 2.20% |
| 39.402 | 2.28502 | 2.40% |
| 40.013 | 2.2515 | 2.30% |
| 40.274 | 2.23752 | 2.10% |
| 40.7 | 2.2151 | 4.70% |
| 41.447 | 2.17686 | 3.10% |

Example 28

Crystalline, Form 2 material of 5-(3,4-dichlorophenyl)-N-((1R,2R)-2-hydroxycyclohexyl)-6-(2,2,2-trifluoroethoxy)nicotinamide, anhydrate, was prepared as follows. A sample of crystalline Form J material of 5-(3,4-dichlorophenyl)-N-((1R,2R)-2-hydroxycyclohexyl)-6-(2,2,2-trifluoroethoxy)nicotinamide, ethanol solvate, was dried under vacuum (<5 mbar) at 25° C. XRPD analysis indicated that the dried material was crystalline with a pattern consistent with Form 2.

Figure 67:
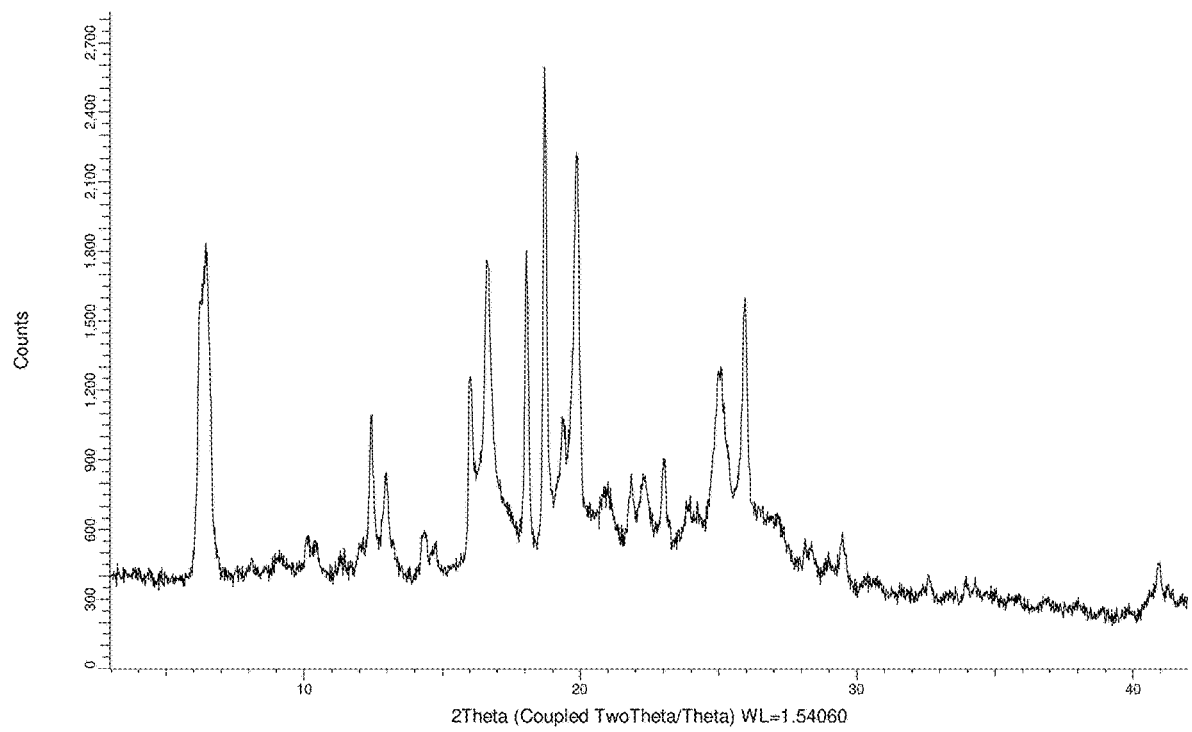
FIG. 67 depicts the X-ray powder diffraction (XRPD) pattern of 5-(3,4-dichlorophenyl)-N-((1R,2R)-2-hydroxycyclohexyl)-6-(2,2,2-trifluoroethoxy)nicotinamide, anhydrate (Form 2).

The XRPD pattern of Form 2 is shown in FIG. 67. Characteristic peaks include one or more of the peaks shown in Table 39.

TABLE 39

| Angle | d Value | Rel. Intensity |
|---|---|---|
| 5.077 | 17.39208 | 54.50% |
| 5.348 | 16.51019 | 23.90% |
| 6.927 | 12.74992 | 24.00% |
| 8.964 | 9.85765 | 28.50% |
| 10.163 | 8.69671 | 12.80% |
| 10.722 | 8.24428 | 11.90% |
| 12.14 | 7.28445 | 15.40% |
| 13.564 | 6.52276 | 7.20% |
| 13.887 | 6.37188 | 3.50% |
| 14.193 | 6.23518 | 3.60% |
| 14.407 | 6.14295 | 3.90% |
| 15.269 | 5.79794 | 7.50% |
| 15.861 | 5.58314 | 8.60% |
| 16.112 | 5.49646 | 9.90% |
| 17.475 | 5.07095 | 2.20% |
| 18.01 | 4.9214 | 31.30% |
| 18.449 | 4.80527 | 19.70% |
| 18.85 | 4.70393 | 44.30% |
| 19.481 | 4.55289 | 12.30% |
| 19.701 | 4.50252 | 23.00% |
| 20.304 | 4.3702 | 20.00% |
| 20.852 | 4.2566 | 100.00% |
| 21.399 | 4.149 | 17.10% |
| 21.994 | 4.03818 | 9.70% |
| 22.199 | 4.00128 | 28.10% |
| 22.528 | 3.94351 | 13.30% |

TABLE 39-continued

| Angle | d Value | Rel. Intensity |
|---|---|---|
| 22.734 | 3.90835 | 12.60% |
| 23.19 | 3.83246 | 19.30% |
| 23.476 | 3.78646 | 31.30% |
| 23.755 | 3.74266 | 6.70% |
| 24.364 | 3.6504 | 21.40% |
| 24.86 | 3.57864 | 16.30% |
| 25.357 | 3.5096 | 3.40% |
| 25.563 | 3.48189 | 16.40% |
| 25.877 | 3.44032 | 10.90% |
| 26.392 | 3.37431 | 2.90% |
| 26.655 | 3.34162 | 6.20% |
| 27.14 | 3.28302 | 9.20% |
| 27.516 | 3.23903 | 3.80% |
| 27.949 | 3.18976 | 2.50% |
| 28.257 | 3.1557 | 13.10% |
| 28.49 | 3.13042 | 8.20% |
| 28.958 | 3.0809 | 5.50% |
| 29.286 | 3.04712 | 7.50% |
| 29.797 | 2.99601 | 7.60% |
| 30.37 | 2.94082 | 1.20% |
| 30.823 | 2.89863 | 1.90% |
| 31.064 | 2.87666 | 5.40% |
| 31.572 | 2.83149 | 3.20% |
| 32.05 | 2.79035 | 5.80% |
| 32.598 | 2.74467 | 2.60% |
| 33.179 | 2.69795 | 1.30% |
| 34.099 | 2.62723 | 3.20% |
| 34.392 | 2.60554 | 4.20% |
| 35.108 | 2.55398 | 3.30% |
| 35.813 | 2.50535 | 2.50% |
| 36.131 | 2.48403 | 5.20% |
| 36.445 | 2.46332 | 6.70% |
| 36.972 | 2.42938 | 5.00% |
| 37.611 | 2.38957 | 5.30% |
| 38.198 | 2.3542 | 6.60% |
| 39.037 | 2.30554 | 2.20% |
| 39.402 | 2.28502 | 2.40% |
| 40.013 | 2.2515 | 2.30% |
| 40.274 | 2.23752 | 2.10% |
| 40.7 | 2.2151 | 4.70% |
| 41.447 | 2.17686 | 3.10% |

Figure 68:
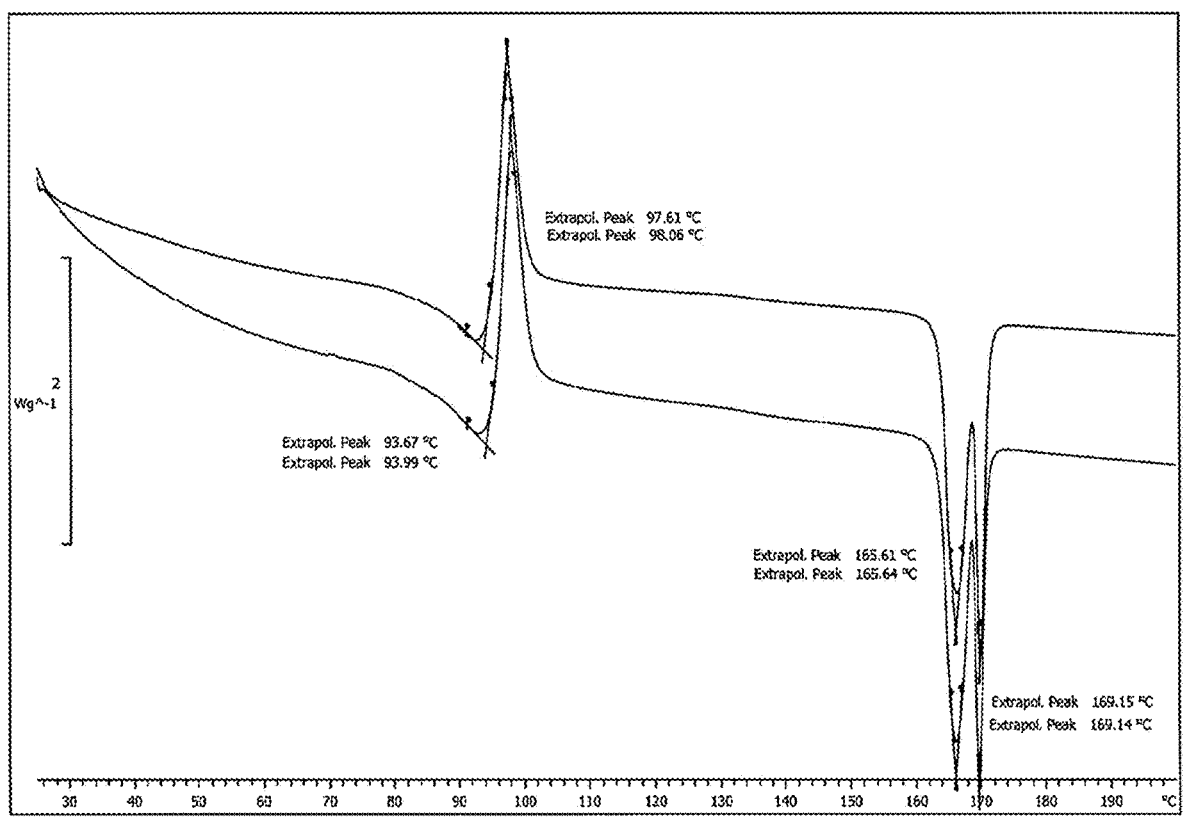
FIG. 68 depicts the characterization of Form 2 by differential scanning calorimetry (DSC).

FIG. 68 depicts the differential scanning calorimetry (DSC) profile of crystalline Form 2. As shown in FIG. 68, crystalline Form 2 shows a characteristic endotherm with an onset of about 94° C.; a characteristic exotherm with an onset of about 98° C.; a characteristic exotherm with an onset of about 165° C.; and a characteristic endotherm with an onset and a peak of about 169° C. Crystalline Form 2 displayed a thermogravimetric analysis (TGA) profile showing a mass loss of about 0.9 wt. % up to about 120° C. Crystalline Form 2 displayed a dynamic vapor sorption (DVS) profile showing a reversable total mass change of about 2.1 wt. % between about 0 to about 90% relative humidity (RH) at 25° C.

Example 29

Figure 71:
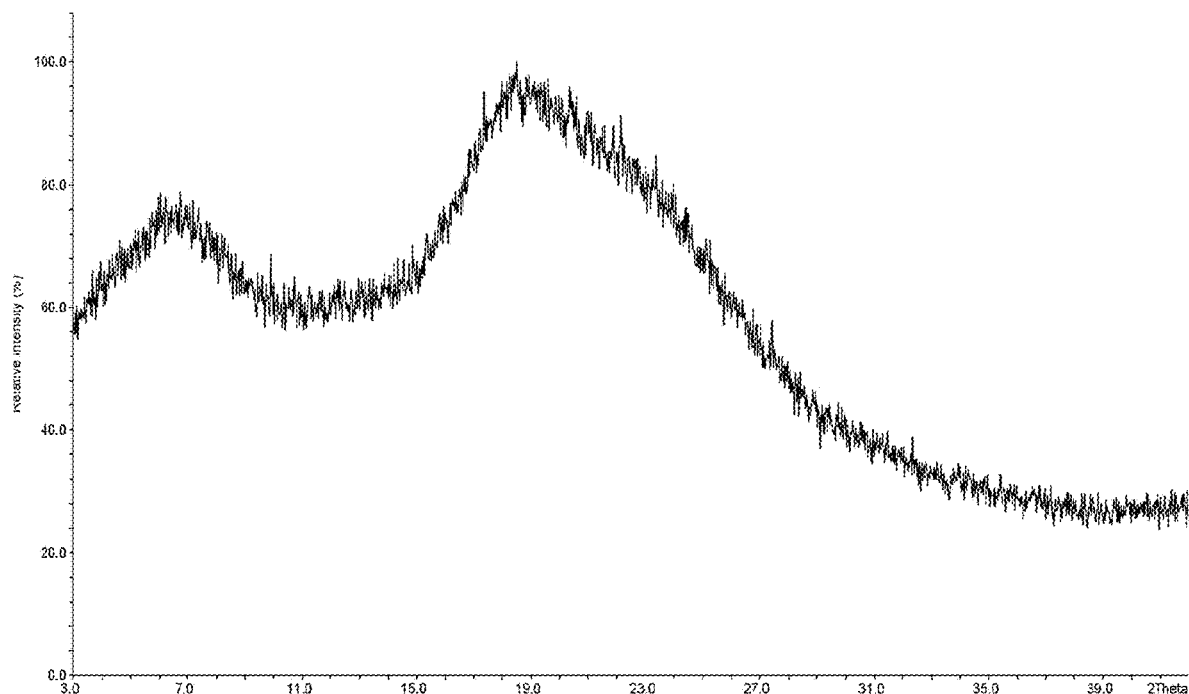
FIG. 71 depicts the X-ray powder diffraction (XRPD) pattern of amorphous 5-(3,4-dichlorophenyl)-N-((1R,2R)-2-hydroxycyclohexyl)-6-(2,2,2-trifluoroethoxy)nicotinamide.

Amorphous material of 5-(3,4-dichlorophenyl)-N-((1R,2R)-2-hydroxycyclohexyl)-6-(2,2,2-trifluoroethoxy)nicotinamide was prepared as follows. A sample of crystalline Form E material of 5-(3,4-dichlorophenyl)-N-((1R,2R)-2-hydroxycyclohexyl)-6-(2,2,2-trifluoroethoxy)nicotinamide, anhydrate, was heated to 164° C. XRPD analysis indicated that the material was amorphous, as shown in FIG. 71.

Example 29

Figure 72:
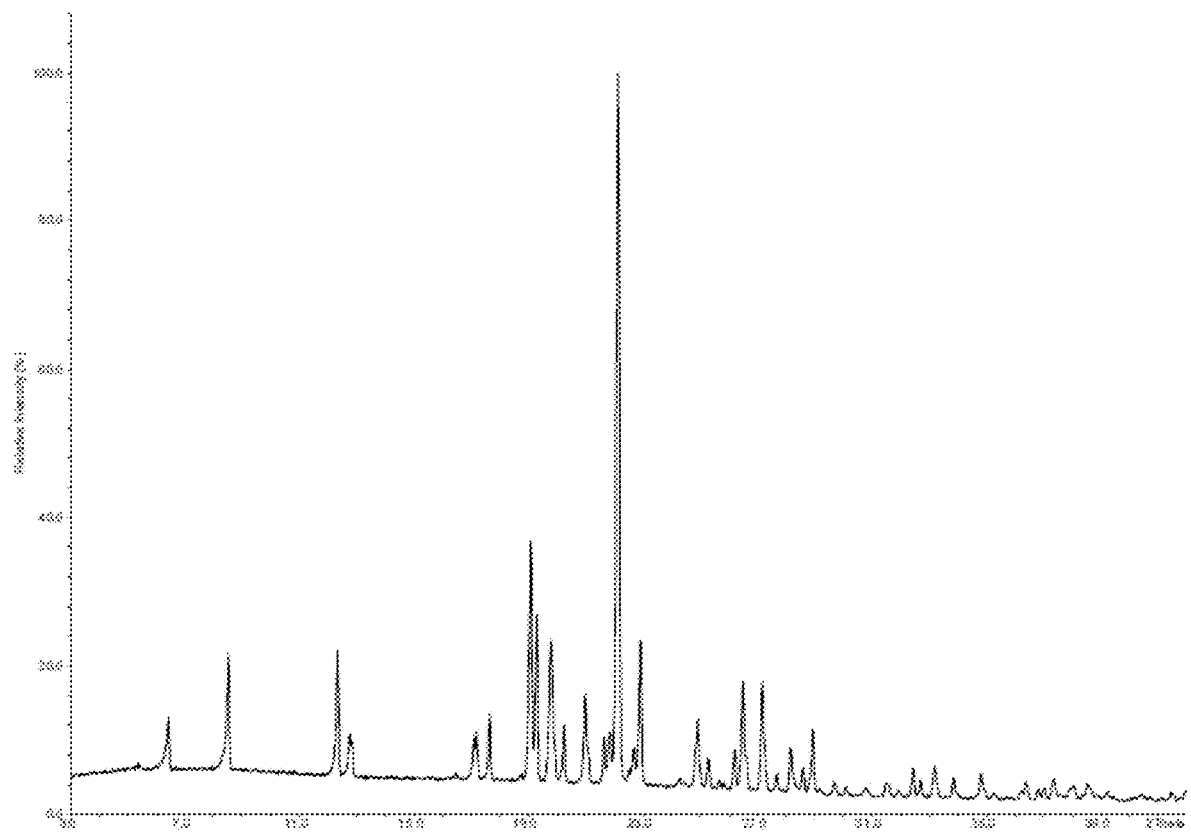
FIG. 72 depicts the X-ray powder diffraction (XRPD) pattern of a 5-(3,4-dichlorophenyl)-N-((1R,2R)-2-hydroxycyclohexyl)-6-(2,2,2-trifluoroethoxy)nicotinamide/sorbic acid cocrystal (4:1 molar ratio).

A cocrystal of 5-(3,4-dichlorophenyl)-N-((1R,2R)-2-hydroxycyclohexyl)-6-(2,2,2-trifluoroethoxy)nicotinamide and sorbic acid (4:1 molar ratio) was prepared as follows. 150 mg of 5-(3,4-dichlorophenyl)-N-((1R,2R)-2-hydroxycyclohexyl)-6-(2,2,2-trifluoroethoxy)nicotinamide as equilibrated in 2000 ul saturated sorbic acid solution in acetonitrile for 24 hours at room temperature by head-over-head rotation with a magnetic stir bar (5×10 mm) in a 4 mL screw cap glass vial. After equilibration the solid phase was separated from the liquid phase by centrifugal filtration. The residual solid was dried at 40° C. in a vacuum tray dryer for 4 h at 40 mbar. XRPD analysis indicated that the dried material was crystalline. NMR, IR and LC-MS analyses indicated the material was a cocrystal of 5-(3,4-dichlorophenyl)-N-((1R,2R)-2-hydroxycyclohexyl)-6-(2,2,2-trifluoroethoxy)nicotinamide and sorbic acid (4:1 molar ratio). The XRPD pattern of Form 2 is shown in FIG. 72.

Figure 73:
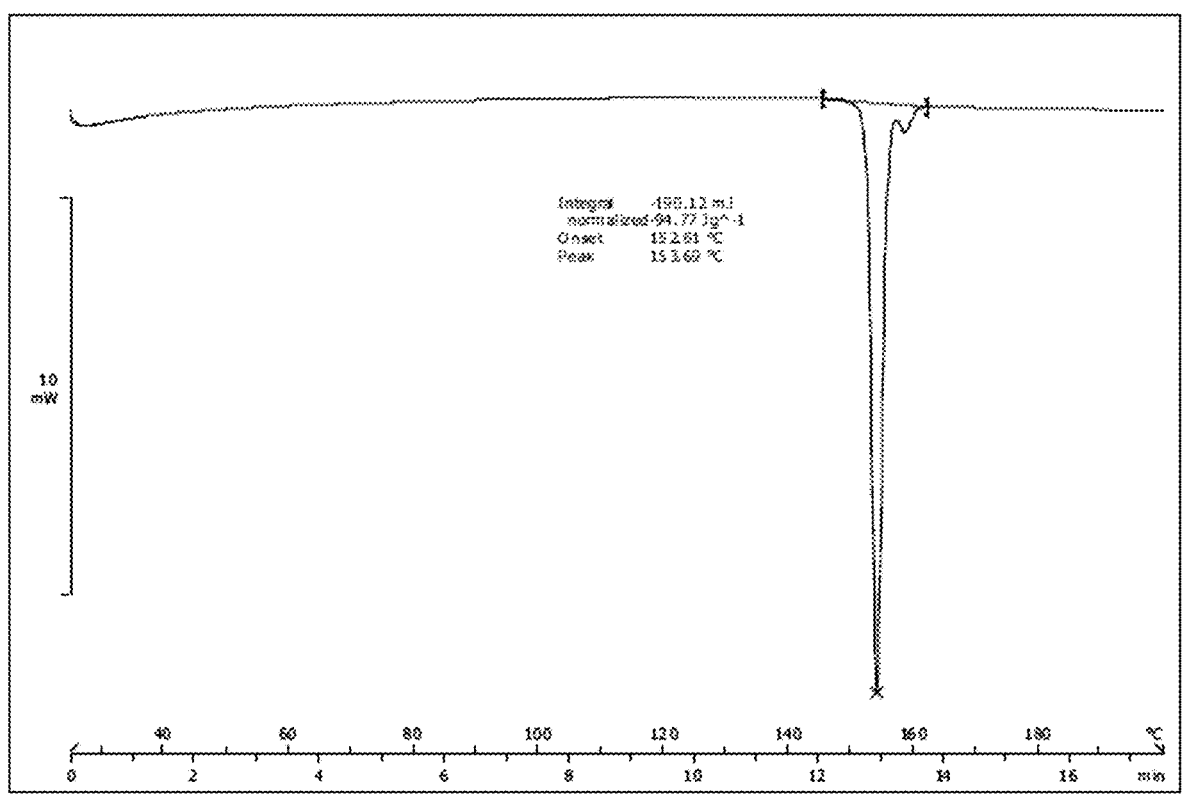
FIG. 73 depicts the differential scanning calorimetry (DSC) profile of a 5-(3,4-dichlorophenyl)-N-((1R,2R)-2-hydroxycyclohexyl)-6-(2,2,2-trifluoroethoxy)nicotinamide/sorbic acid cocrystal (4:1 molar ratio).
Figure 74:
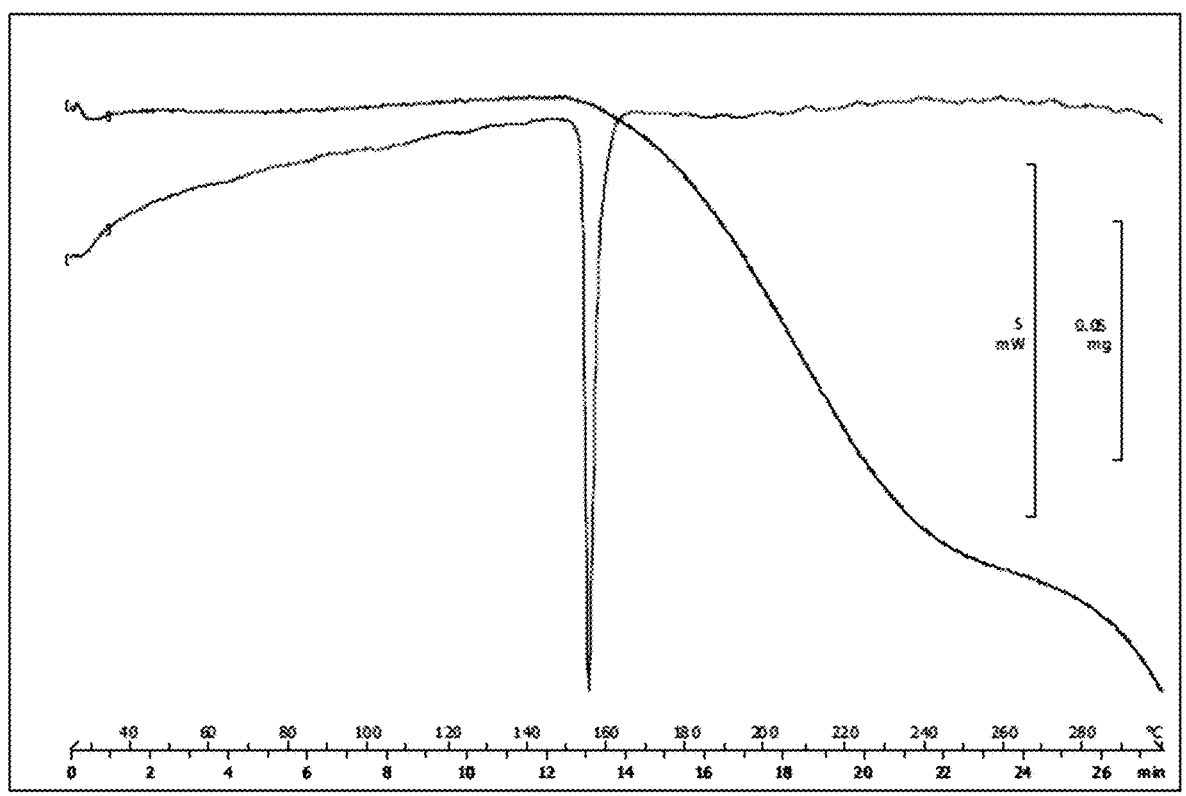
FIG. 74 depicts the thermogravimetric analysis (TGA) profile of a 5-(3,4-dichlorophenyl)-N-((1R,2R)-2-hydroxycyclohexyl)-6-(2,2,2-trifluoroethoxy)nicotinamide/sorbic acid cocrystal (4:1 molar ratio).

FIG. 73 depicts the differential scanning calorimetry (DSC) profile of the cocrystal. As shown in FIG. 73, the cocrystal shows a characteristic endotherm with an onset of about 153° C. and a peak of about 154° C. As shown in FIG. 74, thermogravimetric analysis (TGA) of the cocrystal (sample weight 1.8860 mg) showed no substantial weight loss step (about 0.05 mg) upon heating.

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject disclosure have been discussed, the above specification is illustrative and not restrictive. Many variations of the disclosure will become apparent to those skilled in the art upon review of this specification. The full scope of the disclosure should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure.

The invention claimed is:

1. A crystalline form of 5-(3,4-dichlorophenyl)-N-((1R,2R)-2-hydroxycyclohexyl)-6-(2,2,2-trifluoroethoxy)nicotinamide, anhydrate (Form E), characterized by a powder X-ray diffraction pattern having characteristic peaks in degrees 2θ at about 10.3, 15.9, and 20.6.

2. The crystalline form of claim 1, characterized by a powder X-ray diffraction pattern having characteristic peaks in degrees 2θ at about 10.3, 15.9, 17.7, 20.6, 21.4, and 26.1.

3. The crystalline form of claim 1, characterized by a powder X-ray diffraction pattern having characteristic peaks in degrees 2θ at about 10.3, 14.9, 15.9, 17.7, 18.9, 20.6, 21.4, 21.8, 26.1, 29.7, 33.0, and 39.3.

4. The crystalline form of claim 1, characterized by a powder X-ray diffraction pattern having characteristic peaks in degrees 2θ at about 10.3, 14.9, 15.9, 17.7, 18.9, 20.6, 21.4, 21.8, 23.3, 25.2, 26.1, 26.7, 29.7, 28.0, 33.0, 36.1, 37.2, and 39.3.

5. The crystalline form of claim 1, wherein the powder X-ray diffraction pattern was obtained using Cu Kα radiation.

6. The crystalline form of claim 1, characterized by a differential scanning calorimetry (DSC) profile having a characteristic endotherm with an onset of about 168° C. and a peak of about 169° C.

7. A crystalline form of 5-(3,4-dichlorophenyl)-N-((1R, 2R)-2-hydroxycyclohexyl)-6-(2,2,2-trifluoroethoxy)nicotinamide, anhydrate (Form A), characterized by a powder X-ray diffraction pattern having a characteristic peak in degrees 2θ at about 8.4, 11.7, 14.9, 15.8, 17.5, 18.4, 19.1, 20.4, 21.6, 22.2, 23.4, and 25.1, wherein the powder X-ray diffraction pattern was obtained using Cu Kα radiation.

8. The crystalline form of claim 7, characterized by a differential scanning calorimetry (DSC) profile having a characteristic endotherm with an onset and a peak of about 164° C.; and a characteristic endotherm with an onset of about 168° C. and a peak of about 169° C.

9. A crystalline form of 5-(3,4-dichlorophenyl)-N-((1R, 2R)-2-hydroxycyclohexyl)-6-(2,2,2-trifluoroethoxy)nicotinamide, anhydrate (Form I), characterized by a powder X-ray diffraction pattern having a characteristic peak in degrees 2θ at about 7.6, 12.2, 12.7, 17.7, 20.1, 22.7, 22.9, 23.4, 24.4, 25.2, 28.5, and 36.9, wherein the powder X-ray diffraction pattern was obtained using Cu Kα radiation.

10. The crystalline form of claim 9, characterized by a differential scanning calorimetry (DSC) profile having a characteristic endotherm with an onset of about 154° C.; a characteristic exotherm with an onset of about 156° C.; a characteristic endotherm with an onset of about 164° C.; and a characteristic endotherm with an onset of about 168° C.

11. A pharmaceutical composition comprising the crystalline form of claim 1, and a pharmaceutically acceptable excipient.

12. A pharmaceutical composition comprising the crystalline form of claim 7, and a pharmaceutically acceptable excipient.

13. A pharmaceutical composition comprising the crystalline form of claim 9, and a pharmaceutically acceptable excipient.

14. A pharmaceutical composition formed from the crystalline Form E of claim 1.

15. The pharmaceutical composition of claim 11, wherein the composition is formulated for oral administration.

16. A method of treating a kidney disease in a patient in need thereof, comprising administering to the patient an effective amount of a crystalline form of claim 1.

17. A method of treating a cancer in a patient in need thereof, comprising administering to the patient an effective amount of a crystalline form of claim 1.

* * * * *